(12) United States Patent
Lynch et al.

(10) Patent No.: US 12,018,327 B2
(45) Date of Patent: Jun. 25, 2024

(54) METHODS AND COMPOSITIONS RELATING TO EPOXIDE HYDROLASE GENES

(71) Applicant: The Regents of the University of California, Oakland, CA (US)

(72) Inventors: Susan V. Lynch, Piedmont, CA (US); Sophia Rose Levan, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 954 days.

(21) Appl. No.: 16/976,285

(22) PCT Filed: Mar. 1, 2019

(86) PCT No.: PCT/US2019/020277
§ 371 (c)(1),
(2) Date: Aug. 27, 2020

(87) PCT Pub. No.: WO2019/169258
PCT Pub. Date: Sep. 6, 2019

(65) Prior Publication Data
US 2020/0407796 A1 Dec. 31, 2020

Related U.S. Application Data

(60) Provisional application No. 62/637,175, filed on Mar. 1, 2018.

(51) Int. Cl.
| | |
|---|---|
| *G16H 50/30* | (2018.01) |
| *A61K 31/201* | (2006.01) |
| *A61K 31/47* | (2006.01) |
| *A61K 31/495* | (2006.01) |
| *A61K 31/58* | (2006.01) |
| *A61K 31/59* | (2006.01) |
| *A61K 35/60* | (2006.01) |
| *A61K 35/741* | (2015.01) |
| *A61K 35/745* | (2015.01) |
| *C07K 16/28* | (2006.01) |
| *C12Q 1/6883* | (2018.01) |
| *G16B 20/00* | (2019.01) |
| *G16H 10/40* | (2018.01) |
| *G16H 20/10* | (2018.01) |
| *G16H 50/70* | (2018.01) |

(52) U.S. Cl.
CPC .......... *C12Q 1/6883* (2013.01); *A61K 31/201* (2013.01); *A61K 31/47* (2013.01); *A61K 31/495* (2013.01); *A61K 31/58* (2013.01); *A61K 31/59* (2013.01); *A61K 35/60* (2013.01); *A61K 35/741* (2013.01); *A61K 35/745* (2013.01); *C07K 16/283* (2013.01); *G16B 20/00* (2019.02); *G16H 10/40* (2018.01); *G16H 20/10* (2018.01); *G16H 50/30* (2018.01); *G16H 50/70* (2018.01)

(58) Field of Classification Search
None
See application file for complete search history.

(56) References Cited

U.S. PATENT DOCUMENTS

| 5,445,956 A | 8/1995 | Hammock et al. |
|---|---|---|
| 2002/0061569 A1 | 5/2002 | Haselback et al. |
| 2002/0120116 A1 | 8/2002 | Kunsch et al. |
| 2008/0118484 A1 | 5/2008 | Herz et al. |
| 2009/0076098 A1 | 3/2009 | Hoffmann et al. |
| 2018/0177749 A1 | 6/2018 | Potter et al. |

FOREIGN PATENT DOCUMENTS

| WO | WO-2016/192788 A1 | 12/2016 |
|---|---|---|
| WO | WO-2017/152137 A2 | 9/2017 |
| WO | WO-2017/152137 A3 | 9/2017 |
| WO | WO-2017/152137 A8 | 9/2017 |
| WO | WO-2017/152137 A9 | 9/2017 |

OTHER PUBLICATIONS

Weinstock et al., UniProt accession No. A0A059N0Y6;(EMBL accession No. KDE16932) (Year: 2013).*
Aichbhaumik, N. et al. (Nov. 2008, e-published Aug. 11, 2008). "Prenatal exposure to household pets influences fetal immunoglobulin E production," *Clin Exp Allergy* 38(11):1787-1794.
Altschul, S.F. et al. (Oct. 5, 1990). "Basic local alignment search tool," *J Mol Biol* 215(3):403-410.
Altschul, S.F. et al. (Sep. 1, 1997). "Gapped BLAST and PSI-BLAST: a new generation of protein database search programs," *Nucleic Acids Research* 25(17):3389-3402.
Amin, P. et al. (Nov.-Dec. 2014, e-published Nov. 6, 2014). "Optimum predictors of childhood asthma: persistent wheeze or the Asthma Predictive Index?" *J Allergy Clin Immunol Pract* 2(6):709-715.
Arrieta, M-C. et al. (Sep. 30, 2015). "Early infancy microbial and metabolic alterations affect risk of childhood asthma," *Sci Transl Med* 7(307):307ra152.
Baker, K. et al. (Jun. 2, 2016). "Role of the ion channel, transient receptor potential cation channel subfamily V member 1 (TRPV1), in allergic asthma," *Respir Res* 17(1):67.
Barrett, E.G. (2008, e-published Jul. 12, 2007). "Maternal influence in the transmission of asthma susceptibility," *Pulmonary Pharmacol Ther* 21(3):474-484.
Biswal, B.K. et al. (Sep. 12, 2008, e-published Jun. 17, 2008). "The molecular structure of epoxide hydrolase B from *Mycobacterium tuberculosis* and its complex with a urea-based inhibitor," *J Mol Biol* 381(4):897-912.

(Continued)

*Primary Examiner* — Daniel C Gamett
(74) *Attorney, Agent, or Firm* — Mintz, Levin, Cohn, Ferris, Glovsky and Popeo, P.C.

(57) ABSTRACT

Provided herein are, inter alia, methods and kits for detecting epoxide hydrolase genes. In embodiments, methods and kits for detecting the risk of developing atopy or asthma are included. Also included are methods for preventing or treating atopy or asthma.

18 Claims, 35 Drawing Sheets

Specification includes a Sequence Listing.

(56) References Cited

OTHER PUBLICATIONS

Byndloss, M.X. et al. (Aug. 11, 2017). "Microbiota-activated PPAR-γ signaling inhibits dysbiotic Enterobacteriaceae expansion," *Science* 357(6351):570-575.

Castro-Rodriguez, J.A. et al. (Oct. 2000). "A clinical index to define risk of asthma in young children with recurrent wheezing," *Am J Respir Crit Care Med* 162 (4 Pt 1):1403-1406.

Choo, J. et al. (Oct. 16, 2015, Sep. 4, 2015). "A Novel Peroxisome Proliferator-activated Receptor (PPAR)γ Agonist 2-Hydroxyethyl 5-chloro-4,5-didehydrojasmonate Exerts Anti-Inflammatory Effects in Colitis*," *J Biol Chem* 290(42):25609-25619.

Deangelis, K.M. et al. (Feb. 2009, e-published Nov. 13, 2008). Selective progressive response of soil microbial community to wild oat roots, *ISME J.* 3(2):168-178.

Decker, M. et al. (Apr. 2009, e-published Apr. 2, 2009). "Mammalian epoxide hydrolases in xenobiotic metabolism and signaling," *Arch Toxicol* 83(4):297-318.

Fujimura, K.E. et al. (Jan. 14, 2014, e-published Dec. 16, 2013). House dust exposure mediates gut microbiome Lactobacillus enrichment and airway immune defense against allergens and virus infection *Proc. Natl. Acad. Sci.* 111(2) 805-810.

Fujimura, K.E. et al. (Oct. 2016, e-published Sep. 12, 2016). "Neonatal gut microbiota associates with childhood multisensitized atopy and T cell differentiation," *Nat Med* 22(10):1187-1191.

Gouveia-Figueira, S. et al. (Jul. 17, 2015). "Profiling the Oxylipin and Endocannabinoid Metabolome by UPLC-ESI-MS/MS in Human Plasma to Monitor Postprandial Inflammation," *PLoS One* 10(7):e0132042.

Gouveia-Figueira, S. et al. (Apr. 2017, e-published Feb. 24, 2017). "Mass spectrometry profiling of oxylipins, endocannabinoids, and N-acylethanolamines in human lung lavage fluids reveals responsiveness of prostaglandin E2 and associated lipid metabolites to biodiesel exhaust exposure," *Anal Bioanal Chem* 409(11):2967-2980.

Green, D. et al. (Jul. 12, 2016). "Central activation of TRPV1 and TRPA1 by novel endogenous agonists contributes to mechanical allodynia and thermal hyperalgesia after burn injury," *Mol Pain* 12:1744806916661725.

Guilbert, T.W. et al. (Jun. 2004). "The Prevention of Early Asthma in Kids study: design, rationale and methods for the Childhood Asthma Research and Education network," *Control Clin Trials* 25(3):286-310.

Ha, J. et al. (Jul. 1, 2002). "Effect of linoleic acid metabolites on Na(+)/K(+) pump current in N20.1 oligodendrocytes: role of membrane fluidity," *Toxicol Appl Pharmacol* 182(1):76-83.

Hammad, H. et al. (Jan. 2004). "Activation of peroxisome proliferator-activated receptor-gamma in dendritic cells inhibits the development of eosinophilic airway inflammation in a mouse model of asthma," *Am J Pathol* 164(1):263-271.

Havstad, S. et al. (Oct. 2011, e-published Aug. 5, 2011). "Effect of prenatal indoor pet exposure on the trajectory of total IgE levels in early childhood," *J Allergy Clin Immunol* 128(4):880-885.

Havstad, S. et al. (Sep. 2014, e-published Mar. 15, 2014). "Atopic phenotypes identified with latent class analyses at age 2 years," *J Allergy Clin Immunol* 134(3):722-727.

Henikoff, S. et al. (Nov. 15, 1992). "Amino acid substitution matrices from protein blocks," *Biochemistry* 89(220):10915-10919.

Henke, B.R. et al. (Dec. 3, 1998). "N-(2-Benzoylphenyl)-L-tyrosine PPARgamma agonists. 1. Discovery of a novel series of potent antihyperglycemic and antihyperlipidemic agents," *J Med Chem* 41(25):5020-5036.

International Search Report dated May 28, 2019, for PCT Application No. PCT/US2019/020277, filed Mar. 1, 2019, 5 pages.

Iyer, S.S. et al. (2012). "Role of interleukin 10 transcriptional regulation in inflammation and autoimmune disease," *Crit Rev Immunol* 32(1):23-63.

Kaminski, J. et al. (Dec. 18, 2015). "High-Specificity Targeted Functional Profiling in Microbial Communities with ShortBRED," *PLoS Comput Biol* 11(12):e1004557.

Khare, A. et al. (Jul. 15, 2015, e-published Jun. 10, 2015). "Cutting Edge: Dual Function of PPARγ in CD11c+ Cells Ensures Immune Tolerance in the Airways," *J Immunol* 195(2):431-435.

Lecka-Czernik, B. et al. (Jun. 2002). "Divergent effects of selective peroxisome proliferator-activated receptor-gamma 2 ligands on adipocyte versus osteoblast differentiation," *Endocrinology* 143(6):2376-2384.

Lehmann, J.M. et al. (Jun. 2, 1995). "An antidiabetic thiazolidinedione is a high affinity ligand for peroxisome proliferator-activated receptor gamma (PPAR gamma)," *J Biol Chem* 270(22):12953-12956.

Levan, S.R. et al. (Feb. 2017). "The childhood asthma-associated metabolite 12,13 DiHOME, suppresses regulatory T cells," *J Allergy Clin Immunol* Abstract 266, 1 page.

Levan, S.R. et al. (Apr. 30, 2018). "Neonatal Gut-Microbiome-Derived 12,13 DiHOME Impedes Tolerance and Promotes Childhood Atopy and Asthma," *bioRxiv* pp. 1-14.

Levan, S.R. et al. (Nov. 2019, e-published Jul. 22, 2019). "Elevated faecal 12,13-diHOME concentration in neonates at high risk for asthma is produced by gut bacteria and impedes immune tolerance," *Nat Microbiol* 4(11):1851-1861.

Lundstrom, S.L. et al. (2011, e-published Aug. 29, 2011). "Asthmatics exhibit altered oxylipin profiles compared to healthy individuals after subway air exposure," *PLoS One* 6(8):e23864.

Lynes, M.D. et al. (May 2017). "The cold-induced lipokine 12,13-diHOME promotes fatty acid transport into brown adipose tissue," *Nat Med* 23(5):631-637.

Morisseau, C. et al. (Jan. 2013, e-published Jun. 18, 2012). "Role of epoxide hydrolases in lipid metabolism," *Biochimie* 95(1):91-95.

Needleman, S.B. et al. (Mar. 1970). "A general method applicable to the search for similarities in the amino acid sequence of two proteins," *J Mol Biol* 48(3):443-453.

Nguyen, H.L. et al. (Jun. 2013, e-published Apr. 5, 2013). "Expression of a novel mRNA transcript for human microsomal epoxide hydrolase (EPHX1) is regulated by short open reading frames within its 5'-untranslated region," *RNA* 19(6):752-766.

Nobs, S.P. et al. (Oct. 2, 2017, e-published Aug. 10, 2017. "PPARγ in dendritic cells and T cells drives pathogenic type-2 effector responses in lung inflammation," *J Exp Med* 214(10)3015-3035.

Pearson, W.R. et al. (Apr. 1988). "Improved tools for biological sequence comparison," *Proc. Nat'l. Acad. Sci. USA* 85(8):2444-2448.

Perzanowski, M. et al. (Sep. 1, 2002). "Effect of cat and dog ownership on sensitization and development of asthma among preteenage children," *Am J Respir Crit Care Med* 166(5):696-702.

Prabhu, N. et al. (Mar. 2010). "First trimester maternal tobacco smoking habits and fetal growth," *Thorax* 65(3):235-240.

Salam, M.T. et al. (Dec. 2007, e-published Aug. 21, 2007). "Microsomal epoxide hydrolase, glutathione S-transferase P1, traffic and childhood asthma," *Thorax* 62(12):1050-1057.

Schmelzer, K.R. et al. (Jul. 12, 2005, e-published Jun. 30, 2005). "Soluble epoxide hydrolase is a therapeutic target for acute inflammation," *PNAS USA* 102(28):9772-9777.

Smith, T.F. et al. (1981). "Comparison of Biosequences," *Adv. Appl. Math* 2:482-489.

Strassburg, K. et al. (Sep. 2012, e-published Jul. 20, 2012). "Quantitative profiling of oxylipins through comprehensive LC-MS/MS analysis: application in cardiac surgery," *Anal Bioanal Chem* 404(5):1413-1426.

Suzek, B.E. (Mar. 2015, e-published Nov. 13, 2014). "UniRef clusters: a comprehensive and scalable alternative for improving sequence similarity searches," *Bioinformatics* 31(6):926-932.

Szatmari, I. et al. (Nov. 1, 2007, e-published Jul. 30, 2007). "PPARgamma regulates the function of human dendritic cells primarily by altering lipid metabolism," *Blood* 110(9):3271-3280.

Tang, L. et al. (Jul.-Aug. 2015, Jul. 26, 2015). "A high-throughput adrenaline test for the exploration of the catalytic potential of halohydrin dehalogenases in epoxide ring-opening reactions," *Biotechnol Appl Biochem* 62(4):451-457.

Vangaveti, V.N. et al. (Dec. 2014, e-published Oct. 21, 2014). "Hydroxyoctadecadienoic acids regulate apoptosis in human THP-1 cells in a PPARγ-dependent manner," *Lipids* 49(12):1181-1192.

(56) References Cited

OTHER PUBLICATIONS

Wahli, W. et al. (Jul. 2012, e-published Jun. 14, 2012). "PPARs at the crossroads of lipid signaling and inflammation," *Trends Endocrinol Metab* 23(7):351-363.
Wang, Q. et al. (Sep. 2009). "[TRPV1 UTR-3 polymorphism and susceptibility of childhood asthma of the Han Nationality in Beijing]," *Wei Sheng Yan Jiu* 38(5):516-521. (English Translation of Abstract Only).
Wegienka, G. et al. (Mar. 2015). Combined effects of prenatal medication use and delivery type are associated with eczema at age 2 years, *Clin Exp Allergy* 45(3):660-668.
Wegienka, G. et al. (Jan. 2017, e-published Oct. 10, 2016). "Subgroup differences in the associations between dog exposure during the first year of life and early life allergic outcomes," *Clin Exp Allergy* 47(1):97-105.
Woerly, G. et al. (Aug. 4, 2003). "Peroxisome proliferator-activated receptors alpha and gamma down-regulate allergic inflammation and eosinophil activation," *J Exp Med* 198(3):411-421.
Written Opinion dated May 28, 2019, for PCT Application No. PCT/US2019/020277, filed Mar. 1, 2019, 12 pages.
Yang, J. et al. (Jan. 2015). "Soluble epoxide hydrolase inhibitor attenuates inflammation and airway hyperresponsiveness in mice," *Am J Respir Cell Mol Biol* 52(1):46-55.
Ye, F. et al. (Jan. 2006). "The dipeptide H-Trp-Glu-OH shows highly antagonistic activity against PPARgamma: bioassay with molecular modeling simulation," *ChemBioChem* 7(1):74-82.

\* cited by examiner

FIG. 2A
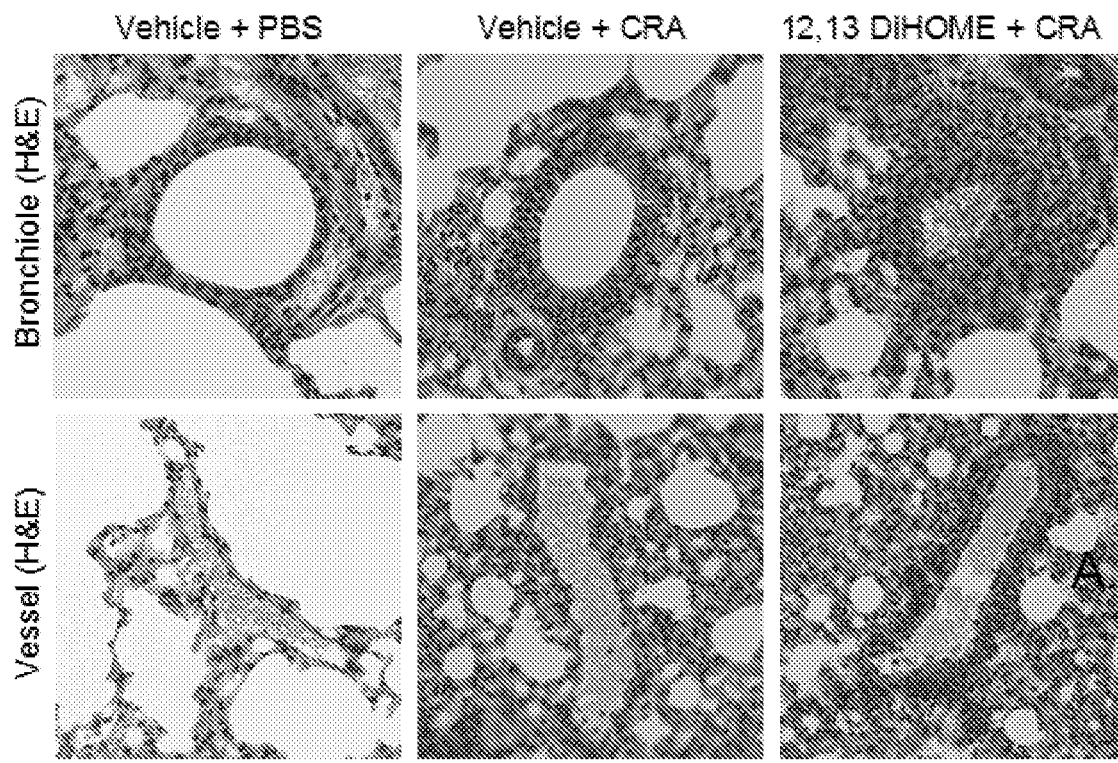
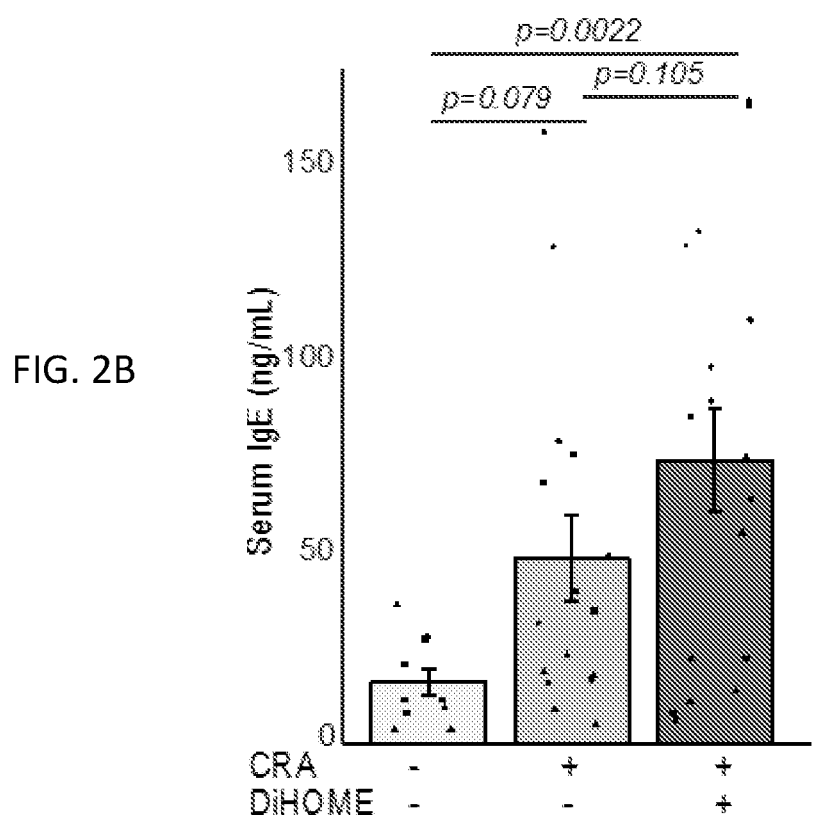
FIG. 2B

METHODS AND COMPOSITIONS RELATING TO EPOXIDE HYDROLASE GENES

CROSS-REFERENCE

This application claims the benefit of priority to U.S. Provisional Application No. 62/637,175, filed Mar. 1, 2018, which is hereby incorporated by reference in its entirety for all purposes.

STATEMENT REGARDING FEDERALLY SPONSORED RESEARCH OR DEVELOPMENT

This invention was made with government support under grant no. AI089473 awarded by the National Institutes of Health. The government has certain rights in the invention.

SEQUENCE LISTING

The instant application contains a Sequence Listing written in file 048536-612001WO_SL_ST25, which was created on Feb. 27, 2019, is 33,899 byes in size, is in ASCII format, and is hereby incorporated by reference in its entirety.

BACKGROUND

Asthma is the most common chronic disease worldwide. It disproportionately affects children, families living below the poverty line, and minorities. Risk is greatest between birth and age 4. Childhood allergic asthma specifically refers to the development of severe asthma before age 12. These patients often have a history of allergic sensitization (atopy) and a family history of asthma. Diagnosis of atopy and asthma currently relies on both objective clinical measures and patient- and family-reported clinical symptoms, limiting early detection. Current asthma screening tools, such as the asthma predictive index, have limited utility before three years of age. Additionally, the asthma predictive index is only approximately 40% sensitive and 90% specific. While metrics like this can be used to rule out asthma in toddlers, they have limited utility in identifying potential asthmatics before they develop clinical symptoms.

BRIEF SUMMARY

Provided herein are, inter alia, methods and kits for detecting epoxide hydrolase (EH) genes. In embodiments, methods and kits for detecting the risk of developing atopy or asthma are provided. Also included are methods for preventing or treating atopy or asthma.

In aspects, included herein is a method of detecting an epoxide hydrolase gene in a biological sample from a subject, the method comprising detecting (i) an epoxide hydrolase gene comprising a nucleotide sequence with at least about 95%, 96%, 97%, 98%, or 99% identity to SEQ ID NO:50, or the expression thereof, in the biological sample; (ii) an epoxide hydrolase gene comprising a nucleotide sequence with at least about 95%, 96%, 97%, 98%, or 99% identity to SEQ ID NO:51, or the expression thereof, in the biological sample; and/or (iii) an epoxide hydrolase gene comprising a nucleotide sequence with at least about 95%, 96%, 97%, 98%, or 99% identity to SEQ ID NO:52, or the expression thereof, in the biological sample.

In aspects, included herein is a method of detecting an epoxide hydrolase gene in a biological sample from a subject, the method comprising detecting (i) an epoxide hydrolase gene comprising the nucleotide sequence of SEQ ID NO:50 (Gene 1), or the expression thereof, in the biological sample; (ii) an epoxide hydrolase gene comprising the nucleotide sequence of SEQ ID NO:51 (Gene 2), or the expression thereof, in the biological sample; and/or (iii) an epoxide hydrolase gene comprising the nucleotide sequence of SEQ ID NO:52 (Gene 3), or the expression thereof, in the biological sample.

In aspects, included herein is a method of detecting an epoxide hydrolase gene in a biological sample from a subject. In embodiments, the method comprises detecting (i) a gene that encodes an epoxide hydrolase having an amino acid sequence with at least about 95%, 96%, 97%, 98%, or 99% identity to SEQ ID NO:46, or the expression thereof, in the biological sample; (ii) a gene that encodes an epoxide hydrolase having an amino acid sequence with at least about 95%, 96%, 97%, 98%, or 99% identity to SEQ ID NO:47, or the expression thereof, in the biological sample; and/or (iii) a gene that encodes an epoxide hydrolase having an amino acid sequence with at least about 95%, 96%, 97%, 98%, or 99% identity to SEQ ID NO:48, or the expression thereof, in the biological sample.

In aspects, included herein is a method of detecting an epoxide hydrolase gene in a biological sample from a subject. In embodiments, the method comprises detecting (i) a gene that encodes an epoxide hydrolase having an amino acid sequence with at least about 95%, 96%, 97%, 98%, or 99% identity to SEQ ID NO:46, or the expression thereof, in feces of the subject (e.g. a fecal sample obtained from the subject); (ii) a gene that encodes an epoxide hydrolase having an amino acid sequence with at least about 95%, 96%, 97%, 98%, or 99% identity to SEQ ID NO:47, or the expression thereof, in feces of the subject (e.g., a fecal sample obtained from the subject); and/or (iii) a gene that encodes an epoxide hydrolase having an amino acid sequence with at least about 95%, 96%, 97%, 98%, or 99% identity to SEQ ID NO:48, or the expression thereof, in feces of the subject (e.g., a fecal sample obtained from the subject).

In aspects, included herein is a method of detecting an epoxide hydrolase gene in a biological sample from a subject. In embodiments, the method comprises detecting any combination of, or each of: (i) a gene that encodes an epoxide hydrolase having an amino acid sequence with at least about 95%, 96%, 97%, 98%, or 99% identity to SEQ ID NO:46, or the expression thereof, in feces of the subject (e.g., a fecal sample obtained from the subject); (ii) a gene that encodes an epoxide hydrolase having an amino acid sequence with at least about 95%, 96%, 97%, 98%, or 99% identity to SEQ ID NO:47, or the expression thereof, in feces of the subject (e.g. a fecal sample obtained from the subject); and (iii) a gene that encodes an epoxide hydrolase having an amino acid sequence with at least about 95%, 96%, 97%, 98%, or 99% identity to SEQ ID NO:48, or the expression thereof, in feces of the subject (e.g. a fecal sample obtained from the subject).

In aspects, included herein is a method of detecting an epoxide hydrolase gene in a biological sample from a subject wherein the subject is less than 1, 2, 3, 4, or 5 years old. In embodiments, the method comprises detecting any combination of, or each of: (i) a gene that encodes an epoxide hydrolase having an amino acid sequence with at least about 95%, 96%, 97%, 98%, or 99% identity to SEQ ID NO:46, or the expression thereof, in feces of the subject (e.g., a fecal sample obtained from the subject); (ii) a gene that encodes an epoxide hydrolase having an amino acid sequence with at least about 95%, 96%, 97%, 98%, or 99% identity to SEQ ID NO:47, or the expression thereof, in feces of the subject (e.g. a fecal sample obtained from the subject); and (iii) a gene that encodes an epoxide hydrolase having an amino acid sequence with at least about 95%, 96%, 97%, 98%, or 99% identity to SEQ ID NO:48, or the expression thereof, in feces of the subject (e.g. a fecal sample obtained from the subject).

In aspects, included herein is a method of detecting dysbiosis. In embodiments, the method comprises detecting (i) a gene that encodes an epoxide hydrolase having an amino acid sequence with at least about 95%, 96%, 97%, 98%, or 99% identity to SEQ ID NO:46, or the expression thereof, in a biological sample; (ii) a gene that encodes an epoxide hydrolase having an amino acid sequence with at least about 95%, 96%, 97%, 98%, or 99% identity to SEQ ID NO:47, or the expression thereof, in a biological sample; and/or (iii) a gene that encodes an epoxide hydrolase having an amino acid sequence with at least about 95%, 96%, 97%, 98%, or 99% identity to SEQ ID NO:48, or the expression thereof, in a biological sample.

In aspects, included herein is a method of determining whether a subject is at risk of atopy or asthma. In embodiments, the method comprises (a) detecting (i) a gene that encodes an epoxide hydrolase having an amino acid sequence with at least about 95%, 96%, 97%, 98%, or 99% identity to SEQ ID NO:46, or the expression thereof, in a biological sample from the subject; (ii) a gene that encodes an epoxide hydrolase having an amino acid sequence with at least about 95%, 96%, 97%, 98%, or 99% identity to SEQ ID NO:47, or the expression thereof, in a biological sample from the subject; and/or (iii) a gene that encodes an epoxide hydrolase having an amino acid sequence with at least about 95%, 96%, 97%, 98%, or 99% identity to SEQ ID NO:48, or the expression thereof, in a biological sample from the subject, and (b) identifying the subject as at risk of atopy or asthma if a level of the first epoxide hydrolase gene, the second epoxide hydrolase gene, and/or the third epoxide hydrolase gene is detected.

In embodiments, a method provided herein comprises detecting the level of (i) an epoxide hydrolase gene that encodes an enzyme that has the amino acid sequence of SEQ ID NO:46 (Gene 1), or the expression thereof, in the biological sample; (ii) an epoxide hydrolase gene that encodes an enzyme that has the amino acid sequence of SEQ ID NO:47 (Gene 2), or the expression thereof, in the biological sample; and/or (iii) an epoxide hydrolase gene that encodes an enzyme that has the amino acid sequence of SEQ ID NO:48 (Gene 3), or the expression thereof, in the biological sample.

In aspects, included herein is a method of reducing the likelihood that a subject will develop asthma or atopy. In embodiments, the method comprises administering to the subject a treatment that reduces the likelihood that the subject will develop atopy, wherein Gene 1, Gene 2, and/or Gene 3 has been detected in a biological sample from the subject.

In aspects, included herein is a method of treating or preventing atopy or asthma in a subject in need thereof. In embodiments, the method comprises administering to the subject a treatment that prevents or treats atopy or asthma, wherein Gene 1, Gene 2, and/or Gene 3 has been detected in a biological sample from the subject.

In aspects, included herein is a kit for detecting (i) a gene that encodes an epoxide hydrolase having an amino acid sequence with at least about 95%, 96%, 97%, 98%, or 99% identity to SEQ ID NO:46, or the expression thereof (ii) a gene that encodes an epoxide hydrolase having an amino acid sequence with at least about 95%, 96%, 97%, 98%, or 99% identity to SEQ ID NO:47, or the expression thereof and/or (iii) a gene that encodes an epoxide hydrolase having an amino acid sequence with at least about 95%, 96%, 97%, 98%, or 99% identity to SEQ ID NO:48, or the expression thereof. In embodiments, the kit comprises a probe or primer that hybridizes to the gene. In embodiments, the kit comprises a probe or primer that hybridizes to a mRNA molecule transcribed from the gene or a cDNA corresponding to the gene. In embodiments, the kit comprises an agent (such as antibody or a fragment thereof) that binds to a protein expressed by the gene.

BRIEF DESCRIPTION OF THE DRAWINGS

FIG. 1A-1H were performed with n=3 treatment replicates using cells isolated from 2 independent donors (biological replicates; ▲ and ●). Raw264.7 cells were transfected with a PPARγ-activated luciferase reporter and treated with 12,13 DiHOME and known PPARγ agonists GW1929 (Ki=1.4 nM)[39] and Rosiglitazone (Kd=40 nM)[40] (n=3) (FIG. 1J). All error bars represent the standard error of the mean (SEM).

FIG. 2A-2H show example results illustrating that peritoneal treatment with 12,13 DiHOME exacerbated lung inflammation in CRA-challenged mice. FIG. 2A shows haematoxylin and eosin (H&E) stained bronchioles and blood vessels from the lungs of mice treated with vehicle (10% DMSO) or 30 mg kg$^{-1}$ 12,13 DiHOME (solubilized in 10% DMSO) and airway challenged with PBS or CRA. FIG. 2B is an example bar graph showing that peritoneal treatment of mice with 12,13 DiHOME (n=17) increased serum IgE compared to CRA-challenged (n=16; LME; $p=0.105$) and PBS-challenged animals (n=10; LME; $p=0.0022$). FIGS. 2C and 2D are example bar graphs showing that 12,13 DiHOME treatment increased the number of infiltrating cells surrounding the bronchioles and veins of CRA-challenged mice compared with vehicle treated, PBS challenged [n=5; LME; $p=0.00263$ (bronchial), $p=0.00087$ (venous)] or vehicle treated, CRA challenged [n=13; LME; $p=0.0298$ (bronchial), $p=0.0170$ (venous)] animals. FIG. 2E is an example bar graph showing that peritoneal 12,13 DiHOME treatment increased the frequency of lung resident T cells (CD3+) in CRA challenged mice (n=9) compared with vehicle treated, PBS challenged (n=10; LME; $p=4.69\times10^{-6}$)

or vehicle treated, CRA challenged (n=10; LME; p=0.016) animals. FIG. 2F is an example bar graph showing that 12,13 DiHOME treatment (n=8) increased the expression of IL1β compared with vehicle treated, PBS challenged (n=9; LME; p=0.0010) or vehicle treated, CRA challenged (n=9; LME; p=0.030) animals. FIG. 2G is an example bar graph showing that 12,13 DiHOME treatment of CRA-challenged mice (n=18) decreased Treg frequency compared to vehicle-treated CRA-challenged mice (n=18; LME; p=0.031). FIG. 2H is an example bar graph showing that peritoneal treatment with 12,13 DiHOME significantly increased the concentration of 12,13 DiHOME in the lungs (n=6; Student t-test: p=0.0048) at 3 hours post-delivery. Unique symbols (▲, ■, ♦, ●) represent mice from independent assays. All error bars represent the SEM.

FIGS. 3F and 3G are example plots showing that specific combinations of known early-life and microbial risk factors identified in neonates (n=41) increased the relative odds of developing allergic disease in childhood. While 3EH>13, 318 copies ng fecal DNA significantly increased the odds of atopy at age 2 [Odds Ratio=12.2; 95% confidence interval (CI)=2.07-98.3; Fisher Exact Test; p=0.0014], a Neonatal Atopy Score (NAtS)≥2 increased the relative odds of atopy to 16.4 (95% CI=2.52-194; Fisher Exact Test; p=0.0014). These odds were greater than the odds of any of the individual risk factors (shown in bold) that comprised NAtS. Similarly, 12,13 DiHOME in excess of 398 ng g$^{-1}$ neonatal stool significantly increased the relative odds of developing asthma at age 4 (Odds Ratio=8.96; 95% CI=1.50-99.7; Fisher Exact Test; p=0.0063); however, a Neonatal Asthma Predictive Score (NAPS)≥6 increased the relative odds of asthma beyond any of the individual risk factors that comprised the score (NAPS factors shown in bold; Odds Ratio=10.4; 95% CI=1.72-117; Fisher Exact Test; p=0.0047) PD indicates risk factors assess pre-delivery. Error bars in FIGS. 3A, 3B, 3E represent the SEM. Error bars in FIGS. 3E-G represent the 95% CI. The following symbols, ▲, ■, ♦, ● represent neonates who developed into healthy, atopic, asthmatic, and atopic asthmatic children, respectively.

FIG. 4B shows a plot of results for a gating strategy used to assess T cell subsets following co-culture of 12,13 DiHOME treated DCs with autologous T cells. FIG. 4C shows an example plot illustrating the frequency of live CD3+ cells following co-culture with vehicle or 130 μM 12,13 DiHOME-treated DCs (n=3; biological replicates=2; LME; p=0.0442). FIG. 4D shows example plots illustrating the frequency of CD4+ T cells following co-culture with vehicle or 130 μM 12,13 DiHOME-treated DCs (n=3; biological replicates=2). FIG. 4E shows example plots illustrating the gating strategy used to assess CD3−CD19−CD11c+ cells. FIG. 4F shows an example plot illustrating the frequency of live CD3− cells following PBMC treatment with vehicle or 130 μM 12,13 DiHOME (n=3; biological replicates=2 (▲ and ●); LME; 130 μM p=0.127; 200 μM p=0.0124). FIG. 4G is a an example plot illustrating the frequency of CD3−CD19−CD11c+ live cells following PBMC treatment with vehicle or 130 μM 12,13 DiHOME (n=3; biological replicates=2 (▲ and ●); LME; 130 μM p=0.0107; 200 μM p=0.0020).

FIG. 5C shows example plots illustrating the gating strategy used to assess resident immune cells in mouse lungs. FIG. 5D shows a representative flow plot displaying lung Tregs in mice (FoxP3+ CD25+CD4+CD3+). 12,13 DiHOME treatment of CRA-challenged mice (n=7) decreased the frequency of resident lung cells compared to vehicle treated, PBS challenged (n=9; LME; p=0.016) or vehicle treated, CRA challenged animals (n=9; LME; p=0.042) (FIG. 5E). 12,13 DiHOME treatment of CRA-challenged mice (n=7) did not increase the frequency of live resident cells in the lungs (vehicle treated, PBS challenged n=9; vehicle treated, CRA challenged n=9) (FIG. 5F). 12,13 DiHOME treatment of CRA-challenged mice (n=7) significantly increased the frequency of lung resident monocytes (F4-80+Ly6C+Ly6G-CD11b+) compared to vehicle treated, PBS challenged (n=9; LME; p=8.3×10$^{-7}$) or vehicle treated, CRA challenged animals (n=9; LME; p=0.021) (FIG. 5G). 12,13 DiHOME treatment of CRA-challenged mice (n=7) significantly increased the frequency of lung resident neutrophils (Ly6G+CD11b+) compared to vehicle treated, PBS challenged (n=9; LME; p=8.47×10$^{-10}$ or vehicle treated, CRA challenged animals (n=9; LME; p=0.0172) (FIG. 5H). 12,13 DiHOME treatment of CRA-challenged mice (n=6) decreased the frequency of lung resident alveolar macrophages (CD11c+ CD11b+F4/80+Siglec-F+) compared to vehicle treated, CRA challenged animals (n=6; LME; p=0.122) but increased the frequency compared to vehicle treated, PBS challenged animals (n=6; LME; p=0.0072) (FIG. 5I). 12,13 DiHOME treatment increased the expression of IL1α and TNF in 12,13 DiHOME treated, CRA challenged mice (n=8) compared to vehicle treated, PBS challenged [n=9; LME; p=0.0245 (IL1α), p=0.040 (TNF)] or vehicle treated, CRA challenged animals [n=9; LME; p=0.0456 (IL1α), p=0.145 (TNF)] (FIGS. 5J and 5K). Peritoneal treatment with 12,13 DiHOME significantly increased the concentration of 12,13 DiHOME in the plasma (n=6, Student t-test: p=0.0327)

(FIG. 5L). Unique symbols (▲, ■, ♦, ●) represent mice from independent assays. All error bars represent the SEM.

FIGS. 6B, 6C, and 6D show example calibration curves generated using a modified colorimetric assay for glycidol, 9,10 DiHOME, and 12,13 DiHOME, respectively. Error bars represent the standard deviation. Best fit curves were generated using the lm (linear modeling) function in R. The Neonatal Atopy Score (NAtS; curve labeled "Atopy") combined fecal 3EH copy number>13,318 copies $ng^{-1}$ fecal DNA, maternal asthma, and lack of cat exposure at one month of age to predict atopy at age 2 (n=41; pROC; AUC=0.817) (FIG. 6E). The Neonatal Asthma Predictive Score (NAPS; curve labeled "Asthma") combined fecal 12,13 DiHOME>398 ng $g^1$, fecal 9,10 DiHOME>425 ng $g^1$, 3EH>1,598 copies ng of stool, maternal smoking during pregnancy, formula feeding, lack of dogs pre-delivery, and lack of dogs at one month to predict asthma at age 4 (n=41; pROC; AUC=0.813) (FIG. 6E).

Figure 7A:
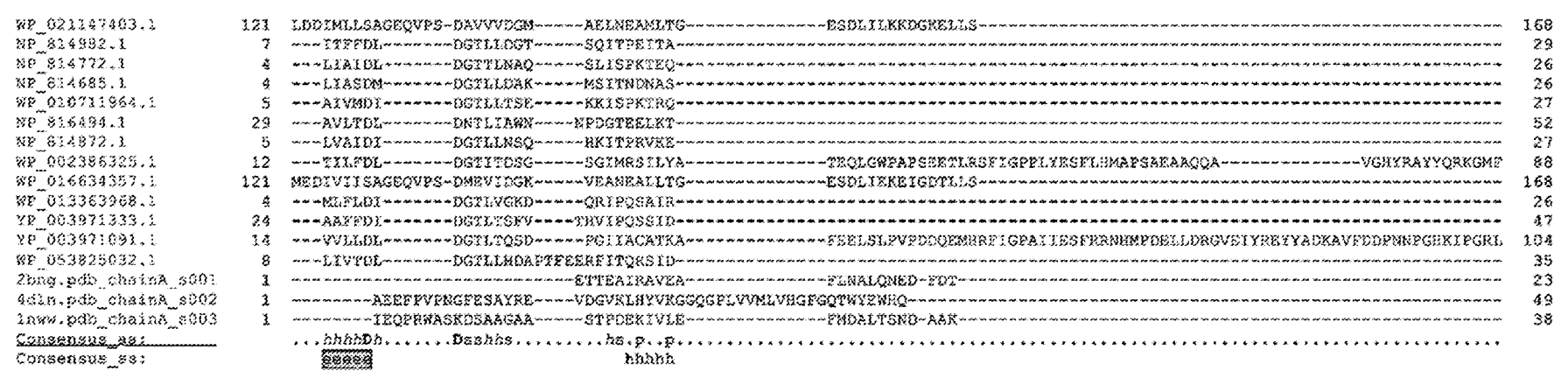
Figure 7C:
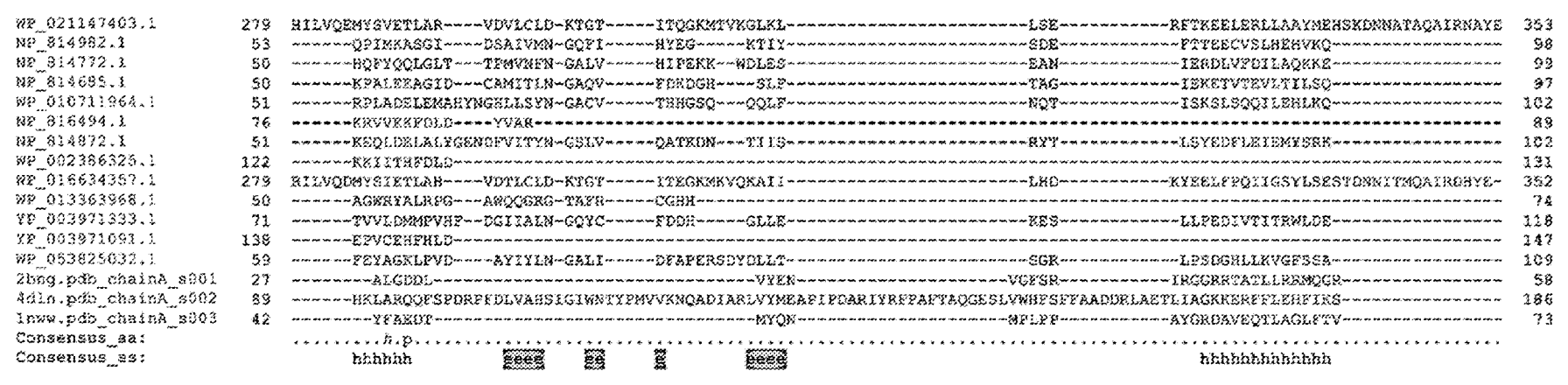
Figure 7D:
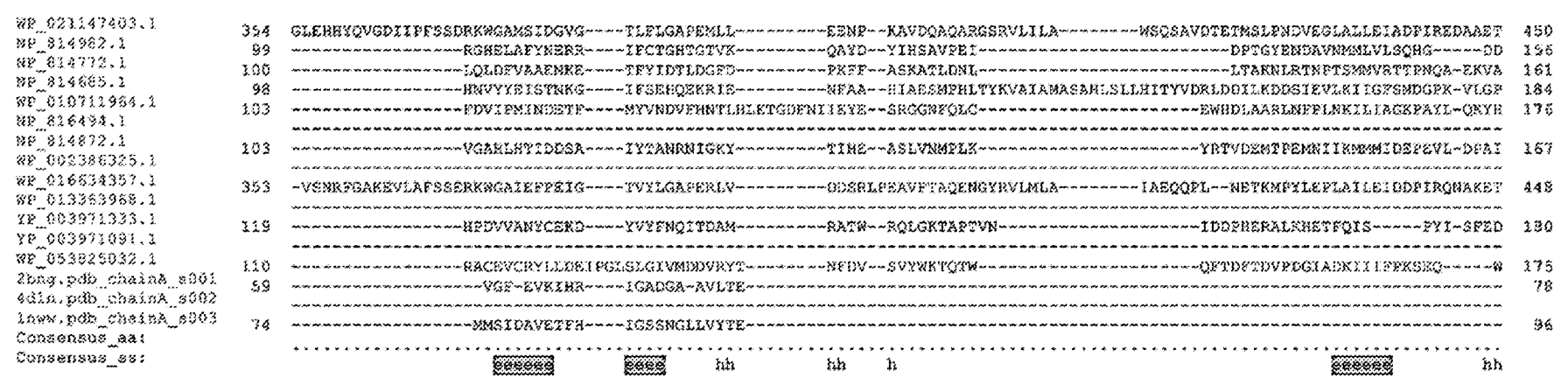
Figure 7E:
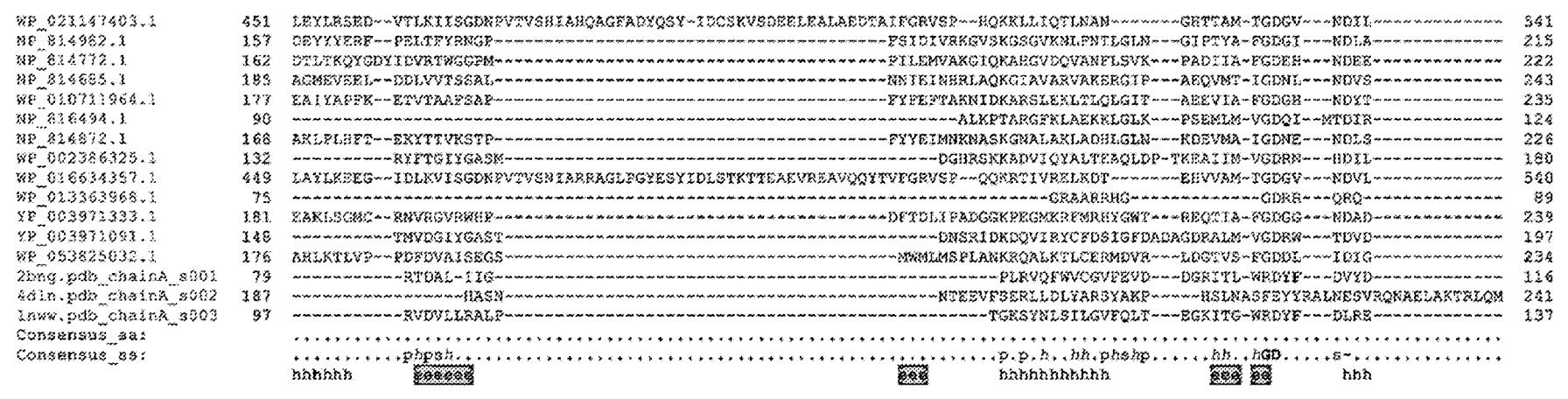
Figure 7F:
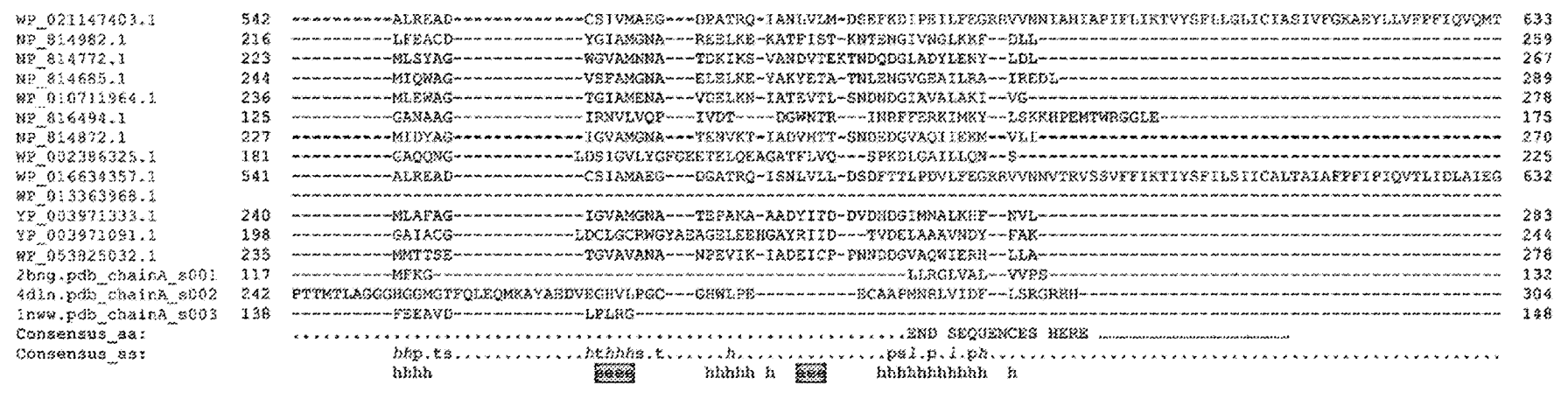

FIGS. 7A-7F show example results of alignment of thirteen EH candidate genes with *Mycobacterium tuberculosis* (pdbid: 2bng), *Pseudomonas aeruginosa* (pbdid: 4d1n), and *Rhodococcus erythopolis* (pdbid: 1nww), the crystal structure of which has been solved. Alignment was performed using Promals3D. The key for consensus amino acid symbols (consensus_aa) is as follows: conserved amino acid residues: bold and uppercase letters; aliphatic residues (I, V, L): 1; aromatic residues (Y, H, W, F): @; hydrophobic residues (W, F, Y, M, L, I, V, A, C, T, H): h; alcohol residues (S, T): o; polar residues (D, E, H, K, N, Q, R, S, T): p; tiny residues (A, G, C, S): t; small residues (A, G, C, S, V, N, D, T, P): s; bulky residues (E, F, I, K, L, M, Q, R, W, Y): b; positively charged residues (K, R, H): +; negatively charged residues (D, E): −; charged (D, E, K, R, H): c. The key for consensus secondary structure symbols (consensus_ss) is as follows: alpha-helix: h; beta-strand: e.

DETAILED DESCRIPTION

Figure 1A:
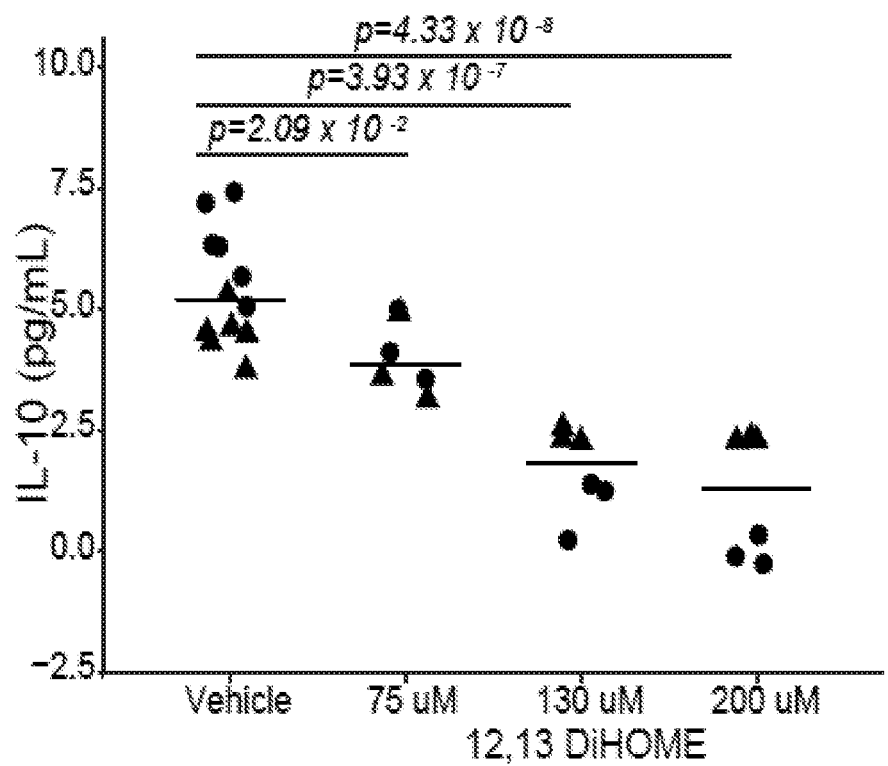
FIGS. 1A-1J show example results illustrating that 12,13 DiHOME acts via PPARγ on DCs to decrease Tregs. 12,13 DiHOME treatment caused a dose-dependent decrease in IL-10 secretion from human DCs (Linear Mixed Effects (LME); $p=0.0209$, $p=3.93\times10^{-7}$, $p=4.33\times10^{-8}$ for concentrations of 75, 130, 200 μM, respectively) (FIG. 1A). Treatment of DCs with 130 μM 12,13 DiHOME induced a significant shift in the distribution of helper T cells (MANOVA; $p=0.00034$) and caused a specific decrease in the frequency of Tregs (CD3+CD4+CD25+FoxP3+; LME; $p=0.00025$) (FIGS. 1B and 1C). Increasing doses of 12,13 DiHOME caused a significant decrease in the expression of CD80, CD1a, and CCR7 on DCs (CD3-CD19-CD11c+; LME; $p<0.001$ for all comparisons) and an increase in the expression of CD36 at high concentrations (LME; $p=0.0225$ for 200 μM) (FIG. 1D, 1E, 1F, 1G). Treatment of human DCs with 130 μM 12,13 DiHOME caused a significant decrease in the expression of CD1a and significant increases in the expression of CD36, FABP4, and HADH consistent with 12,13 DiHOME acting as an activator of PPARγ (LME; $p=0.0021$, $p=0.0022$, $p=0.0024$, $p=0.0029$ for CD1a, CD36, FABP4, and HADH, respectively) (FIGS. 1.H and 1I).
Figure 1B:
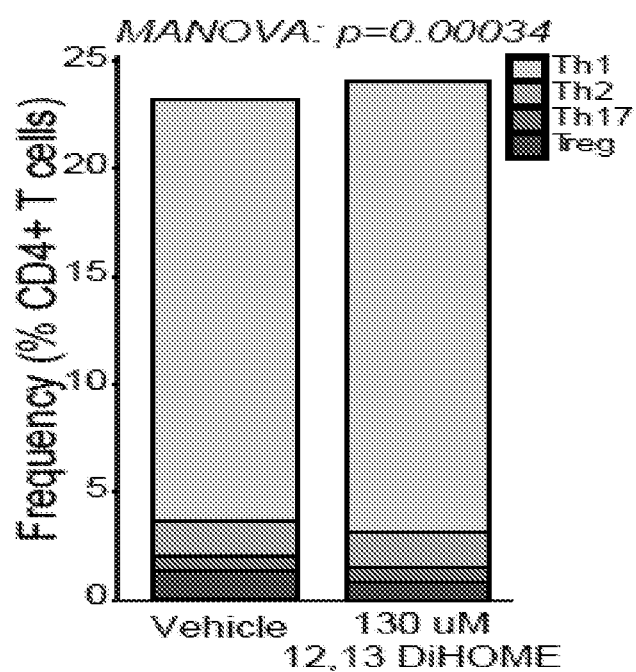
Figure 1C:
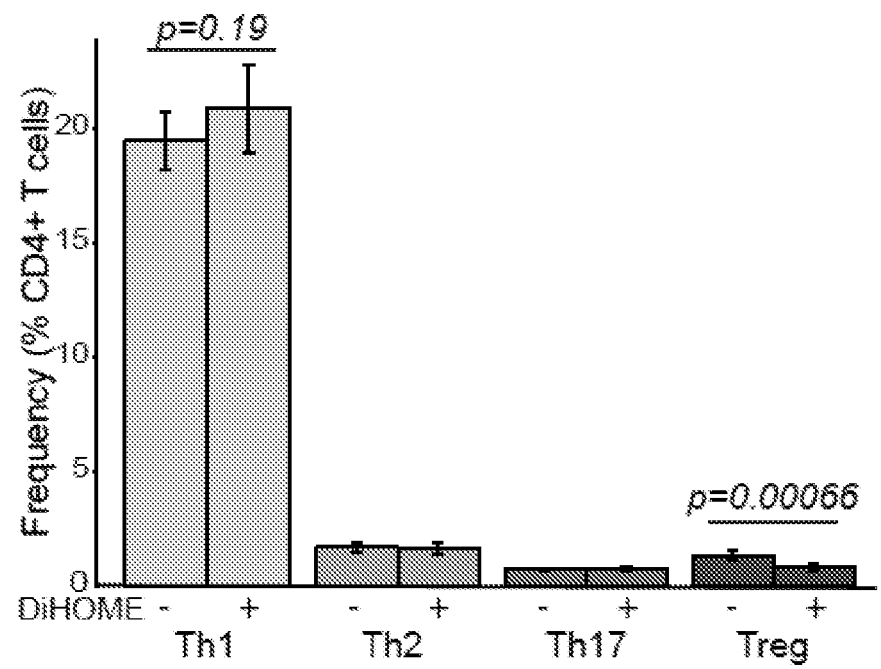
Figure 1D:
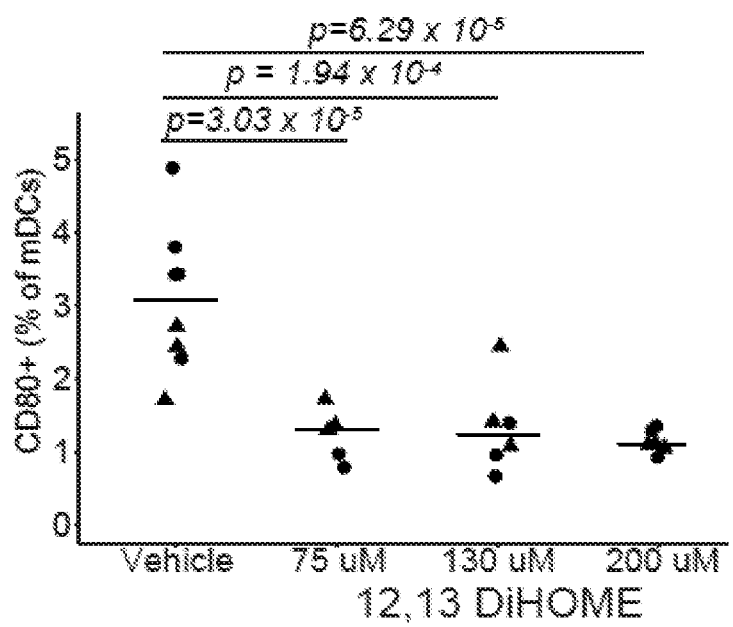
Figure 1E:
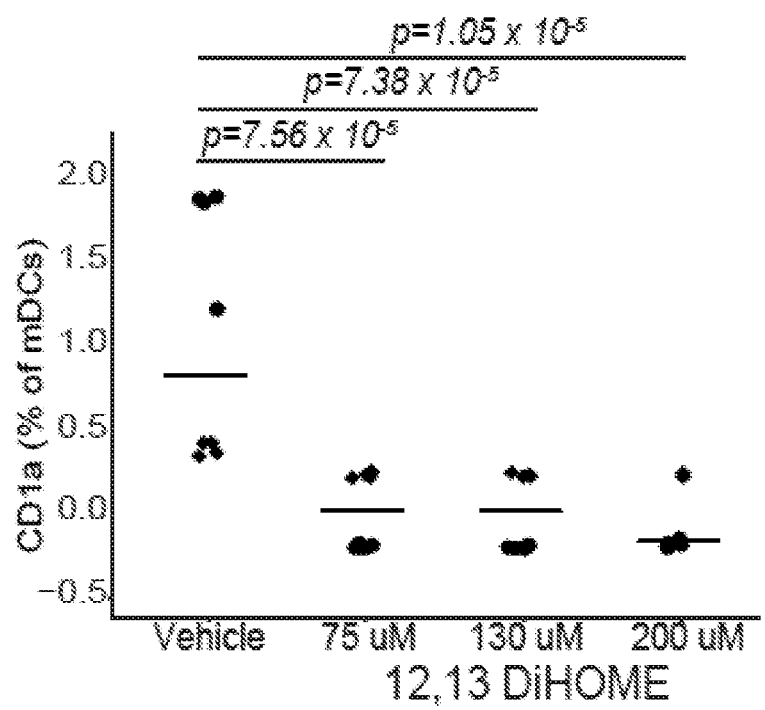
Figure 1F:
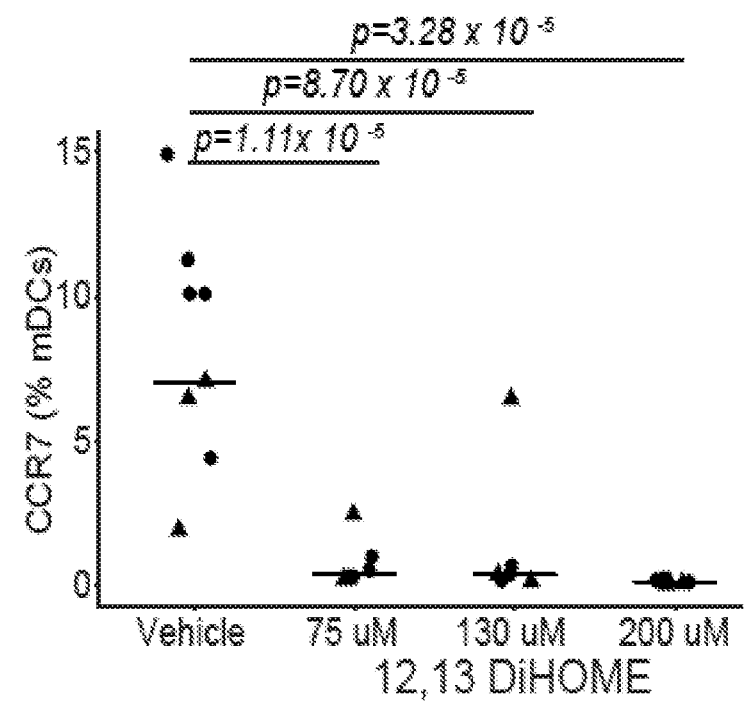
Figure 1G:
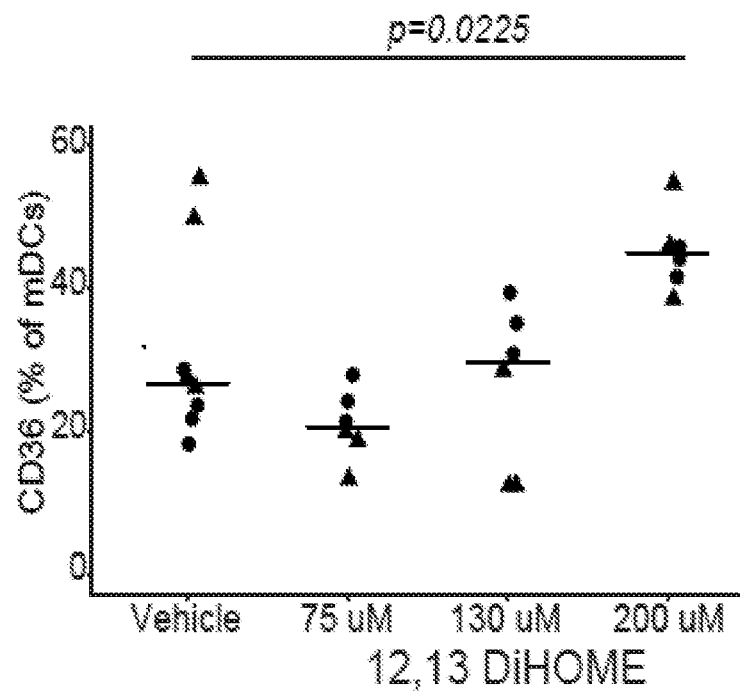

Provided herein are, inter alia, methods and kits for detecting epoxide hydrolase genes. In embodiments, methods and kits for detecting the risk of developing atopy or asthma are included. Also included are methods for preventing or treating atopy or asthma. In embodiments, methods and kits (such as gut-microbiome-based tests) for detecting risk of developing atopy or asthma are provided. In embodiments, methods and kits for detecting risk of developing atopy or asthma in childhood (e.g., before the age of 18, 17, 16, 14, 13, 12, 11, 10, 9, 8, 7, 6, 5, 4, or 3 years) are included. In embodiments, a method or kit provided herein may be used for the early-life identification (e.g., in a neonate, infant, or toddler) of those at risk of developing atopy or asthma.

Asthma currently affects more than 300 million people worldwide and is the most prevalent childhood disease in western countries [1]. Current asthma screening tools, such as the asthma predictive index, have limited utility before three years of age. The University of Cincinnati asthma predictive index is publicly available and is currently used in children age two and up. Atopy diagnosis currently relies on blood based IgE (which is limited by the volume obtainable in infants) and patient-/family-reported clinical symptoms. There is an unmet need for diagnostic tools for early detection of children with high-risk for developing atopy or asthma. Such tools provide the opportunity for earlier disease intervention and prevention.

An emerging body of scientific evidence suggests that the gut microbiome plays a role in the early origins of atopy and asthma and that ideal window for intervention to prevent disease development may be much earlier in life. Earlier and more accurate detection of those at risk will shift the window of opportunity for intervention and create opportunities for disease prevention. In aspects, the technology disclosed herein, including embodiments thereof, is useful for early detection of those at high-risk for asthma and/or atopy in childhood using neonatal stool samples.

In aspects, methods and kits provided herein identify those at risk in the earliest stages of post-natal life (e.g., 1 month of age). In embodiments, the diagnostic approach provided herein is far more sensitive than existing strategies, uses objective microbiome-associated biomarkers, and can be applied to neonatal stool samples, advancing the age of diagnosis by several years.

Three bacterial epoxide hydrolase (EH) genes that produce elevated 12,13 DiHOME levels have been identified (*E. faecalis* NP_814872, *B. bifidum* YP_003971091, and *B. bifidum* YP_003971333). Included herein is a diagnostic technology that uses measurements of the three bacterial epoxide hydrolase (EH) genes, the level of 12,13 DiHOME, and known early-life risk factors to identify neonates with high-risk for developing atopy and asthma. The currently used asthma screening tools are not effective for predicting the onset of asthma prior to the age of 3 or 2. However, in embodiments, diagnostic tests and kits provided herein can be used as early as 1 month after birth to predict atopy at age 2 and asthma at age 4.

Recent studies demonstrate that compositionally distinct gut microbiotas of neonates produce specific biological products that relate to the risk of developing childhood atopy or asthma [42, 1]. Notably, neonates with heightened risk of developing childhood atopy are characterized by an altered gut microbiome that results in fecal enrichment of the oxylipin 12,13-DiHOME. 12,13 DiHOME is structurally similar to ligands of peroxisome proliferator-activated receptor gamma (PPARγ), which is a nuclear receptor important for developing immune tolerance and regulating regulatory T-cell (Treg) maturation. The enrichment of microbial-derived 12,13-DiHOME and its interaction with PPARγ leads to suppressed regulatory T-cell (Treg) levels and impaired immune tolerance [1].

In embodiments, neonates at heightened risk of childhood atopy and asthma are characterized by metabolic dysfunction, inter-kingdom perturbation of their fecal microbiota, and fecal enrichment of the linoleic acid metabolite, 12,13 DiHOME. In embodiments, this lipid prevents the development of immune tolerance by reducing the frequency of anti-inflammatory regulatory T cells. In embodiments, microbial genes that lead to 12,13 DiHOME production are significantly increased in copy number in neonates who subsequently develop atopy and/or asthma in childhood. In embodiments, such bacterial genes encode functional epoxide hydrolases that specifically produce 12,13 DiHOME in vitro. In embodiments, the abundance of fecal oxylipins (12,13 DiHOME and its enantiomer 9,10 DiHOME) and bacterial EH genes in biological samples (e.g., stool samples, such as stool samples from 0.1 to 6 month old subjects) can be combined with known early-life risk factors to predict atopy at age 2 and asthma at age 4, years before traditional diagnostics are applicable. Included herein are tests that can be applied to early-life stool samples (e.g., ~1 month of age) that employ a combination of novel gut-microbiome-associated biomarkers together with risk factors to identify with good sensitivity and specificity, neonates who are at risk of developing atopy and asthma years in advance of clinical symptoms. In embodiments, methods and kits herein are useful for early diagnosis and interventions, particularly those targeting the gut microbiome, to prevent allergy and asthma development in childhood.

I. DEFINITIONS

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "isolated", when applied to a bacterium, refers to a bacterium that has been (1) separated from at least some of the components with which it was associated when initially produced (whether in nature or in an experimental setting), and/or (2) produced, prepared, purified, and/or manufactured by the hand of man, e.g. using artificial culture conditions such as (but not limited to) culturing on a plate and/or in a fermenter. Isolated bacteria include those bacteria that are cultured, even if such cultures are not monocultures. Isolated bacteria may be separated from at least about 10%, about 20%, about 30%, about 40%, about 50%, about 60%, about 70%, about 80%, about 90%, or more of the other components with which they were initially associated. In embodiments, isolated bacteria are more than about 80%, about 85%, about 90%, about 91%, about 92%, about 93%, about 94%, about 95%, about 96%, about 97%, about 98%, about 99%, or more than about 99% pure. In embodiments, a bacterial population administered to a subject comprises isolated bacteria. In embodiments, a composition administered to a subject comprises isolated bacteria. In embodiments, the bacteria that are administered are isolated bacteria.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Subject" "Patient" or "subject in need thereof" refer to a living member of the animal kingdom suffering from or that may suffer from the indicated disorder (e.g., is a member of a species comprising individuals who naturally suffer from the indicated disorder such as asthma or atopy). In embodiments, the subject is a member of a species comprising individuals who naturally suffer from asthma or atopy. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer. In embodiments, the subject is a human. In embodiments, the subject is a non-mammalian animal such as a turkey, a duck, or a chicken. In embodiments, a subject is a living organism suffering from or prone to a disease or condition that can be treated by administration of a treatment or composition as provided herein.

As used herein, a "symptom" of a disease includes any clinical or laboratory manifestation associated with the disease, and is not limited to what a subject can feel or observe.

As used herein the term "dysbiosis" means a difference in a microbiota compared to a healthy or general population. In embodiments, dysbiosis comprises a difference in microbiota commensal species diversity compared to a healthy or general population. In embodiments, dysbiosis comprises a decrease of beneficial microorganisms and/or increase of pathobionts (pathogenic or potentially pathogenic microorganisms) and/or decrease of overall microbiota species diversity. Many factors can harm the beneficial members of the microbiota leading to dysbiosis, including (but not limited to) infection, antibiotic use, psychological and physical stress, radiation, and dietary changes. In embodiments, the microbiota is the small intestine microbiota. In embodiments, the microbiota is the large intestine microbiota. In embodiments, dysbiosis comprises or promotes the overgrowth of a bacterial opportunistic pathogen such as *Enterococcus faecalis, Enterococcus faecium*, or *Clostridium difficile*. In embodiments, the dysbiosis comprises a reduced amount (absolute number or proportion of the total microbial population) of bacterial or fungal cells of a species or genus (e.g., 5%, 10%, 15%, 20%, 25%, 30%, 35%, 40%, 45%, 50%, 55%, 60%, 65%, 70%, 75%, 80%, 85%, 90%, 95% or more lower) compared to a healthy subject (e.g., a corresponding subject who does not have an inflammatory disease, an infection, and who has not been administered an antibiotic within about 1, 2, 3, 4, 5, or 6 months, and/or compared to a healthy or general population). In embodiments, the dysbiosis comprises an increased amount (absolute number or proportion of the total microbial population) of bacterial or fungal cells within a species or genus (e.g., 5%, 10%, 15%, 20%, 25%, 30%, 35%, 40%, 45%, 50%, 55%, 60%, 65%, 70%, 75%, 80%, 85%, 90%, 95% or more higher) compared to a healthy subject (e.g., a corresponding subject who does not have an inflammatory disease, an infection, and who has not been administered an antibiotic within about 1, 2, 3, 4, 5, or 6 months, and/or compared to a healthy or general population). In embodiments, a subject who comprises a gastrointestinal infection, gastrointestinal inflammation, diarrhea, colitis, or who has received an antibiotic within about 1, 2, 3, 4, 5, 6, 7, 8, 9, or 10 weeks is deemed to comprise dysbiosis. In embodiments, antibiotic administration (e.g., systemically, such as by intravenous injection or orally) is causing or has caused a major alteration in the normal microbiota. Thus, as used herein, the term "antibiotic-induced dysbiosis" refers to dysbiosis caused by or following the administration of an antibiotic.

A "control" or "standard control" refers to a sample, measurement, or value that serves as a reference, usually a known reference, for comparison to a test sample, measurement, or value. For example, a test sample can be taken from a patient suspected of having a given disease or being assessed for risk of the disease (e.g. dysbiosis, asthma, or atopy) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. In embodiments, a standard control represents an average measurement or value gathered from a general population of similar individuals (e.g. standard control subjects) that have a given disease (i.e. standard control population), e.g., with a similar medical background, same age, weight, etc. (such as individuals with atopy and/or asthma). A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. microbiome, genomic DNA levels, RNA levels, protein levels, specific cell types, specific bodily fluids, specific tissues, metabolites, etc.).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

The term "diagnosis" refers to a relative probability that a disease (e.g. dysbiosis, an infection, or other disease) is present in the subject. Similarly, the term "prognosis" refers to a relative probability that a certain future outcome may occur in the subject with respect to a disease state. For example, in the context of the present invention, prognosis can refer to the likelihood that an individual will develop a disease (e.g. dysbiosis, atopy, or asthma), or the likely severity of the disease (e.g., duration of disease, a symptom, or severity within a given timeframe). The terms are not intended to be absolute, as will be appreciated by any one of skill in the field of medical diagnostics.

"Biological sample" or "sample" refer to materials obtained from or derived from a subject or patient. In embodiments, a biological sample includes sections of tissues such as biopsy and autopsy samples, and frozen sections taken for histological purposes. In embodiments, a biological sample is a bodily fluid such as blood or a blood fraction or product (e.g., serum, plasma, platelets, red blood cells, and the like), feces or a feces fraction or product (e.g., fecal water, such as but not limited to fecal water separated from other fecal components and solids by methods such as centrifugation and filtration), sputum, tissue, cultured cells (e.g., primary cultures, explants, and transformed cells), stool, urine, etc. In embodiments, a biological sample is obtained from a subject. In embodiments, a biological sample is feces. In embodiments, a biological sample is a feces fraction or product (e.g., fecal water, such as but not limited to fecal water separated from other fecal components and solids by methods such as centrifugation and filtration).

As used herein the abbreviation "sp." for species means at least one species (e.g., 1, 2, 3, 4, 5, or more species) of the indicated genus. The abbreviation "spp." for species means 2 or more species (e.g., 2, 3, 4, 5, 6, 7, 8, 9, 10 or more) of the indicated genus. In embodiments, methods and compositions provided herein comprise a single species within an indicated genus or indicated genera, or 2 or more (e.g., a plurality comprising more than 2) species within an indicated genus or indicated genera. In embodiments, 1, 2, 3, 4, 5, or more or all or the indicated species is or are isolated. In embodiments, the indicated species are administered together. In embodiments, each of the indicated species is present in a single composition that comprises each of the species. In embodiments, each of the species is administered concurrently, e.g., within about 1, 2, 3, 4, 5, 6, 7, 8, 9, 10, 30, or 60, 1-5, 1-10, 1-30, 1-60, or 5-15 seconds or minutes of each other.

The terms "identical" or percent "identity," in the context of two or more nucleic acids or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region, e.g., of the entire sequence), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. In embodiments, the identity exists over the entire length of the two sequences being aligned. In embodiments, the identity exists over the entire length of a reference sequence. In embodiments, the identity exists over the entire length of an amino acid sequence, e.g., the amino acid sequence of a protein encoded by Gene 1, Gene 2, or Gene 3. In embodiments, the identity exists over the entire length of a nucleotide sequence, e.g., the nucleotide sequence of a mRNA transcribed from Gene 1, Gene 2, or Gene 3. In embodiments, the identity exists over the entire length of a nucleotide sequence, e.g., the DNA sequence of Gene 1, Gene 2, or Gene 3. In embodiments, the identity exists over a region that is at least about 10 to about 100, about 20 to about 75, about 30 to about 50, about 200 to about 250, or about 200 to about 300, amino acids or nucleotides in length. In embodiments, the identity exists over a region that is at least about 50 amino acids in length, or more preferably over a region that is 100 to 500 or 1000 or more amino acids or nucleotides in length.

In embodiments, percentage of sequence identity may be determined by comparing two optimally aligned sequences over a comparison window. In embodiments, the comparison window is the entire length of the shorter of the two sequences being aligned. In embodiments, a portion of the polynucleotide or polypeptide sequence in the comparison window may comprise additions or deletions (i.e., gaps) as compared to a reference sequence (which does not comprise additions or deletions). In embodiments, the percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. In embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions in which a sequence may be compared to a reference sequence of the same number of contiguous positions after the two sequences are optimally aligned. In embodiments, the comparison window is the entire length of an amino acid sequence, e.g., the amino acid sequence of a protein encoded by Gene 1, Gene 2, or Gene 3. In embodiments, the comparison window is the entire length of a nucleotide sequence, e.g., the nucleotide sequence of a mRNA transcribed from Gene 1, Gene 2, or Gene 3. In embodiments, the comparison window is the entire length of a nucleotide sequence, e.g., the DNA sequence of Gene 1, Gene 2, or Gene 3. Methods of alignment of sequences for comparison are well-known in the art. Optimal alignment of sequences for comparison can be conducted, e.g., by the local homology algorithm of Smith & Waterman, $Adv. Appl. Math.$ 2:482 (1981), by the homology alignment algorithm of Needleman & Wunsch, $J. Mol. Biol.$ 48:443 (1970), by the search for similarity method of Pearson & Lipman, $Proc. Nat'l. Acad. Sci. USA$ 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., $Current Protocols in Molecular Biology$ (Ausubel et al., eds. 1995 supplement)).

A preferred example of algorithm that is suitable for determining percent sequence identity and sequence similarity are the BLAST and BLAST 2.0 algorithms, which are described in Altschul et al., $Nuc. Acids Res.$ 25:3389-3402 (1977) and Altschul et al., $J. Mol. Biol.$ 215:403-410 (1990), respectively. BLAST and BLAST 2.0 are used, with the parameters described herein, to determine percent sequence identity for the nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, $Proc. Natl. Acad. Sci. USA$ 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues.

The phrase "stringent hybridization conditions" refers to conditions under which a primer or probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium).

Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

In embodiments, nucleic acids that do not hybridize to each other under stringent conditions are still considered substantially identical if the polypeptides which they encode are substantially identical. This occurs, for example, when a copy of a nucleic acid is created using the maximum codon degeneracy permitted by the genetic code. In embodiments, the nucleic acids hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al., supra.

In this disclosure, "comprises," "comprising," "containing," and "having" and the like can have the meaning ascribed to them in U.S. Patent law and can mean "includes," "including," and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. By contrast, the transitional phrase "consisting of" excludes any element, step, or ingredient not specified.

As used herein, the term "about" in the context of a numerical value or range means±10% of the numerical value or range recited or claimed, unless the context requires a more limited range.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

As used in the description herein and throughout the claims that follow, the meaning of "a," "an," and "the" includes plural reference unless the context clearly dictates otherwise.

II. METHODS OF DETECTION

In an aspect, provided herein is a method of detecting an epoxide hydrolase gene in a biological sample from a subject, the method including detecting (i) a gene that encodes an epoxide hydrolase having an amino acid sequence with at least about 95%, 96%, 97%, 98%, or 99% identity to SEQ ID NO:46, or the expression thereof, in the biological sample; (ii) a gene that encodes an epoxide hydrolase having an amino acid sequence with at least about 95%, 96%, 97%, 98%, or 99% identity to SEQ ID NO:47, or the expression thereof, in the biological sample; and/or (iii) a gene that encodes an epoxide hydrolase having an amino acid sequence with at least about 95%, 96%, 97%, 98%, or 99% identity to SEQ ID NO:48, or the expression thereof, in the biological sample.

In an aspect included herein is a method of detecting dysbiosis. In embodiments, the method comprises detecting (i) a gene that encodes an epoxide hydrolase having an amino acid sequence with at least about 95%, 96%, 97%, 98%, or 99% identity to SEQ ID NO:46, or the expression thereof, in a biological sample; (ii) a gene that encodes an epoxide hydrolase having an amino acid sequence with at least about 95%, 96%, 97%, 98%, or 99% identity to SEQ ID NO:47, or the expression thereof, in a biological sample; and/or (iii) a gene that encodes an epoxide hydrolase having an amino acid sequence with at least about 95%, 96%, 97%, 98%, or 99% identity to SEQ ID NO:48, or the expression thereof, in a biological sample.

In aspects, included herein is a method of detecting an epoxide hydrolase gene in a biological sample from a subject, the method comprising detecting (i) an epoxide hydrolase gene comprising a nucleotide sequence with at least about 95%, 96%, 97%, 98%, or 99% identity to SEQ ID NO:50, or the expression thereof, in the biological sample; (ii) an epoxide hydrolase gene comprising a nucleotide sequence with at least about 95%, 96%, 97%, 98%, or 99% identity to SEQ ID NO:51, or the expression thereof, in the biological sample; and/or (iii) an epoxide hydrolase gene comprising a nucleotide sequence with at least about 95%, 96%, 97%, 98%, or 99% identity to SEQ ID NO:52, or the expression thereof, in the biological sample.

In aspects, included herein is a method of detecting an epoxide hydrolase gene in a biological sample from a subject, the method comprising detecting (i) an epoxide hydrolase gene comprising the nucleotide sequence of SEQ ID NO:50 (Gene 1), or the expression thereof, in the biological sample; (ii) an epoxide hydrolase gene comprising the nucleotide sequence of SEQ ID NO:51 (Gene 2), or the expression thereof, in the biological sample; and/or (iii) an epoxide hydrolase gene comprising the nucleotide sequence of SEQ ID NO:52 (Gene 3), or the expression thereof, in the biological sample.

In embodiments, 1 gene is detected. In embodiments, 2 genes are detected. In embodiments, 3 genes are detected. In embodiments, at least 1, 5, 10, 100, 500, or 1000 additional genes are detected. In embodiments, no more than 1000 genes are detected. In embodiments, no more than 500 genes are detected. In embodiments, no more than 100 genes are detected. In embodiments, no more than 50 genes are detected. In embodiments, no more than 25 genes are detected. In embodiments, no more than 10 genes are detected. In embodiments, no more than 5 genes are detected. In embodiments, no more than 3 genes are detected. In embodiments, detecting a gene comprises detecting the level of a gene. In embodiments, detecting the level of a gene comprises detecting the copy number of the gene. In embodiments detecting the copy number of the gene comprises detecting the copy number of the gene per a given amount of or level DNA in the biological sample. In embodiments, detecting a gene or a level thereof comprises detecting mRNA transcribed from the gene or the level thereof. In embodiments, detecting a gene or a level thereof comprises detecting protein expressed from the gene or the level thereof.

The term "detecting" encompasses quantitative and qualitative detection. In embodiments, detecting is quantitative detecting. In embodiments, detecting is quantitative detecting. As used herein, "detecting a gene" includes determining whether the gene is present. In embodiments, detecting a gene comprises measuring the level of the gene (e.g., the number of copies of DNA comprising the gene or the number of copies of DNA comprising a portion or fragment of the gene). In embodiments, detecting a gene comprises detecting expression of the gene. In embodiments, detecting the expression of the gene comprises measuring the level of expression of the gene (e.g., by measuring the level of an mRNA transcribed from or protein expressed from the gene). Numerous methods detecting genomic DNA, mRNA, proteins, and cells are known in the art. Non-limiting examples of detection assays include immune assays such as an enzyme-linked immunosorbent assay (ELISA), enzyme-linked immunofiltration assay (ELIFA), fluorescence activated cell sorting (FACS), MassARRAY®, proteomic assays, biochemical enzymatic activity assays, in situ hybridization, Southern analysis, Northern analysis, whole genome sequencing, polymerase chain reaction ("PCR") including quantitative PCT, quantitative real time PCR, and reverse transcription PCR, and other amplification type detection methods [such as, for example, branched DNA, single-primer amplification (SISBA), transcription-mediated amplification (TMA) and the like], RNA-Seq, fuorescent in situ hybridization (FISH), microarray analysis, gene expression profiling, and/or serial analysis of gene expression (SAGE), as well as any one of the wide variety of assays that can be performed by protein, mRNA, and/or genomic array analysis. Non-limiting examples of protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). In embodiments, multiplexed immunoassays such as those available from Rules Based Medicine or Meso Scale Discovery may be used.

In embodiments, (i) the gene that encodes an epoxide hydrolase having an amino acid sequence with at least about 95%, 96%, 97%, 98%, or 99% identity to SEQ ID NO:46 is an *Enterococcus* sp. gene; (ii) the gene that encodes an epoxide hydrolase having an amino acid sequence with at least about 95%, 96%, 97%, 98%, or 99% identity to SEQ ID NO:47 is a *Bifidobacterium* sp. gene; and/or (iii) the gene that encodes an epoxide hydrolase having an amino acid sequence with at least about 95%, 96%, 97%, 98%, or 99% identity to SEQ ID NO:48 is a *Bifidobacterium* sp. gene.

In embodiments, (i) the gene that encodes an epoxide hydrolase having an amino acid sequence with at least about 95%, 96%, 97%, 98%, or 99% identity to SEQ ID NO:46 is an *Enterococcus faecalis* gene; (ii) the gene that encodes an epoxide hydrolase having an amino acid sequence with at least about 95%, 96%, 97%, 98%, or 99% identity to SEQ ID NO:47 is a *Bifidobacterium* bifidum gene; and/or (iii) the gene that encodes an epoxide hydrolase having an amino acid sequence with at least about 95%, 96%, 97%, 98%, or 99% identity to SEQ ID NO:48 is a *Bifidobacterium bifidum* gene.

In embodiments, the method includes detecting the level of (i) an epoxide hydrolase gene that encodes an enzyme that has the amino acid sequence of SEQ ID NO:46 (Gene 1), or the expression thereof, in the biological sample; (ii) an epoxide hydrolase gene that encodes an enzyme that has the amino acid sequence of SEQ ID NO:47 (Gene 2), or the expression thereof, in the biological sample; and/or (iii) an epoxide hydrolase gene that encodes an enzyme that has the amino acid sequence of SEQ ID NO:48 (Gene 3), or the expression thereof, in the biological sample. In embodiments, Gene 1 comprises the nucleotide sequence of SEQ ID NO:50. In embodiments, Gene 1 has a nucleotide sequence other than SEQ ID NO:50, but encodes an enzyme having the same amino acid sequence as an enzyme encoded by SEQ ID NO:50. In embodiments, Gene 2 comprises the nucleotide sequence of SEQ ID NO:51. In embodiments, Gene 2 has a nucleotide sequence other than SEQ ID NO:51, but encodes an enzyme having the same amino acid sequence as an enzyme encoded by SEQ ID NO:51. In embodiments, Gene 3 comprises the nucleotide sequence of SEQ ID NO:52. In embodiments, Gene 3 has a nucleotide sequence other than SEQ ID NO:52, but encodes an enzyme having the same amino acid sequence as an enzyme encoded by SEQ ID NO:52.

In embodiments, the biological sample is a fecal sample. In embodiments, the biological sample is a fecal fraction or product. In embodiments, the fecal sample is a stool sample.

In embodiments, the subject is less than 1, 2, 3, 4, or 5 years old. In embodiments, the subject is less than 1 years old. In embodiments, the subject is less than 2 years old. In embodiments, the subject is less than 3 years old. In embodiments, the subject is less than 3 years old. In embodiments, the subject is less than 4 years old. In embodiments, the subject is less than 5 years old. In embodiments, the subject is 1 years old. In embodiments, the subject is 2 years old. In embodiments, the subject is 3 years old. In embodiments, the subject is 3 years old. In embodiments, the subject is 4 years old. In embodiments, the subject is 5 years old.

In embodiments, the subject is from 0 to 1 month old, from 0.5 to 2 months old, from 0 to 3 months old, 0.5 to 3 months old, from 3 to 6 months old, or from 0 to 6 months old. In embodiments, the subject is from 0 to 1 month old. In embodiments, the subject is from 0.5 to 2 months old. In embodiments, the subject is from 0 to 3 months old. In embodiments, the subject is 0.5 to 3 months old. In embodiments, the subject is from 3 to 6 months old. In embodiments, the subject is from 0 to 6 months old.

In embodiments, the mother of the subject has or has had asthma. In embodiments, the mother of the subject has asthma. In embodiments, the mother of the subject has had asthma.

In embodiments, the subject has been in a room with a cat 0 times during the first month after the subject was born. In embodiments, the subject has been in a room with a cat 1 time during the first month after the subject was born. In embodiments, the subject has been in a room with a cat 2 times during the first month after the subject was born. In embodiments, the subject has been in a room with a cat 3 times during the first month after the subject was born. In embodiments, the subject has been in a room with a cat 4 times during the first month after the subject was born. In embodiments, the subject has been in a room with a cat 5 times during the first month after the subject was born. In embodiments, the subject has been in a room with a cat 6 times during the first month after the subject was born. In embodiments, the subject has been in a room with a cat 7 times during the first month after the subject was born. In embodiments, the subject has been in a room with a cat 8 times during the first month after the subject was born. In embodiments, the subject has been in a room with a cat 9 times during the first month after the subject was born. In embodiments, the subject has been in a room with a cat 10 times during the first month after the subject was born. In embodiments, the subject has been in a room with a cat 11 times during the first month after the subject was born. In embodiments, the subject has been in a room with a cat 12 times during the first month after the subject was born. In embodiments, the subject has been in a room with a cat 13 times during the first month after the subject was born. In embodiments, the subject has been in a room with a cat 14 times during the first month after the subject was born. In embodiments, the subject has been in a room with a cat 15 times during the first month after the subject was born. In embodiments, the subject has been in a room with a cat 16 times during the first month after the subject was born. In embodiments, the subject has been in a room with a cat 17 times during the first month after the subject was born. In embodiments, the subject has been in a room with a cat 18 times during the first month after the subject was born. In embodiments, the subject has been in a room with a cat 19 times during the first month after the subject was born. In embodiments, the subject has been in a room width a cat 20 times during the first month after the subject was born.

In embodiments, the subject has not lived in a residence with a cat for at least 7, 14, or 21 days of the first month after the subject was born. In embodiments, the subject has not lived in a residence with a cat for at least 7 days of the first month after the subject was born. In embodiments, the subject has not lived in a residence with a cat for at least 14 days of the first month after the subject was born. In embodiments, the subject has not lived in a residence with a cat for at least 21 days of the first month after the subject was born.

In embodiments, the subject has been in a room with a dog 0 times during the first month after the subject was born. In embodiments, the subject has been in a room with a dog 1 time during the first month after the subject was born. In embodiments, the subject has been in a room with a dog 2 times during the first month after the subject was born. In embodiments, the subject has been in a room with a dog 3 times during the first month after the subject was born. In embodiments, the subject has been in a room with a dog 4 times during the first month after the subject was born. In embodiments, the subject has been in a room with a dog 5 times during the first month after the subject was born. In embodiments, the subject has been in a room with a dog 6 times during the first month after the subject was born. In embodiments, the subject has been in a room with a dog 7 times during the first month after the subject was born. In embodiments, the subject has been in a room with a dog 8 times during the first month after the subject was born. In embodiments, the subject has been in a room with a dog 9 times during the first month after the subject was born. In embodiments, the subject has been in a room with a dog 10 times during the first month after the subject was born. In embodiments, the subject has been in a room with a dog 11 times during the first month after the subject was born. In embodiments, the subject has been in a room with a dog 12 times during the first month after the subject was born. In embodiments, the subject has been in a room with a dog 13 times during the first month after the subject was born. In embodiments, the subject has been in a room with a dog 14 times during the first month after the subject was born. In embodiments, the subject has been in a room with a dog 15 times during the first month after the subject was born. In embodiments, the subject has been in a room with a dog 16 times during the first month after the subject was born. In embodiments, the subject has been in a room with a dog 17 times during the first month after the subject was born. In embodiments, the subject has been in a room with a dog 18 times during the first month after the subject was born. In embodiments, the subject has been in a room with a dog 19 times during the first month after the subject was born. In embodiments, the subject has been in a room with a dog 20 times during the first month after the subject was born.

In embodiments, the subject has not lived in a residence with a dog for at least 7, 14, or 21 days of the first month after the subject was born. In embodiments, the subject has not lived in a residence with a dog for at least 7 days of the first month after the subject was born. In embodiments, the subject has not lived in a residence with a dog for at least 14 days of the first month after the subject was born. In embodiments, the subject has not lived in a residence with a dog for at least 21 days of the first month after the subject was born.

In embodiments, the subject's mother has not lived in a residence with a dog for at least 30, 60, 90, 120, 150, 180, 210, 240, or 270 days between when the subject was conceived and when the subject was born. In embodiments, the subject's mother has not lived in a residence with a dog for at least 30 days between when the subject was conceived and when the subject was born. In embodiments, the subject's mother has not lived in a residence with a dog for at least 60 days between when the subject was conceived and when the subject was born. In embodiments, the subject's mother has not lived in a residence with a dog for at least 90 days between when the subject was conceived and when the subject was born. In embodiments, the subject's mother has not lived in a residence with a dog for at least 120 days between when the subject was conceived and when the subject was born. In embodiments, the subject's mother has not lived in a residence with a dog for at least 150 days between when the subject was conceived and when the subject was born. In embodiments, the subject's mother has not lived in a residence with a dog for at least 180 days between when the subject was conceived and when the subject was born. In embodiments, the subject's mother has not lived in a residence with a dog for at least 210 days between when the subject was conceived and when the subject was born. In embodiments, the subject's mother has not lived in a residence with a dog for at least 240 days between when the subject was conceived and when the subject was born. In embodiments, the subject's mother has not lived in a residence with a dog for at least 270 days between when the subject was conceived and when the subject was born.

In embodiments, the subject's mother has smoked at least once on a total of at least about 30, 60, 90, 120, 150, 180, 210, 240, or 270 days between when the subject was conceived and when the subject was born. In embodiments, the subject's mother has smoked at least once on a total of at least about 30 days between when the subject was conceived and when the subject was born. In embodiments, the subject's mother has smoked at least once on a total of at least about 60 days between when the subject was conceived and when the subject was born. In embodiments, the subject's mother has smoked at least once on a total of at least about 90 days between when the subject was conceived and when the subject was born. In embodiments, the subject's mother has smoked at least once on a total of at least about 120 days between when the subject was conceived and when the subject was born. In embodiments, the subject's mother has smoked at least once on a total of at least about 150 days between when the subject was conceived and when the subject was born. In embodiments, the subject's mother has smoked at least once on a total of at least about 180 days between when the subject was conceived and when the subject was born. In embodiments, the subject's mother has smoked at least once on a total of at least about 210 days between when the subject was conceived and when the subject was born. In embodiments, the subject's mother has smoked at least once on a total of at least about 240 days between when the subject was conceived and when the subject was born. In embodiments, the subject's mother has smoked at least once on a total of at least about 270 days between when the subject was conceived and when the subject was born.

In embodiments, the subject's mother has smoked at least once on a total of at least 30, 60, 90, 120, 150, 180, 210, 240, or 270 days between when the subject was conceived and when the subject was born. In embodiments, the subject's mother has smoked at least once on a total of at least 30 days between when the subject was conceived and when the subject was born. In embodiments, the subject's mother has smoked at least once on a total of at least 60 days between when the subject was conceived and when the subject was born. In embodiments, the subject's mother has smoked at least once on a total of at least 90 days between when the subject was conceived and when the subject was born. In embodiments, the subject's mother has smoked at least once on a total of at least 120 days between when the subject was conceived and when the subject was born. In embodiments, the subject's mother has smoked at least once on a total of at least 150 days between when the subject was conceived and when the subject was born. In embodiments, the subject's mother has smoked at least once on a total of at least 180 days between when the subject was conceived and when the subject was born. In embodiments, the subject's mother has smoked at least once on a total of at least 210 days between when the subject was conceived and when the subject was born. In embodiments, the subject's mother has smoked at least once on a total of at least 240 days between when the subject was conceived and when the subject was born. In embodiments, the subject's mother has smoked at least once on a total of at least 270 days between when the subject was conceived and when the subject was born.

In embodiments, the days are consecutive days.

In embodiments, he subject has been fed formula in the first month of life. In embodiments, the subject has been fed more formula than breast milk in the first month of life. In embodiments, the subject has not been fed breast milk in the first month of live. In embodiments, the subject has been fed at least twice as much formula as breast milk in the first month of life. In embodiments, the subject has been fed at least three times as much formula as breast milk in the first month of life.

In embodiments, the subject has not been fed breast milk in the first month of life.

In embodiments, the level of 12,13 DiHOME in feces of the subject is at least about 250 ng/g. In embodiments, the level of 12,13 DiHOME in feces of the subject is at least about 260 ng/g. In embodiments, the level of 12,13 DiHOME in feces of the subject is at least about 270 ng/g. In embodiments, the level of 12,13 DiHOME in feces of the subject is at least about 280 ng/g. In embodiments, the level of 12,13 DiHOME in feces of the subject is at least about 290 ng/g. In embodiments, the level of 12,13 DiHOME in feces of the subject is at least about 300 ng/g. In embodiments, the level of 12,13 DiHOME in feces of the subject is at least about 310 ng/g. In embodiments, the level of 12,13 DiHOME in feces of the subject is at least about 320 ng/g. In embodiments, the level of 12,13 DiHOME in feces of the subject is at least about 330 ng/g. In embodiments, the level of 12,13 DiHOME in feces of the subject is at least about 340 ng/g. In embodiments, the level of 12,13 DiHOME in feces of the subject is at least about 350 ng/g. In embodiments, the level of 12,13 DiHOME in feces of the subject is at least about 360 ng/g. In embodiments, the level of 12,13 DiHOME in feces of the subject is at least about 370 ng/g. In embodiments, the level of 12,13 DiHOME in feces of the subject is at least about 380 ng/g. In embodiments, the level of 12,13 DiHOME in feces of the subject is at least about 390 ng/g. In embodiments, the level of 12,13 DiHOME in feces of the subject is at least about 400 ng/g. In embodiments, the level of 12,13 DiHOME in feces of the subject is at least about 410 ng/g. In embodiments, the level of 12,13 DiHOME in feces of the subject is at least about 420 ng/g. In embodiments, the level of 12,13 DiHOME in feces of the subject is at least about 430 ng/g. In embodiments, the level of 12,13 DiHOME in feces of the subject is at least about 440 ng/g. In embodiments, the level of 12,13 DiHOME in feces of the subject is at least about 450 ng/g. In embodiments, the level of 12,13 DiHOME in feces of the subject is at least about 460 ng/g. In embodiments, the level of 12,13 DiHOME in feces of the subject is at least about 470 ng/g. In embodiments, the level of 12,13 DiHOME in feces of the subject is at least about 480 ng/g. In embodiments, the level of 12,13 DiHOME in feces of the subject is at least about 490 ng/g. In embodiments, the level of 12,13 DiHOME in feces of the subject is at least about 500 ng/g.

In embodiments, the level of 12,13 DiHOME in feces of the subject is at least 250 ng/g. In embodiments, the level of 12,13 DiHOME in feces of the subject is at least 260 ng/g. In embodiments, the level of 12,13 DiHOME in feces of the subject is at least 270 ng/g. In embodiments, the level of 12,13 DiHOME in feces of the subject is at least 280 ng/g. In embodiments, the level of 12,13 DiHOME in feces of the subject is at least 290 ng/g. In embodiments, the level of 12,13 DiHOME in feces of the subject is at least 300 ng/g. In embodiments, the level of 12,13 DiHOME in feces of the subject is at least 310 ng/g. In embodiments, the level of 12,13 DiHOME in feces of the subject is at least 320 ng/g. In embodiments, the level of 12,13 DiHOME in feces of the subject is at least 330 ng/g. In embodiments, the level of 12,13 DiHOME in feces of the subject is at least 340 ng/g. In embodiments, the level of 12,13 DiHOME in feces of the subject is at least 350 ng/g. In embodiments, the level of 12,13 DiHOME in feces of the subject is at least 360 ng/g. In embodiments, the level of 12,13 DiHOME in feces of the subject is at least 370 ng/g. In embodiments, the level of 12,13 DiHOME in feces of the subject is at least 380 ng/g. In embodiments, the level of 12,13 DiHOME in feces of the subject is at least 390 ng/g. In embodiments, the level of 12,13 DiHOME in feces of the subject is at least 400 ng/g. In embodiments, the level of 12,13 DiHOME in feces of the subject is at least 410 ng/g. In embodiments, the level of 12,13 DiHOME in feces of the subject is at least 420 ng/g. In embodiments, the level of 12,13 DiHOME in feces of the subject is at least 430 ng/g. In embodiments, the level of 12,13 DiHOME in feces of the subject is at least 440 ng/g. In embodiments, the level of 12,13 DiHOME in feces of the subject is at least 450 ng/g. In embodiments, the level of 12,13 DiHOME in feces of the subject is at least 460 ng/g. In embodiments, the level of 12,13 DiHOME in feces of the subject is at least 470 ng/g. In embodiments, the level of 12,13 DiHOME in feces of the subject is at least 480 ng/g. In embodiments, the level of 12,13 DiHOME in feces of the subject is at least 490 ng/g. In embodiments, the level of 12,13 DiHOME in feces of the subject is at least 500 ng/g.

In embodiments, the level of 12,13 DiHOME in feces of the subject is 250 ng/g. In embodiments, the level of 12,13 DiHOME in feces of the subject is 260 ng/g. In embodiments, the level of 12,13 DiHOME in feces of the subject is 270 ng/g. In embodiments, the level of 12,13 DiHOME in feces of the subject is 280 ng/g. In embodiments, the level of 12,13 DiHOME in feces of the subject is 290 ng/g. In embodiments, the level of 12,13 DiHOME in feces of the subject is 300 ng/g. In embodiments, the level of 12,13 DiHOME in feces of the subject is 310 ng/g. In embodiments, the level of 12,13 DiHOME in feces of the subject is 320 ng/g. In embodiments, the level of 12,13 DiHOME in feces of the subject is 330 ng/g. In embodiments, the level of 12,13 DiHOME in feces of the subject is 340 ng/g. In embodiments, the level of 12,13 DiHOME in feces of the subject is 350 ng/g. In embodiments, the level of 12,13 DiHOME in feces of the subject is 360 ng/g. In embodiments, the level of 12,13 DiHOME in feces of the subject is 370 ng/g. In embodiments, the level of 12,13 DiHOME in feces of the subject is 380 ng/g. In embodiments, the level of 12,13 DiHOME in feces of the subject is 390 ng/g. In embodiments, the level of 12,13 DiHOME in feces of the subject is 400 ng/g. In embodiments, the level of 12,13 DiHOME in feces of the subject is 410 ng/g. In embodiments, the level of 12,13 DiHOME in feces of the subject is 420 ng/g. In embodiments, the level of 12,13 DiHOME in feces of the subject is 430 ng/g. In embodiments, the level of 12,13 DiHOME in feces of the subject is 440 ng/g. In embodiments, the level of 12,13 DiHOME in feces of the subject is 450 ng/g. In embodiments, the level of 12,13 DiHOME in feces of the subject is 460 ng/g. In embodiments, the level of 12,13 DiHOME in feces of the subject is 470 ng/g. In embodiments, the level of 12,13 DiHOME in feces of the subject is 480 ng/g. In embodiments, the level of 12,13 DiHOME in feces of the subject is 490 ng/g. In embodiments, the level of 12,13 DiHOME in feces of the subject is 500 ng/g.

In embodiments, the level of 12,13 DiHOME in feces of the subject is from about 250 ng/g to about 500 ng/g. In embodiments, the level of 12,13 DiHOME in feces of the subject is from about 250 ng/g to about 450 ng/g. In embodiments, the level of 12,13 DiHOME in feces of the subject is from about 250 ng/g to about 400 ng/g. In embodiments, the level of 12,13 DiHOME in feces of the subject is from about 250 ng/g to about 350 ng/g. In embodiments, the level of 12,13 DiHOME in feces of the subject is from about 250 ng/g to about 300 ng/g. In embodiments, the level of 12,13 DiHOME in feces of the subject is from about 300 ng/g to about 500 ng/g. In embodiments, the level of 12,13 DiHOME in feces of the subject is from about 350 ng/g to about 500 ng/g. In embodiments, the level of 12,13 DiHOME in feces of the subject is from about 400 ng/g to about 500 ng/g. In embodiments, the level of 12,13 DiHOME in feces of the subject is from about 450 ng/g to about 500 ng/g.

In embodiments, the level of 12,13 DiHOME in feces of the subject is from 250 ng/g to 500 ng/g. In embodiments, the level of 12,13 DiHOME in feces of the subject is from 250 ng/g to 450 ng/g. In embodiments, the level of 12,13 DiHOME in feces of the subject is from 250 ng/g to 400 ng/g. In embodiments, the level of 12,13 DiHOME in feces of the subject is from 250 ng/g to 350 ng/g. In embodiments, the level of 12,13 DiHOME in feces of the subject is from 250 ng/g to 300 ng/g. In embodiments, the level of 12,13 DiHOME in feces of the subject is from 300 ng/g to 500 ng/g. In embodiments, the level of 12,13 DiHOME in feces of the subject is from 350 ng/g to 500 ng/g. In embodiments, the level of 12,13 DiHOME in feces of the subject is from 400 ng/g to 500 ng/g. In embodiments, the level of 12,13 DiHOME in feces of the subject is from 450 ng/g to 500 ng/g.

In embodiments, the level of 12,13 DiHOME in feces of the subject is at least about 398 ng/g.

In embodiments, the level of 12,13 DiHOME in feces of the subject is detected using mass spectrometry. In embodiments, the level of 12,13 DiHOME in feces of the subject is detected using high-performance liquid chromatography (HPLC). In embodiments, the level of 12,13 DiHOME in feces of the subject is detected using an immunoassay. In embodiments, the level of 12,13 DiHOME in feces of the subject is detected using ELISA. In embodiments, the level of 12,13 DiHOME in feces of the subject is detected using sandwich ELISA. In embodiments, the level of 12,13 DiHOME in feces of the subject is detected using a cloned enzyme donor immunoassay (CEDIA). In embodiments, the level of 12,13 DiHOME in feces of the subject is detected using a lateral flow test. In embodiments, the level of 12,13 DiHOME in feces of the subject is detected using a magnetic immunoassay. In embodiments, the level of 12,13 DiHOME in feces of the subject is detected using a radioimmunoassay. In embodiments, the level of 12,13 DiHOME in feces of the subject is detected using a surround optical-fiber immunoassay (SOFIA). In embodiments, the level of 12,13 DiHOME in feces of the subject is detected using a CD/DVD based immunoassay. It is contemplated that any suitable method known in the art for detecting concentrations of an analyte (e.g., 12,13 DiHOME) in a biological sample may be used to determine a level of 12,13 DiHOME in feces of the subject.

In embodiments, the level of 9,10 DiHOME in the feces of the subject is at least about 425 ng/g.

In embodiments, the level of 9,10 DiHOME in feces of the subject is at least about 350 ng/g. In embodiments, the level of 9,10 DiHOME in feces of the subject is at least about 360 ng/g. In embodiments, the level of 9,10 DiHOME in feces of the subject is at least about 370 ng/g. In embodiments, the level of 9,10 DiHOME in feces of the subject is at least about 380 ng/g. In embodiments, the level of 9,10 DiHOME in feces of the subject is at least about 390 ng/g. In embodiments, the level of 9,10 DiHOME in feces of the subject is at least about 400 ng/g. In embodiments, the level of 9,10 DiHOME in feces of the subject is at least about 410 ng/g. In embodiments, the level of 9,10 DiHOME in feces of the subject is at least about 420 ng/g. In embodiments, the level of 9,10 DiHOME in feces of the subject is at least about 430 ng/g. In embodiments, the level of 9,10 DiHOME in feces of the subject is at least about 440 ng/g. In embodiments, the level of 9,10 DiHOME in feces of the subject is at least about 450 ng/g. In embodiments, the level of 9,10 DiHOME in feces of the subject is at least about 460 ng/g. In embodiments, the level of 9,10 DiHOME in feces of the subject is at least about 470 ng/g. In embodiments, the level of 9,10 DiHOME in feces of the subject is at least about 480 ng/g. In embodiments, the level of 9,10 DiHOME in feces of the subject is at least about 490 ng/g. In embodiments, the level of 9,10 DiHOME in feces of the subject is at least about 500 ng/g. In embodiments, the level of 9,10 DiHOME in feces of the subject is at least about 510 ng/g. In embodiments, the level of 9,10 DiHOME in feces of the subject is at least about 520 ng/g. In embodiments, the level of 9,10 DiHOME in feces of the subject is at least about 530 ng/g. In embodiments, the level of 9,10 DiHOME in feces of the subject is at least about 540 ng/g. In embodiments, the level of 9,10 DiHOME in feces of the subject is at least about 550 ng/g. In embodiments, the level of 9,10 DiHOME in feces of the subject is at least about 560 ng/g. In embodiments, the level of 9,10 DiHOME in feces of the subject is at least about 570 ng/g. In embodiments, the level of 9,10 DiHOME in feces of the subject is at least about 580 ng/g. In embodiments, the level of 9,10 DiHOME in feces of the subject is at least about 590 ng/g. In embodiments, the level of 9,10 DiHOME in feces of the subject is at least about 600 ng/g.

In embodiments, the level of 9,10 DiHOME in feces of the subject is at least 350 ng/g. In embodiments, the level of 9,10 DiHOME in feces of the subject is at least 360 ng/g. In embodiments, the level of 9,10 DiHOME in feces of the subject is at least 370 ng/g. In embodiments, the level of 9,10 DiHOME in feces of the subject is at least 380 ng/g. In embodiments, the level of 9,10 DiHOME in feces of the subject is at least 390 ng/g. In embodiments, the level of 9,10 DiHOME in feces of the subject is at least 400 ng/g. In embodiments, the level of 9,10 DiHOME in feces of the subject is at least 410 ng/g. In embodiments, the level of 9,10 DiHOME in feces of the subject is at least 420 ng/g. In embodiments, the level of 9,10 DiHOME in feces of the subject is at least 430 ng/g. In embodiments, the level of 9,10 DiHOME in feces of the subject is at least 440 ng/g. In embodiments, the level of 9,10 DiHOME in feces of the subject is at least 450 ng/g. In embodiments, the level of 9,10 DiHOME in feces of the subject is at least 460 ng/g. In embodiments, the level of 9,10 DiHOME in feces of the subject is at least 470 ng/g. In embodiments, the level of 9,10 DiHOME in feces of the subject is at least 480 ng/g. In embodiments, the level of 9,10 DiHOME in feces of the subject is at least 490 ng/g. In embodiments, the level of 9,10 DiHOME in feces of the subject is at least 500 ng/g. In embodiments, the level of 9,10 DiHOME in feces of the subject is at least 510 ng/g. In embodiments, the level of 9,10 DiHOME in feces of the subject is at least 520 ng/g. In embodiments, the level of 9,10 DiHOME in feces of the subject is at least 530 ng/g. In embodiments, the level of 9,10 DiHOME in feces of the subject is at least 540 ng/g. In embodiments, the level of 9,10 DiHOME in feces of the subject is at least 550 ng/g. In embodiments, the level of 9,10 DiHOME in feces of the subject is at least 560 ng/g. In embodiments, the level of 9,10 DiHOME in feces of the subject is at least 570 ng/g. In embodiments, the level of 9,10 DiHOME in feces of the subject is at least 580 ng/g. In embodiments, the level of 9,10 DiHOME in feces of the subject is at least 590 ng/g. In embodiments, the level of 9,10 DiHOME in feces of the subject is at least 600 ng/g.

In embodiments, the level of 9,10 DiHOME in feces of the subject is 350 ng/g. In embodiments, the level of 9,10 DiHOME in feces of the subject is 360 ng/g. In embodiments, the level of 9,10 DiHOME in feces of the subject is 370 ng/g. In embodiments, the level of 9,10 DiHOME in feces of the subject is 380 ng/g. In embodiments, the level of 9,10 DiHOME in feces of the subject is 390 ng/g. In embodiments, the level of 9,10 DiHOME in feces of the subject is 400 ng/g. In embodiments, the level of 9,10 DiHOME in feces of the subject is 410 ng/g. In embodiments, the level of 9,10 DiHOME in feces of the subject is 420 ng/g. In embodiments, the level of 9,10 DiHOME in feces of the subject is 430 ng/g. In embodiments, the level of 9,10 DiHOME in feces of the subject is 440 ng/g. In embodiments, the level of 9,10 DiHOME in feces of the subject is 450 ng/g. In embodiments, the level of 9,10 DiHOME in feces of the subject is 460 ng/g. In embodiments, the level of 9,10 DiHOME in feces of the subject is 470 ng/g. In embodiments, the level of 9,10 DiHOME in feces of the subject is 480 ng/g. In embodiments, the level of 9,10 DiHOME in feces of the subject is 490 ng/g. In embodiments, the level of 9,10 DiHOME in feces of the subject is 500 ng/g. In embodiments, the level of 9,10 DiHOME in feces of the subject is 510 ng/g. In embodiments, the level of 9,10 DiHOME in feces of the subject is 520 ng/g. In embodiments, the level of 9,10 DiHOME in feces of the subject is 530 ng/g. In embodiments, the level of 9,10 DiHOME in feces of the subject is 540 ng/g. In embodiments, the level of 9,10 DiHOME in feces of the subject is 550 ng/g. In embodiments, the level of 9,10 DiHOME in feces of the subject is 560 ng/g. In embodiments, the level of 9,10 DiHOME in feces of the subject is 570 ng/g. In embodiments, the level of 9,10 DiHOME in feces of the subject is 580 ng/g. In embodiments, the level of 9,10 DiHOME in feces of the subject is 590 ng/g. In embodiments, the level of 9,10 DiHOME in feces of the subject is 600 ng/g.

In embodiments, the level of 9,10 DiHOME in feces of the subject is from about 350 ng/g to about 600 ng/g. In embodiments, the level of 9,10 DiHOME in feces of the subject is from about 350 ng/g to about 550 ng/g. In embodiments, the level of 9,10 DiHOME in feces of the subject is from about 350 ng/g to about 500 ng/g. In embodiments, the level of 9,10 DiHOME in feces of the subject is from about 350 ng/g to about 450 ng/g. In embodiments, the level of 9,10 DiHOME in feces of the subject is from about 350 ng/g to about 400 ng/g. In embodiments, the level of 9,10 DiHOME in feces of the subject is from about 400 ng/g to about 600 ng/g. In embodiments, the level of 9,10 DiHOME in feces of the subject is from about 450 ng/g to about 600 ng/g. In embodiments, the level of 9,10 DiHOME in feces of the subject is from about 500 ng/g to about 600 ng/g. In embodiments, the level of 9,10 DiHOME in feces of the subject is from about 550 ng/g to about 600 ng/g.

In embodiments, the level of 9,10 DiHOME in feces of the subject is from 350 ng/g to 600 ng/g. In embodiments, the level of 9,10 DiHOME in feces of the subject is from 350 ng/g to 550 ng/g. In embodiments, the level of 9,10 DiHOME in feces of the subject is from 350 ng/g to 500 ng/g. In embodiments, the level of 9,10 DiHOME in feces of the subject is from 350 ng/g to 450 ng/g. In embodiments, the level of 9,10 DiHOME in feces of the subject is from 350 ng/g to 400 ng/g. In embodiments, the level of 9,10 DiHOME in feces of the subject is from 400 ng/g to 600 ng/g. In embodiments, the level of 9,10 DiHOME in feces of the subject is from 450 ng/g to 600 ng/g. In embodiments, the level of 9,10 DiHOME in feces of the subject is from 500 ng/g to 600 ng/g. In embodiments, the level of 9,10 DiHOME in feces of the subject is from 550 ng/g to 600 ng/g.

In embodiments, the level of 9,10 DiHOME in feces of the subject is detected using mass spectrometry. In embodiments, the level of 9,10 DiHOME in feces of the subject is detected using high-performance liquid chromatography (HPLC). In embodiments, the level of 9,10 DiHOME in feces of the subject is detected using immunoassay techniques. In embodiments, the level of 9,10 DiHOME in feces of the subject is detected using an enzyme-linked immunosorbent assay (ELISA). In embodiments, the level of 9,10 DiHOME in feces of the subject is detected using sandwich ELISA. In embodiments, the level of 9,10 DiHOME in feces of the subject is detected using a cloned enzyme donor immunoassay (CEDIA). In embodiments, the level of 9,10 DiHOME in feces of the subject is detected using a lateral flow test. In embodiments, the level of 9,10 DiHOME in feces of the subject is detected using a magnetic immunoassay. In embodiments, the level of 9,10 DiHOME in feces of the subject is detected using a radioimmunoassay. In embodiments, the level of 9,10 DiHOME in feces of the subject is detected using a surround optical-fiber immunoassay (SOFIA). In embodiments, the level of 9,10 DiHOME in feces of the subject is detected using a CD/DVD based immunoassay. It is contemplated that any suitable method known in the art for detecting concentrations of an analyte (e.g., 9,10 DiHOME) in a biological sample may be used to determine a level of 9,10 DiHOME in feces of the subject.

In embodiments, detecting a gene includes detecting the level of the gene. In embodiments, the method includes detecting the level of Gene 1 in the biological sample. In embodiments, the method includes detecting the level of Gene 2 in the biological sample. In embodiments, the method includes detecting the level of Gene 3 in the biological sample.

In embodiments, the level of a gene that encodes an epoxide hydrolase is the copy number of the gene or a portion thereof (e.g., a portion or fragment listed in Table 9 of Example 2). In embodiments, the portion comprises SEQ ID NO:43. In embodiments, the portion comprises SEQ ID NO:44. In embodiments, the portion comprises SEQ ID NO:45. In embodiments, the portion comprises SEQ ID NO:49. In embodiments, the level of a gene that encodes an epoxide hydrolase is the copy number of the gene or a portion thereof per an amount of weight of the biological sample. In embodiments, the level of a gene that encodes an epoxide hydrolase is the copy number of the gene or a portion thereof per an amount or level of DNA in the biological sample. In embodiments, the level of a gene that encodes an epoxide hydrolase is the copy number of the gene or a portion thereof per an amount of DNA in the biological sample.

In embodiments, the method includes determining whether there are at least about 1,598 or 13,318 copies of genomic DNA sequences encoding Gene 1, Gene 2, and/or Gene 3 per nanogram (ng) of fecal DNA in the fecal sample.

In embodiments, the method includes determining whether there are at least about 1,250 copies of genomic DNA sequences encoding Gene 1, Gene 2, and/or Gene 3 per nanogram (ng) of fecal DNA in the fecal sample. In embodiments, the method includes determining whether there are at least about 1,300 copies of genomic DNA sequences encoding Gene 1, Gene 2, and/or Gene 3 per nanogram (ng) of fecal DNA in the fecal sample. In embodiments, the method includes determining whether there are at least about 1,400 copies of genomic DNA sequences encoding Gene 1, Gene 2, and/or Gene 3 per nanogram (ng) of fecal DNA in the fecal sample. In embodiments, the method includes determining whether there are at least about 1,500 copies of genomic DNA sequences encoding Gene 1, Gene 2, and/or Gene 3 per nanogram (ng) of fecal DNA in the fecal sample. In embodiments, the method includes determining whether there are at least about 1,600 copies of genomic DNA sequences encoding Gene 1, Gene 2, and/or Gene 3 per nanogram (ng) of fecal DNA in the fecal sample. In embodiments, the method includes determining whether there are at least about 1,700 copies of genomic DNA sequences encoding Gene 1, Gene 2, and/or Gene 3 per nanogram (ng) of fecal DNA in the fecal sample. In embodiments, the method includes determining whether there are at least about 1,800 copies of genomic DNA sequences encoding Gene 1, Gene 2, and/or Gene 3 per nanogram (ng) of fecal DNA in the fecal sample. In embodiments, the method includes determining whether there are at least about 1,900 copies of genomic DNA sequences encoding Gene 1, Gene 2, and/or Gene 3 per nanogram (ng) of fecal DNA in the fecal sample. In embodiments, the method includes determining whether there are at least about 2,000 copies of genomic DNA sequences encoding Gene 1, Gene 2, and/or Gene 3 per nanogram (ng) of fecal DNA in the fecal sample. In embodiments, the method includes determining whether there are at least about 2,500 copies of genomic DNA sequences encoding Gene 1, Gene 2, and/or Gene 3 per nanogram (ng) of fecal DNA in the fecal sample. In embodiments, the method includes determining whether there are at least about 3,000 copies of genomic DNA sequences encoding Gene 1, Gene 2, and/or Gene 3 per nanogram (ng) of fecal DNA in the fecal sample. In embodiments, the method includes determining whether there are at least about 3,500 copies of genomic DNA sequences encoding Gene 1, Gene 2, and/or Gene 3 per nanogram (ng) of fecal DNA in the fecal sample. In embodiments, the method includes determining whether there are at least about 4,000 copies of genomic DNA sequences encoding Gene 1, Gene 2, and/or Gene 3 per nanogram (ng) of fecal DNA in the fecal sample. In embodiments, the method includes determining whether there are at least about 4,500 copies of genomic DNA sequences encoding Gene 1, Gene 2, and/or Gene 3 per nanogram (ng) of fecal DNA in the fecal sample. In embodiments, the method includes determining whether there are at least about 5,000 copies of genomic DNA sequences encoding Gene 1, Gene 2, and/or Gene 3 per nanogram (ng) of fecal DNA in the fecal sample. In embodiments, the method includes determining whether there are at least about 5,500 copies of genomic DNA sequences encoding Gene 1, Gene 2, and/or Gene 3 per nanogram (ng) of fecal DNA in the fecal sample. In embodiments, the method includes determining whether there are at least about 6,000 copies of genomic DNA sequences encoding Gene 1, Gene 2, and/or Gene 3 per nanogram (ng) of fecal DNA in the fecal sample. In embodiments, the method includes determining whether there are at least about 6,500 copies of genomic DNA sequences encoding Gene 1, Gene 2, and/or Gene 3 per nanogram (ng) of fecal DNA in the fecal sample. In embodiments, the method includes determining whether there are at least about 7,000 copies of genomic DNA sequences encoding Gene 1, Gene 2, and/or Gene 3 per nanogram (ng) of fecal DNA in the fecal sample. In embodiments, the method includes determining whether there are at least about 7,500 copies of genomic DNA sequences encoding Gene 1, Gene 2, and/or Gene 3 per nanogram (ng) of fecal DNA in the fecal sample. In embodiments, the method includes determining whether there are at least about 8,000 copies of genomic DNA sequences encoding Gene 1, Gene 2, and/or Gene 3 per nanogram (ng) of fecal DNA in the fecal sample. In embodiments, the method includes determining whether there are at least about 8,500 copies of genomic DNA sequences encoding Gene 1, Gene 2, and/or Gene 3 per nanogram (ng) of fecal DNA in the fecal sample. In embodiments, the method includes determining whether there are at least about 9,000 copies of genomic DNA sequences encoding Gene 1, Gene 2, and/or Gene 3 per nanogram (ng) of fecal DNA in the fecal sample. In embodiments, the method includes determining whether there are at least about 9,500 copies of genomic DNA sequences encoding Gene 1, Gene 2, and/or Gene 3 per nanogram (ng) of fecal DNA in the fecal sample. In embodiments, the method includes determining whether there are at least about 10,000 copies of genomic DNA sequences encoding Gene 1, Gene 2, and/or Gene 3 per nanogram (ng) of fecal DNA in the fecal sample. In embodiments, the method includes determining whether there are at least about 10,500 copies of genomic DNA sequences encoding Gene 1, Gene 2, and/or Gene 3 per nanogram (ng) of fecal DNA in the fecal sample. In embodiments, the method includes determining whether there are at least about 11,000 copies of genomic DNA sequences encoding Gene 1, Gene 2, and/or Gene 3 per nanogram (ng) of fecal DNA in the fecal sample. In embodiments, the method includes determining whether there are at least about 11,500 copies of genomic DNA sequences encoding Gene 1, Gene 2, and/or Gene 3 per nanogram (ng) of fecal DNA in the fecal sample. In embodiments, the method includes determining whether there are at least about 12,000 copies of genomic DNA sequences encoding Gene 1, Gene 2, and/or Gene 3 per nanogram (ng) of fecal DNA in the fecal sample. In embodiments, the method includes determining whether there are at least about 12,500 copies of genomic DNA sequences encoding Gene 1, Gene 2, and/or Gene 3 per nanogram (ng) of fecal DNA in the fecal sample. In embodiments, the method includes determining whether there are at least about 13,000 copies of genomic DNA sequences encoding Gene 1, Gene 2, and/or Gene 3 per nanogram (ng) of fecal DNA in the fecal sample. In embodiments, the method includes determining whether there are at least about 13,500 copies of genomic DNA sequences encoding Gene 1, Gene 2, and/or Gene 3 per nanogram (ng) of fecal DNA in the fecal sample. In embodiments, the method includes determining whether there are at least about 14,000 copies of genomic DNA sequences encoding Gene 1, Gene 2, and/or Gene 3 per nanogram (ng) of fecal DNA in the fecal sample. In embodiments, the method includes determining whether there are at least about 14,500 copies of genomic DNA sequences encoding Gene 1, Gene 2, and/or Gene 3 per nanogram (ng) of fecal DNA in the fecal sample. In embodiments, the method includes determining whether there are at least about 15,000 copies of genomic DNA sequences encoding Gene 1, Gene 2, and/or Gene 3 per nanogram (ng) of fecal DNA in the fecal sample. In embodiments, the method includes determining whether there are at least about 15,500 copies of genomic DNA sequences encoding Gene 1, Gene 2, and/or Gene 3 per nanogram (ng) of fecal DNA in the fecal sample. In embodiments, the method includes determining whether there are at least about 16,000 copies of genomic DNA sequences encoding Gene 1, Gene 2, and/or Gene 3 per nanogram (ng) of fecal DNA in the fecal sample. In embodiments, the method includes determining whether there are at least about 16,500 copies of genomic DNA sequences encoding Gene 1, Gene 2, and/or Gene 3 per nanogram (ng) of fecal DNA in the fecal sample. In embodiments, the method includes determining whether there are at least about 17,000 copies of genomic DNA sequences encoding Gene 1, Gene 2, and/or Gene 3 per nanogram (ng) of fecal DNA in the fecal sample. In embodiments, the method includes determining whether there are at least about 17,500 copies of genomic DNA sequences encoding Gene 1, Gene 2, and/or Gene 3 per nanogram (ng) of fecal DNA in the fecal sample. In embodiments, the method includes determining whether there are at least about 18,000 copies of genomic DNA sequences encoding Gene 1, Gene 2, and/or Gene 3 per nanogram (ng) of fecal DNA in the fecal sample. In embodiments, the method includes determining whether there are at least about 18,500 copies of genomic DNA sequences encoding Gene 1, Gene 2, and/or Gene 3 per nanogram (ng) of fecal DNA in the fecal sample. In embodiments, the method includes determining whether there are at least about 19,000 copies of genomic DNA sequences encoding Gene 1, Gene 2, and/or Gene 3 per nanogram (ng) of fecal DNA in the fecal sample. In embodiments, the method includes determining whether there are at least about 19,500 copies of genomic DNA sequences encoding Gene 1, Gene 2, and/or Gene 3 per nanogram (ng) of fecal DNA in the fecal sample. In embodiments, the method includes determining whether there are at least about 20,000 copies of genomic DNA sequences encoding Gene 1, Gene 2, and/or Gene 3 per nanogram (ng) of fecal DNA in the fecal sample.

In embodiments, the method includes determining whether there are at least 1,250 copies of genomic DNA sequences encoding Gene 1, Gene 2, and/or Gene 3 per nanogram (ng) of fecal DNA in the fecal sample. In embodiments, the method includes determining whether there are at least 1,300 copies of genomic DNA sequences encoding Gene 1, Gene 2, and/or Gene 3 per nanogram (ng) of fecal DNA in the fecal sample. In embodiments, the method includes determining whether there are at least 1,400 copies of genomic DNA sequences encoding Gene 1, Gene 2, and/or Gene 3 per nanogram (ng) of fecal DNA in the fecal sample. In embodiments, the method includes determining whether there are at least 1,500 copies of genomic DNA sequences encoding Gene 1, Gene 2, and/or Gene 3 per nanogram (ng) of fecal DNA in the fecal sample. In embodiments, the method includes determining whether there are at least 1,600 copies of genomic DNA sequences encoding Gene 1, Gene 2, and/or Gene 3 per nanogram (ng) of fecal DNA in the fecal sample. In embodiments, the method includes determining whether there are at least 1,700 copies of genomic DNA sequences encoding Gene 1, Gene 2, and/or Gene 3 per nanogram (ng) of fecal DNA in the fecal sample. In embodiments, the method includes determining whether there are at least 1,800 copies of genomic DNA sequences encoding Gene 1, Gene 2, and/or Gene 3 per nanogram (ng) of fecal DNA in the fecal sample. In embodiments, the method includes determining whether there are at least 1,900 copies of genomic DNA sequences encoding Gene 1, Gene 2, and/or Gene 3 per nanogram (ng) of fecal DNA in the fecal sample. In embodiments, the method includes determining whether there are at least 2,000 copies of genomic DNA sequences encoding Gene 1, Gene 2, and/or Gene 3 per nanogram (ng) of fecal DNA in the fecal sample. In embodiments, the method includes determining whether there are at least 2,500 copies of genomic DNA sequences encoding Gene 1, Gene 2, and/or Gene 3 per nanogram (ng) of fecal DNA in the fecal sample. In embodiments, the method includes determining whether there are at least 3,000 copies of genomic DNA sequences encoding Gene 1, Gene 2, and/or Gene 3 per nanogram (ng) of fecal DNA in the fecal sample. In embodiments, the method includes determining whether there are at least 3,500 copies of genomic DNA sequences encoding Gene 1, Gene 2, and/or Gene 3 per nanogram (ng) of fecal DNA in the fecal sample. In embodiments, the method includes determining whether there are at least 4,000 copies of genomic DNA sequences encoding Gene 1, Gene 2, and/or Gene 3 per nanogram (ng) of fecal DNA in the fecal sample. In embodiments, the method includes determining whether there are at least 4,500 copies of genomic DNA sequences encoding Gene 1, Gene 2, and/or Gene 3 per nanogram (ng) of fecal DNA in the fecal sample. In embodiments, the method includes determining whether there are at least 5,000 copies of genomic DNA sequences encoding Gene 1, Gene 2, and/or Gene 3 per nanogram (ng) of fecal DNA in the fecal sample. In embodiments, the method includes determining whether there are at least 5,500 copies of genomic DNA sequences encoding Gene 1, Gene 2, and/or Gene 3 per nanogram (ng) of fecal DNA in the fecal sample. In embodiments, the method includes determining whether there are at least 6,000 copies of genomic DNA sequences encoding Gene 1, Gene 2, and/or Gene 3 per nanogram (ng) of fecal DNA in the fecal sample. In embodiments, the method includes determining whether there are at least 6,500 copies of genomic DNA sequences encoding Gene 1, Gene 2, and/or Gene 3 per nanogram (ng) of fecal DNA in the fecal sample. In embodiments, the method includes determining whether there are at least 7,000 copies of genomic DNA sequences encoding Gene 1, Gene 2, and/or Gene 3 per nanogram (ng) of fecal DNA in the fecal sample. In embodiments, the method includes determining whether there are at least 7,500 copies of genomic DNA sequences encoding Gene 1, Gene 2, and/or Gene 3 per nanogram (ng) of fecal DNA in the fecal sample. In embodiments, the method includes determining whether there are at least 8,000 copies of genomic DNA sequences encoding Gene 1, Gene 2, and/or Gene 3 per nanogram (ng) of fecal DNA in the fecal sample. In embodiments, the method includes determining whether there are at least 8,500 copies of genomic DNA sequences encoding Gene 1, Gene 2, and/or Gene 3 per nanogram (ng) of fecal DNA in the fecal sample. In embodiments, the method includes determining whether there are at least 9,000 copies of genomic DNA sequences encoding Gene 1, Gene 2, and/or Gene 3 per nanogram (ng) of fecal DNA in the fecal sample. In embodiments, the method includes determining whether there are at least 9,500 copies of genomic DNA sequences encoding Gene 1, Gene 2, and/or Gene 3 per nanogram (ng) of fecal DNA in the fecal sample. In embodiments, the method includes determining whether there are at least 10,000 copies of genomic DNA sequences encoding Gene 1, Gene 2, and/or Gene 3 per nanogram (ng) of fecal DNA in the fecal sample. In embodiments, the method includes determining whether there are at least 10,500 copies of genomic DNA sequences encoding Gene 1, Gene 2, and/or Gene 3 per nanogram (ng) of fecal DNA in the fecal sample. In embodiments, the method includes determining whether there are at least 11,000 copies of genomic DNA sequences encoding Gene 1, Gene 2, and/or Gene 3 per nanogram (ng) of fecal DNA in the fecal sample. In embodiments, the method includes determining whether there are at least 11,500 copies of genomic DNA sequences encoding Gene 1, Gene 2, and/or Gene 3 per nanogram (ng) of fecal DNA in the fecal sample. In embodiments, the method includes determining whether there are at least 12,000 copies of genomic DNA sequences encoding Gene 1, Gene 2, and/or Gene 3 per nanogram (ng) of fecal DNA in the fecal sample. In embodiments, the method includes determining whether there are at least 12,500 copies of genomic DNA sequences encoding Gene 1, Gene 2, and/or Gene 3 per nanogram (ng) of fecal DNA in the fecal sample. In embodiments, the method includes determining whether there are at least 13,000 copies of genomic DNA sequences encoding Gene 1, Gene 2, and/or Gene 3 per nanogram (ng) of fecal DNA in the fecal sample. In embodiments, the method includes determining whether there are at least 13,500 copies of genomic DNA sequences encoding Gene 1, Gene 2, and/or Gene 3 per nanogram (ng) of fecal DNA in the fecal sample. In embodiments, the method includes determining whether there are at least 14,000 copies of genomic DNA sequences encoding Gene 1, Gene 2, and/or Gene 3 per nanogram (ng) of fecal DNA in the fecal sample. In embodiments, the method includes determining whether there are at least 14,500 copies of genomic DNA sequences encoding Gene 1, Gene 2, and/or Gene 3 per nanogram (ng) of fecal DNA in the fecal sample. In embodiments, the method includes determining whether there are at least 15,000 copies of genomic DNA sequences encoding Gene 1, Gene 2, and/or Gene 3 per nanogram (ng) of fecal DNA in the fecal sample. In embodiments, the method includes determining whether there are at least 15,500 copies of genomic DNA sequences encoding Gene 1, Gene 2, and/or Gene 3 per nanogram (ng) of fecal DNA in the fecal sample. In embodiments, the method includes determining whether there are at least 16,000 copies of genomic DNA sequences encoding Gene 1, Gene 2, and/or Gene 3 per nanogram (ng) of fecal DNA in the fecal sample. In embodiments, the method includes determining whether there are at least 16,500 copies of genomic DNA sequences encoding Gene 1, Gene 2, and/or Gene 3 per nanogram (ng) of fecal DNA in the fecal sample. In embodiments, the method includes determining whether there are at least 17,000 copies of genomic DNA sequences encoding Gene 1, Gene 2, and/or Gene 3 per nanogram (ng) of fecal DNA in the fecal sample. In embodiments, the method includes determining whether there are at least 17,500 copies of genomic DNA sequences encoding Gene 1, Gene 2, and/or Gene 3 per nanogram (ng) of fecal DNA in the fecal sample. In embodiments, the method includes determining whether there are at least 18,000 copies of genomic DNA sequences encoding Gene 1, Gene 2, and/or Gene 3 per nanogram (ng) of fecal DNA in the fecal sample. In embodiments, the method includes determining whether there are at least 18,500 copies of genomic DNA sequences encoding Gene 1, Gene 2, and/or Gene 3 per nanogram (ng) of fecal DNA in the fecal sample. In embodiments, the method includes determining whether there are at least 19,000 copies of genomic DNA sequences encoding Gene 1, Gene 2, and/or Gene 3 per nanogram (ng) of fecal DNA in the fecal sample. In embodiments, the method includes determining whether there are at least 19,500 copies of genomic DNA sequences encoding Gene 1, Gene 2, and/or Gene 3 per nanogram (ng) of fecal DNA in the fecal sample. In embodiments, the method includes determining whether there are at least 20,000 copies of genomic DNA sequences encoding Gene 1, Gene 2, and/or Gene 3 per nanogram (ng) of fecal DNA in the fecal sample.

In embodiments, the method includes determining whether there are from about 1,250 to about 20,000 copies of genomic DNA sequences encoding Gene 1, Gene 2, and/or Gene 3 per nanogram (ng) of fecal DNA in the fecal sample. In embodiments, the method includes determining whether there are from about 1,500 to about 20,000 copies of genomic DNA sequences encoding Gene 1, Gene 2, and/or Gene 3 per nanogram (ng) of fecal DNA in the fecal sample. In embodiments, the method includes determining whether there are from about 2,000 to about 20,000 copies of genomic DNA sequences encoding Gene 1, Gene 2, and/or Gene 3 per nanogram (ng) of fecal DNA in the fecal sample. In embodiments, the method includes determining whether there are from about 2,500 to about 20,000 copies of genomic DNA sequences encoding Gene 1, Gene 2, and/or Gene 3 per nanogram (ng) of fecal DNA in the fecal sample. In embodiments, the method includes determining whether there are from about 3,000 to about 20,000 copies of genomic DNA sequences encoding Gene 1, Gene 2, and/or Gene 3 per nanogram (ng) of fecal DNA in the fecal sample. In embodiments, the method includes determining whether there are from about 3,500 to about 20,000 copies of genomic DNA sequences encoding Gene 1, Gene 2, and/or Gene 3 per nanogram (ng) of fecal DNA in the fecal sample. In embodiments, the method includes determining whether there are from about 4,000 to about 20,000 copies of genomic DNA sequences encoding Gene 1, Gene 2, and/or Gene 3 per nanogram (ng) of fecal DNA in the fecal sample. In embodiments, the method includes determining whether there are from about 4,500 to about 20,000 copies of genomic DNA sequences encoding Gene 1, Gene 2, and/or Gene 3 per nanogram (ng) of fecal DNA in the fecal sample. In embodiments, the method includes determining whether there are from about 5,000 to about 20,000 copies of genomic DNA sequences encoding Gene 1, Gene 2, and/or Gene 3 per nanogram (ng) of fecal DNA in the fecal sample. In embodiments, the method includes determining whether there are from about 5,500 to about 20,000 copies of genomic DNA sequences encoding Gene 1, Gene 2, and/or Gene 3 per nanogram (ng) of fecal DNA in the fecal sample. In embodiments, the method includes determining whether there are from about 6,000 to about 20,000 copies of genomic DNA sequences encoding Gene 1, Gene 2, and/or Gene 3 per nanogram (ng) of fecal DNA in the fecal sample. In embodiments, the method includes determining whether there are from about 6,500 to about 20,000 copies of genomic DNA sequences encoding Gene 1, Gene 2, and/or Gene 3 per nanogram (ng) of fecal DNA in the fecal sample. In embodiments, the method includes determining whether there are from about 7,000 to about 20,000 copies of genomic DNA sequences encoding Gene 1, Gene 2, and/or Gene 3 per nanogram (ng) of fecal DNA in the fecal sample. In embodiments, the method includes determining whether there are from about 7,500 to about 20,000 copies of genomic DNA sequences encoding Gene 1, Gene 2, and/or Gene 3 per nanogram (ng) of fecal DNA in the fecal sample. In embodiments, the method includes determining whether there are from about 8,000 to about 20,000 copies of genomic DNA sequences encoding Gene 1, Gene 2, and/or Gene 3 per nanogram (ng) of fecal DNA in the fecal sample. In embodiments, the method includes determining whether there are from about 8,500 to about 20,000 copies of genomic DNA sequences encoding Gene 1, Gene 2, and/or Gene 3 per nanogram (ng) of fecal DNA in the fecal sample. In embodiments, the method includes determining whether there are from about 9,000 to about 20,000 copies of genomic DNA sequences encoding Gene 1, Gene 2, and/or Gene 3 per nanogram (ng) of fecal DNA in the fecal sample. In embodiments, the method includes determining whether there are from about 9,500 to about 20,000 copies of genomic DNA sequences encoding Gene 1, Gene 2, and/or Gene 3 per nanogram (ng) of fecal DNA in the fecal sample. In embodiments, the method includes determining whether there are from about 10,000 to about 20,000 copies of genomic DNA sequences encoding Gene 1, Gene 2, and/or Gene 3 per nanogram (ng) of fecal DNA in the fecal sample. In embodiments, the method includes determining whether there are from about 10,500 to about 20,000 copies of genomic DNA sequences encoding Gene 1, Gene 2, and/or Gene 3 per nanogram (ng) of fecal DNA in the fecal sample. In embodiments, the method includes determining whether there are from about 11,000 to about 20,000 copies of genomic DNA sequences encoding Gene 1, Gene 2, and/or Gene 3 per nanogram (ng) of fecal DNA in the fecal sample. In embodiments, the method includes determining whether there are from about 11,500 to about 20,000 copies of genomic DNA sequences encoding Gene 1, Gene 2, and/or Gene 3 per nanogram (ng) of fecal DNA in the fecal sample. In embodiments, the method includes determining whether there are from about 12,000 to about 20,000 copies of genomic DNA sequences encoding Gene 1, Gene 2, and/or Gene 3 per nanogram (ng) of fecal DNA in the fecal sample. In embodiments, the method includes determining whether there are from about 12,500 to about 20,000 copies of genomic DNA sequences encoding Gene 1, Gene 2, and/or Gene 3 per nanogram (ng) of fecal DNA in the fecal sample. In embodiments, the method includes determining whether there are from about 13,000 to about 20,000 copies of genomic DNA sequences encoding Gene 1, Gene 2, and/or Gene 3 per nanogram (ng) of fecal DNA in the fecal sample. In embodiments, the method includes determining whether there are from about 13,500 to about 20,000 copies of genomic DNA sequences encoding Gene 1, Gene 2, and/or Gene 3 per nanogram (ng) of fecal DNA in the fecal sample. In embodiments, the method includes determining whether there are from about 14,000 to about 20,000 copies of genomic DNA sequences encoding Gene 1, Gene 2, and/or Gene 3 per nanogram (ng) of fecal DNA in the fecal sample. In embodiments, the method includes determining whether there are from about 14,500 to about 20,000 copies of genomic DNA sequences encoding Gene 1, Gene 2, and/or Gene 3 per nanogram (ng) of fecal DNA in the fecal sample. In embodiments, the method includes determining whether there are from about 15,000 to about 20,000 copies of genomic DNA sequences encoding Gene 1, Gene 2, and/or Gene 3 per nanogram (ng) of fecal DNA in the fecal sample. In embodiments, the method includes determining whether there are from about 15,500 to about 20,000 copies of genomic DNA sequences encoding Gene 1, Gene 2, and/or Gene 3 per nanogram (ng) of fecal DNA in the fecal sample. In embodiments, the method includes determining whether there are from about 16,000 to about 20,000 copies of genomic DNA sequences encoding Gene 1, Gene 2, and/or Gene 3 per nanogram (ng) of fecal DNA in the fecal sample. In embodiments, the method includes determining whether there are from about 16,500 to about 20,000 copies of genomic DNA sequences encoding Gene 1, Gene 2, and/or Gene 3 per nanogram (ng) of fecal DNA in the fecal sample. In embodiments, the method includes determining whether there are from about 17,000 to about 20,000 copies of genomic DNA sequences encoding Gene 1, Gene 2, and/or Gene 3 per nanogram (ng) of fecal DNA in the fecal sample. In embodiments, the method includes determining whether there are from about 17,500 to about 20,000 copies of genomic DNA sequences encoding Gene 1, Gene 2, and/or Gene 3 per nanogram (ng) of fecal DNA in the fecal sample. In embodiments, the method includes determining whether there are from about 18,000 to about 20,000 copies of genomic DNA sequences encoding Gene 1, Gene 2, and/or Gene 3 per nanogram (ng) of fecal DNA in the fecal sample. In embodiments, the method includes determining whether there are from about 18,500 to about 20,000 copies of genomic DNA sequences encoding Gene 1, Gene 2, and/or Gene 3 per nanogram (ng) of fecal DNA in the fecal sample. In embodiments, the method includes determining whether there are from about 19,000 to about 20,000 copies of genomic DNA sequences encoding Gene 1, Gene 2, and/or Gene 3 per nanogram (ng) of fecal DNA in the fecal sample. In embodiments, the method includes determining whether there are from about 19,500 to about 20,000 copies of genomic DNA sequences encoding Gene 1, Gene 2, and/or Gene 3 per nanogram (ng) of fecal DNA in the fecal sample.

In embodiments, the method includes determining whether there are from 1,250 to 20,000 copies of genomic DNA sequences encoding Gene 1, Gene 2, and/or Gene 3 per nanogram (ng) of fecal DNA in the fecal sample. In embodiments, the method includes determining whether there are from 1,500 to 20,000 copies of genomic DNA sequences encoding Gene 1, Gene 2, and/or Gene 3 per nanogram (ng) of fecal DNA in the fecal sample. In embodiments, the method includes determining whether there are from 2,000 to 20,000 copies of genomic DNA sequences encoding Gene 1, Gene 2, and/or Gene 3 per nanogram (ng) of fecal DNA in the fecal sample. In embodiments, the method includes determining whether there are from 2,500 to 20,000 copies of genomic DNA sequences encoding Gene 1, Gene 2, and/or Gene 3 per nanogram (ng) of fecal DNA in the fecal sample. In embodiments, the method includes determining whether there are from 3,000 to 20,000 copies of genomic DNA sequences encoding Gene 1, Gene 2, and/or Gene 3 per nanogram (ng) of fecal DNA in the fecal sample. In embodiments, the method includes determining whether there are from 3,500 to 20,000 copies of genomic DNA sequences encoding Gene 1, Gene 2, and/or Gene 3 per nanogram (ng) of fecal DNA in the fecal sample. In embodiments, the method includes determining whether there are from 4,000 to 20,000 copies of genomic DNA sequences encoding Gene 1, Gene 2, and/or Gene 3 per nanogram (ng) of fecal DNA in the fecal sample. In embodiments, the method includes determining whether there are from 4,500 to 20,000 copies of genomic DNA sequences encoding Gene 1, Gene 2, and/or Gene 3 per nanogram (ng) of fecal DNA in the fecal sample. In embodiments, the method includes determining whether there are from 5,000 to 20,000 copies of genomic DNA sequences encoding Gene 1, Gene 2, and/or Gene 3 per nanogram (ng) of fecal DNA in the fecal sample. In embodiments, the method includes determining whether there are from 5,500 to 20,000 copies of genomic DNA sequences encoding Gene 1, Gene 2, and/or Gene 3 per nanogram (ng) of fecal DNA in the fecal sample. In embodiments, the method includes determining whether there are from 6,000 to 20,000 copies of genomic DNA sequences encoding Gene 1, Gene 2, and/or Gene 3 per nanogram (ng) of fecal DNA in the fecal sample. In embodiments, the method includes determining whether there are from 6,500 to 20,000 copies of genomic DNA sequences encoding Gene 1, Gene 2, and/or Gene 3 per nanogram (ng) of fecal DNA in the fecal sample. In embodiments, the method includes determining whether there are from 7,000 to 20,000 copies of genomic DNA sequences encoding Gene 1, Gene 2, and/or Gene 3 per nanogram (ng) of fecal DNA in the fecal sample. In embodiments, the method includes determining whether there are from 7,500 to 20,000 copies of genomic DNA sequences encoding Gene 1, Gene 2, and/or Gene 3 per nanogram (ng) of fecal DNA in the fecal sample. In embodiments, the method includes determining whether there are from 8,000 to 20,000 copies of genomic DNA sequences encoding Gene 1, Gene 2, and/or Gene 3 per nanogram (ng) of fecal DNA in the fecal sample. In embodiments, the method includes determining whether there are from 8,500 to 20,000 copies of genomic DNA sequences encoding Gene 1, Gene 2, and/or Gene 3 per nanogram (ng) of fecal DNA in the fecal sample. In embodiments, the method includes determining whether there are from 9,000 to 20,000 copies of genomic DNA sequences encoding Gene 1, Gene 2, and/or Gene 3 per nanogram (ng) of fecal DNA in the fecal sample. In embodiments, the method includes determining whether there are from 9,500 to 20,000 copies of genomic DNA sequences encoding Gene 1, Gene 2, and/or Gene 3 per nanogram (ng) of fecal DNA in the fecal sample. In embodiments, the method includes determining whether there are from 10,000 to 20,000 copies of genomic DNA sequences encoding Gene 1, Gene 2, and/or Gene 3 per nanogram (ng) of fecal DNA in the fecal sample. In embodiments, the method includes determining whether there are from 10,500 to 20,000 copies of genomic DNA sequences encoding Gene 1, Gene 2, and/or Gene 3 per nanogram (ng) of fecal DNA in the fecal sample. In embodiments, the method includes determining whether there are from 11,000 to 20,000 copies of genomic DNA sequences encoding Gene 1, Gene 2, and/or Gene 3 per nanogram (ng) of fecal DNA in the fecal sample. In embodiments, the method includes determining whether there are from 11,500 to 20,000 copies of genomic DNA sequences encoding Gene 1, Gene 2, and/or Gene 3 per nanogram (ng) of fecal DNA in the fecal sample. In embodiments, the method includes determining whether there are from 12,000 to 20,000 copies of genomic DNA sequences encoding Gene 1, Gene 2, and/or Gene 3 per nanogram (ng) of fecal DNA in the fecal sample. In embodiments, the method includes determining whether there are from 12,500 to 20,000 copies of genomic DNA sequences encoding Gene 1, Gene 2, and/or Gene 3 per nanogram (ng) of fecal DNA in the fecal sample. In embodiments, the method includes determining whether there are from 13,000 to 20,000 copies of genomic DNA sequences encoding Gene 1, Gene 2, and/or Gene 3 per nanogram (ng) of fecal DNA in the fecal sample. In embodiments, the method includes determining whether there are from 13,500 to 20,000 copies of genomic DNA sequences encoding Gene 1, Gene 2, and/or Gene 3 per nanogram (ng) of fecal DNA in the fecal sample. In embodiments, the method includes determining whether there are from 14,000 to 20,000 copies of genomic DNA sequences encoding Gene 1, Gene 2, and/or Gene 3 per nanogram (ng) of fecal DNA in the fecal sample. In embodiments, the method includes determining whether there are from 14,500 to 20,000 copies of genomic DNA sequences encoding Gene 1, Gene 2, and/or Gene 3 per nanogram (ng) of fecal DNA in the fecal sample. In embodiments, the method includes determining whether there are from 15,000 to 20,000 copies of genomic DNA sequences encoding Gene 1, Gene 2, and/or Gene 3 per nanogram (ng) of fecal DNA in the fecal sample. In embodiments, the method includes determining whether there are from 15,500 to 20,000 copies of genomic DNA sequences encoding Gene 1, Gene 2, and/or Gene 3 per nanogram (ng) of fecal DNA in the fecal sample. In embodiments, the method includes determining whether there are from 16,000 to 20,000 copies of genomic DNA sequences encoding Gene 1, Gene 2, and/or Gene 3 per nanogram (ng) of fecal DNA in the fecal sample. In embodiments, the method includes determining whether there are from 16,500 to 20,000 copies of genomic DNA sequences encoding Gene 1, Gene 2, and/or Gene 3 per nanogram (ng) of fecal DNA in the fecal sample. In embodiments, the method includes determining whether there are from 17,000 to 20,000 copies of genomic DNA sequences encoding Gene 1, Gene 2, and/or Gene 3 per nanogram (ng) of fecal DNA in the fecal sample. In embodiments, the method includes determining whether there are from 17,500 to 20,000 copies of genomic DNA sequences encoding Gene 1, Gene 2, and/or Gene 3 per nanogram (ng) of fecal DNA in the fecal sample. In embodiments, the method includes determining whether there are from 18,000 to 20,000 copies of genomic DNA sequences encoding Gene 1, Gene 2, and/or Gene 3 per nanogram (ng) of fecal DNA in the fecal sample. In embodiments, the method includes determining whether there are from 18,500 to 20,000 copies of genomic DNA sequences encoding Gene 1, Gene 2, and/or Gene 3 per nanogram (ng) of fecal DNA in the fecal sample. In embodiments, the method includes determining whether there are from 19,000 to 20,000 copies of genomic DNA sequences encoding Gene 1, Gene 2, and/or Gene 3 per nanogram (ng) of fecal DNA in the fecal sample. In embodiments, the method includes determining whether there are from 19,500 to 20,000 copies of genomic DNA sequences encoding Gene 1, Gene 2, and/or Gene 3 per nanogram (ng) of fecal DNA in the fecal sample.

In embodiments, the method includes determining whether there are from about 1,250 to about 19,500 copies of genomic DNA sequences encoding Gene 1, Gene 2, and/or Gene 3 per nanogram (ng) of fecal DNA in the fecal sample. In embodiments, the method includes determining whether there are from about 1,250 to about 19,000 copies of genomic DNA sequences encoding Gene 1, Gene 2, and/or Gene 3 per nanogram (ng) of fecal DNA in the fecal sample. In embodiments, the method includes determining whether there are from about 1,250 to about 18,500 copies of genomic DNA sequences encoding Gene 1, Gene 2, and/or Gene 3 per nanogram (ng) of fecal DNA in the fecal sample. In embodiments, the method includes determining whether there are from about 1,250 to about 18,000 copies of genomic DNA sequences encoding Gene 1, Gene 2, and/or Gene 3 per nanogram (ng) of fecal DNA in the fecal sample. In embodiments, the method includes determining whether there are from about 1,250 to about 17,500 copies of genomic DNA sequences encoding Gene 1, Gene 2, and/or Gene 3 per nanogram (ng) of fecal DNA in the fecal sample. In embodiments, the method includes determining whether there are from about 1,250 to about 17,000 copies of genomic DNA sequences encoding Gene 1, Gene 2, and/or Gene 3 per nanogram (ng) of fecal DNA in the fecal sample. In embodiments, the method includes determining whether there are from about 1,250 to about 16,500 copies of genomic DNA sequences encoding Gene 1, Gene 2, and/or Gene 3 per nanogram (ng) of fecal DNA in the fecal sample. In embodiments, the method includes determining whether there are from about 1,250 to about 16,000 copies of genomic DNA sequences encoding Gene 1, Gene 2, and/or Gene 3 per nanogram (ng) of fecal DNA in the fecal sample. In embodiments, the method includes determining whether there are from about 1,250 to about 15,500 copies of genomic DNA sequences encoding Gene 1, Gene 2, and/or Gene 3 per nanogram (ng) of fecal DNA in the fecal sample. In embodiments, the method includes determining whether there are from about 1,250 to about 15,000 copies of genomic DNA sequences encoding Gene 1, Gene 2, and/or Gene 3 per nanogram (ng) of fecal DNA in the fecal sample. In embodiments, the method includes determining whether there are from about 1,250 to about 14,500 copies of genomic DNA sequences encoding Gene 1, Gene 2, and/or Gene 3 per nanogram (ng) of fecal DNA in the fecal sample. In embodiments, the method includes determining whether there are from about 1,250 to about 14,000 copies of genomic DNA sequences encoding Gene 1, Gene 2, and/or Gene 3 per nanogram (ng) of fecal DNA in the fecal sample. In embodiments, the method includes determining whether there are from about 1,250 to about 13,500 copies of genomic DNA sequences encoding Gene 1, Gene 2, and/or Gene 3 per nanogram (ng) of fecal DNA in the fecal sample. In embodiments, the method includes determining whether there are from about 1,250 to about 13,000 copies of genomic DNA sequences encoding Gene 1, Gene 2, and/or Gene 3 per nanogram (ng) of fecal DNA in the fecal sample. In embodiments, the method includes determining whether there are from about 1,250 to about 12,500 copies of genomic DNA sequences encoding Gene 1, Gene 2, and/or Gene 3 per nanogram (ng) of fecal DNA in the fecal sample. In embodiments, the method includes determining whether there are from about 1,250 to about 12,000 copies of genomic DNA sequences encoding Gene 1, Gene 2, and/or Gene 3 per nanogram (ng) of fecal DNA in the fecal sample. In embodiments, the method includes determining whether there are from about 1,250 to about 11,500 copies of genomic DNA sequences encoding Gene 1, Gene 2, and/or Gene 3 per nanogram (ng) of fecal DNA in the fecal sample. In embodiments, the method includes determining whether there are from about 1,250 to about 11,000 copies of genomic DNA sequences encoding Gene 1, Gene 2, and/or Gene 3 per nanogram (ng) of fecal DNA in the fecal sample. In embodiments, the method includes determining whether there are from about 1,250 to about 10,500 copies of genomic DNA sequences encoding Gene 1, Gene 2, and/or Gene 3 per nanogram (ng) of fecal DNA in the fecal sample. In embodiments, the method includes determining whether there are from about 1,250 to about 10,000 copies of genomic DNA sequences encoding Gene 1, Gene 2, and/or Gene 3 per nanogram (ng) of fecal DNA in the fecal sample. In embodiments, the method includes determining whether there are from about 1,250 to about 9,500 copies of genomic DNA sequences encoding Gene 1, Gene 2, and/or Gene 3 per nanogram (ng) of fecal DNA in the fecal sample. In embodiments, the method includes determining whether there are from about 1,250 to about 9,000 copies of genomic DNA sequences encoding Gene 1, Gene 2, and/or Gene 3 per nanogram (ng) of fecal DNA in the fecal sample. In embodiments, the method includes determining whether there are from about 1,250 to about 8,500 copies of genomic DNA sequences encoding Gene 1, Gene 2, and/or Gene 3 per nanogram (ng) of fecal DNA in the fecal sample. In embodiments, the method includes determining whether there are from about 1,250 to about 8,000 copies of genomic DNA sequences encoding Gene 1, Gene 2, and/or Gene 3 per nanogram (ng) of fecal DNA in the fecal sample. In embodiments, the method includes determining whether there are from about 1,250 to about 7,500 copies of genomic DNA sequences encoding Gene 1, Gene 2, and/or Gene 3 per nanogram (ng) of fecal DNA in the fecal sample. In embodiments, the method includes determining whether there are from about 1,250 to about 7,000 copies of genomic DNA sequences encoding Gene 1, Gene 2, and/or Gene 3 per nanogram (ng) of fecal DNA in the fecal sample. In embodiments, the method includes determining whether there are from about 1,250 to about 6,500 copies of genomic DNA sequences encoding Gene 1, Gene 2, and/or Gene 3 per nanogram (ng) of fecal DNA in the fecal sample. In embodiments, the method includes determining whether there are from about 1,250 to about 6,000 copies of genomic DNA sequences encoding Gene 1, Gene 2, and/or Gene 3 per nanogram (ng) of fecal DNA in the fecal sample. In embodiments, the method includes determining whether there are from about 1,250 to about 5,500 copies of genomic DNA sequences encoding Gene 1, Gene 2, and/or Gene 3 per nanogram (ng) of fecal DNA in the fecal sample. In embodiments, the method includes determining whether there are from about 1,250 to about 5,000 copies of genomic DNA sequences encoding Gene 1, Gene 2, and/or Gene 3 per nanogram (ng) of fecal DNA in the fecal sample. In embodiments, the method includes determining whether there are from about 1,250 to about 4,500 copies of genomic DNA sequences encoding Gene 1, Gene 2, and/or Gene 3 per nanogram (ng) of fecal DNA in the fecal sample. In embodiments, the method includes determining whether there are from about 1,250 to about 4,000 copies of genomic DNA sequences encoding Gene 1, Gene 2, and/or Gene 3 per nanogram (ng) of fecal DNA in the fecal sample. In embodiments, the method includes determining whether there are from about 1,250 to about 3,500 copies of genomic DNA sequences encoding Gene 1, Gene 2, and/or Gene 3 per nanogram (ng) of fecal DNA in the fecal sample. In embodiments, the method includes determining whether there are from about 1,250 to about 3,000 copies of genomic DNA sequences encoding Gene 1, Gene 2, and/or Gene 3 per nanogram (ng) of fecal DNA in the fecal sample. In embodiments, the method includes determining whether there are from about 1,250 to about 2,500 copies of genomic DNA sequences encoding Gene 1, Gene 2, and/or Gene 3 per nanogram (ng) of fecal DNA in the fecal sample. In embodiments, the method includes determining whether there are from about 1,250 to about 2,000 copies of genomic DNA sequences encoding Gene 1, Gene 2, and/or Gene 3 per nanogram (ng) of fecal DNA in the fecal sample. In embodiments, the method includes determining whether there are from about 1,250 to about 1,500 copies of genomic DNA sequences encoding Gene 1, Gene 2, and/or Gene 3 per nanogram (ng) of fecal DNA in the fecal sample.

In embodiments, the method includes determining whether there are from 1,250 to 19,500 copies of genomic DNA sequences encoding Gene 1, Gene 2, and/or Gene 3 per nanogram (ng) of fecal DNA in the fecal sample. In embodiments, the method includes determining whether there are from 1,250 to 19,000 copies of genomic DNA sequences encoding Gene 1, Gene 2, and/or Gene 3 per nanogram (ng) of fecal DNA in the fecal sample. In embodiments, the method includes determining whether there are from about 1,250 to 18,500 copies of genomic DNA sequences encoding Gene 1, Gene 2, and/or Gene 3 per nanogram (ng) of fecal DNA in the fecal sample. In embodiments, the method includes determining whether there are from 1,250 to 18,000 copies of genomic DNA sequences encoding Gene 1, Gene 2, and/or Gene 3 per nanogram (ng) of fecal DNA in the fecal sample. In embodiments, the method includes determining whether there are from 1,250 to 17,500 copies of genomic DNA sequences encoding Gene 1, Gene 2, and/or Gene 3 per nanogram (ng) of fecal DNA in the fecal sample. In embodiments, the method includes determining whether there are from 1,250 to 17,000 copies of genomic DNA sequences encoding Gene 1, Gene 2, and/or Gene 3 per nanogram (ng) of fecal DNA in the fecal sample. In embodiments, the method includes determining whether there are from 1,250 to 16,500 copies of genomic DNA sequences encoding Gene 1, Gene 2, and/or Gene 3 per nanogram (ng) of fecal DNA in the fecal sample. In embodiments, the method includes determining whether there are from 1,250 to 16,000 copies of genomic DNA sequences encoding Gene 1, Gene 2, and/or Gene 3 per nanogram (ng) of fecal DNA in the fecal sample. In embodiments, the method includes determining whether there are from 1,250 to 15,500 copies of genomic DNA sequences encoding Gene 1, Gene 2, and/or Gene 3 per nanogram (ng) of fecal DNA in the fecal sample. In embodiments, the method includes determining whether there are from 1,250 to 15,000 copies of genomic DNA sequences encoding Gene 1, Gene 2, and/or Gene 3 per nanogram (ng) of fecal DNA in the fecal sample. In embodiments, the method includes determining whether there are from 1,250 to 14,500 copies of genomic DNA sequences encoding Gene 1, Gene 2, and/or Gene 3 per nanogram (ng) of fecal DNA in the fecal sample. In embodiments, the method includes determining whether there are from 1,250 to 14,000 copies of genomic DNA sequences encoding Gene 1, Gene 2, and/or Gene 3 per nanogram (ng) of fecal DNA in the fecal sample. In embodiments, the method includes determining whether there are from 1,250 to 13,500 copies of genomic DNA sequences encoding Gene 1, Gene 2, and/or Gene 3 per nanogram (ng) of fecal DNA in the fecal sample. In embodiments, the method includes determining whether there are from 1,250 to 13,000 copies of genomic DNA sequences encoding Gene 1, Gene 2, and/or Gene 3 per nanogram (ng) of fecal DNA in the fecal sample. In embodiments, the method includes determining whether there are from 1,250 to 12,500 copies of genomic DNA sequences encoding Gene 1, Gene 2, and/or Gene 3 per nanogram (ng) of fecal DNA in the fecal sample. In embodiments, the method includes determining whether there are from 1,250 to 12,000 copies of genomic DNA sequences encoding Gene 1, Gene 2, and/or Gene 3 per nanogram (ng) of fecal DNA in the fecal sample. In embodiments, the method includes determining whether there are from 1,250 to 11,500 copies of genomic DNA sequences encoding Gene 1, Gene 2, and/or Gene 3 per nanogram (ng) of fecal DNA in the fecal sample. In embodiments, the method includes determining whether there are from 1,250 to 11,000 copies of genomic DNA sequences encoding Gene 1, Gene 2, and/or Gene 3 per nanogram (ng) of fecal DNA in the fecal sample. In embodiments, the method includes determining whether there are from 1,250 to 10,500 copies of genomic DNA sequences encoding Gene 1, Gene 2, and/or Gene 3 per nanogram (ng) of fecal DNA in the fecal sample. In embodiments, the method includes determining whether there are from 1,250 to 10,000 copies of genomic DNA sequences encoding Gene 1, Gene 2, and/or Gene 3 per nanogram (ng) of fecal DNA in the fecal sample. In embodiments, the method includes determining whether there are from 1,250 to 9,500 copies of genomic DNA sequences encoding Gene 1, Gene 2, and/or Gene 3 per nanogram (ng) of fecal DNA in the fecal sample. In embodiments, the method includes determining whether there are from 1,250 to 9,000 copies of genomic DNA sequences encoding Gene 1, Gene 2, and/or Gene 3 per nanogram (ng) of fecal DNA in the fecal sample. In embodiments, the method includes determining whether there are from 1,250 to 8,500 copies of genomic DNA sequences encoding Gene 1, Gene 2, and/or Gene 3 per nanogram (ng) of fecal DNA in the fecal sample. In embodiments, the method includes determining whether there are from 1,250 to 8,000 copies of genomic DNA sequences encoding Gene 1, Gene 2, and/or Gene 3 per nanogram (ng) of fecal DNA in the fecal sample. In embodiments, the method includes determining whether there are from 1,250 to 7,500 copies of genomic DNA sequences encoding Gene 1, Gene 2, and/or Gene 3 per nanogram (ng) of fecal DNA in the fecal sample. In embodiments, the method includes determining whether there are from 1,250 to 7,000 copies of genomic DNA sequences encoding Gene 1, Gene 2, and/or Gene 3 per nanogram (ng) of fecal DNA in the fecal sample. In embodiments, the method includes determining whether there are from 1,250 to 6,500 copies of genomic DNA sequences encoding Gene 1, Gene 2, and/or Gene 3 per nanogram (ng) of fecal DNA in the fecal sample. In embodiments, the method includes determining whether there are from 1,250 to 6,000 copies of genomic DNA sequences encoding Gene 1, Gene 2, and/or Gene 3 per nanogram (ng) of fecal DNA in the fecal sample. In embodiments, the method includes determining whether there are from 1,250 to 5,500 copies of genomic DNA sequences encoding Gene 1, Gene 2, and/or Gene 3 per nanogram (ng) of fecal DNA in the fecal sample. In embodiments, the method includes determining whether there are from 1,250 to 5,000 copies of genomic DNA sequences encoding Gene 1, Gene 2, and/or Gene 3 per nanogram (ng) of fecal DNA in the fecal sample. In embodiments, the method includes determining whether there are from 1,250 to 4,500 copies of genomic DNA sequences encoding Gene 1, Gene 2, and/or Gene 3 per nanogram (ng) of fecal DNA in the fecal sample. In embodiments, the method includes determining whether there are from 1,250 to 4,000 copies of genomic DNA sequences encoding Gene 1, Gene 2, and/or Gene 3 per nanogram (ng) of fecal DNA in the fecal sample. In embodiments, the method includes determining whether there are from 1,250 to 3,500 copies of genomic DNA sequences encoding Gene 1, Gene 2, and/or Gene 3 per nanogram (ng) of fecal DNA in the fecal sample. In embodiments, the method includes determining whether there are from 1,250 to 3,000 copies of genomic DNA sequences encoding Gene 1, Gene 2, and/or Gene 3 per nanogram (ng) of fecal DNA in the fecal sample. In embodiments, the method includes determining whether there are from 1,250 to 2,500 copies of genomic DNA sequences encoding Gene 1, Gene 2, and/or Gene 3 per nanogram (ng) of fecal DNA in the fecal sample. In embodiments, the method includes determining whether there are from 1,250 to 2,000 copies of genomic DNA sequences encoding Gene 1, Gene 2, and/or Gene 3 per nanogram (ng) of fecal DNA in the fecal sample. In embodiments, the method includes determining whether there are from 1,250 to 1,500 copies of genomic DNA sequences encoding Gene 1, Gene 2, and/or Gene 3 per nanogram (ng) of fecal DNA in the fecal sample.

In embodiments, the method includes detecting the expression of: (i) the gene that encodes an epoxide hydrolase having an amino acid sequence with at least about 95%, 96%, 97%, 98%, or 99% identity to SEQ ID NO:46 in the biological sample; (ii) the gene that encodes an epoxide hydrolase having an amino acid sequence with at least about 95%, 96%, 97%, 98%, or 99% identity to SEQ ID NO:47 in the biological sample; and/or (iii) a gene that encodes an epoxide hydrolase having an amino acid sequence with at least about 95%, 96%, 97%, 98%, or 99% identity to SEQ ID NO:48 in the biological sample.

In embodiments, detecting the expression of a gene includes detecting an epoxide hydrolase mRNA transcribed from the gene or an epoxide hydrolase protein encoded by the gene.

In embodiments, detecting the expression of a gene includes detecting the level of the expression of the gene.

In embodiments, the level of expression is the level of mRNA transcribed from the gene or the level of an epoxide hydrolase protein encoded by the gene.

In embodiments, detecting includes measuring with an assay. In embodiments, the assay includes high-throughput sequencing, quantitative PCR, or microarray analysis. In embodiments, the assay includes high-throughput sequencing. In embodiments, the assay includes quantitative PCR. In embodiments, the assay includes microarray analysis.

In embodiments, the assay includes one or more probes or primers that hybridize to at least a portion of the gene or an mRNA transcribed from the gene under stringent conditions.

In embodiments, the assay includes one or more probes or primers that hybridize to a portion of a genome within about 0.1, 0.5, 1, 2, 3, 4, or 5 kilobases of the gene under stringent conditions. In embodiments, the assay includes one or more probes or primers that hybridize to a portion of a genome within about 0.1 kilobases of the gene under stringent conditions. In embodiments, the assay includes one or more probes or primers that hybridize to a portion of a genome within about 0.5 kilobases of the gene under stringent conditions. In embodiments, the assay includes one or more probes or primers that hybridize to a portion of a genome within about 1 kilobases of the gene under stringent conditions. In embodiments, the assay includes one or more probes or primers that hybridize to a portion of a genome within about 2 kilobases of the gene under stringent conditions. In embodiments, the assay includes one or more probes or primers that hybridize to a portion of a genome within about 3 kilobases of the gene under stringent conditions. In embodiments, the assay includes one or more probes or primers that hybridize to a portion of a genome within about 4 kilobases of the gene under stringent conditions. In embodiments, the assay includes one or more probes or primers that hybridize to a portion of a genome within about 5 kilobases of the gene under stringent conditions.

In embodiments, the assay includes one or more probes or primers that hybridize to a portion of a genome within 0.1, 0.5, 1, 2, 3, 4, or 5 kilobases of the gene under stringent conditions. In embodiments, the assay includes one or more probes or primers that hybridize to a portion of a genome within 0.1 kilobases of the gene under stringent conditions. In embodiments, the assay includes one or more probes or primers that hybridize to a portion of a genome within 0.5 kilobases of the gene under stringent conditions. In embodiments, the assay includes one or more probes or primers that hybridize to a portion of a genome within 1 kilobases of the gene under stringent conditions. In embodiments, the assay includes one or more probes or primers that hybridize to a portion of a genome within 2 kilobases of the gene under stringent conditions. In embodiments, the assay includes one or more probes or primers that hybridize to a portion of a genome within 3 kilobases of the gene under stringent conditions. In embodiments, the assay includes one or more probes or primers that hybridize to a portion of a genome within 4 kilobases of the gene under stringent conditions. In embodiments, the assay includes one or more probes or primers that hybridize to a portion of a genome within 5 kilobases of the gene under stringent conditions.

In embodiments, the method further includes detecting the level of an oxylipin in the biological sample. In embodiments, the oxylipin is 12,13 DiHOME and/or 9,10 DiHOME.

In embodiments, the method further includes calculating a Neonatal Atopy Score (NAtS) for the subject, wherein the subject's NAtS score includes one point for each of the following: (i) having at least about 13,318 copies of a genomic DNA sequence that encodes Gene 1, Gene 2, and/or Gene 3 per nanogram (ng) of fecal DNA in a fecal sample; (ii) having a mother who has or has had asthma; and (iii) having not lived in a residence with a cat for at least 7, 14, or 21 days of the first month after being born.

In embodiments, the method further includes calculating a Neonatal Atopy Score (NAtS) for the subject, wherein the subject's NAtS score consists of one point for each of the following: (i) having at least about 13,318 copies of a genomic DNA sequence that encodes Gene 1, Gene 2, and/or Gene 3 per nanogram (ng) of fecal DNA in a fecal sample; (ii) having a mother who has or has had asthma; and (iii) having not lived in a residence with a cat for at least 7, 14, or 21 days of the first month after being born.

In embodiments, the method further includes calculating a Neonatal Atopy Score (NAtS) for the subject, wherein the subject's NAtS score consists essentially of one point for each of the following: (i) having at least about 13,318 copies of a genomic DNA sequence that encodes Gene 1, Gene 2, and/or Gene 3 per nanogram (ng) of fecal DNA in a fecal sample; (ii) having a mother who has or has had asthma; and (iii) having not lived in a residence with a cat for at least 7, 14, or 21 days of the first month after being born.

In embodiments, the subject's risk of developing atopy increases incrementally as the NAtS increases. In embodiments, a subject with a NAtS of 3 has a higher risk of atopy than a subject with a NAtS of 2. In embodiments, a subject with a NAtS of 2 has a higher risk of atopy than a subject with a NAtS of 1. In embodiments, a subject with a NAtS of 1 has a higher risk of atopy than a subject with a NAtS of 0. In embodiments, a NAtS of ≥2 identifies the subject as at risk of atopy.

In embodiments, a NAtS of ≥2 is calculated for the subject.

In embodiments, the method further includes identifying the subject as at risk of developing atopy compared to a corresponding subject with a NAtS of 1 or 0.

In embodiments, a NAtS of 1 or 0 is calculated for the subject.

In embodiments, the method further includes identifying the subject as less likely to develop atopy than a corresponding subject with a NAts of ≥2.

In embodiments, the method further includes calculating a Neonatal Asthma Predictive Score (NAPS) for the subject, wherein the subject's NAPS score includes one point for each of the following: (i) having not lived in a residence with a dog for at least about 7, 14, or 21 days of the first month after being born; (ii) having a mother who has not lived in a residence with a dog for at least 30, 60, 90, 120, 150, 180, 210, 240, or 270 days between when the subject was conceived and when the subject was born; (iii) having a mother who has smoked at least once on a total of at least 30, 60, 90, 120, 150, 180, 210, 240, or 270 days between when the subject was conceived and when the subject was born; (iv) being fed formula in the first month of life; (v) having a fecal level of 12,13 DiHOME of at least about >398 ng/g; (vi) having a fecal level of 9,10 DiHOME of at least about >425 ng/g; and (vii) having at least about 1,598 copies of a genomic DNA sequence that encodes Gene 1, Gene 2, and/or Gene 3 per nanogram (ng) of fecal DNA in a fecal sample.

In embodiments, the method further includes calculating a Neonatal Asthma Predictive Score (NAPS) for the subject, wherein the subject's NAPS score consists of one point for each of the following: (i) having not lived in a residence with a dog for at least about 7, 14, or 21 days of the first month after being born; (ii) having a mother who has not lived in a residence with a dog for at least 30, 60, 90, 120, 150, 180, 210, 240, or 270 days between when the subject was conceived and when the subject was born; (iii) having a mother who has smoked at least once on a total of at least 30, 60, 90, 120, 150, 180, 210, 240, or 270 days between when the subject was conceived and when the subject was born; (iv) being fed formula in the first month of life; (v) having a fecal level of 12,13 DiHOME of at least about >398 ng/g; (vi) having a fecal level of 9,10 DiHOME of at least about >425 ng/g; and (vii) having at least about 1,598 copies of a genomic DNA sequence that encodes Gene 1, Gene 2, and/or Gene 3 per nanogram (ng) of fecal DNA in a fecal sample.

In embodiments, the method further includes calculating a Neonatal Asthma Predictive Score (NAPS) for the subject, wherein the subject's NAPS score consists essentially of one point for each of the following: (i) having not lived in a residence with a dog for at least about 7, 14, or 21 days of the first month after being born; (ii) having a mother who has not lived in a residence with a dog for at least 30, 60, 90, 120, 150, 180, 210, 240, or 270 days between when the subject was conceived and when the subject was born; (iii) having a mother who has smoked at least once on a total of at least 30, 60, 90, 120, 150, 180, 210, 240, or 270 days between when the subject was conceived and when the subject was born; (iv) being fed formula in the first month of life; (v) having a fecal level of 12,13 DiHOME of at least about >398 ng/g; (vi) having a fecal level of 9,10 DiHOME of at least about >425 ng/g; and (vii) having at least about 1,598 copies of a genomic DNA sequence that encodes Gene 1, Gene 2, and/or Gene 3 per nanogram (ng) of fecal DNA in a fecal sample.

In embodiments, the subject's risk of developing asthma increases incrementally as the NAPS increases. In embodiments, a subject with a NAPS of 7 has a higher risk of asthma than a subject with a NAPS of 6. In embodiments, a subject with a NAPS of 6 has a higher risk of asthma than a subject with a NAPS of 5. In embodiments, a subject with a NAPS of 5 has a higher risk of asthma than a subject with a NAPS of 4. In embodiments, a subject with a NAPS of 4 has a higher risk of asthma than a subject with a NAPS of 3. In embodiments, a subject with a NAPS of 3 has a higher risk of asthma than a subject with a NAPS of 2. In embodiments, a subject with a NAPS of 2 has a higher risk of asthma than a subject with a NAPS of 1. In embodiments, a subject with a NAPS of 1 has a higher risk of asthma than a subject with a NAPS of 0. In embodiments, a NAPS of ≥2 identifies the subject as at risk of asthma.

In embodiments, a NAPS of ≥6 is calculated for the subject. In embodiments, the method further includes identifying the subject as at risk of developing atopy compared to a corresponding subject with a NAPS of <6.

In embodiments, a NAPS of <6 is calculated for the subject.

In embodiments, the method further includes identifying the subject as less likely to develop atopy than a corresponding subject with a NAPS of ≥6.

III. METHODS OF DIAGNOSIS AND SCREENING

In an aspect is provided a method of determining whether a subject is at risk of atopy or asthma, the method including: (a) detecting (i) a gene that encodes an epoxide hydrolase having an amino acid sequence with at least about 95%, 96%, 97%, 98%, or 99% identity to SEQ ID NO:46, or the expression thereof, in a biological sample from the subject; (ii) a gene that encodes an epoxide hydrolase having an amino acid sequence with at least about 95%, 96%, 97%, 98%, or 99% identity to SEQ ID NO:47, or the expression thereof, in a biological sample from the subject; and/or (iii) a gene that encodes an epoxide hydrolase having an amino acid sequence with at least about 95%, 96%, 97%, 98%, or 99% identity to SEQ ID NO:48, or the expression thereof, in a biological sample from the subject, and (b) identifying the subject as at risk of atopy or asthma if a level of the first epoxide hydrolase gene, the second epoxide hydrolase gene, and/or the third epoxide hydrolase gene is detected.

In embodiments is provided a method of determining whether a subject is at risk of atopy or asthma, the method consisting of: (a) detecting (i) a gene that encodes an epoxide hydrolase having an amino acid sequence with at least about 95%, 96%, 97%, 98%, or 99% identity to SEQ ID NO:46, or the expression thereof, in a biological sample from the subject; (ii) a gene that encodes an epoxide hydrolase having an amino acid sequence with at least about 95%, 96%, 97%, 98%, or 99% identity to SEQ ID NO:47, or the expression thereof, in a biological sample from the subject; and/or (iii) a gene that encodes an epoxide hydrolase having an amino acid sequence with at least about 95%, 96%, 97%, 98%, or 99% identity to SEQ ID NO:48, or the expression thereof, in a biological sample from the subject, and (b) identifying the subject as at risk of atopy or asthma if a level of the first epoxide hydrolase gene, the second epoxide hydrolase gene, and/or the third epoxide hydrolase gene is detected.

In embodiments is provided a method of determining whether a subject is at risk of atopy or asthma, the method consisting essentially of: (a) detecting (i) a gene that encodes an epoxide hydrolase having an amino acid sequence with at least about 95%, 96%, 97%, 98%, or 99% identity to SEQ ID NO:46, or the expression thereof, in a biological sample from the subject; (ii) a gene that encodes an epoxide hydrolase having an amino acid sequence with at least about 95%, 96%, 97%, 98%, or 99% identity to SEQ ID NO:47, or the expression thereof, in a biological sample from the subject; and/or (iii) a gene that encodes an epoxide hydrolase having an amino acid sequence with at least about 95%, 96%, 97%, 98%, or 99% identity to SEQ ID NO:48, or the expression thereof, in a biological sample from the subject, and (b) identifying the subject as at risk of atopy or asthma if a level of the first epoxide hydrolase gene, the second epoxide hydrolase gene, and/or the third epoxide hydrolase gene is detected.

In embodiments, the method further includes monitoring the subject for atopy if the subject is identified as at risk for atopy, wherein the monitoring is more frequent than a corresponding subject who is identified as having less risk or a lower likelihood of developing atopy. In embodiments, the method further includes monitoring the subject for atopy if the subject is identified as at risk for atopy, wherein the monitoring includes an examination or diagnostic assay that is not administered to a corresponding subject who is identified as having less risk or a lower likelihood of developing atopy.

In embodiments, monitoring the subject for atopy comprises skin or blood testing for one or more allergies to a panel of food or aeroallergens. In embodiments, a positive NAtS screen or score (e.g., a score indicating an increased risk as disclosed herein) increases the likelihood of blood or skin testing. In embodiments, monitoring or assessing a subject with a positive NAtS screen or score (e.g., a score indicating an increased risk as disclosed herein) comprises blood or skin testing. In embodiments, atopy is assessed or monitored following observation of symptoms by either the child or the parents.

In embodiments, the method further includes monitoring the subject for asthma if the subject is identified as at risk for asthma, wherein the monitoring is more frequent than a corresponding subject who is identified as having less risk or a lower likelihood of developing asthma. In embodiments, the method further includes monitoring the subject for asthma if the subject is identified as at risk for asthma, wherein the monitoring includes an examination or diagnostic assay that is not administered to a corresponding subject who is identified as having less risk or a lower likelihood of developing asthma.

In embodiments, a positive NAPS screen or score (e.g., a score indicating an increased risk as disclosed herein) indicates a need for a pulmonary function test. In embodiments, a positive NAPS screen or score (e.g., a score indicating an increased risk as disclosed herein) indicates increased suspicion or likelihood of asthma, especially following a parental report of wheezing. In embodiments, monitoring or assessing a subject with a positive NAP screen or score (e.g., a score indicating an increased risk as disclosed herein) comprises a pulmonary function test. In embodiments, asthma is assessed or diagnosed in a child (e.g., a subject between 4 and 5 years old) using a pulmonary function test. In embodiments, a child under the age of 4 cannot perform a pulmonary function test).

In embodiments, the method further includes administering a treatment to treat, reduce the likelihood of, or prevent atopy to the subject if the subject is identified as at risk for atopy.

In embodiments, the method further includes administering a treatment to treat, reduce the likelihood of, or prevent asthma to the subject if the subject is identified as at risk for asthma.

IV. METHODS OF TREATMENT

In an aspect, provided herein is a method of reducing the likelihood that a subject will develop asthma or atopy, the method including administering to the subject a treatment that reduces the likelihood that the subject will develop atopy, wherein (i) a gene that encodes an epoxide hydrolase having an amino acid sequence with at least about 95%, 96%, 97%, 98%, or 99% identity to SEQ ID NO:46, or the expression thereof, has been detected in a biological sample from the subject; (ii) a gene that encodes an epoxide hydrolase having an amino acid sequence with at least about 95%, 96%, 97%, 98%, or 99% identity to SEQ ID NO:47, or the expression thereof, has been detected in a biological sample from the subject; and/or (iii) a gene that encodes an epoxide hydrolase having an amino acid sequence with at least about 95%, 96%, 97%, 98%, or 99% identity to SEQ ID NO:48, or the expression thereof, has been detected in a biological sample from the subject.

In an aspect, provided herein is a method of reducing the likelihood that a subject will develop asthma or atopy, the method including administering to the subject a treatment that reduces the likelihood that the subject will develop atopy, wherein Gene 1, Gene 2, and/or Gene 3, or the expression thereof, has been detected in a biological sample from the subject.

In an aspect is provided a method of treating or preventing atopy or asthma in a subject in need thereof, the method including administering to the subject a treatment that reduces the likelihood that the subject will develop atopy, wherein (i) a gene that encodes an epoxide hydrolase having an amino acid sequence with at least about 95%, 96%, 97%, 98%, or 99% identity to SEQ ID NO:46, or the expression thereof, has been detected in a biological sample from the subject; (ii) a gene that encodes an epoxide hydrolase having an amino acid sequence with at least about 95%, 96%, 97%, 98%, or 99% identity to SEQ ID NO:47, or the expression thereof, has been detected in a biological sample from the subject; and/or (iii) a gene that encodes an epoxide hydrolase having an amino acid sequence with at least about 95%, 96%, 97%, 98%, or 99% identity to SEQ ID NO:48, or the expression thereof, has been detected in a biological sample from the subject.

In an aspect is provided a method of treating or preventing atopy or asthma in a subject in need thereof, the method including administering to the subject a treatment that prevents or treats atopy or asthma, wherein Gene 1, Gene 2, and/or Gene 3, or the expression thereof, has been detected in a biological sample from the subject.

In embodiments, a level of Gene 1, Gene 2, and/or Gene 3 has been detected in the biological sample, wherein the level is at least about 1,598 or 13,318 copies of genomic DNA sequences encoding Gene 1, Gene 2, and/or Gene 3 per nanogram (ng) of fecal DNA of the subject.

In embodiments, the subject has been identified as at risk of atopy or asthma according to the methods described herein, including embodiments thereof.

In embodiments, the treatment includes immunotherapy for a food allergen, immunotherapy for an aeroallergen, or a monoclonal antibody. In embodiments, the treatment includes immunotherapy for a food allergen. In embodiments, the treatment includes immunotherapy for an aeroallergen. In embodiments, the treatment includes a monoclonal antibody.

In embodiments, the treatment includes the administration of an effective amount of omalizumab, montelukast, budesonide, levocetirizine, vitamin D supplementation, a probiotic organism, fish oil, or linoleic acid. In embodiments, the treatment includes the administration of an effective amount of omalizumab. In embodiments, the treatment includes the administration of an effective amount of montelukast. In embodiments, the treatment includes the administration of an effective amount of budesonide. In embodiments, the treatment includes the administration of an effective amount of levocetirizine. In embodiments, the treatment includes the administration of an effective amount of vitamin D supplementation. In embodiments, the treatment includes the administration of an effective amount of a probiotic organism. In embodiments, the treatment includes the administration of an effective amount of fish oil. In embodiments, the treatment includes the administration of an effective amount of linoleic acid.

In embodiments, the treatment includes oral mucosal immunoprophylaxis with a house dust mite, cat dander, or a grass pollen, vitamin E, supplementation with *Lactobacillus reuteri* with or without one or more leukotrienes, sublingual supplementation with grass pollen extract, or dust mite immunotherapy.

In embodiments, the treatment includes administering an effective amount of at least one probiotic organism to the subject. In embodiments, the at least one probiotic organism comprises *Lactobacillus* sp., *Faecalibacterium* sp., *Akkermansia* sp., *Myxococcus* sp., *Pediococcus* sp., *Bifidobacterium* sp., and/or *Streptococcus* sp.

In embodiments, (i) the *Lactobacillus* sp. is *Lactobacillus zeae, Lactobacillus acidipiscis, Lactobacillus acidophilus, Lactobacillus agilis, Lactobacillus aviarius, Lactobacillus brevis, Lactobacillus coleohominis, Lactobacillus crispatus, Lactobacillus crustorum, Lactobacillus curvatus, Lactobacillus dioliverans, Lactobacillus farraginis, Lactobacillus fermentum, Lactobacillus fuchuensis, Lactobacillus harbinensis, Lactobacillus helveticus, Lactobacillus hilgardii, Lactobacillus intestinalis, Lactobacillus jensenii, Lactobacillus kefiranofaciens, Lactobacillus kefiri, Lactobacillus lindneri, Lactobacillus mali, Lactobacillus manihotivorans, Lactobacillus mucosae, Lactobacillus oeni, Lactobacillus oligofermentans, Lactobacillus panis, Lactobacillus pantheris, Lactobacillus parabrevis, Lactobacillus paracollinoides, Lactobacillus parakefiri, Lactobacillus paraplantarum, Lactobacillus pentosus, Lactobacillus pontis, Lactobacillus reuteri, Lactobacillus rossiae, Lactobacillus salivarius, Lactobacillus siliginis, Lactobacillus sucicola, Lactobacillus vaccinostercus, Lactobacillus vaginalis, Lactobacillus vini, Lactococcus garvieae,* or *Lactococcus lactis*; (ii) the *Faecalibacterium* sp., is *Faecalibacterium prausnitzii*; (iii) the *Akkermansia* sp. is *Akkermansia muciniphila*; (iv) the *Myxococcus* sp. is *Myxococcus xanthus*; (v) the *Pediococcus* sp. is *Pediococcus pentosaceus, Pediococcus acidilactici, Pediococcus damnosus, Pediococcus ethanolidurans,* or *Pediococcus parvulus*; (vi) the *Bifidobacterium* sp. is *B. bifidum, B. infantis, B. reuteri, B. breve,* or *B. longum*; and/or (vii) the *Streptococcus* sp. is *Streptococcus thermophilis*. In embodiments, the *Lactobacillus* sp. is *Lactobacillus zeae, Lactobacillus acidipiscis, Lactobacillus acidophilus, Lactobacillus agilis, Lactobacillus aviarius, Lactobacillus brevis, Lactobacillus coleohominis, Lactobacillus crispatus, Lactobacillus crustorum, Lactobacillus curvatus, Lactobacillus dioliverans, Lactobacillus farraginis, Lactobacillus fermentum, Lactobacillus fuchuensis, Lactobacillus harbinensis, Lactobacillus helveticus, Lactobacillus hilgardii, Lactobacillus intestinalis, Lactobacillus jensenii, Lactobacillus kefiranofaciens, Lactobacillus kefiri, Lactobacillus lindneri, Lactobacillus mali, Lactobacillus manihotivorans, Lactobacillus mucosae, Lactobacillus oeni, Lactobacillus oligofermentans, Lactobacillus panis, Lactobacillus pantheris, Lactobacillus parabrevis, Lactobacillus paracollinoides, Lactobacillus parakefiri, Lactobacillus paraplantarum, Lactobacillus pentosus, Lactobacillus pontis, Lactobacillus reuteri, Lactobacillus rossiae, Lactobacillus salivarius, Lactobacillus siliginis, Lactobacillus sucicola, Lactobacillus vaccinostercus, Lactobacillus vaginalis, Lactobacillus vini, Lactococcus garvieae,* or *Lactococcus lactis*. In embodiments, the *Faecalibacterium* sp., is *Faecalibacterium prausnitzii*. In embodiments, the *Akkermansia* sp. is *Akkermansia mucimphila*. In embodiments, the *Myxococcus* sp. is *Myxococcus xanthus*. In embodiments, the *Pediococcus* sp. is *Pediococcus pentosaceus, Pediococcus acidilactici, Pediococcus damnosus, Pediococcus ethanolidurans,* or *Pediococcus parvulus*. In embodiments, the *Bifidobacterium* sp. is *B. bifidum, B. infantis, B. reuteri, B. breve,* or *B. longum*. In embodiments, the *Streptococcus* sp. is *Streptococcus thermophilis*.

In embodiments, the treatment includes at least one antibiotic compound. In embodiments, the antibiotic is a cephalosporin, a penicillin, a carbapenem, or a glycopeptide. In embodiments, the antibiotic is a cephalosporin. In embodiments, the antibiotic is a penicillin. In embodiments, the antibiotic is a carbapenem. In embodiments, the antibiotic is a glycopeptide.

V. EXAMPLES

Diagnostic tools provided herein were validated in a pilot study consisting of 41 neonatal stool samples. The data show the present disclosure provides a viable method for identifying neonates at high-risk for developing atopy or asthma.

We have shown both in vitro and in vivo that 12,13 DiHOME prevents the development of immune tolerance by reducing the frequency of anti-inflammatory regulatory T cells. Using metagenomic sequencing of neonatal stool we have shown that the microbial genes that lead to 12,13 DiHOME production are significantly increased in copy number in neonates who subsequently develop atopy and/or asthma in childhood and confirmed that three of these bacterial genes encode functional epoxide hydrolases that specifically produce 12,13 DiHOME in vitro. In pilot studies of 1 month old stool samples, we've found that the abundance of fecal oxylipins (12,13 DiHOME and its enantiomer 9,10 DiHOME) and bacterial EH genes can be combined with known early-life risk factors to predict atopy at age 2 and asthma at age 4, years before traditional diagnostics are applicable. Hence the present disclosure describes two new tests that can be applied to early-life stool samples (~1 month of age) that employ a combination of novel gut-microbiome-associated biomarkers together with risk factors to identify with good sensitivity and specificity, neonates who are at risk of developing atopy and asthma years in advance of clinical symptoms. These new tests offer the opportunity for early diagnosis and interventions, particularly those targeting the gut microbiome, to prevent allergy and asthma development in childhood.

Embodiments herein are further illustrated by the following examples. However, the examples are merely intended to illustrate embodiments and are not to be construed to limit the scope herein. The contents of all references and published patents and patent applications cited throughout this application are hereby incorporated by reference.

Example 1: Illustrative Example of how to Calculate the Neotnatal Atopy Score (NAtS) and the Neonatal Asthma Predictive Score (NAPS)

Calculating the Neonatal Atopy Score (NAtS). A patient scores one point for meeting each of the following criteria. A total score≥2 is considered a positive test.
3EH>13,318 copies/ng of fecal DNA
Maternal asthma
Lack of cat exposure at one month For example, an one-month-old child with born into a pet-free household with an non-asthmatic mother and a fecal 3EH concentration of 22,000 copies/ng of DNA would receive a NAtS of 2, and would be considered high-risk for atopy at age 2.

TABLE 1

Example calculation of NAtS for the example scenario above.

| Criteria | Points |
|---|---|
| 3EH >13,318 copies/ng of fecal DNA | 1 |
| Maternal asthma | 0 |
| Lack of cat exposure at one month | 1 |
| Total Score | 2 |

Calculating the Neonatal Asthma Predictive Score (NAPS). A patient scores one point for meeting each of the following criteria. A total score≥6 is considered a positive test.
Lack of dog exposure at one month
Lack of dog exposure pre-delivery
Maternal smoking during pregnancy
Formula feeding at one month
12,13 DiHOME>398 ng/g feces
9,10 DiHOME>425 ng/g feces
3EH>1,598 copies/ng of fecal DNA For example, an formula-fed one-month-old child with that was born into a dog-owning household to a non-smoking mother with fecal concentrations of 12,13 DiHOME=600 ng/g, 9,10 DiHOME=500 ng/g, and 3EH=500 copies/ng would receive a NAPS of 3, indicating that they are at low-risk of asthma at age 4.

TABLE 2

Example calculation of NAPS for the example scenario above.

| Criteria | Points |
|---|---|
| Lack of dog exposure at one month | 0 |
| Lack of dog exposure pre-delivery | 0 |
| Maternal smoking during pregnancy | 0 |
| Formula feeding at one month | 1 |
| 12, 13 DiHOME >398 ng/g feces | 1 |
| 9, 10 DiHOME >425 ng/g feces | 1 |
| 3EH >1,598 copies/ng of fecal DNA | 0 |
| Total Score | 3 |

TABLE 3

Risk of atopy based on abundance of the individual epoxide hydrolase genes (NP_814874, YP_003971091, YP_00397133) and the combined 3EH abundance

| | Atopy | | | |
|---|---|---|---|---|
| | Gene 1: NP_814872 | Gene 2: YP_003971091 | Gene 3: YP_003971333 | 3EH |
| Sensitivity | 50% | 67% | 67% | 67% |
| Specificity | 94% | 66% | 63% | 84% |
| PPV | 75% | 42% | 40% | 62% |
| NPV | 83% | 84% | 83% | 87% |
| PLR | 8.00 | 1.94 | 1.78 | 4.27 |
| NLR | 0.53 | 0.51 | 0.53 | 0.40 |
| OR | 13.72 | 3.70 | 3.24 | 10.02 |
| p-value | 0.003 | 0.088 | 0.102 | 0.002 |

TABLE 4

Risk of asthma based on abundance of the individual epoxide hydrolase genes (NP_814874, YP_003971091, YP_00397133) and the combined 3EH abundance

| | Asthma | | | |
|---|---|---|---|---|
| | Gene 1: NP_814872 | Gene 2: YP_003971091 | Gene 3: YP_003971333 | 3EH |
| Sensitivity | 75% | 67% | 58% | 83% |
| Specificity | 63% | 56% | 56% | 44% |
| PPV | 43% | 36% | 33% | 36% |
| NPV | 87% | 82% | 78% | 88% |
| PLR | 2.00 | 1.52 | 1.33 | 1.48 |
| NLR | 0.40 | 0.59 | 0.74 | 0.38 |
| OR | 4.81 | 2.52 | 1.78 | 3.78 |
| p-value | 0.042 | 0.310 | 0.504 | 0.160 |

Applications of the technology. NAtS and NAPS may be used to identify one-month-old babies at high risk of atopy and asthma. Early identification of high-risk neonates may provide opportunities for early diagnosis and intervention. Ongoing clinical trials focused on early-life intervention, such as immunotherapy for food and aeroallergens or monoclonal antibodies for asthma, are often underpowered and require large sample sizes and broad enrollment criteria to assess the efficacy of intervention. The two tools developed in our lab would allow clinicians to assess risk of atopy and asthma with greater sensitivity several years before the current predictive models can be applied. Additionally, they may help identify high-risk neonates who could benefit from early-life microbial or immune interventions whose effects may be undetectable in population-based clinical trials.

Example 2: Neonatal Gut-Microbiome-Derived 12,13 DiHOME Impedes Tolerance and Promotes Childhood Atopy and Asthma Summary Here we show that 12,13 DiHOME treatment of human DCs decreased IL-10 production, altered expression of PPARγ-regulated genes, and decreased Treg frequency ex vivo. Mice treated with 12,13 DiHOME prior to airway allergic sensitization exhibited exacerbated pulmonary inflammation and decreased lung Tregs. Fecal metagenomic analysis of neonates who developed childhood atopy and/or asthma revealed a significant increase in bacterial epoxide hydrolase (EH) genes, three of which specifically produce 12,13 DiHOME in vitro. Lastly, we show that elevated neonatal fecal DiHOME concentration and bacterial EH gene copy number combined with specific known early-life risk factors significantly increased neonatal odds of atopy at age two and asthma at age four years.

Experiments.

Figure 1H:
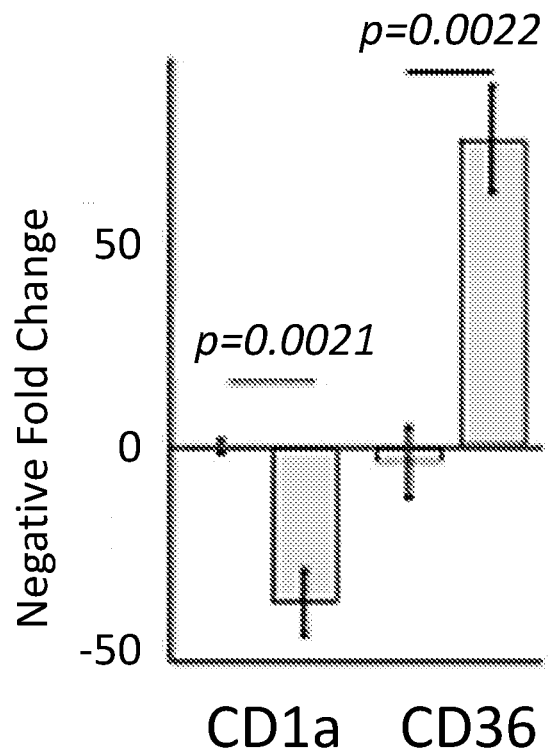
Figure 1I:
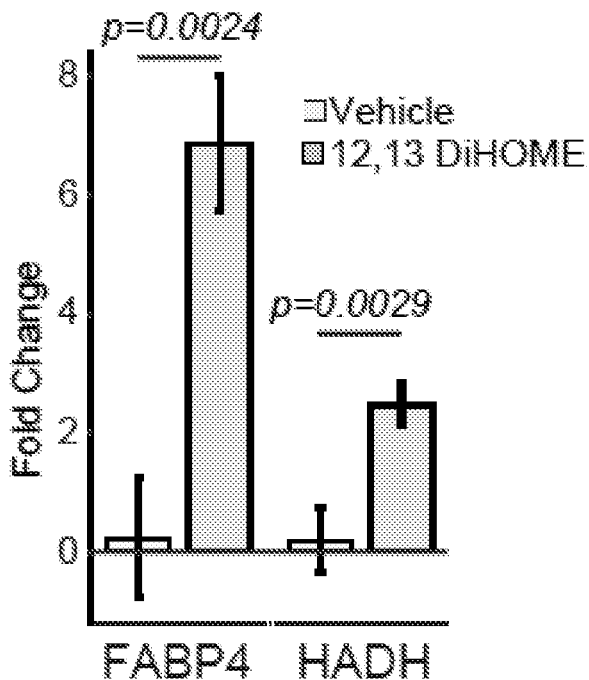
Figure 1J:
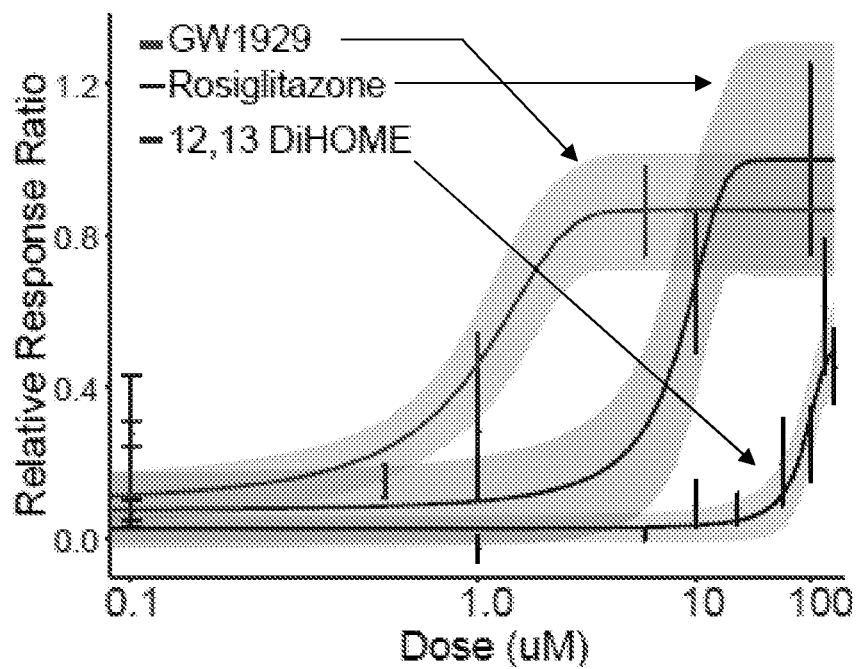

We treated human DCs with 12,13 DiHOME or vehicle and examined the effect on both DCs and autologous T cells. 12,13 DiHOME treatment decreased DC secretion of IL-10, an anti-inflammatory cytokine that protects against allergic inflammation [6], and altered the distribution of helper T cells, by specifically decreasing the frequency of Tregs without decreasing cell viability (FIGS. 1A-C, FIGS. 4 A-C). To evaluate whether 12,13 DiHOME exerted this effect via PPARγ, flow cytometry was used to compare effects on expression of PPARγ-regulated proteins in human DCs. While 12,13 DiHOME did not alter cell viability, it did mimic previously characterized effects of PPARγ activation: increased expression of CD36, a fatty-acid transporter implicated in 12,13 DiHOME-regulation of brown adipocytes [7], and decreased expression of CD80, CD1a, and CCR7, immune markers involved in antigen presentation, lipid presentation, and cell trafficking [8] (FIGS. 1D-G, FIGS. 4F-G). To confirm these observations, RNA was isolated from human DCs treated with 12,13 DiHOME, and examined for the expression of CD1a and CD36 as well as FABP4 and HADH, genes up-regulated by PPARγ and involved in fatty acid uptake and metabolism [8]. 12,13 DiHOME treated DCs exhibited significantly increased expression of CD36, FABP4, and HADH and decreased expression of CD (FIG. 1H-I). To test whether 12,13 DiHOME directly acted on PPARγ, we utilized a modified PPARγ reporter assay [9] to demonstrate that treatment with concentrations of 12,13 DiHOME in excess of 50 µM lead to PPARγ activation (FIG. 1J). While PPARγ activation in DCs is traditionally considered anti-inflammatory [10,11], recent studies suggest that PPARγ may in fact promote allergic inflammation [12]. Alternatively, 12,13 DiHOME may act as a weak agonist of PPARγ and compete with endogenous PPARγ ligands found in serum [13].

Figure 2C:
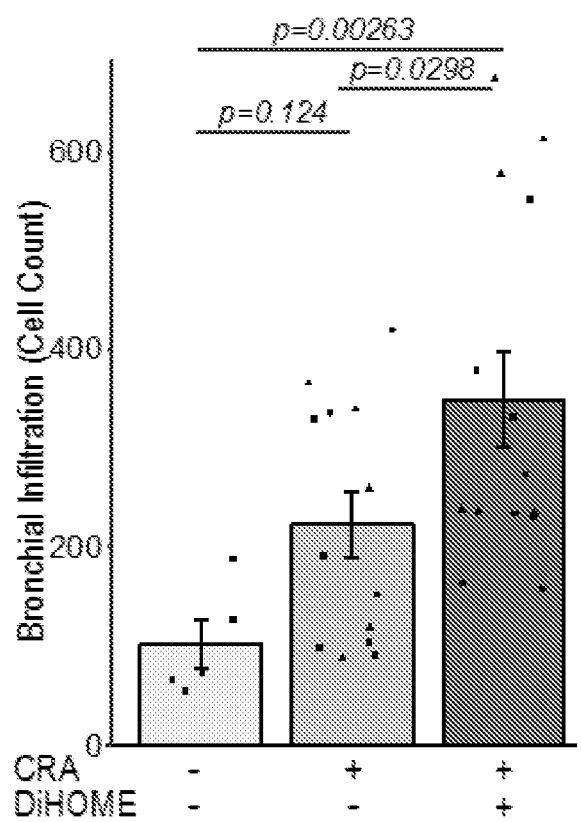
Figure 2D:
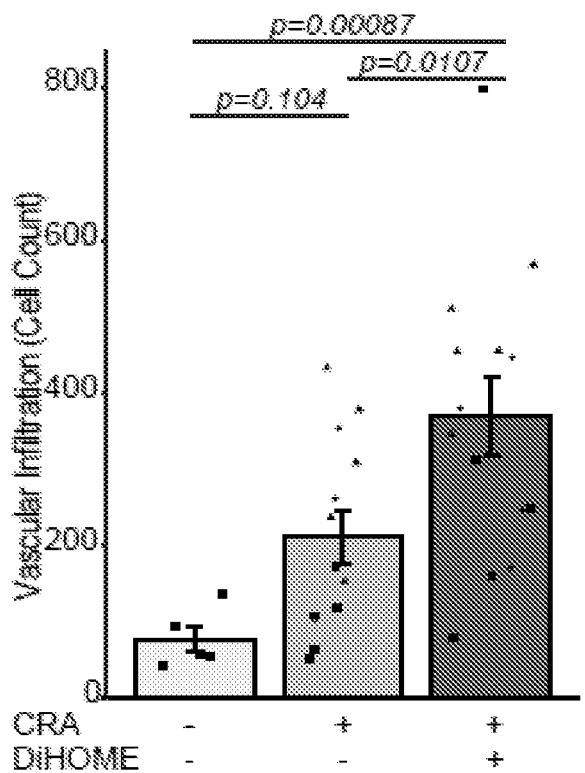
Figure 2E:
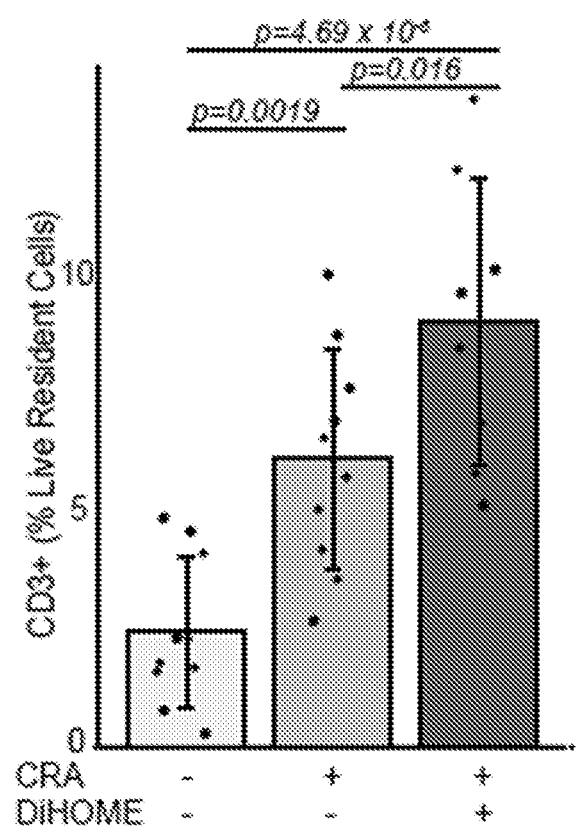
Figure 2F:
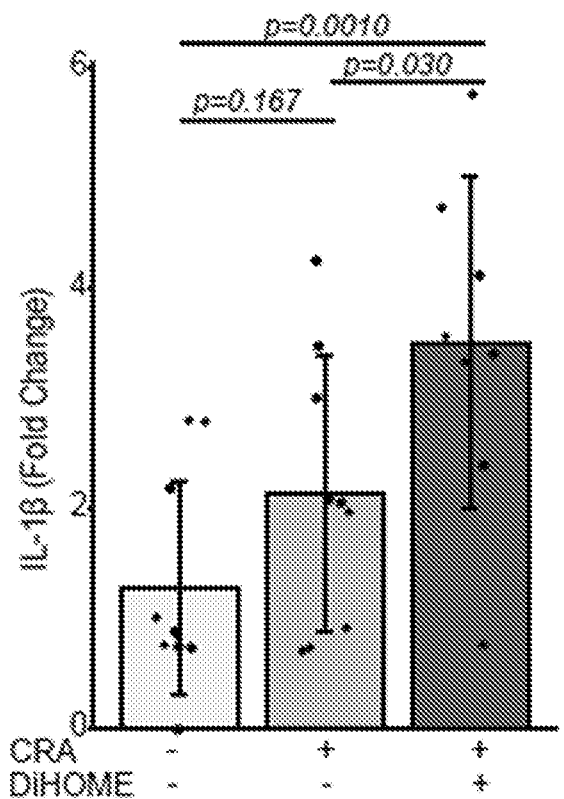
Figure 2G:
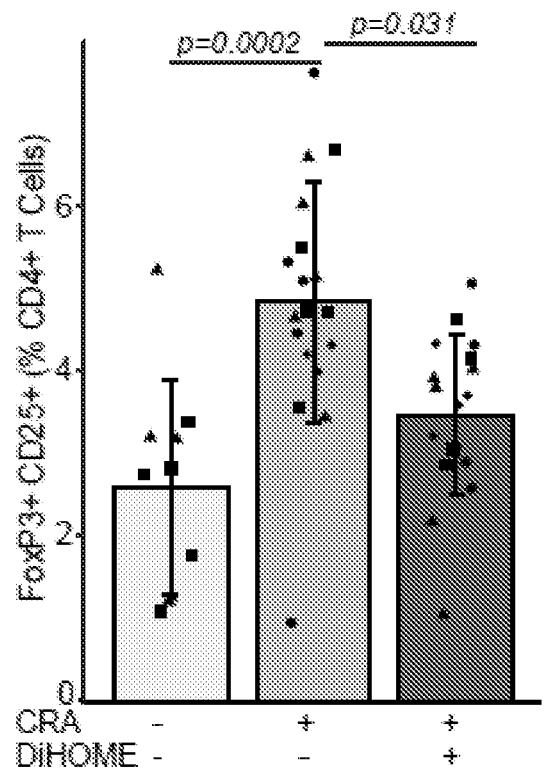

We next examined whether 12,13 DiHOME exacerbated allergic sensitization in vivo, by treating mice with 12,13 DiHOME (30 mg/kg) or vehicle (10% DMSO) via peritoneal injection prior to airway sensitization and challenge with cockroach antigen (CRA) [14]. Lipid-treated animals exhibited increases in both peribronchial and perivascular inflammatory infiltrates and serum IgE compared to those treated with vehicle alone (FIGS. 2A-D, FIGS. 5A-B). 12,13 DiHOME-treated animals also exhibited increases in lung resident T cells, neutrophils, and monocytes, and pulmonary expression of pro-inflammatory innate cytokines, IL1β, IL1α, and TNF, as well as a significant decrease in the frequency of lung Tregs and a trend towards decreased lung resident alveolar macrophages (FIGS. 2E-G, FIGS. 5E-K). These immunologic changes may be explained by the effect of 12,13 DiHOME on PPARγ observed ex vivo. Alternatively, 12,13 DiHOME has been identified as an activator of transient receptor potential vanilloid 1 (TRPV1) [15], loss of which is associated with decreased asthma prevalence in humans and protection against airway inflammation in animal models [16,17]. To evaluate whether 12,13 DiHOME acted directly on the lungs, it was quantified by liquid-chromatography mass spectrometry (LC-MS) [18] in mouse lungs and plasma three hours after peritoneal injection and was significantly enriched in both tissues when compared with vehicle-treated animals (FIG. 2J, FIG. 5I), indicating a direct effect of this lipid on the lungs of mice to exacerbate allergic airway inflammation.

Figure 3A:
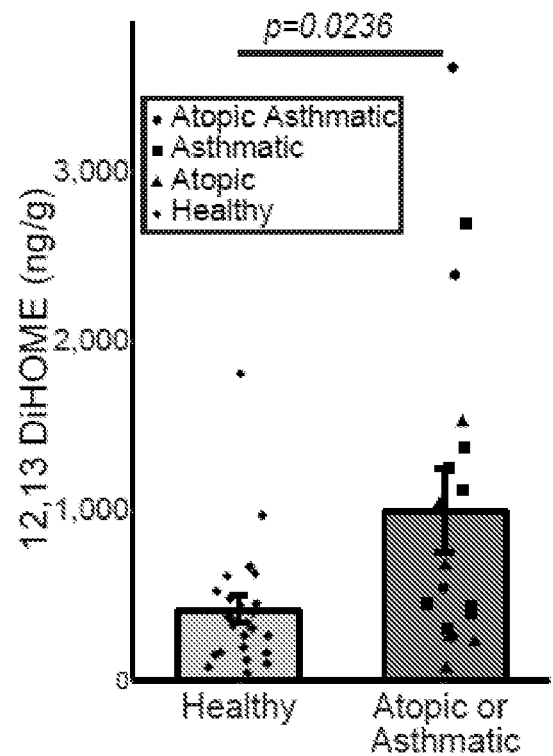
FIGS. 3A-3G show example results that illustrate that neonatal gut microbiome *Enterococcus faecalis* and *Bifidobacterium bifidum* strains encoded the capacity to produce 12,13 DiHOME and increased the odds of developing atopy and/or asthma. Neonates who developed childhood atopy and/or asthma exhibited increased fecal concentrations of 12,13 DiHOME (n=41; Wilcox Test; p=0.0182) (FIG. 3A). Neonates who developed atopy at age two had more bacterial EH genes in their stool (n=26; Wilcox Test; p=0.002) (FIG. 3B). The 30 most abundant EH genes identified in stool were enriched in neonates who developed atopy (FIG. 3C). Three of the candidate EH genes, *E. faecalis* NP_814872, *B. bifidum* YP_003971091, and *B. bifidum* YP_003971333, converted 12,13 EpOME to its conjugate diol, 12,13 DiHOME (FIG. 3D). 3EH copy number mimicked the significant increase in overall fecal EH genes observed in neonates who went on to develop atopy and/or asthma (n=41; Wilcox Test; p=0.0158) (FIG. 3E).
Figure 6A:
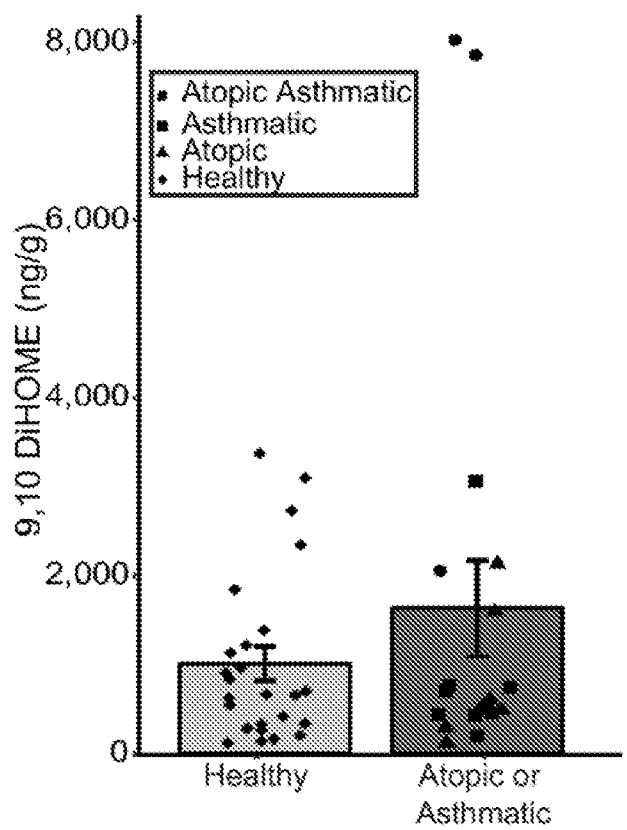
FIGS. 6A-6E show example results that illustrate that bacterial EH enzymes can generate 9,10 and 12,13 DiHOME in vitro and can be combined with known risk factors to predict development of allergic disease in childhood. The fecal concentration of 9,10 DiHOME did not significantly differ between healthy neonates and those who develop atopy and/or asthma (n=41) (FIG. 6A). The following symbols, ▲, ■, ♦, ●, represent neonates who developed into healthy, atopic, asthmatic, and atopic asthmatic children, respectively. Error bars represent the SEM.

Given the apparent role of this lipid in driving pro-allergic immune dysfunction both ex vivo and in mice, we focused on determining the concentration and microbial sources of 12,13 DiHOME in the feces of neonates who develop childhood atopy and/or asthma. We began by quantifying 12,13 DiHOME and 9,10 DiHOME (its enantiomer, a known agonist of PPARγ [19]) using LC-MS in a subset of one-month-old neonates from the Wayne County Health, Environment, Allergy & Asthma Longitudinal Study (WHEALS) who had atopy and/or asthma outcomes in childhood available, had previously undergone fecal microbiota profiling [1], and had more than 50 mg of stool and 10 ng of extracted fecal DNA remaining (n=41; atopic=7; asthmatic=8; atopic asthmatic=4). 12,13 DiHOME was present in all neonatal stool, but was detected at significantly higher concentrations in the stool of neonates who subsequently developed atopy and/or asthma (FIG. 3A). In contrast the concentration of 9,10 DiHOME did not significantly differ between the two groups (FIG. 6A).

Figure 3B:
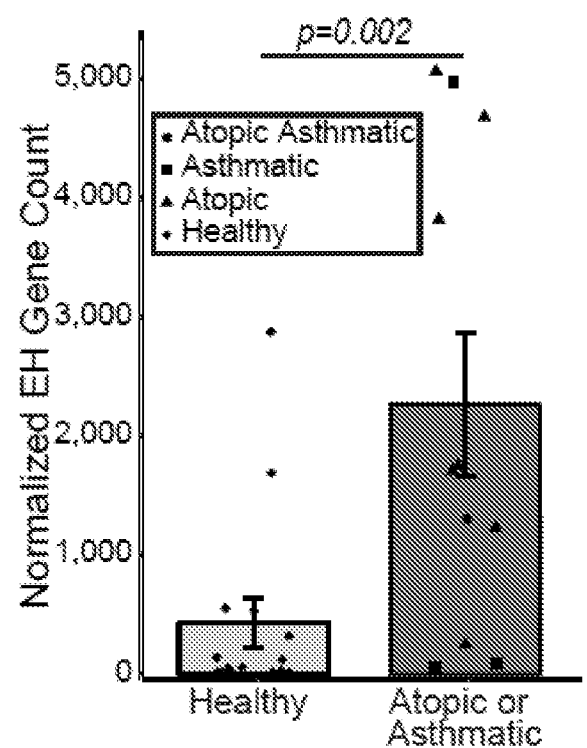
Figure 3C:
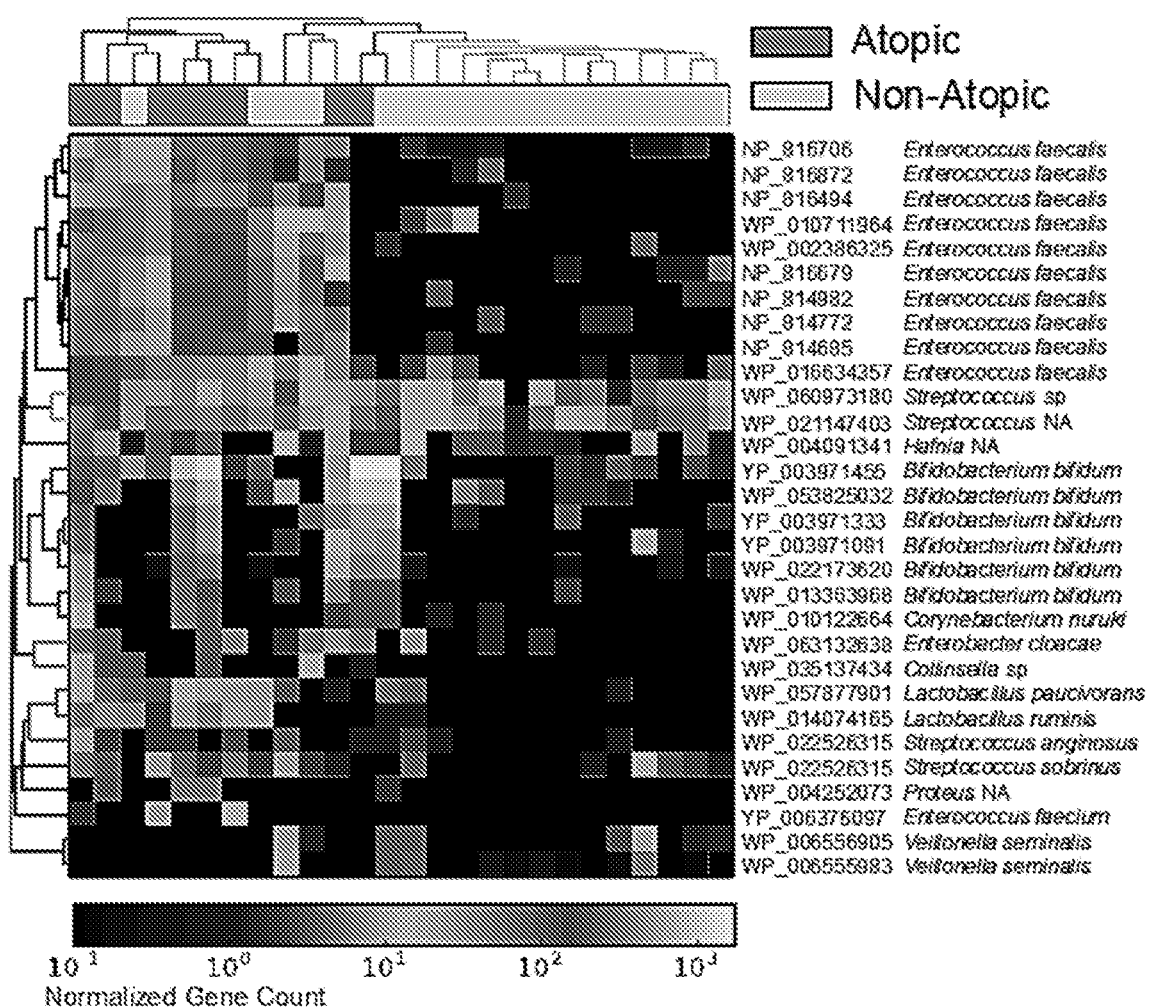

12,13 DiHOME is a terminal metabolic product of linoleic acid, which is initially converted to 12,13 EpOME either spontaneously via oxidation or enzymatically via a cytochrome P450 epoxygenase [20]; 12,13 EpOME is then converted to 12,13 DiHOME via an epoxide hydrolase (EH); an enzyme encoded by humans, bacteria and fungi [21-23]. To identify potential sources of 12,13 DiHOME in the stool of high-risk neonates, 26 neonatal stool samples from the WHEALS cohort underwent shotgun metagenomic sequencing. A database of known bacterial (~73,000), fungal (~5,000), and human (~50) EH genes was assembled and used in conjunction with ShortBred, a bioinformatics tool [24], to probe the neonatal metagenomic data for sequence reads with EH homology. No fungal or human EH genes were detected; however, approximately 1,400 bacterial EH genes were identified. Bacterial EH genes are significantly more abundant in the stool of neonates who developed atopy and/or asthma (FIG. 3B), the thirty most abundant of which are primarily encoded by *Enterococcus faecalis, Streptococcus, Bifidobacterium bifidum*, and *Lactobacillus* strains (FIG. 3C).

To evaluate whether these putative EH genes are capable of hydrolyzing epoxides and producing 12,13 DiHOME, a cell-based assay was developed. A subset (n=11) of the most frequently detected putative bacterial EH genes, with ≥75% of homologous EH marker regions identified in the metagenomic data, were selected (Table 5).

TABLE 5

Conserved marker regions for the top differential epoxide hydrolase genes found in the metagenomic sequencing data. Fold changes were calculated comparing neonates who developed atopy to those who did not. P-values were generated using a Wilcox Test and adjusted using the Benjamini & Hochberg (BH) correction. The frequency of conserved markers found in the metagenomic data were used to select candidate genes for further analysis.

| Gene | Taxa | Fold Change | Adjusted p-value | Markers | % Markers |
|---|---|---|---|---|---|
| NP 814685 | *Enterococcus faecalis* | 4.79 | 0.0237 | 3 of 4 | 75% |
| NP 814772 | *Enterococcus faecalis* | 3.85 | 0.0237 | 5 of 6 | 83% |
| NP 814872 | *Enterococcus faecalis* | 4.03 | 0.0237 | 4 of 5 | 80% |
| NP 814982 | *Enterococcus faecalis* | 3.92 | 0.0237 | 5 of 6 | 83% |
| NP 816494 | *Enterococcus faecalis* | 4.12 | 0.0237 | 2 of 2 | 100% |
| NP 816679 | *Enterococcus faecalis* | 3.73 | 0.0237 | 4 of 6 | 67% |
| NP 816706 | *Enterococcus faecalis* | 4.45 | 0.0237 | 3 of 5 | 60% |
| WP 002386325 | *Enterococcus faecalis* | 3.29 | 0.0237 | 6 of 7 | 86% |
| WP 010711964 | *Enterococcus faecalis* | 3.9 | 0.0237 | 6 of 7 | 86% |
| WP 016634357 | *Enterococcus faecalis* | 4.21 | 0.0237 | 14 of 15 | 93% |
| WP 021147403 | *Streptococcus* | 2.16 | 0.042 | 7 of 9 | 78% |
| WP 060973180 | *Streptococcus* sp | 2.17 | 0.038 | 4 of 6 | 67% |
| WP 010122664 | *Corynebacterium nuruki* | 5.33 | 0.0131 | 1 of 7 | 14% |
| WP 013363968 | *Bifidobacterium bifidum* | 5.05 | 0.004 | 1 of 1 | 100% |
| WP 022173620 | *Bifidobacterium bifidum* | 5.39 | 0.0253 | 1 of 3 | 33% |
| WP 053825032 | *Bifidobacterium bifidum* | 5.2 | 0.0262 | 6 of 6 | 100% |
| YP 003971091 | *Bifidobacterium bifidum* | 6.82 | 0.0185 | 3 of 3 | 100% |
| YP 003971333 | *Bifidobacterium bifidum* | 4.87 | 0.0393 | 5 of 5 | 100% |
| YP 003971455 | *Bifidobacterium bifidum* | 4.92 | 0.0028 | 9 of 13 | 69% |
| WP 035137434 | *Collinsella* sp | 2.52 | 0.0422 | 4 of 6 | 67% |
| WP 063132638 | *Enterobacter cloacae* | 7.33 | 0.0095 | 4 of 6 | 67% |
| WP 014074165 | *Lactobacillus ruminis* | 2.62 | 0.0093 | 1 of 9 | 11% |
| WP 057877901 | Lactobacillus paucivorans | 2.57 | 0.009 | 1 of 7 | 14% |

Figure 3D:
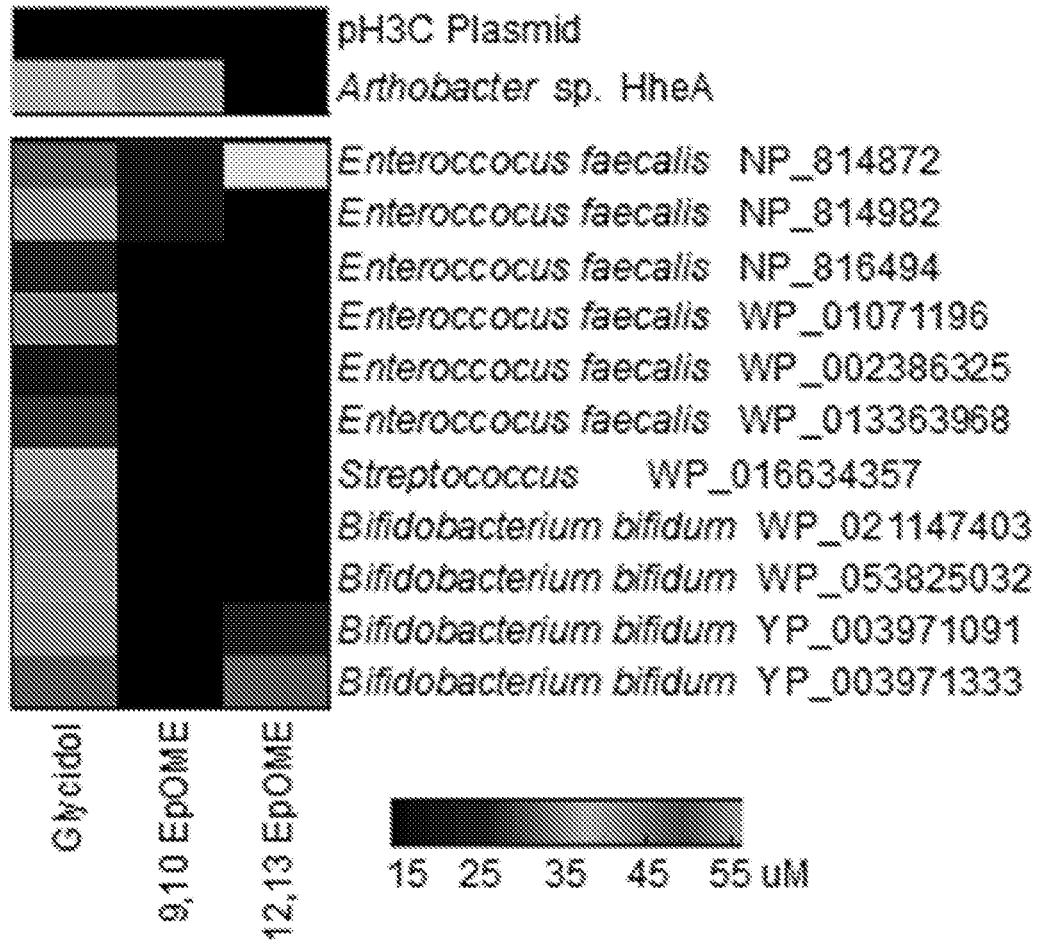

These genes were synthesized and cloned into *Escherichia coli* for expression. EH activity was measured using modifications of a previously described colorimetric assay [25]. All 11 genes were capable of hydrolyzing glycidol, a generic epoxide, to its conjugate diol, glycerol, and three could hydrolyze 9,10 EpOME to 9,10 DiHOME. However, only NP_814872 (*E. faecalis*), YP_003971091 (*B. bifidum*), and YP_003971333 (*B. bifidum*) could convert 12,13 EpOME into 12,13 DiHOME (FIG. 3D), indicating that while EH activity was common, the specific capacity to produce 9,10 or 12,13 DiHOME appeared bacterial strain specific.

Figure 3E:
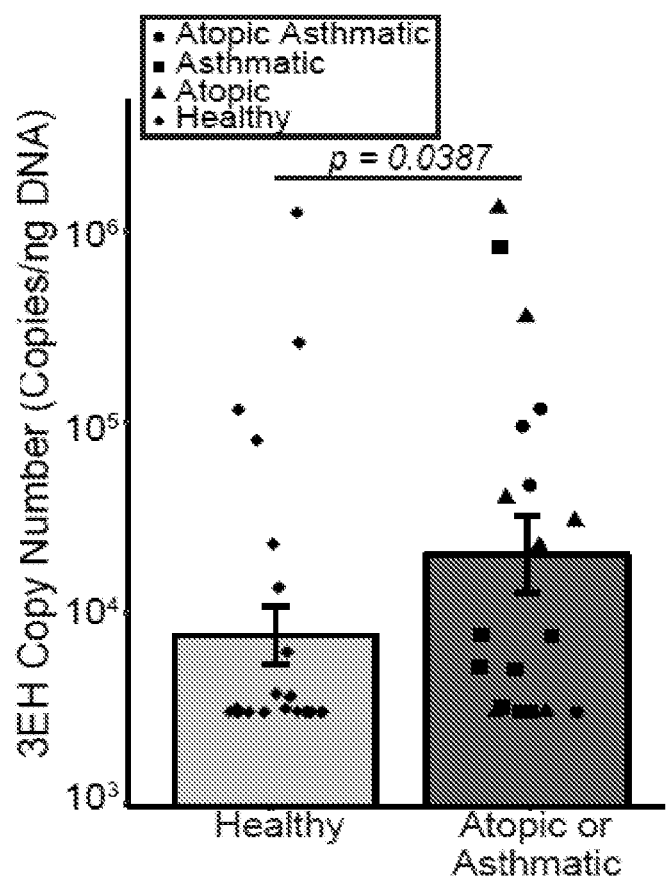
Figure 3F:
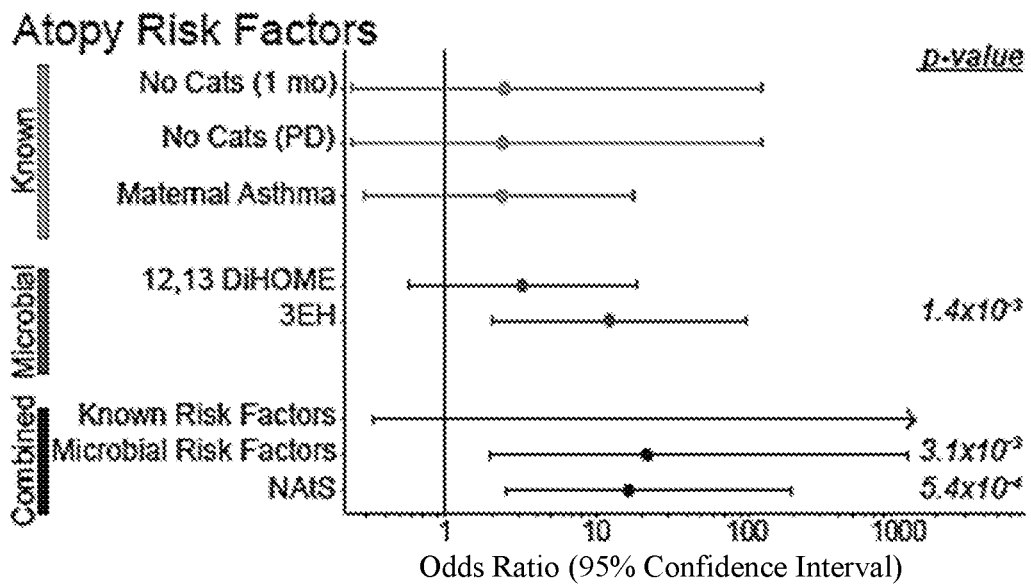
Figure 3G:
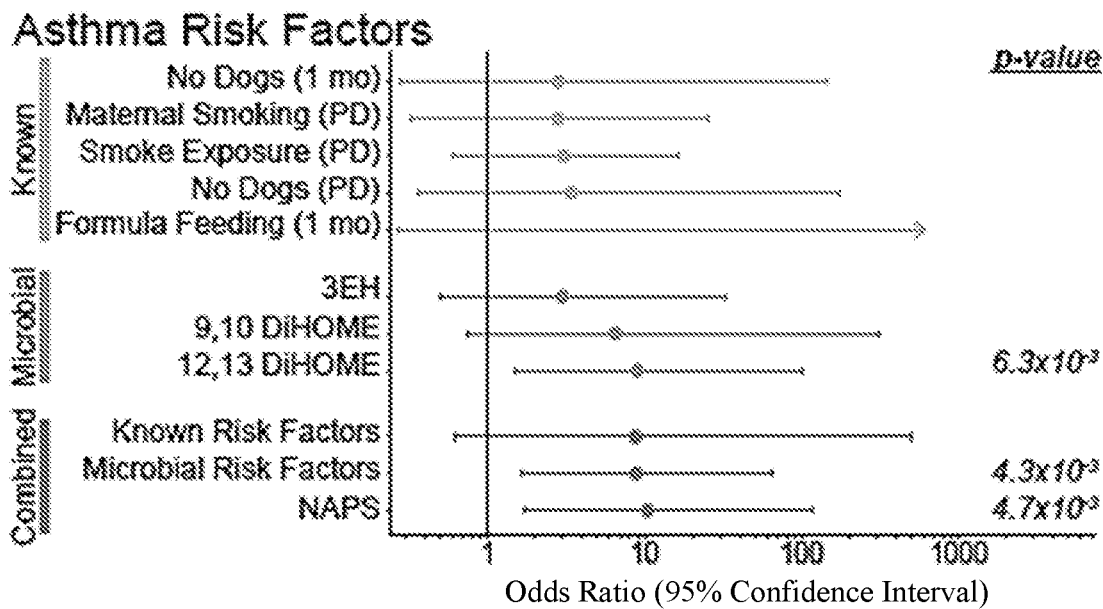
Figure 4A:
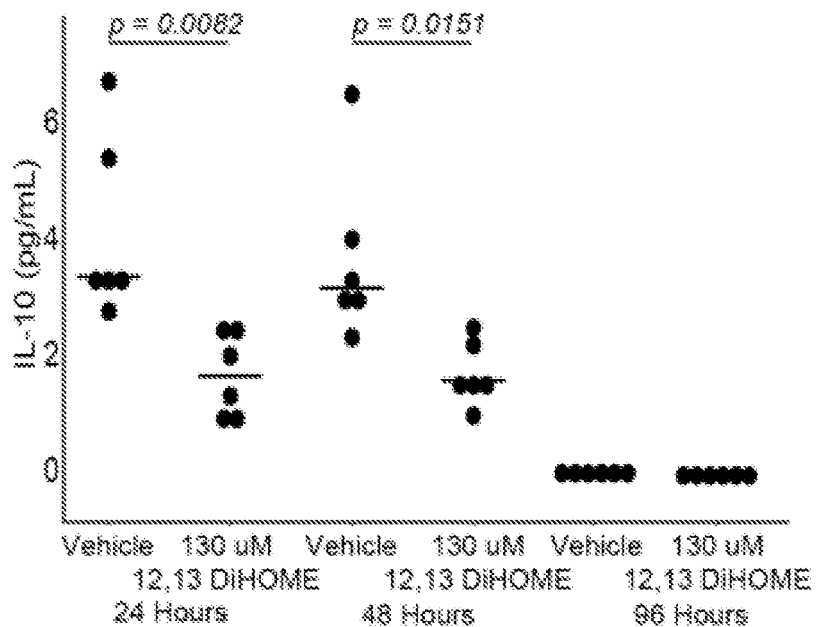
FIGS. 4A-4G show example results that illustrate that 12,13 DiHOME treatment of DCs decreased IL-10 secretion and Treg frequency without affecting cell viability. Treatment of DCs with 130 μM 12,13 DiHOME caused significant decreases in IL-10 secretion 24 and 48 hours after treatment (n=3; biological replicates=2 (▲ and ●; LME; 24 hr p=0.0082; 48 hr p=0.151) (FIG. 4A).
Figure 4B:
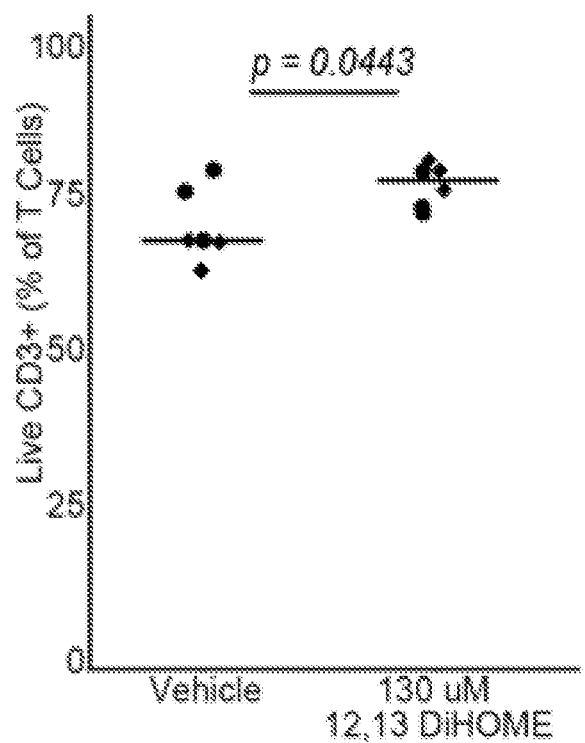
Figure 4C:
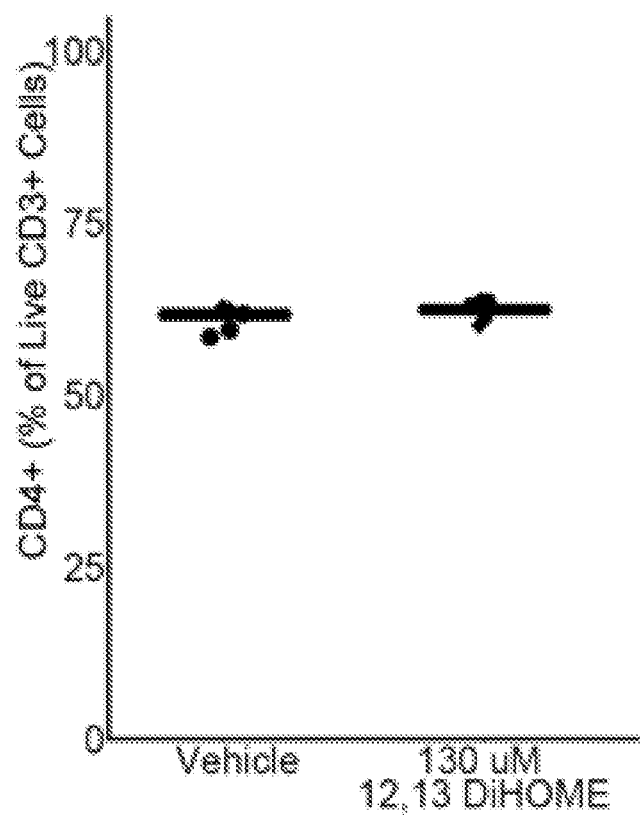
Figure 4D:
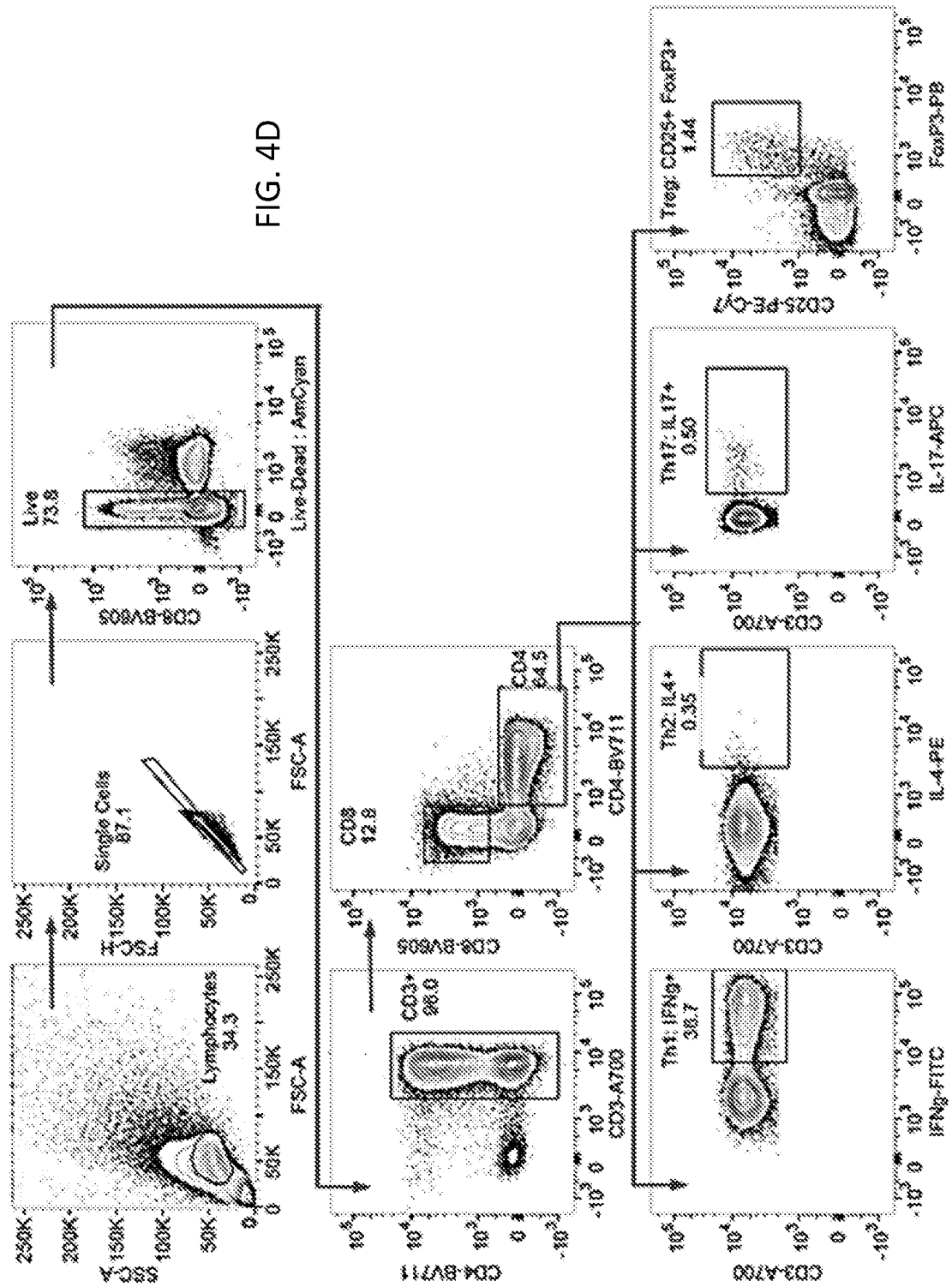
Figure 4E:
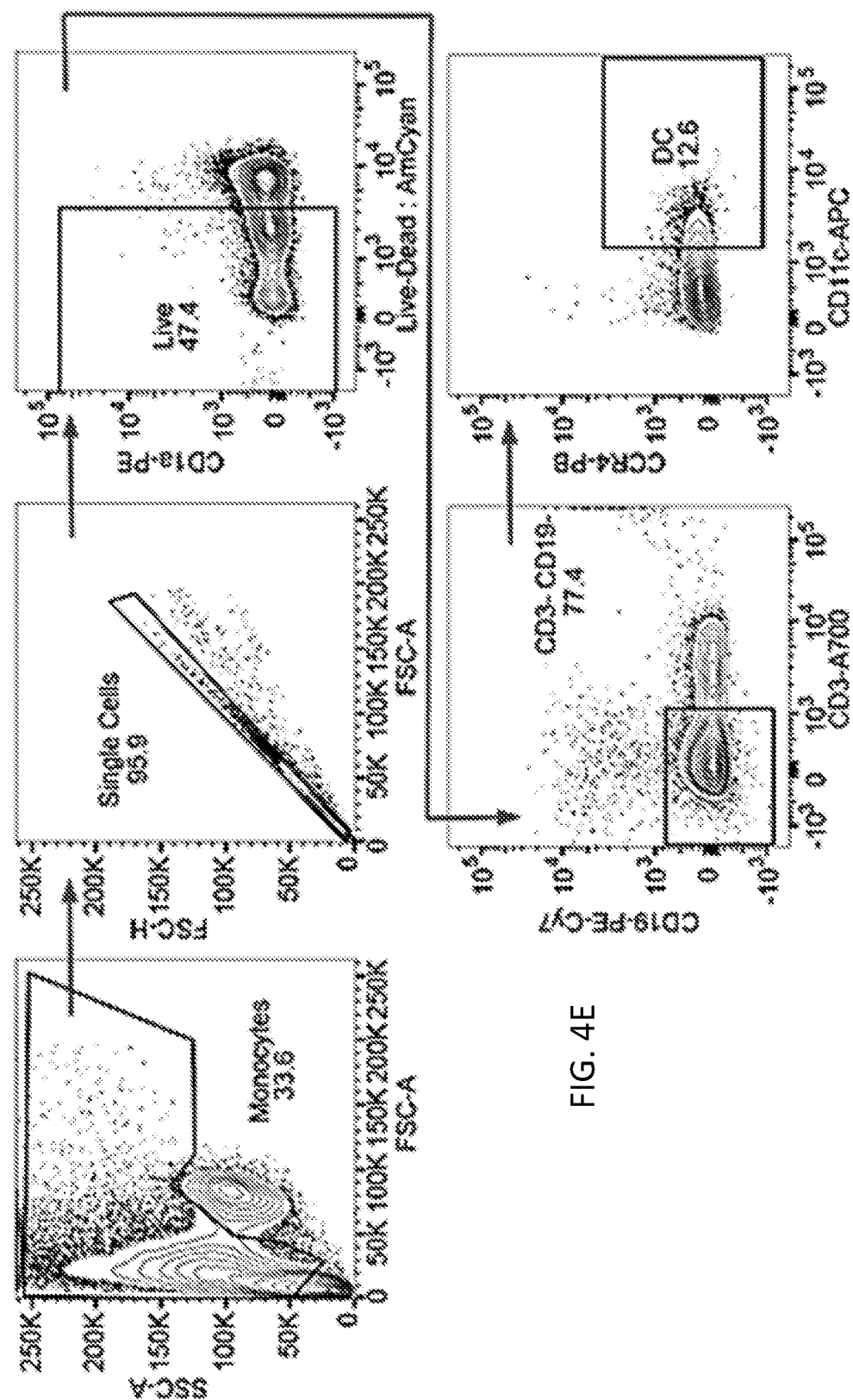
Figure 4F:
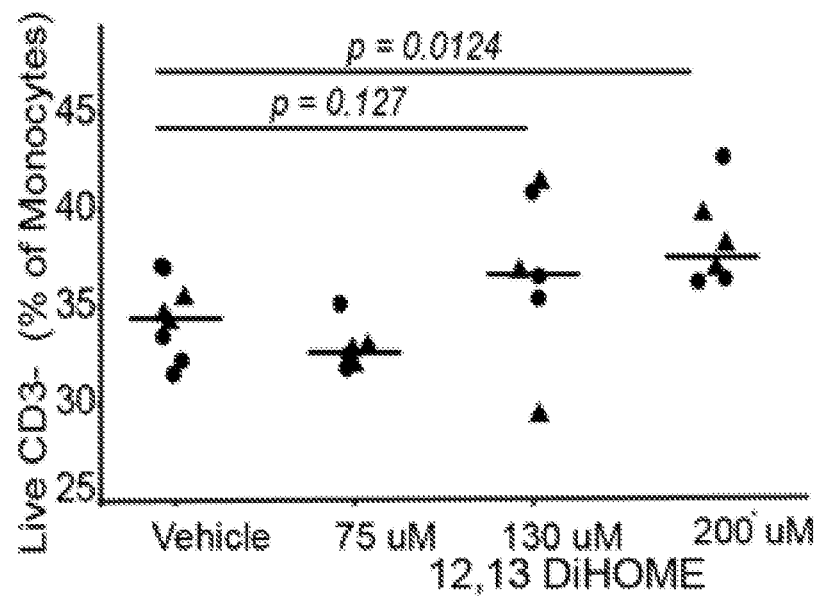
Figure 4G:
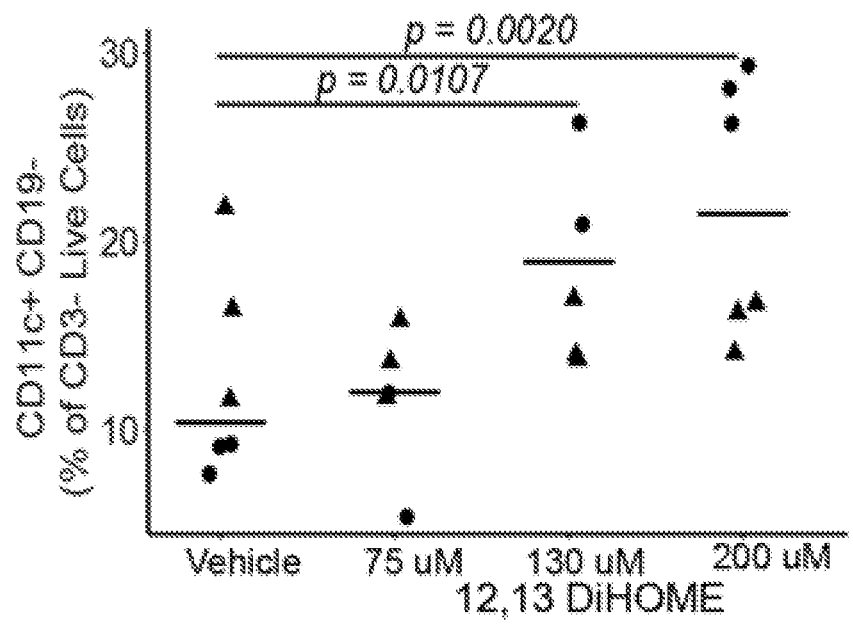
Figure 6B:
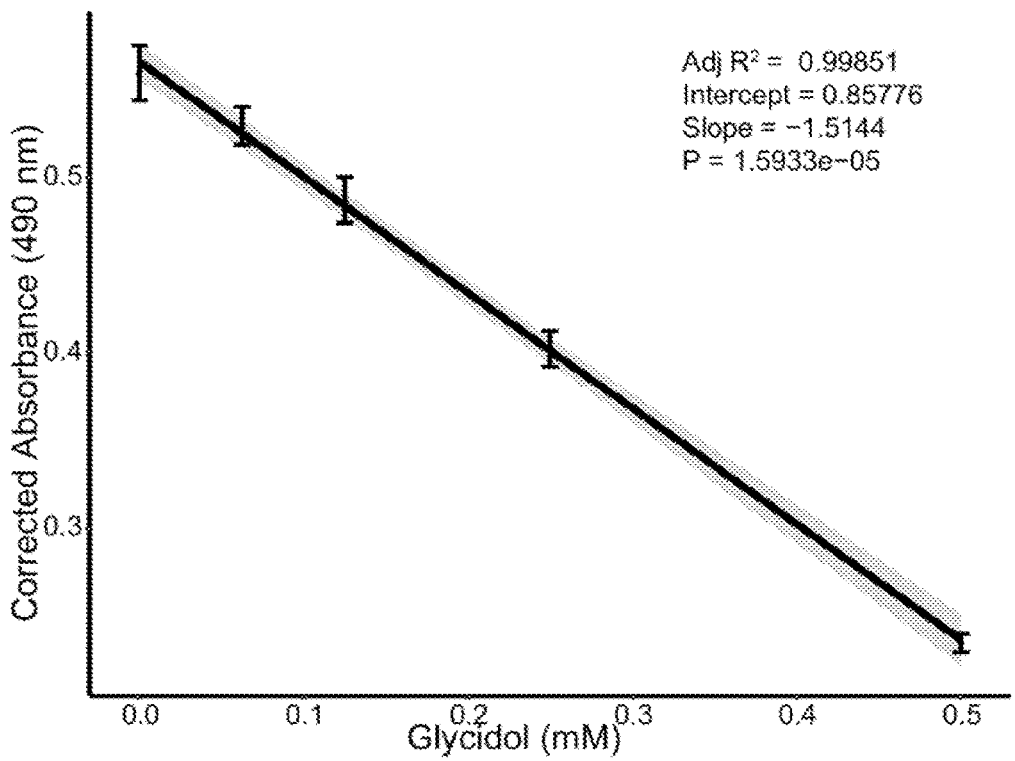
Figure 6C:
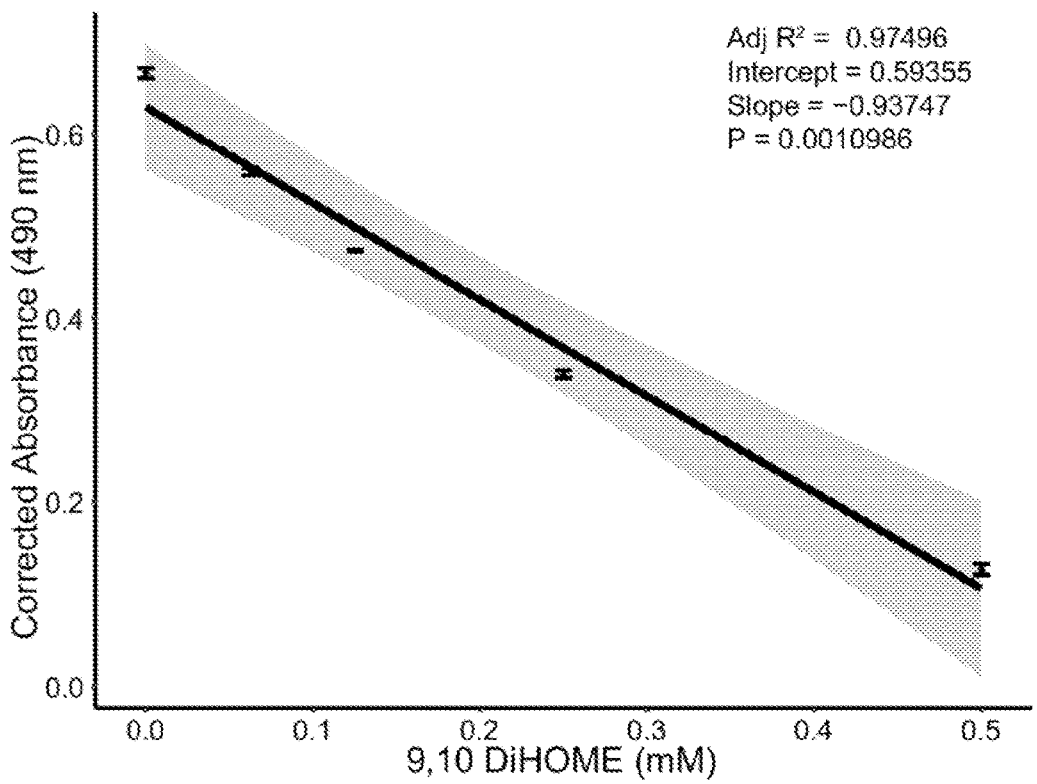
Figure 6D:
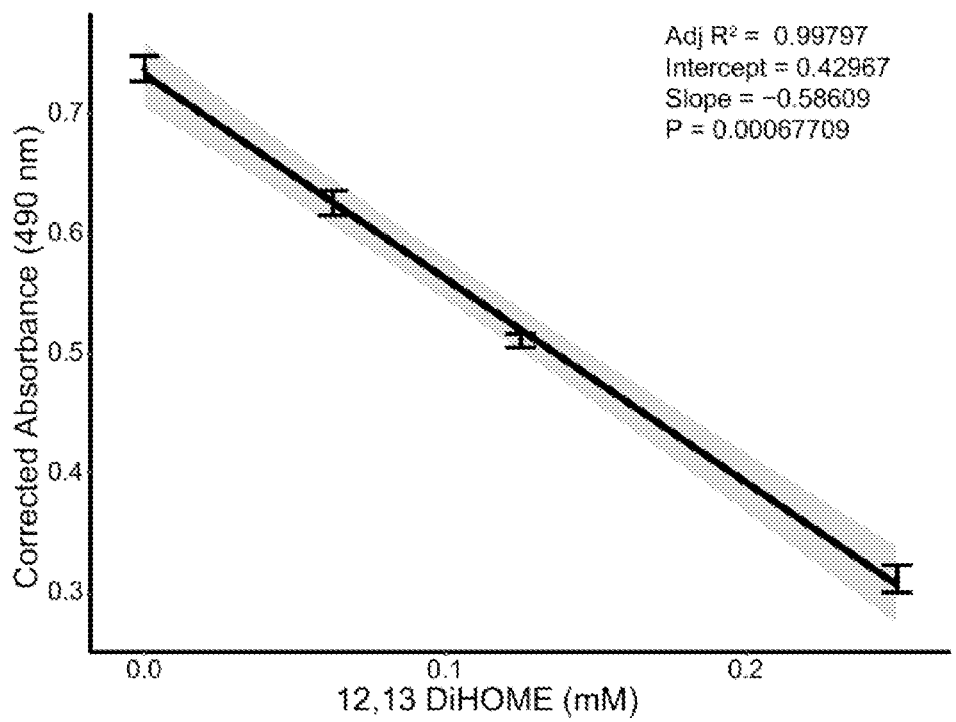
Figure 6E:
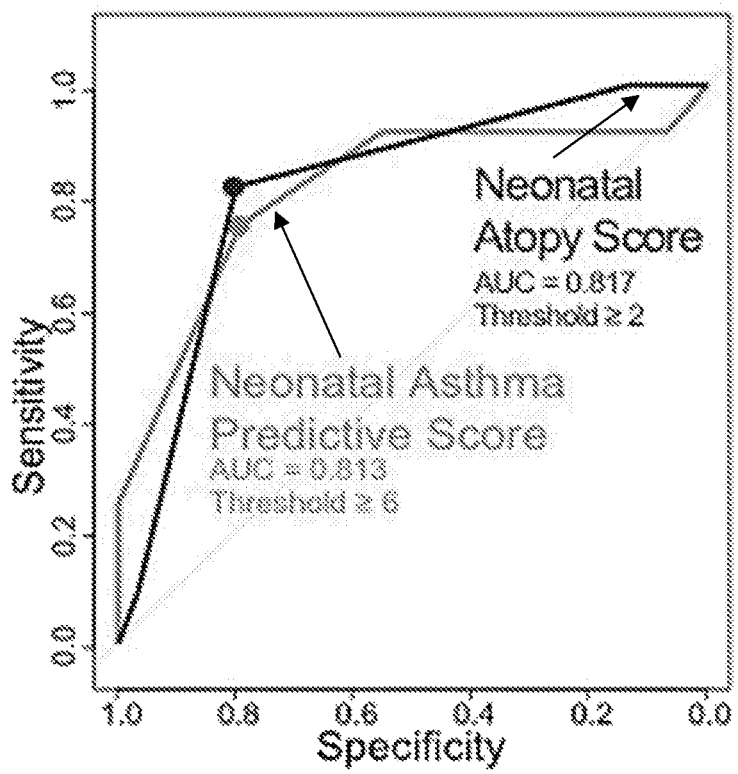

To test whether the three 12,13 DiHOME-producing bacterial EH genes (3EH) were sufficient to distinguish neonates who developed atopy and/or asthma in childhood from those who did not, we developed qPCR assays to quantify the 3EH copy number in neonatal stool. 3EH copy number was measured in the 41 stool samples analyzed by LC-MS and was significantly increased in the stool of neonates who subsequently developed atopy or asthma in childhood (FIG. 3E). We also evaluated whether high fecal oxylipin concentrations and 3EH copy number were associated with increased odds of childhood atopy or asthma. To test this, threshold values were determined using receiver-operator characteristic (ROC) analysis, and the relative odds of developing atopy or asthma were initially calculated for neonates that underwent fecal 3EH and oxylipin profiling. Elevated fecal 3EH in neonatal stool significantly increased the odds of atopy at age two (OR=12.2), while high fecal concentrations of 12,13 DiHOME significantly increased the odds of asthma at age four (OR=8.96; FIG. 3F-G). We next hypothesized that these microbial factors coupled with known early-life risk factors would further increase the relative odds of developing allergic disease in childhood. To test this hypothesis we identified several known early-life risk factors [26-29] associated with increased likelihood of either atopy at age two or asthma at age four years in our subset of WHEALS participants (n=41). These known risk factors were combined with our newly identified microbial risk factors. ROC curves were generated for all possible combinations, and the area under the curve was used to compare them. We found that atopy at age two was most accurately predicted by two or more of the following criteria: 3EH copy number>13,318 copies $ng^{-1}$ of fecal DNA; maternal asthma; and no cat exposure at one month (OR=16.4), while asthma at age four was most accurately predicted by six or more of the following criteria: fecal 12,13 DiHOME>398 ng $g^{-1}$; fecal 9,10 DiHOME>425 ng $g^1$; 3EH>1,598 copies $ng^{-1}$ of fecal DNA; no dog exposure pre-delivery; no dog exposure at one month; maternal smoking during pregnancy; and formula feeding (OR=10.4; FIG. 6E. We deemed these combined scoring systems the neonatal atopy score (NAtS) and the neonatal asthma predictive score (NAPS), respectively, and found that a NAtS≥2 or a NAPS≥6 increased the relative odds of atopy or asthma respectively when compared to individual microbial or known risk factors (FIG. 3F-G). Our findings indicated that combining objective neonatal microbial risk factors with known very early-life environmental exposures not only permitted identification of neonates at risk of developing atopy and asthma years in advance of clinical symptoms, but also identified microbial and host targets for early intervention and disease prevention.

Methods.

Human Immune Assays.

IL-10 secretion was measured using a cytometric bead array (BD Biosciences, San Jose, CA). Human DCs were isolated from the peripheral blood mononuclear cells (PBMCs) of two healthy human donors as previously described [1] and treated with increasing concentrations of 12,13 DiHOME (Cayman Chemical, Ann Arbor, MI) solubilized in 0.2% dimethylsulfoxide (DMSO). Supernatant was collected after 24 hours. IL-10 concentrations were determined according to the manufacturer's instructions.

Co-culture of human DCs and T cells in the presence of 12,13 DiHOME was performed as previously described [1]. In brief, DCs were isolated from the PBMCs of two healthy human donors and treated for five days with 130 μM 12,13 DiHOME solubilized in 0.2% DMSO or vehicle (0.2% DMSO) in the presence of 20 ng mL$^{-1}$ IL-4 (R&D Systems, Minneapolis, MN) and 10 ng mL$^{-1}$ GM-CSF (R&D Systems, Minneapolis, MN). Fresh treatment media was added every 48 hrs throughout the course of the study. Eighteen hours prior to co-culture, DCs were stimulated with 10 ng mL$^{-1}$ TNFα, IL1β, and IL-6 (Peprotech, Rocky Hill, NJ) and 1 mM prostaglandin E2 (Stemcell Technologies, Cambridge, MA). DCs were subsequently washed and co-cultured with autologous T cells in the presence of 10 ng mL$^{-1}$ anti-CD28 and anti-CD49d (BD Bioscience, San Jose, CA).

After five days of co-culture, T cell subsets were analyzed by flow cytometry. To assess cytokine secretion, cells were stimulated for 16 hrs with Phorbol Myristate Acetate-Ionomycin (ACROS, Morris Planes, NJ) and GolgiPlug (Gplug; BD Biosciences, San Jose, CA). Antibodies used for staining are summarized in Table 6. Flow cytometry data was collected on a BD LSR II flow cytometer. Helper T cell subsets were defined as follows: Th1 CD3+CD4+IFNγ+; Th2 CD3+CD4+IL-4+; Th17 CD3+CD4+IL-17+, Treg CD3+CD4+CD25+FoxP3+. The human T cell gating strategy can be found in FIG. 4D.

TABLE 6

Listing of antibodies used for staining in Example 2.

| Antibody | Clone | Vendor | Dilution |
|---|---|---|---|
| Human T Cell Panel | | | |
| anti-CD4 | L200 | BD | 1:100 |
| anti-CD25 | M-A251 | BD | 1:25 |
| LIVE-DEAD Aqua | | Life Technologies | 1:300 |
| anti-CD3 | SP34-2 | BD | 1:100 |
| anti-FoxP3 | PCH101 | eBioscience | 1:20 |
| anti-IFNg | B27 | BD | 1:200 |
| anti-IL4 | 7A3-3 | Miltenyi Biotec | 1:20 |
| anti-IL-17 | 64DEC17 | eBioscience | 1:20 |
| Human DC Panel | | | |
| anti-CD11c | B-ly6 | BD | 1:50 |
| anti-CD19 | SJ25C1 | BD | 1:100 |
| LIVE-DEAD Aqua | | Life Technologies | 1:300 |
| anti-CD3 | SP34-2 | BD | 1:100 |
| anti-CCR7 | 3D12 | BD | 1:35 |
| anti-CD80 | 2D10 | Biolegend | 1:50 |
| anti-CD86 | 2331 | BD | 1:50 |
| anti-HLA-DR | G46-6 | BD | 1:50 |
| anti-CD36 | CB38 | BD | 1:50 |
| Anti-CD1a | HI149 | BD | 1:40 |

Human DC maturation was assessed by flow cytometry. PBMCs were isolated from two healthy human donors using Ficoll-Hypaque gradient centrifugation as previously described [1] and cultured for five days in the presence of 20 ng mL$^{-1}$ IL-4 and 10 ng mL$^{-1}$ GM-CSF. Monocytic DCs (DCs) were defined as CD3-CD19-CD11c+. The DC gating strategy can be found in FIG. 4E.

Gene expression was examined in human DCs. DCs were isolated as described above and treated for two days with 130 μM 12,13 DiHOME. Cells were washed twice in PBS, and RNA was extracted using the RNAqueous™ Micro Kit (Ambion, Foster City, CA). The RT2 First Strand Kit (Qiagen, Germantown, MD) was used to synthesize cDNA, and expression of CD36, CD1a, FABP4, and HADH relative to beta-actin was measured using Power SYBR Green PCR Master Mix (ThermoFisher Scientific, Waltham, MA) and a QuantStudio 6 Real-Time PCR system (ThermoFisher Scientific, Waltham, MA). Primers are summarized in Table 7.

TABLE 7

Listing of primers used in Example 2.

| Gene | Primer | SEQ ID NO: |
|---|---|---|
| Human qPCR Primers | | |
| HADH | Forward | 3 |
| HADH | Reverse | 4 |
| FABP4 | Forward | 5 |
| FABP4 | Reverse | 6 |
| CD1a | Forward | 7 |
| CD1a | Reverse | 8 |
| CD36 | Forward | 9 |
| CD36 | Reverse | 10 |
| Beta-actin | Forward | 11 |
| Beta-actin | Reverse | 12 |
| Mouse qPCR Primers | | |
| IL1a | Forward | 13 |
| IL1a | Reverse | 14 |
| IL1b | Forward | 15 |
| IL1b | Reverse | 16 |
| TNF | Forward | 17 |
| TNF | Reverse | 18 |
| GAPDH | Forward | 19 |
| GAPDH | Reverse | 20 |
| Bacterial EH qPCR Primers and Probes | | |
| NP_814872 | Forward | 21 |
| NP_814872 | Reverse | 22 |
| NP_814872 | Probe | 23 |
| YP_003971091 | Forward | 24 |
| YP_003971091 | Reverse | 25 |
| YP_003971091 | Probe | 26 |
| YP_003971333 | Forward | 27 |
| YP_003971333 | Reverse | 28 |
| YP_003971333 | Probe | 29 |

Luciferase Assay

A modified PPARγ luciferase assay was performed as described in Ye et. al. [33]. A PPRE-luciferase reporter plasmid, PPRE X3-TK-luc from Bruce Spiegelman (Plasmid #1015; Addgene, Cambridge, MA), and a PPARγ overexpression plasmid, pGST-PPARgamma from Bert Vogelstein (Plasmid #16549; Addgene, Cambridge, MA), were ordered from Addgene and purified with the Plasmid Plus Maxi Kit (Qiagen, Germantown, MD). Raw264.7 cells grown in R10 media (Roswell Park Memorial Institute (RPMI) media 1640 with 10% heat-inactivated Fetal Bovine SerμMand 2 mM L-glutamine and 100 U mL$^{-1}$ penicillin—streptomycin) were transfected with the PPRE-reporter, PPARγ, and Renilla luciferase plasmid DNA in a 1:20:40 ratio, using 50 ng/well of reporter plasmid DNA. Fugene HD Transfection reagent (Promega, Madison, WI) was combined with plasmid DNA in a 4:1 ratio, and the total volume was brought to 5 μL/well with RPMI. The transfection mixture was gently combined with dilute Raw264.7 cells and plated in black, clear-bottom, 96-well plates at a density of 50,000 cells per well. Twenty-four hours after transfection, cells were treated with 12,13 DiHOME, Rosiglitazone, or GW1929 (Cayman Chemical, Ann Arbor, MI) solubilized in 0.1% DMSO. Twenty-four hours after treatment luciferase and Renilla luminescence were measured using the Dual-Glo Luciferase Assay kit (Promega, Madison, WI) on a Cytation 3 plate reader (BioTek Instruments, Winooski, VT).

Animal Models.

Six-week-old female C57B6 mice were obtained from Jackson Laboratories (Sacramento, CA). Mice were treated on days 1, 2, 3, 14, and 21 with 30 mg kg$^{-1}$ 12,13 DiHOME solubilized in 10% DMSO or vehicle (10% DMSO) by peritoneal injection. Three hours after injection, mice were challenged intra-tracheally with either PBS or CRA (20,000 PNU mL$^{-1}$; Greer, Lenoir, NC). Twenty-four hours after the final challenge mice were anesthetized, injected retro-orbitally with 100 μL CD45-APC (1:10), allowed to recover from anesthesia, and subsequently sacrificed. Lungs and plasma were collected. Serum was isolated, and serum IgE levels were measured using a Mouse IgE ELISA Max kit (Biolegend, San Diego, CA).

Lungs were sent to the Mouse Pathology Core at UCSF for H&E staining of paraffin-embedded tissue sections. Two bronchioles and two vessels from each stained tissue section were scored on a 0-4 scale with 0, representing structures with no inflammatory infiltrates; 1, representing few inflammatory cells; 2, representing a ring 1 cell-layer wide; 3, representing a ring 2-4 cells wide; and 4, representing a ring of inflammatory cells more than 4 cells wide. Each structure was scored by two blinded-individuals, and scores were averaged for each animal. Cell counts were determined for each structure. In brief, the ImageJ freehand selection tool was used to trace the perimeter of each bronchiole and vessel. The area extending beyond the perimeter of the vessel was cleared, and the color threshold of the image was adjusted using the default method with the following parameters: hue=0-255, saturation=0-255, brightness=130-255, threshold color=white, background=dark, color space=HSB. The image was converted to an 8-bit grey scale, and the threshold was adjusted using the B&W defaults and a range of 0-150. Counts were outlined and summarized using the analyze particles window (size=0-infinity, circularity=0.0-1.00).

Figure 5A:
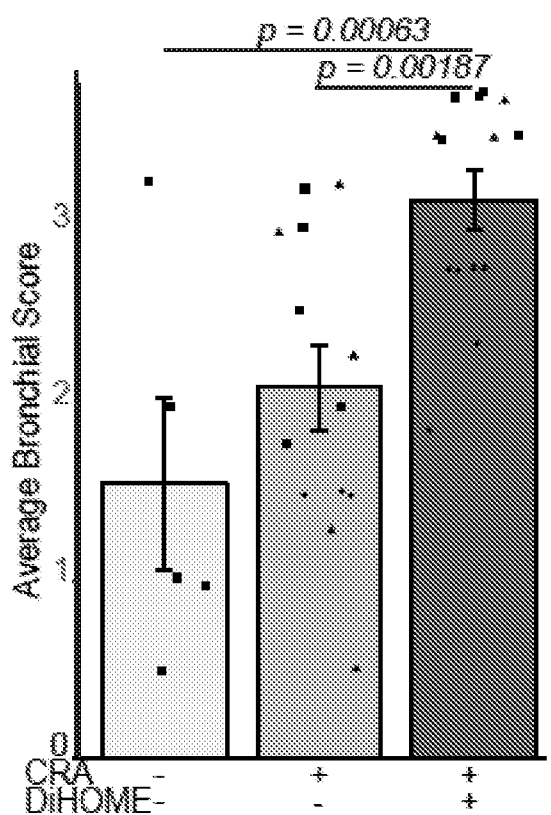
FIGS. 5A-5L show example results that illustrate that peritoneal treatment with 12,13 DiHOME exacerbated innate immune infiltration in the lungs of CRA-challenged mice. Peribronchial and perivascular infiltration were scored in H&E stained lung sections (0—no inflammatory infiltrates; 1—few inflammatory cells; 2—ring 1 cell-layer wide; 3—ring 2-4 cells wide; 4—ring>4 cells wide). 12,13 DiHOME treatment (n=14) increased the peribronchial and perivascular inflammation score compared to vehicle treated, PBS challenged [n=5; LME; p=0.00062 (bronchial), p=9.60×10$^{-7}$ (venous)] or vehicle treated, CRA-challenged [n=13; LME; p=0.00187 (bronchial), p=7.08×10$^{-5}$ (venous)] (FIGS. 5A and 5B).
Figure 5B:
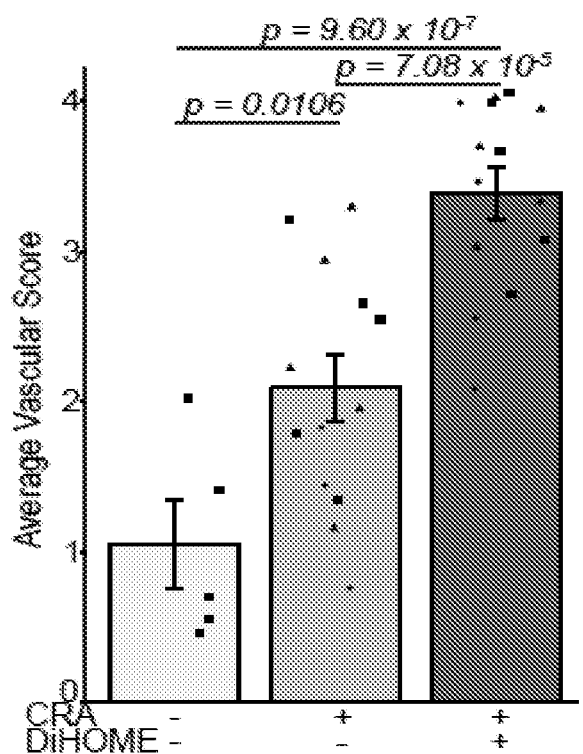
Figure 5C:
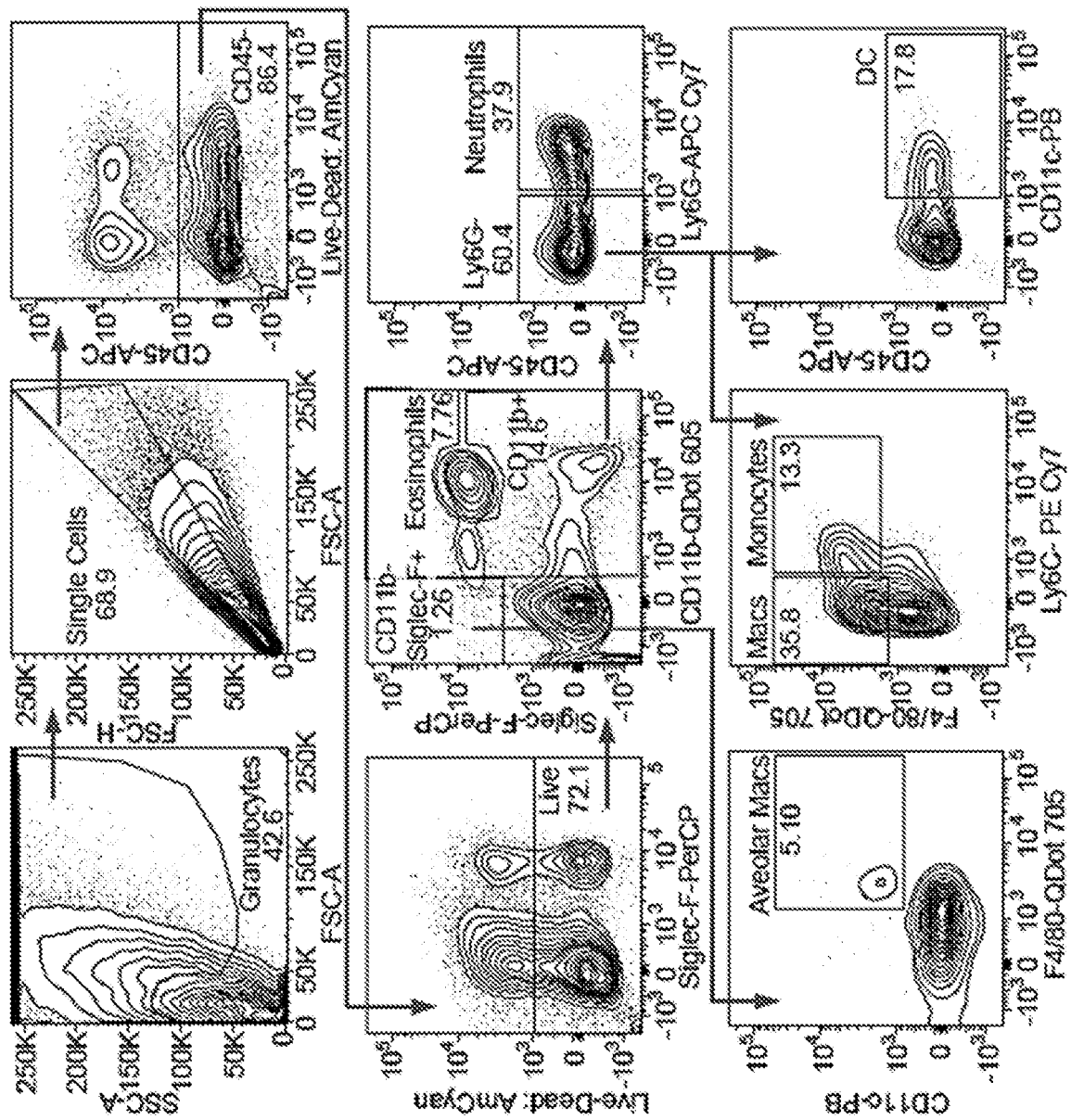
Figure 5D:
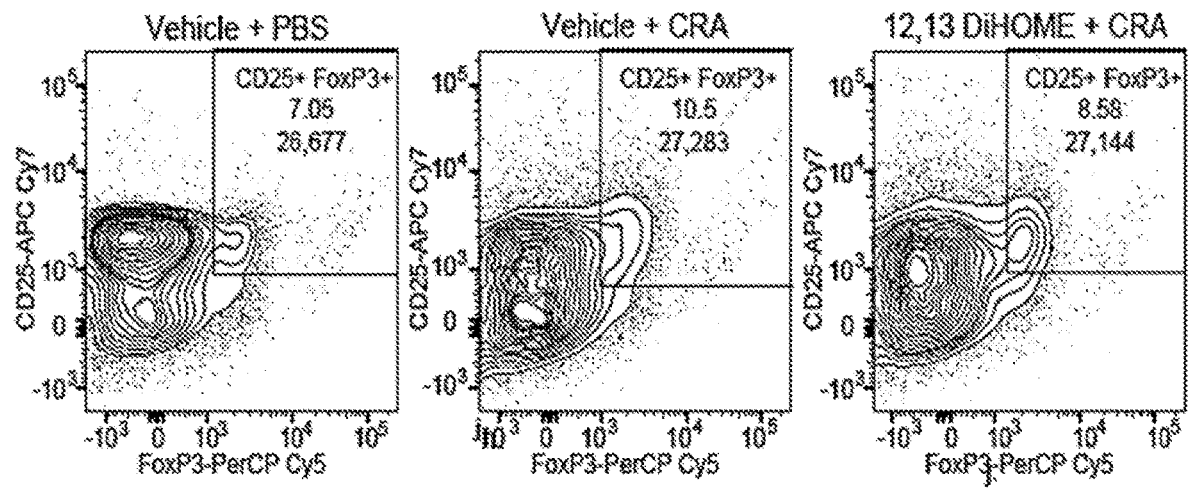
Figure 5E:
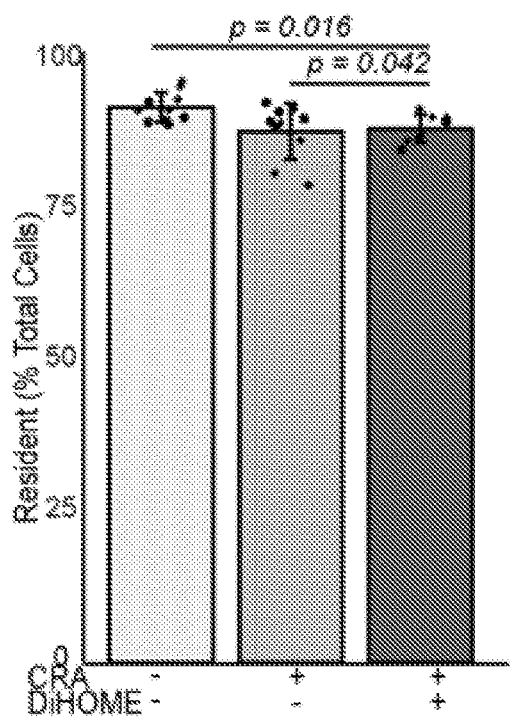
Figure 5F:
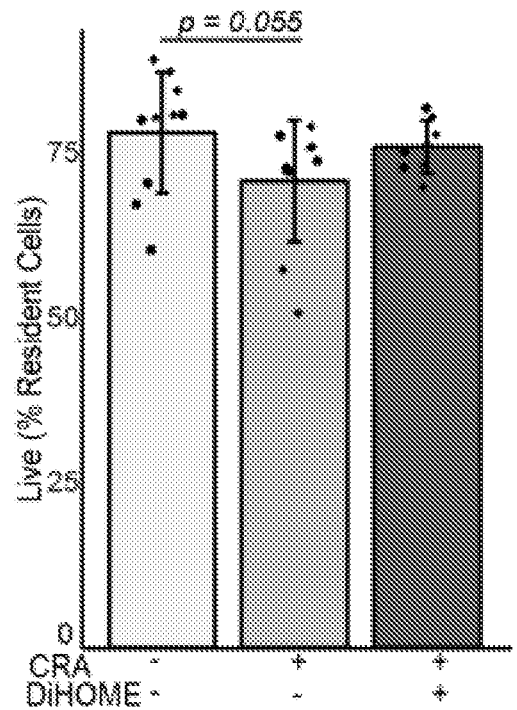
Figure 5G:
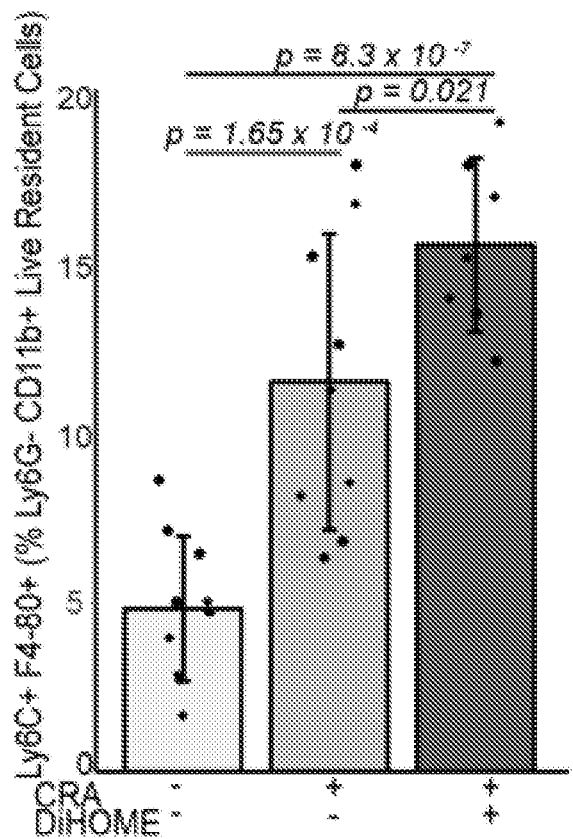
Figure 5H:
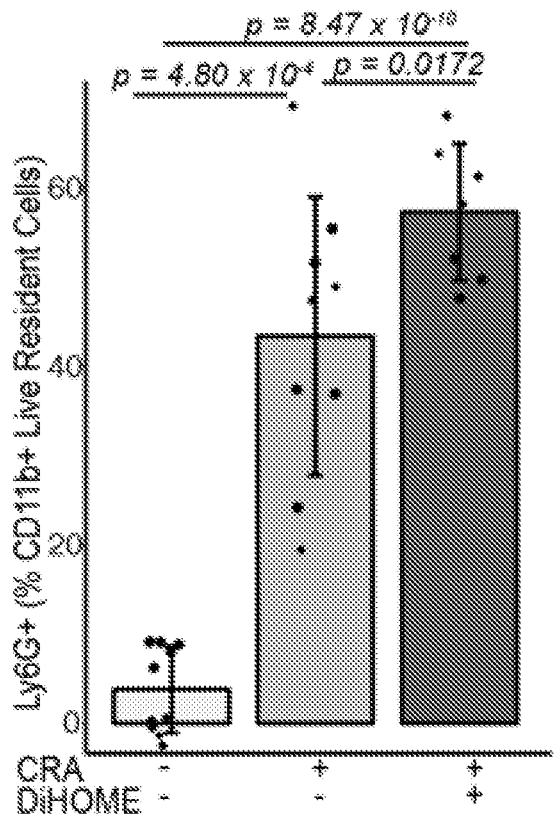
Figure 5I:
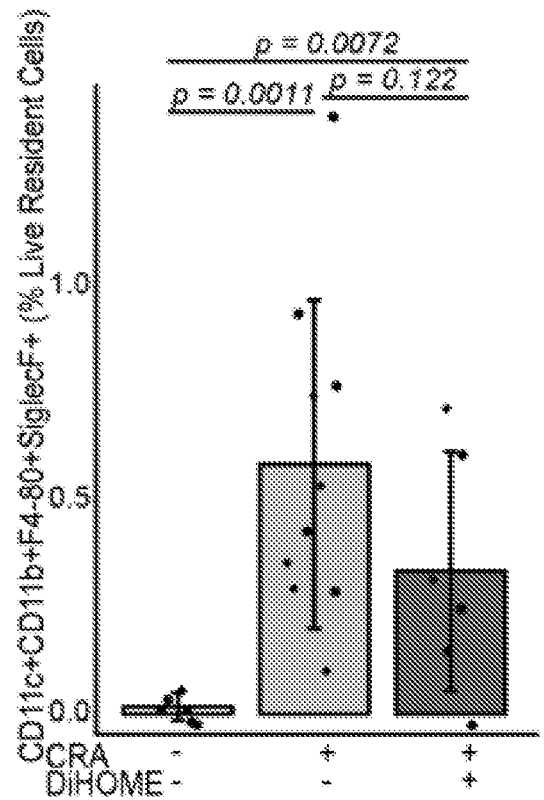
Figure 5J:
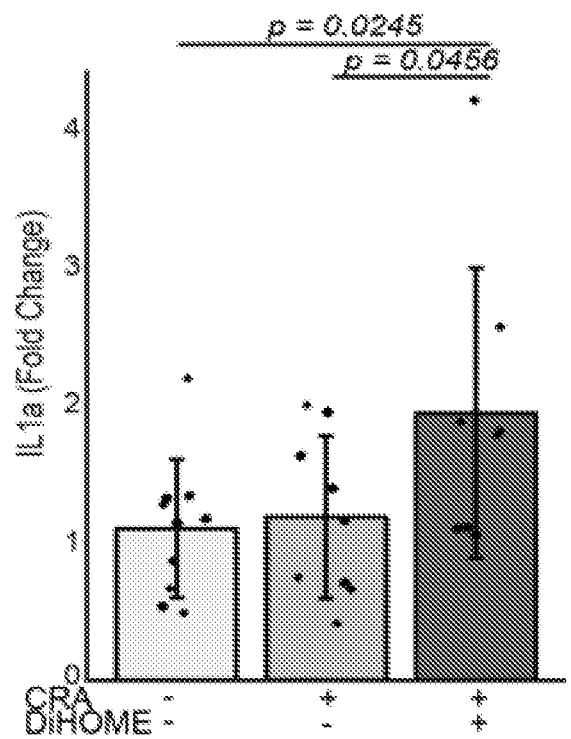
Figure 5K:
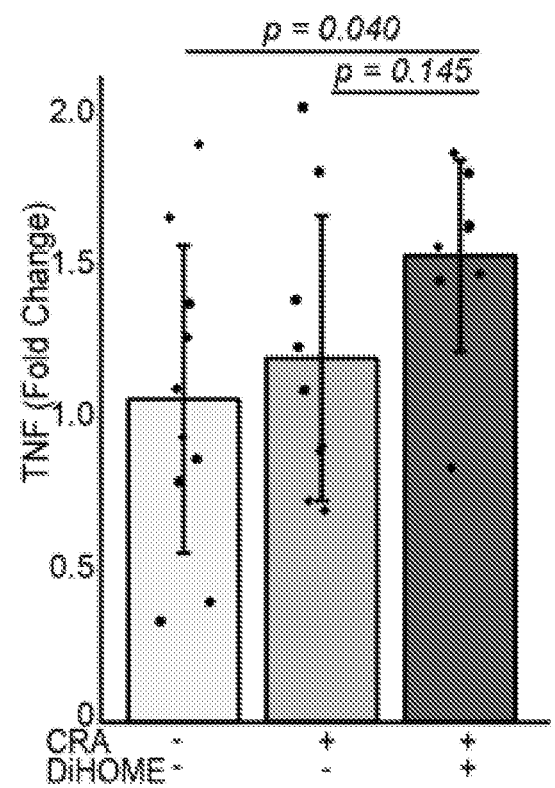
Figure 5L:
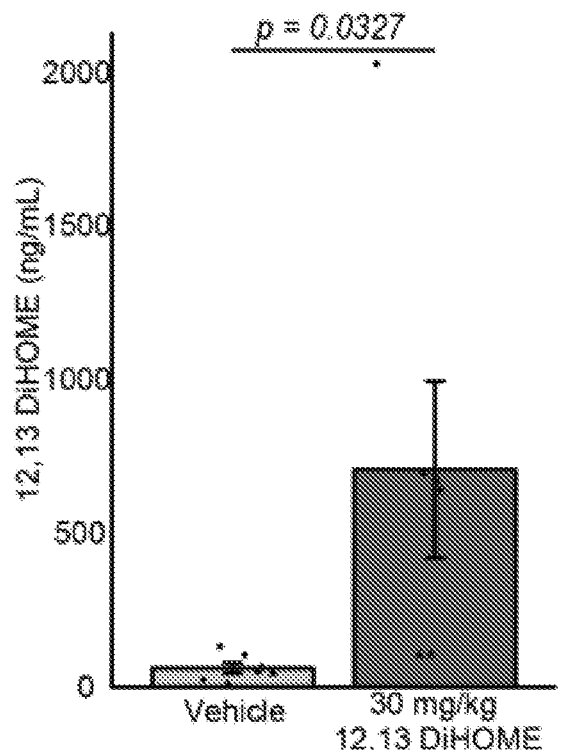

Lung cell subsets were assessed by flow cytometry. Lung tissue was manually dissected, digested with 5 mg per sample collagenase (Sigma-Aldrich, St. Louis, MO), and passed through a 40 μM filter to generate single cell suspensions. CD45− lung cells were considered resident cells and further classified as T cells (CD3+), neutrophils (Ly6G+CD11b+), monocytes (F4/80+Ly6C+Ly6G−CD11b+), and alveolar macrophages (Siglec-F+F4/80+CD11c+CD11b−). Gating strategy can be found in FIG. 5C. Regulatory T cells were identified as CD3+CD4+CD25+FoxP3+ cells. The human T cell gating strategy was also applied to mouse lungs. A representative flow plot can be found in FIG. 5D.

Lung tissue was preserved in RNAlater (Ambion, Foster City, CA). Preserved lung tissue was homogenized in Lysing Matrix E Tubes using a FastPrep 24 Homogenizer (MP Biomedicals, Santa Ana, CA) and extracted using an RNAeasy Mini Kit (Qiagen, Germantown, MD). qPCR was performed on lung tissue, as described above, to evaluate expression of IL1α, IL1β, and TNF relative to GAPDH. Primers are summarized in Table 7.

For quantification of 12,13 DiHOME in the lungs and plasma, six-week-old female C57B6 mice were purchased from Jackson Laboratories (Sacramento, CA) and treated with 30 mg kg$^{-1}$ 12,13 DiHOME solubilized in 10% DMSO or vehicle (10% DMSO) by peritoneal injection. Three hours after a single injection mice were sacrificed, and lung tissue and plasma were collected and frozen immediately in liquid nitrogen. 12,13 DiHOME was extracted from tissue and plasma using an established solid phase extraction protocol [34,35]. In brief, flash frozen tissue was massed and added to a Lysing Matrix E Tube (MP Biomedicals, Santa Ana, CA) containing 1 mL of methanol, 10 μL 0.2 mg mL$^{-1}$ BHT/EDTA, and 1.25 ng 12,13 DiHOME-D4 (Cayman Chemical, Ann Arbor, MI) then homogenized as described above. Tissue samples were spun for 10 minutes at 2125×g, and supernatant was transferred to a falcon tube containing 19 mL deionized water to generate a 5% methanol solution. Plasma samples were thawed on ice, and 10 μL 0.2 mg mL$^{-1}$ BHT/EDTA and 1.25 ng 12,13 DiHOME-D4 were added to 250 μL of thawed plasma. All samples were extracted using a Waters Oasis HLB Cartridges (60 mg of sorbent, 30 μM particle size; Waters, Milford, MA) as previously described. Extracted samples were re-suspended in methanol, and LC-MS was performed on a Thermo LTQ-Orbitrap-XL mass spectrometer equipped with an electrospray ionization (ESI) source (ThermoFisher Scientific, Waltham, MA) as previously described [18]. Linear standard curves were generated using 6 injections of 12,13 DiHOME, 9,10 DiHOME, and 12,13 DiHOME-D4 (internal standard). Peaks were manually integrated, and recovery of the internal standard was used to correct for extraction efficiency.

Study Population and Definitions.

A subset of 41 children from the Wayne County Health, Environment, Allergy and Asthma Longitudinal Study (WHEALS) cohort that had undergone fecal fungal and bacterial profiling [1] and had more than 50 mg of stool and 10 ng of extracted fecal DNA remaining from the one-month home visits were selected. The original WHEALS cohort [36] recruited pregnant women (n=1,258) between the ages of 21 and 49 from August 2003-November 2007 in southeastern Michigan. Women were considered eligible if they lived in a predefined cluster of contiguous zip codes near Detroit, Michigan, had no intention of moving out of the area, and provided informed written consent. Follow-up interviews were conducted at 1, 6, 12, 24 and 48 months after birth. The 24-month appointment occurred at a standardized study clinic, where the child underwent evaluation by a board-certified allergist. Stool samples from children were collected at one-month home visits and used in this study.

Samples were randomized before being shipped to the University of California, San Francisco (UCSF), on dry ice, where they were also stored at −80° C. until processing. Fecal DNA extracted via the modified CTAB method [37] and used for fungal and bacterial profiling was stored at −20° C. for further analysis. Latent class analysis of blood drawn during the 2-year clinic visit was used to define atopy as described by Fujimura et. al. [1]. Asthmatic children were identified by parent-reported doctor diagnosis of asthma at the 4-year interview. Maternal smoking, household smoke exposure, formula feeding, pet exposure (to either dogs or cats), and maternal doctor-diagnosed asthma were reported during pre-delivery and one month interviews with the mother.

Mass Spectrometry in Human Samples.

Fecal oxylipin (9,10 DiHOME and 12,13 DiHOME) concentrations were assessed in forty-one samples from the WHEALS cohort that had undergone fungal and bacterial profiling [1]. Oxylipins were extracted from approximately 50 mg of neonatal stool and quantified by LC-MS using the protocol described above. The concentrations of 12,13 DiHOME used in our ex vivo cell assays (~40 μg g$^1$) and in vivo animal models (~0.2 μg g$^{-1}$) were within an order of magnitude of the concentrations measured in high-risk neonatal stool (0.2-4 μg g$^{-1}$).

Metagenomic Data Analysis.

DNA from a subset of 26 stool samples from the WHEALS cohort that had previously undergone untargeted LC-MS [1] and targeted oxylipin quantification (described above) was extracted using the modified CTAB method [37] and sent to the Vincent J. Coates Genomic Sequencing Laboratory at the California Institute for Quantitative Biosciences for 150 base pair, paired-end sequencing on an Illumina HiSeq 4000 (www.qb3.berkeley.edu/gs1). Sequencing reads were quality-trimmed to Q17 with BBDuk (sourceforge.net/projects/bbmap/). A database of approximately 78,000 known bacterial (~73,000), fungal (~5,000), and human (~50) EH genes was generated using the NCBI protein database. All genes that had been tagged as "epoxide hydrolases" were included in the database. The EH database and the UniRef50 database [38] were input into the Short-Bred identify pipeline [24] and used to generate EH-specific markers. These markers were input into Shortbred quantify and were used to probe the quality-trimmed metagenomes for EH markers. Normalized marker abundance for each gene was summed and used to generate the Normalized EH gene counts in FIG. 3C. The thirty most abundant EH genes were visualized using a heatmap generated by HClust2 (bitbucket.org/nsegata/hclust2) and Canberra distance matrices.

Colorimetric Detection of EH Activity.

A subset of thirteen of the most abundant EH genes were selected for functional investigation based on the number of EH markers per gene identified in the metagenomic analysis (Table 5). Genes with fewer than 75% of markers were excluded from further analysis. The thirteen genes were structurally aligned with EH genes with known crystal structures from *Mycobacterium tuberculosis* (pdbid: 2bng), *Pseudomonas aeruginosa* (pdbid: 4d1n), and *Rhodococcus erythopolis* (pdbid: 1nww) using the Promals3D server (prodata.swmed.edu/promals3d/) (FIGS. 7A-F). Amino acids extending beyond the EH domain were trimmed. Amino acid sequences were converted into DNA sequences using the default codon usage table for *E. coli* (www.bioinformatics.org/sms2/rev_trans.html), and restriction enzyme sites for EcoRI and SalI were added to the 5'- and 3'-ends of the DNA fragment, respectively. Genes were synthesized as gBlock gene fragments by IDT (www.idtdna.com). Sequences of the synthetic constructs are summarized in Table 8.

TABLE 8

Synthetic constructs used in Example 2.
Synthetic Epoxide Hydrolase Genes

| Gene | SEQ |
|---|---|
| NP_814685 | 30 |
| NP_814772 | 31 |
| NP_814872 | 32 |
| NP_814982 | 33 |
| NP_816494 | 34 |
| WP_01071196 | 35 |
| WP_002386325 | 36 |
| WP_013363968 | 37 |
| WP_016634357 | 38 |
| WP_021147403 | 39 |
| WP_053825032 | 40 |
| YP_003971091 | 41 |
| YP_003971333 | 42 |

Synthetic genes were sub-cloned into the EcoRI and SalI sites of a pH3C plasmid, graciously provided by Dr. Oren Rosenberg, to generate proteins with an N-terminal 8×His fusion. Constructs were verified by forward and reverse sequencing of the T7 promoter (5'-TAATACGACTCAC-TATAGGG-3', SEQ ID NO:1) and terminator (5'-GCTAGT-TATTGCTCAGCGG-3', SEQ ID NO:2) performed by Quintara Bio (Berkeley, CA). Eleven of the thirteen plasmids (NP_814872, NP_814982, NP_816494, WP_01071196, WP_002386325, WP_013363968, WP_01663157, WP_021147403, WP_053825032, YP_003971091, YP_003971333) were validated and transformed into BL21(DE3) competent *E. coli* (New England Biolabs, Ipswich, MA) for expression. BL21 cells containing recombinant plasmids were streaked onto Lauria-Bertani (LB) agar plates supplemented with 50 μg mL$^{-1}$ kanamycin and grown overnight. Isolated colonies were selected and used to inoculate 200 μl, LB supplemented with 50 μg mL$^{-1}$ kanamycin and 1 mM isopropyl-β-D-1-thiogalactopyranoside (IPTG; Sigma-Aldrich, St. Louis, MO). Ninety-six well v-bottom plates containing inoculate were incubated for 18 hrs at 37° C. at 200 rpm. Following incubation, plates were centrifuged for 10 minutes at 3000 rpm and washed with 20 mM HEPES pH 7.5. Cells were re-suspended, and 40 μL of re-suspended cells per well were added to 96-well flat bottom plates. The OD600 was measured to estimate protein concentration, and 40 μL of 13 mM epoxide was added to each well. Known concentrations of the conjugate diol plated in triplicate were included on each plate and used to generate standard curves (FIGS. 6B-D). To each well, 20 μL of sodium nitrite was added (final concentration 20 mM). Plates were incubated for 1 hr at 37° C. at 200 rpm. The reaction was stopped by centrifugation for 10 minutes at 4° C. at 3000×g. To a new 96-well flat bottom plate containing 50 μL 8 mM sodium periodate (final concentration 2 mM), 85 μL of supernatant was added. Plates were incubated for 30 min at room temperature while shaking. Background absorbance at 490 nm was recorded prior to the addition of 50 μL 12 mM adrenaline (final concentration 3 mM; Sigma-Aldrich, St. Louis, MO). Plates were incubated for 5 minutes at room temperature while shaking, and the absorbance at 490 nm was recorded. BL21 cells containing the pH3C plasmid or expressing HheA, a previously characterized EH [25], were included on each plate as controls. Enzymatic activity was assessed in triplicate for three epoxides, glycidol (Sigma-Aldrich, St. Louis, MO); 9,10 EpOME; and 12,13 EpOME (Cayman Chemical, Ann Arbor, MI), and their conjugate diols; glycerol, 9,10 DiHOME, and 12,13 DiHOME.

Quantification of 3EH Copy Number by qPCR.

The abundance of the three active EH genes, NP_814872, YP_003971091, and YP_003971333, was quantified in fecal DNA extracted using the modified CTAB method [37] from all 41 neonates. Gene fragments containing the target sequences (Table 9) were ordered from IDT (www.idtdna.com/) and used to generate a standard curve. In brief, gene fragments were amplified by PCR, normalized to 2×10$^8$ copies μL$^{-1}$, and eight 1:10 serial dilutions were made for use as standards. qPCR was performed using the TaqMan Universal PCR Master Mix (Applied Biosystems, Foster City, CA) and a QuantStudio 6 Real-Time PCR system (ThermoFisher Scientific, Waltham, MA). The 3EH copy number represents the total number of copies of all three genes per nanogram of fecal DNA. Sequences of gene fragments, primers, and probes are summarized in Tables 7 and 9.

TABLE 9

Listing target sequences in Bacterial
EH genes used in Example 2.

Bacterial EH Gene Fragments

| Gene | SEQ ID NO: |
|---|---|
| NP_814872 | 43 |
| YP_003971091 | 44 |
| YP_003971333 | 45 |

Development of the Neonatal Atopy Score (NAtS) and the Neonatal Asthma Predictive Score (NAPS).

ROC analysis using the pROC package (expasy.org/tools/pROC/) of all 41 neonatal samples was used to determine threshold values for the concentrations of oxylipins (12,13 DiHOME and 9,10 DiHOME) and 3EH copy number that best predicted atopy at age two or asthma at age four. Fisher exact tests were conducted in R and used to determine the odds ratio, 95% confidence interval, and significance of tests above this threshold value. Microbial risk factors were combined with epidemiologic data collected on the WHEALS cohort pre-delivery and at the one-month interview. Risk factors with a positive likelihood ratio greater than 2 or a negative likelihood ratio less than 0.5 were included in the analysis. For asthma, out of 34 epidemiologic factors examined, three known risk factors (lack of cats pre-delivery, lack of cats at one month, maternal asthma) and two microbial risk factors (fecal 12,13 DiHOME concentration, fecal 3EH copy number) met the inclusion criteria (FIG. 3F). For asthma, five known risk factors (maternal smoking during pregnancy, household smoke exposure during pregnancy, formula feeding at one month, no dogs pre-delivery, no dogs at the one month interview) met the inclusion criteria, along with all three microbial risk factors (FIG. 3G). All risk factors were expressed as either 0 or 1, with 0 referring to the low-risk condition, and 1 referring to the high-risk condition. ROC curves and thresholds were generated for all possible combinations of risk factors. We defined the most accurate curves as those with the greatest area under the curve. The NAtS and NAPS represent the most accurate curves for our subset of the WHEALS cohort (FIG. 6E). Fisher exact tests were used to determine the odds ratio, 95% confidence interval, and significance of combined microbial or known risk factors and positive tests. Scripts used for the ROC analysis can be found on GitHub (github.com/srlevan/1213DiHOME_ROC.git).

Statistical Analysis.

Figure 2H:
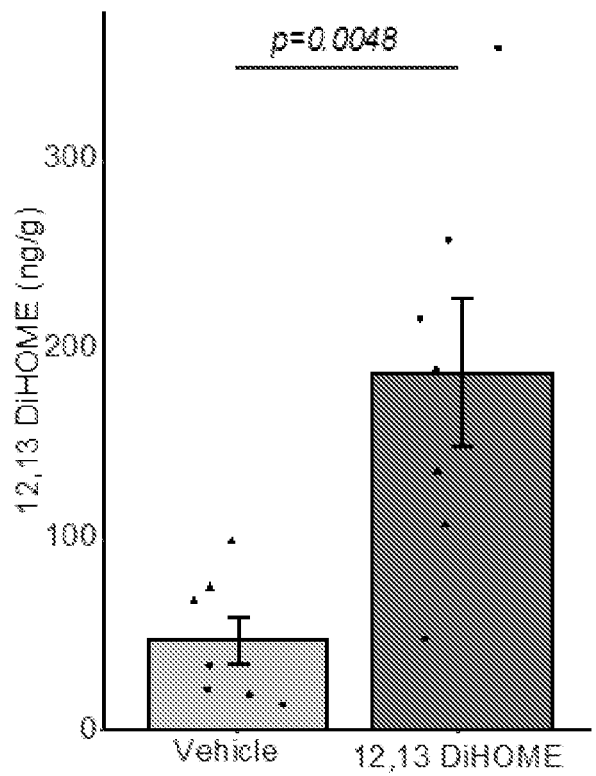

All analyses were conducted in the R statistical programming environment. All human cytokine, T cell, DC, and gene expression differences (FIG. 1, FIG. 4) were tested using a linear mixed-effects model (LME; R package lmerTest) and adjusted for donors, with the exception of the distribution of autologous T cells, which was tested using a multivariate analysis of variance (MANOVA). All comparisons made in mouse models (FIG. 2, FIG. 5) were made using a LME with the exception of 12,13 DiHOME concentration (FIG. 2H, FIG. 5I), which was compared using a Student T-test. Fecal concentrations of 12,13 DiHOME and 9,10 DiHOME, normalized EH gene count, and 3EH copy number differences were tested using a wilcox rank sum test because a Shapiro test revealed that these data sets were not normally distributed. ROC curves and confidence intervals (ci.coords) were calculated using the pROC package (cran.r-project.org/web/packages/pROC/pROC.pdf) in R. The odds ratios and p-value for known risk factors, microbial risk factors, NAPS, and NAtS (FIG. 3F-G) were determined using a fisher exact test.

Data Availability.

Metagenomic data generated in this study is available in the EMBLI repository Accession #PRJEB24006 (www.ebi.ac.uk/). R scripts used for risk analysis and statistics can be found on GitHub (github.com/srlevan/).

VI. REFERENCES

1. Fujimura, K. E. et al. Neonatal gut microbiota associates with childhood multisensitized atopy and T cell differentiation. Nat. Med. 22, 1187-1191 (2016).
2. Vangaveti, V. N. et al. Hydroxyoctadecadienoic Acids Regulate Apoptosis in Human THP-1 Cells in a PPARγ-Dependent Manner. Lipids 49, 1181-1192 (2014).
3. Byndloss, M. X. et al. Microbiota-activated PPAR-γ signaling inhibits dysbiotic Enterobacteriaceae expansion. Science 357, 570-575 (2017).
4. Khare, A., Chakraborty, K., Raundhal, M., Ray, P. & Ray, A. Cutting Edge: Dual Function of PPARγ in CD11c+ Cells Ensures Immune Tolerance in the Airways. J. Immunol. 195, 431-435 (2015).
5. Wahli, W. & Michalik, L. PPARs at the crossroads of lipid signaling and inflammation. Trends in Endocrinology & Metabolism 23, 351-363 (2012).
6. Iyer, S. S. & Cheng, G. Role of interleukin 10 transcriptional regulation in inflammation and autoimmune disease. Crit. Rev. Immunol. 32, 23-63 (2012).
7. Lynes, M. D. et al. The cold-induced lipokine 12,13-diHOME promotes fatty acid transport into brown adipose tissue. Nat. Med. 37, 1685 (2017).
8. SZATMARI, I. et al. PPAR regulates the function of human dendritic cells primarily by altering lipid metabolism. Blood 110, 3271-3280 (2007).
9. Choo, J. et al. A Novel Peroxisome Proliferator-activated Receptor (PPAR)γ Agonist 2-Hydroxyethyl 5-chloro-4,5-didehydrojasmonate Exerts Anti-Inflammatory Effects in Colitis. J. Biol. Chem. 290, 25609-25619 (2015).
10. Woerly, G. et al. Peroxisome proliferator-activated receptors alpha and gamma down-regulate allergic inflammation and eosinophil activation. J Exp Med 198, 411-421 (2003).
11. Hammad, H. et al. Activation of peroxisome proliferator-activated receptor-gamma in dendritic cells inhibits the development of eosinophilic airway inflammation in a mouse model of asthma. The American Journal of Pathology 164, 263-271 (2004).
12. Nobs, S. P. et al. PPARγ in dendritic cells and T cells drives pathogenic type-2 effector responses in lung inflammation. J Exp Med 8, jem.20162069 (2017).
13. SZATMARI, I. et al. PPAR regulates the function of human dendritic cells primarily by altering lipid metabolism. Blood 110, 3271-3280 (2007).
14. Fujimura, K. E. et al. House dust exposure mediates gut microbiome Lactobacillus enrichment and airway immune defense against allergens and virus infection. Proc. Natl. Acad. Sci. U.S.A. 111, 805-810 (2014).
15. Green, D. et al. Central activation of TRPV1 and TRPA1 by novel endogenous agonists contributes to mechanical allodynia and thermal hyperalgesia after burn injury. Mol Pain 12, 174480691666172 (2016).
16. Wang, Q. et al. [TRPV1 UTR-3 polymorphism and susceptibility of childhood asthma of the Han Nationality in Beijing]. Wei Sheng Yan Jiu 38, 516-521 (2009).

17. Baker, K. et al. Role of the ion channel, transient receptor potential cation channel subfamily V member 1 (TRPV1), in allergic asthma. *Respiratory Research* 17, 143 (2016).
18. Gouveia-Figueira, S. et al. Mass spectrometry profiling of oxylipins, endocannabinoids, and N-acylethanolamines in human lung lavage fluids reveals responsiveness of prostaglandin E2 and associated lipid metabolites to biodiesel exhaust exposure. *Anal Bioanal Chem* 409, 2967-2980 (2017).
19. Lecka-Czemik, B. et al. Divergent effects of selective peroxisome proliferator-activated receptor-gamma 2 ligands on adipocyte versus osteoblast differentiation. *Endocrinology* 143, 2376-2384 (2002).
20. Ha, J., Dobretsov, M., Kurten, R. C., Grant, D. F. & Stimers, J. R. Effect of linoleic acid metabolites on Na(+)/K(+) pump current in N20.1 oligodendrocytes: role of membrane fluidity. *Toxicol. Appl. Pharmacol.* 182, 76-83 (2002).
21. Morisseau, C. Role of epoxide hydrolases in lipid metabolism. *Biochimie* 95, 91-95 (2013).
22. Biswal, B. K. et al. The molecular structure of epoxide hydrolase B from *Mycobacterium tuberculosis* and its complex with a urea-based inhibitor. *J. Mol. Biol.* 381, 897-912 (2008).
23. Decker, M., Arand, M. & Cronin, A. Mammalian epoxide hydrolases in xenobiotic metabolism and signalling. *Arch. Toxicol.* 83, 297-318 (2009).
24. Kaminski, J. et al. High-Specificity Targeted Functional Profiling in Microbial Communities with ShortBRED. *PLoS Comput Biol* 11, e1004557 (2015).
25. Tang, L. et al. A high-throughput adrenaline test for the exploration of the catalytic potential of halohydrin dehalogenases in epoxide ring-opening reactions. *Biotechnology and Applied Biochemistry* 62, 451-457 (2015).
26. Wegienka, G. et al. Combined effects of prenatal medication use and delivery type are associated with eczema at age 2 years. *Clin. Exp. Allergy* 45, 660-668 (2015).
27. Haystad, S. et al. Atopic phenotypes identified with latent class analyses at age 2 years. *J. Allergy Clin. Immunol.* 134, 722-727.e2 (2014).
28. Wegienka, G. et al. Subgroup differences in the associations between dog exposure during the first year of life and early life allergic outcomes. *Clin. Exp. Allergy* 47, 97-105 (2017).
29. Haystad, S. et al. Effect of prenatal indoor pet exposure on the trajectory of total IgE levels in early childhood. *J. Allergy Clin. Immunol.* 128, 880-885.e4 (2011).
30. Castro-Rodriguez, J. A., Holberg, C. J., Wright, A. L. & Martinez, F. D. A clinical index to define risk of asthma in young children with recurrent wheezing. *Am. J Respir. Crit. Care Med.* 162, 1403-1406 (2000).
31. GUILBERT, T. The Prevention of Early Asthma in Kids study: design, rationale and methods for the Childhood Asthma Research and Education network*1. *Controlled Clinical Trials* 25, 286-310 (2004).
32. Amin, P. et al. Optimum predictors of childhood asthma: persistent wheeze or the Asthma Predictive Index? *J Allergy Clin Immunol Pract* 2, 709-715 (2014).
33. Ye, F. et al. The Dipeptide H-Trp-Glu-OH Shows Highly Antagonistic Activity against PPARγ: Bioassay with Molecular Modeling Simulation. *ChemBioChem* 7, 74-82 (2005).
34. Gouveia-Figueira, S., Spath, J., Zivkovic, A. M. & Nording, M. L. Profiling the Oxylipin and Endocannabinoid Metabolome by UPLC-ESI-MS/MS in Human Plasma to Monitor Postprandial Inflammation. *PLoS ONE* 10, e0132042 (2015).
35. Lundström, S. L. et al. Asthmatics exhibit altered oxylipin profiles compared to healthy individuals after subway air exposure. *PLoS ONE* 6, e23864 (2011).
36. Aichbhaumik, N. et al. Prenatal exposure to household pets influences fetal immunoglobulin E production. *Clin. Exp. Allergy* 38, 1787-1794 (2008).
37. DeAngelis, K. M. et al. Selective progressive response of soil microbial community to wild oat roots. *The ISME Journal* 3, 168-178 (2009).
38. Suzek, B. E. et al. UniRef clusters: a comprehensive and scalable alternative for improving sequence similarity searches. *Bioinformatics* 31, 926-932 (2015).
39. Brad R Henke et al. N-(2-Benzoylphenyl)-1-tyrosine PPARγ Agonists. 1. Discovery of a Novel Series of Potent Antihyperglycemic and Antihyperlipidemic Agents. *Journal of Medicinal Chemistry* 41, 5020-5036 (1998).
40. Lehmann, J. M. et al. An antidiabetic thiazolidinedione is a high affinity ligand for peroxisome proliferator-activated receptor gamma (PPAR gamma). *J. Biol. Chem.* 270, 12953-12956 (1995).
41. Arrieta, M. et al. Early infancy microbial and metabolic alterations affect risk of childhood asthma. Science Translational Medicine. 2015

VII. EXEMPLARY EPOXIDE HYDROLASE SEQUENCE INFORMATION

```
NP_814872.1 HAD superfamily hydrolase
[Enterococcus faecalis V583]
                                        (SEQ ID NO: 46)
MSIKLVAIDIDGILLNSQHKITPRVKEALQKANEQGVRIVLCTGRPLPGV

KEQLDELALYGENDFVITYNGSLVQATKDNIIISRYTLSYEDFLEIEMYS

RKVGAHLHTIDDSAIYTANRNIGKYTIHEASLVNMPLKYRTVDEMTPEMN

IIKMMMIDEPEVLDPAIAKLPLHFTEKYTTVKSTPFYYEIMNKNASKGNA

LAKLADHLGLNKDEVMAIGDNENDLSMIDYAGIGVAMGNATENVKTIADV

HITSNDEDGVAQIIEKMVLI
```

The entire entry for National Center for Biotechnology Information (NCBI) Reference Sequence: NP_814872.1 is incorporated herein by reference.

```
NC_004668.1:c1112081-1111269 Enterococcus faecalis
V583 chromosome, complete genome:
                                        (SEQ ID NO: 50)
ATGTCAATTAAGTTAGTTGCTATTGATATCGACGGAACATTGCTAAATTC

ACAACACAAGATTACCCCACGGGTCAAAGAAGCGCTCCAAAAAGCAAATG

AGCAAGGTGTTCGTATTGTTTTATGTACAGGCCGTCCTTTGCCAGGCGTG

AAAGAACAATTGGATGAATTAGCCTTATATGGTGAAAATGATTTCGTGAT

TACCTACAACGGTTCGCTTGTCCAAGCAACCAAAGATAATACGATTATTT

CACGCTATACCTTGAGTTATGAGGATTTTTTAGAAATTGAAATGTATTCT

CGTAAAGTCGGCGCTCACTTGCATACAATTGATGATTCCGCTATTTACAC

TGCCAATCGCAATATTGGTAAATATACGATTCACGAAGCATCTTTAGTGA

ACATGCCTTTAAAATATCGTACGGTGGATGAAATGACACCAGAGATGAAC
```

-continued
ATTATTAAAATGATGATGATTGATGAGCCGGAAGTTTTAGATCCTGCCAT

TGCAAAATTACCATTACATTTTACCGAAAAATATACGACTGTTAAAGTA

CGCCTTTTTACTATGAAATCATGAATAAAAATGCTAGCAAAGGCAATGCT

CTAGCAAAATTGGCAGACCATTTAGGCTTAAATAAAGACGAAGTGATGGC

CATTGGTGACAATGAAAATGACTTATCCATGATTGATTACGCTGGGATTG

-continued
GTGTTGCGATGGGCAATGCGACAGAAAATGTTAAAACAATTGCCGATGTG

CATACCACTAGTAATGACGAAGATGGTGTCGCTCAAATTATTGAAAAAAT

GGTTTTAATTTAA

The entire entry for NCBI Reference Sequence: NC 004668.1 is incorporated herein by reference.

```
NC_004668.1:c1112081-1111269 Enterococcus faecalis V583 chromosome,
complete genome (SEQ ID NO: 46, amino acid sequence; SEQ ID NO: 50,
nucleic acid sequence)
  1 M   S   I   K   L   V   A   I   D   I   D   G   T   L   L   N   S   Q   H   K

1 ATGTCAATTAAGTTAGTTGCTATTGATATCGACGGAACATTGCTAAATTCACAACACAAG

21 I   T   P   R   V   K   E   A   L   Q   K   A   N   E   Q   G   V   R   I   V

61 ATTACCCCACGGGTCAAAGAAGCGCTCCAAAAAGCAAATGAGCAAGGTGTTCGTATTGTT

41 L   C   T   G   R   P   L   P   G   V   K   E   Q   L   D   E   L   A   L   Y

121 TTATGTACAGGCCGTCCTTTGCCAGGCGTGAAAGAACAATTGGATGAATTAGCCTTATAT

61 G   E   N   D   F   V   I   T   Y   N   G   S   L   V   Q   A   T   K   D   N

181 GGTGAAAATGATTTCGTGATTACCTACAACGGTTCGCTTGTCCAAGCAACCAAAGATAAT

81 T   I   I   S   R   Y   T   L   S   Y   E   D   F   L   E   I   E   M   Y   S

241 ACGATTATTTCACGCTATACCTTGAGTTATGAGGATTTTTTAGAAATTGAAATGTATTCT

101 R   K   V   G   A   H   L   H   T   I   D   D   S   A   I   Y   T   A   N   R

301 CGTAAAGTCGGCGCTCACTTGCATACAATTGATGATTCCGCTATTTACACTGCCAATCGC

121 N   I   G   K   Y   T   I   H   E   A   S   L   V   N   M   P   L   K   Y   R

361 AATATTGGTAAATATACGATTCACGAAGCATCTTTAGTGAACATGCCTTTAAAATATCGT

141 T   V   D   E   M   T   P   E   M   N   I   I   K   M   M   M   I   D   E   P

421 ACGGTGGATGAAATGACACCAGAGATGAACATTATTAAAATGATGATGATTGATGAGCCG

161 E   V   L   D   P   A   I   A   K   L   P   L   H   F   T   E   K   Y   T   T

481 GAAGTTTTAGATCCTGCCATTGCAAAATTACCATTACATTTTACCGAAAAATATACGACT

181 V   K   S   T   P   F   Y   Y   E   I   M   N   K   N   A   S   K   G   N   A

541 GTTAAAAGTACGCCTTTTTACTATGAAATCATGAATAAAAATGCTAGCAAAGGCAATGCT

201 L   A   K   L   A   D   H   L   G   L   N   K   D   E   V   M   A   I   G   D

601 CTAGCAAAATTGGCAGACCATTTAGGCTTAAATAAAGACGAAGTGATGGCCATTGGTGAC

221 N   E   N   D   L   S   M   I   D   Y   A   G   I   G   V   A   M   G   N   A

661 AATGAAAATGACTTATCCATGATTGATTACGCTGGGATTGGTGTTGCGATGGGCAATGCG

241 T   E   N   V   K   T   I   A   D   V   H   T   T   S   N   D   E   D   G   V

721 ACAGAAAATGTTAAAACAATTGCCGATGTGCATACCACTAGTAATGACGAAGATGGTGTC

261 A   Q   I   I   E   K   M   V   L   I   *

781 GCTCAAATTATTGAAAAAATGGTTTTAATTTAA

NC_004668.1:c1112081-1111269 Enterococcus faecalis V583 chromosome,
complete genome
Primers:
Forward:
                                                             (SEQ ID NO: 21)
CGA CGG AAC ATT GCT AAA TTC AC
```

Reverse:
(SEQ ID NO: 22)
CAA AGG ACG GCC TGT ACA TAA

Probe:
(SEQ ID NO: 23)
/56-FAM/ACGGGTCAA/ZEN/A GAA GCG CTC CAA A/3IABkFQ/

Oligo:
(SEQ ID NO: 43)
ATGTCAATTAAGTTAGTTGCTATTGATATCGACGGAACATTGCTAAATTCACAACACA

AGATTACCCCACGGGTCAAAGAAGCGCTCCAAAAAGCAAATGAGCAAGGTGTTCGTATTGTTTT

ATGTACAGGCCGTCCTTT

YP_003971091.1 hydrolase [*Bifidobacterium bifidum* PRL2010]
(SEQ ID NO: 47)
MSQHQVTTRQRRNVVLLDLDGTLTQSDPGIIACATKAFEELSLPVPDDQEMHRFIGPAIIESFR

RNHMPDELLDRGVEIYREYYADKAVFDDPNNPGHKIPGRLYNSVYAGIPEQLAALRADGLHLAI

ATCKPQYQAEPVCEHFHLDTMVDGIYGASTDNSRIDKDQVIRYCFDSIGFDADAGDRALMVGDR

WTDVDGAIACGLDCLGCRWGYAEAGELEEHGAYRIIDTVDELAAAVNDYFAK

The entire entry for NCBI Reference Sequence: YP_003971091.1 is incorporated herein by reference.

NC_014638.1:1162676-1163410 *Bifidobacterium bifidum* PRL2010 chromosome, complete genome
(SEQ ID NO: 51)
ATGTCTCAGCATCAGGTCACGACCCGGCAGCGCAGGAACGTGGTGCTGCT

CGACCTTGACGGTACGTTGACGCAATCGGACCCGGGCATCATCGCCTGCG

CCACCAAGGCGTTCGAGGAGCTCAGCCTGCCGGTTCCCGACGATCAGGAG

ATGCACCGGTTCATCGGACCGGCCATCATCGAGTCGTTCAGACGCAACCA

TATGCCGGACGAGCTGCTGGACCGCGGCGTGGAGATATACCGCGAATACT

ATGCGGACAAGGCGGTGTTCGACGACCCGAACAATCCCGGCCACAAAATT

CCCGGACGACTGTACAACAGCGTGTACGCCGGTATTCCCGAGCAGCTGGC

GGCATTGCGCGCCGACGGCTTGCACCTGGCAATCGCCACGTGCAAGCCGC

AATATCAGGCCGAGCCAGTGTGCGAGCATTTCCATCTCGATACCATGGTC

GACGGCATCTACGGCGCCAGCACAGACAATTCGCGCATCGACAAGGATCA

GGTCATCCGATACTGCTTCGACAGCATCGGATTCGATGCGGATGCCGGTG

ACCGCGCCCTGATGGTCGGCGACCGTTGGACCGACGTCGACGGCGCCATC

GCATGCGGGCTCGATTGCCTGGGTTGCCGTTGGGGGTACGCCGAAGCCGG

TGAGCTTGAGGAACATGGCGCATACCGCATCATCGATACCGTCGATGAGC

TTGCCGCCGCGGTGAATGATTATTTCGCAAAGTGA

The entire entry for NCBI Reference Sequence: NC_014638.1 is incorporated herein by reference.

(SEQ ID NO: 47, amino acid sequence)
atgtctcagcatcaggtcacgacccggcagcgcaggaacgtggtgctgctcgaccttgac
 M  S  Q  H  Q  V  T  T  R  Q  R  R  N  V  V  L  L  D  L  D ggtacgttgacgcaatcggacccgggcatcatcgcctgcgccaccaaggcgttcgaggag
 G  T  L  T  Q  S  D  P  G  I  I  A  C  A  T  K  A  F  E  E ctcagcctgccggttcccgacgatcaggagatgcaccggttcatcggaccggccatcatc
 L  S  L  P  V  P  D  D  Q  E  M  H  R  F  I  G  P  A  I  I gagtcgttcagacgcaaccatatgccggacgagctgctggaccgcggcgtggagatatac
 E  S  F  R  R  N  H  M  P  D  E  L  L  D  R  G  V  E  I  Y cgcgaatactatgcggacaaggcggtgttcgacgacccgaacaatcccggccacaaaatt
 R  E  Y  Y  A  D  K  A  V  F  D  D  P  N  N  P  G  H  K  I cccggacgactgtacaacagcgtgtacgccggtattcccgagcagctggcggcattgcgc
 P  G  R  L  Y  N  S  V  Y  A  G  I  P  E  Q  L  A  A  L  R gccgacggcttgcacctggcaatcgccacgtgcaagccgcaatatcaggccgagccagtg
 A  D  G  L  H  L  A  I  A  T  C  K  P  Q  Y  Q  A  E  P  V tgcgagcatttccatctcgataccatggtcgacggcatctacggcgccagcacagacaat
 C  E  H  F  H  L  D  T  M  V  D  G  I  Y  G  A  S  T  D  N tcgcgcatcgacaaggatcaggtcatccgatactgcttcgacagcatcggattcgatgcg
 S  R  I  D  K  D  Q  V  I  R  Y  C  F  D  S  I  G  F  D  A -continued

```
gatgccggtgaccgcgccctgatggtcggcgaccgttggaccgacgtcgacggcgccatc
 D  A  G  D  R  A  L  M  V  G  D  R  W  T  D  V  D  G  A  I gcatgcgggctcgattgcctgggttgccgttgggggtacgccgaagccggtgagcttgag
 A  C  G  L  D  C  L  G  C  R  W  G  Y  A  E  A  G  E  L  E gaacatggcgcataccgcatcatcgataccgtcgatgagcttgccgccgcggtgaatgat
 E  H  G  A  Y  R  I  I  D  T  V  D  E  L  A  A  A  V  N  D tatttcgcaaagtga
 Y  F  A  K  -
```

NC_014638.1:1162676-1163410 *Bifidobacterium bifidum* PRL2010 chromosome, complete genome.
Primers:
Forward:
(SEQ ID NO: 24)
GTC GTT CAG ACG CAA CCA TA Reverse:
(SEQ ID NO: 25)
TTT GIG GCC GGG ATT GTT Probe:
(SEQ ID NO: 26)
/56-FAM/TACTATGCG/ZEN/G ACA AGG CGG TGT TC/3IABkFQ/

Fragment:
(SEQ ID NO: 44)
ACCGGCCATCATCGAGTCGTTCAGACGCAACCATATGCCGGACGAGCTGCTGGACCGCGGCGTG

GAGATATACCGCGAATACTATGCGGACAAGGCGGTGTTCGACGACCCGAACAATCCCGGCCACA

AAATTCCCGGACGAC

YP_003971333.1 hydrolase [*Bifidobacterium bifidum* PRL2010]
(SEQ ID NO: 48)
MASDDIMTAGAGGATATVRADIKAAFFDIDGTLTSFVTHVIPQSSIDALHELQDRGVKVFICSG

RAPSHMTVVLDMMPVHFDGIIALNGQYCFDDHGLLEKESLLPEDIVTITRWLDEHPDVVANYCE

KDYVYFNQITDAMRATWRQLGKTAPTVNIDDPHERALKHETFQISPYISFEDEAKLSGMCRNVR

GVRWHPDFTDLIPADGGKPEGMKRFMRHYGWTREQTIAFGDGGNDADMLAFAGIGVAMGNATEP

AKAAADYITDDVDHDGIMNALKHFNVL

The entire entry for NCBI Reference Sequence: YP_003971333.1 is incorporated herein by reference.

NC_014638.1:1449807-1450658 *Bifidobacterium bifidum* PRL2010 chromosome, complete genome
(SEQ ID NO: 52)
ATGGCATCGGACGACATCATGACAGCGGGCGCCGGAGGCGCGACGGCCAC

CGTGCGAGCCGACATCAAGGCGGCGTTCTTCGACATCGACGGCACGCTGA

CGAGTTTCGTGACGCATGTAATCCCGCAGTCCTCCATCGACGCGCTGCAC

GAGCTGCAGGATCGCGGGGTGAAGGTGTTCATCTGCTCCGGTCGGGCGCC

GTCGCACATGACCGTCGTGCTCGACATGATGCCGGTGCACTTCGACGGCA

TCATCGCGCTGAACGGGCAGTACTGCTTCGACGACCACGGGCTCCTGGAG

AAGGAGTCGCTGCTGCCCGAGGACATCGTCACCATCACCCGCTGGCTTGA

CGAGCACCCCGACGTGGTGGCGAACTACTGCGAGAAGGATTACGTCTACT

TCAACCAGATCACCGACGCGATGCGGGCCACGTGGCGCCAACTCGGCAAG

ACCGCACCGACCGTGAACATCGACGATCCGCACGAGAGGGCGCTGAAGCA

TGAGACGTTCCAGATCAGCCCGTACATCAGCTTTGAAGATGAAGCGAAGC

TGTCCGGCATGTGTCGCAATGTCAGAGGCGTGCGCTGGCATCCGGACTTC

ACCGACCTGATTCCCGCCGACGGCGGCAAACCCGAGGGAATGAAGCGGTT

CATGCGGCATTACGGCTGGACGCGCGAGCAGACCATCGCGTTCGGAGACG

GCGGCAACGACGCCGACATGCTCGCCTTCGCCGGCATCGGCGTGGCGATG

GGCAATGCGACCGAACCGGCGAAGGCCGCGGCCGACTACATCACCGATGA

CGTCGACCACGACGGCATCATGAACGCGCTCAAGCACTTCAACGTCCTGT

AG

The entire entry for NCBI Reference Sequence: NC_014638.1 is incorporated herein by reference.

(SEQ ID NO: 48, amino acid sequence)
```
atggcatcggacgacatcatgacagcgggcgccggaggcgcgacggccaccgtgcgagcc
 M  A  S  D  D  I  M  T  A  G  A  G  G  A  T  A  T  V  R  A
```

```
gacatcaaggcggcgttcttcgacatcgacggcacgctgacgagtttcgtgacgcatgta
 D  I  K  A  A  F  F  D  I  D  G  T  L  T  S  F  V  T  H  V atcccgcagtcctccatcgacgcgctgcacgagctgcaggatcgcggggtgaaggtgttc
 I  P  Q  S  S  I  D  A  L  H  E  L  Q  D  R  G  V  K  V  F atctgctccggtcgggcgccgtcgcacatgaccgtcgtgctcgacatgatgccggtgcac
 I  C  S  G  R  A  P  S  H  M  T  V  V  L  D  M  M  P  V  H ttcgacggcatcatcgcgctgaacgggcagtactgcttcgacgaccacgggctcctggag
 F  D  G  I  I  A  L  N  G  Q  Y  C  F  D  D  H  G  L  L  E aaggagtcgctgctgcccgaggacatcgtcaccatcacccgctggcttgacgagcacccc
 K  E  S  L  L  P  E  D  I  V  T  I  T  R  W  L  D  E  H  P gacgtggtggcgaactactgcgagaaggattacgtctacttcaaccagatcaccgacgcg
 D  V  V  A  N  Y  C  E  K  D  Y  V  Y  F  N  Q  I  T  D  A atgcgggccacgtggcgccaactcggcaagaccgcaccgaccgtgaacatcgacgatccg
 M  R  A  T  W  R  Q  L  G  K  T  A  P  T  V  N  I  D  D  P cacgagagggcgctgaagcatgagacgttccagatcagcccgtacatcagctttgaagat
 H  E  R  A  L  K  H  E  T  F  Q  I  S  P  Y  I  S  F  E  D gaagcgaagctgtccggcatgtgtcgcaatgtcagaggcgtgcgctggcatccggacttc
 E  A  K  L  S  G  M  C  R  N  V  R  G  V  R  W  H  P  D  F accgacctgattcccgccgacggcggcaaacccgagggaatgaagcggttcatgcggcat
 T  D  L  I  P  A  D  G  G  K  P  E  G  M  K  R  F  M  R  H tacggctggacgcgcgagcagaccatcgcgttcggagacggcggcaacgacgccgacatg
 Y  G  W  T  R  E  Q  T  I  A  F  G  D  G  G  N  D  A  D  M ctcgccttcgccggcatcggcgtggcgatgggcaatgcgaccgaaccggcgaaggccgcg
 L  A  F  A  G  I  G  V  A  M  G  N  A  T  E  P  A  K  A  A gccgactacatcaccgatgacgtcgaccacgacggcatcatgaacgcgctcaagcacttc
 A  D  Y  I  T  D  D  V  D  H  D  G  I  M  N  A  L  K  H  F aacgtcctgtag
 N  V  L  -

NC_014638.1:1449807-1450658 Bifidobacterium bifidum PRL2010
chromosome, complete genome.
Primers:
Forward:
                                                  (SEQ ID NO: 27)
GCA CCG ACC GIG AAC AT Reverse:
                                                  (SEQ ID NO: 28)
GGA CAG CTT CGC TTC ATC TT Probe:
                                                  (SEQ ID NO: 29)
/56-FAM/CGCTGAAGC/ZEN/ATGAGACGTTCCAGA/3IABkFQ/

Fragment:
                                                  (SEQ ID NO: 49)
CCAACTCGGCAAGACCGCACCGACCGTGAACATCGACGATCCGCACGAGAGGGCGCTGAAGCAT
GAGACGTTCCAGATCAGCCCGTACATCAGCTTTGAAGATGAAGCGAAGCTGTCCGGCAT
```

VIII. INFORMAL SEQUENCE LISTING

```
                                                  SEQ ID NO: 1
TAATACGACTCACTATAGGG

SEQ ID NO: 2
GCTAGTTATTGCTCAGCGG

SEQ ID NO: 3
ATCAACACTGCCAGTGTGGCT

SEQ ID NO: 4
AGTGTCATGCCCACTATTCCC
```

```
                                            SEQ ID NO: 5
GGATGGAAAATCAACCACCA

SEQ ID NO: 6
GGAAGTGACGCCTTTCATGA

SEQ ID NO: 7
ACCTGTCCTGTCGGGTGAA

SEQ ID NO: 8
CCCACGGAACTGTGATGCT

SEQ ID NO: 9
TCTTTCCTGCAGCCCAATG

SEQ ID NO: 10
AGCCTCTGTTCCAACTGATAGTGA

SEQ ID NO: 11
AAGATGACCCAGATCATGTTTGAGACC

SEQ ID NO: 12
AGCCAGTCCAGACGCAGGAT

SEQ ID NO: 13
CGAAGACTACAGTTCTGCCATT

SEQ ID NO: 14
GACGTTTCAGAGGTTCTCAGAG

SEQ ID NO: 15
GAAATGCCACCTTTTGACAGTG

SEQ ID NO: 16
TGGATGCTCTCATCAGGACAG

SEQ ID NO: 17
CCCTCACACTCAGATCATCTTCT

SEQ ID NO: 18
GCTACGACGTGGGCTACAG

SEQ ID NO: 19
CCTCGTCCCGTAGACAAAATG

SEQ ID NO: 20
TCTCCACTTTGCCACTGCAA

SEQ ID NO: 21
CGA CGG AAC ATT GCT AAA TTC AC

SEQ ID NO: 22
CAA AGG ACG GCC TGT ACA TAA

SEQ ID NO: 23
/56-FAM/ACGGGTCAA/ZEN/AGAAGCGCTCCAAA/3IABkFQ/

SEQ ID NO: 24
GTC GTT CAG ACG CAA CCA TA

SEQ ID NO: 25
TTT GTG GCC GGG ATT GTT

SEQ ID NO: 26
/56-FAM/TACTATGCG/ZEN/GACAAGGCGGTGTTC/3IABkFQ/

SEQ ID NO: 27
GCA CCG ACC GTG AAC AT

SEQ ID NO: 28
GGA CAG CTT CGC TTC ATC TT

SEQ ID NO: 29
/56-FAM/CGCTGAAGC/ZEN/ATGAGACGTTCCAGA/3IABkFQ/

SEQ ID NO: 30
AATTGCAGAATTCATGATTAAACTGATTGCGAGCGATATGGATGGCACCCTGCTGGA

TGCGAAAATGAGCATTACCAACGATAACGCGAGCGCGATTCGCGAAGCGGAACGCC
```

-continued

TGGGCATTGAATTTATGGTGGCGACCGGCCGCGCGTATACCGAAGCGAAACCGGCG

CTGGAAGAAGCGGGCATTGATTGCGCGATGATTACCCTGAACGGCGCGCAGGTGTT

TGATAAAGATGGCCATAGCCTGTTTACCGCGGGCATTGAAAAAGAAACCGTGACCG

AAGTGCTGACCATTCTGAGCCAGCATAACGTGTATTATGAAATTAGCACCAACAAA

GGCATTTTTAGCGAACATCAGGAAAAACGCATTGAAAACTTTGCGGCGCATATTGC

GGAAAGCATGCCGCATCTGACCTATAAAGTGGCGATTGCGATGGCGAGCGCGCATC

TGAGCCTGCTGCATATTACCTATGTGGATCGCCTGGATGATATTCTGAAAGATGATA

GCATTGAAGTGCTGAAAATTATTGGCTTTAGCATGGATGGCCCGAAAGTGCTGGGCC

CGGCGGGCATGGAAGTGGAAGAACTGGATGATCTGGTGGTGACCAGCAGCGCGCTG

AACAACATTGAAATTAACCATCGCCTGGCGCAGAAAGGCATTGCGGTGGCGCGCGT

GGCGAAAGAACGCGGCATTCCGGCGGAACAGGTGATGACCATTGGCGATAACCTGA

ACGATGTGAGCATGATTCAGTGGGCGGGCGTGAGCTTTGCGATGGGCAACGCGGAA

CTGGAACTGAAAGAATATGCGAAATATGAAACCGCGACCAACCTGGAAAACGGCGT

GGGCGAAGCGATTCTGCGCGCGATTCGCGAAGATCTGGTTGTCGACTTATCCGGCC

SEQ ID NO: 31
AATTGCAGAATTCATGAAAAAACTGATTGCGATTGATCTGGATGGCACCACCCTGA

ACGCGCAGAGCCTGATTAGCCCGAAAACCGAACAGACCCTGAAAAAAGCGATTGAT

AACGGCCATTATGTGAGCATTGCGACCGGCCGCCCGTATCGCATGAGCCATCAGTTT

TATCAGCAGCTGGGCCTGACCACCCCGATGGTGAACTTTAACGGCGCGCTGGTGCAT

ATTCCGGAAAAAAAATGGGATCTGGAAAGCGAAGCGAACATTGAACGCGATCTGGT

GTTTGATATTCTGGCGCAGAAAAAAGAACTGCAGCTGGATTTTGTGGCGGCGGAAA

ACAAAGAAACCTTTTATATTGATACCCTGGATGGCTTTGATCCGAAATTTTTTGCGA

GCAAAGCGACCCTGGATAACCTGCTGACCGCGAAAAACCTGCGCACCAACCCGACC

AGCATGATGGTGCGCACCACCCCGAACCAGGCGGAAAAAGTGGCGGATACCCTGAC

CAAACAGTATGGCGATTATATTGATGTGCGCACCTGGGGCGGCCCGATGCCGATTCT

GGAAATGGTGGCGAAAGGCATTCAGAAAGCGCATGGCGTGGATCAGGTGGCGAACT

TTCTGAGCGTGAAACCGGCGGATATTATTGCGTTTGGCGATGAACATAACGATGAA

GAAATGCTGAGCTATGCGGGCTGGGGCGTGGCGATGAACAACGCGACCGATAAAAT

TAAAAGCGTGGCGAACGATGTGACCGAAAAAACCAACGATCAGGATGGCCTGGCG

GATTATCTGGAAAACTATCTGGATCTGGTTGTCGACTTATCCGGCC

SEQ ID NO: 32
AATTGCAGAATTCATGAGCATTAAACTGGTGGCGATTGATATTGATGGCACCCTGCT

GAACAGCCAGCATAAAATTACCCCGCGCGTGAAAGAAGCGCTGCAGAAAGCGAAC

GAACAGGGCGTGCGCATTGTGCTGTGCACCGGCCGCCCGCTGCCGGGCGTGAAAGA

ACAGCTGGATGAACTGGCGCTGTATGGCGAAAACGATTTTGTGATTACCTATAACGG

CAGCCTGGTGCAGGCGACCAAAGATAACACCATTATTAGCCGCTATACCCTGAGCT

ATGAAGATTTTCTGGAAATTGAAATGTATAGCCGCAAAGTGGGCGCGCATCTGCAT

ACCATTGATGATAGCGCGATTTATACCGCGAACCGCAACATTGGCAAATATACCATT

CATGAAGCGAGCCTGGTGAACATGCCGCTGAAATATCGCACCGTGGATGAAATGAC

CCCGGAAATGAACATTATTAAAATGATGATGATTGATGAACCGGAAGTGCTGGATC

CGGCGATTGCGAAACTGCCGCTGCATTTTACCGAAAAATATACCACCGTGAAAAGC

-continued

ACCCCGTTTTATTATGAAATTATGAACAAAAACGCGAGCAAAGGCAACGCGCTGGC

GAAACTGGCGGATCATCTGGGCCTGAACAAAGATGAAGTGATGGCGATTGGCGATA

ACGAAAACGATCTGAGCATGATTGATTATGCGGGCATTGGCGTGGCGATGGGCAAC

GCGACCGAAAACGTGAAAACCATTGCGGATGTGCATACCACCAGCAACGATGAAGA

TGGCGTGGCGCAGATTATTGAAAAAATGGTGCTGATTGTTGTCGACTTATCCGGCC

SEQ ID NO: 33
AATTGCAGAATTCATGGATAAAATGAAAGCGATTACCTTTTTTGATCTGGATGGCAC

CCTGCTGGATGGCACCAGCCAGATTACCCCGGAAATTACCGCGGCGGTGGCGGCGC

TGAAAGATAACCAGATTCTGCCGCTGATTGCGACCGGCCGCACCCTGTGCGAAATTC

AGCCGATTATGAAAGCGAGCGGCATTGATAGCGCGATTGTGATGAACGGCCAGTTT

ATTCATTATGAAGGCAAAACCATTTATAGCGATGAATTTACCACCGAAGAATGCGTG

AGCCTGCATGAACATGTGAAACAGCGCGGCCATGAACTGGCGTTTTATAACGAACG

CCGCATTTTTTGCACCGGCCATACCGGCACCGTGAAACAGGCGTATGATTATATTCA

TAGCGCGGTGCCGGAAATTGATCCGACCGGCTATGAAAACGATGCGGTGAACATGA

TGCTGGTGCTGAGCCAGCATGGCGATGATGATGAATATTATTATGAACGCTTTCCGG

AACTGACCTTTTATCGCAACGGCCCGTTTAGCATTGATATTGTGCGCAAAGGCGTGA

GCAAAGGCAGCGGCGTGAAAAAACCTGTTTAACACCCTGGGCCTGAACGGCATTCCG

ACCTATGCGTTTGGCGATGGCATTAACGATCTGGCGCTGTTTGAAGCGTGCGATTAT

GGCATTGCGATGGGCAACGCGCGCGAAGAACTGAAAGAAAAAGCGACCTTTATTAG

CACCAAAAACACCGAAAACGGCATTGTGAACGGCCTGAAAAAATTTGATCTGCTGG

TTGTCGACTTATCCGGCC

SEQ ID NO: 34
AATTGCAGAATTCATGAAAGCGGTGCTGACCGATCTGGATAACACCCTGATTGCGTG

GAACAACCCGGATGGCACCGAAGAACTGAAAACCTGGCTGCTGGAAATGAAAAAC

GCGGGCATTACCGTGCTGGTGGTGAGCAACAACAAAGATAGCCGCATTAAACGCGT

GGTGGAAAAATTTGATCTGGATTATGTGGCGCGCGCGCTGAAACCGACCGCGCGCG

GCTTTAAACTGGCGGAAAAAAAACTGGGCCTGAAACCGAGCGAAATGCTGATGGTG

GGCGATCAGATTATGACCGATATTCGCGGCGCGAACGCGGCGGGCATTCGCAACGT

GCTGGTGCAGCCGATTGTGGATACCGATGGCTGGAACACCCGCATTAACCGCTTTTT

TGAACGCAAAATTATGAAATATCTGAGCAAAAAAGTTGTCGACTTATCCGGCC

SEQ ID NO: 35
AATTGCAGAATTCATGGCGGTGAAAGCGATTGTGATGGATATTGATGGCACCCTGCT

GACCAGCGAAAAAAAATTAGCCCGAAAACCCGCCAGGCGCTGGTGGCGGCGCAG

AAACAGGGCCTGAGCCTGATTCTGGCGAGCGGCCGCCCGACCAACGGCATGCGCCC

GCTGGCGGATGAACTGGAAATGGCGCATTATAACGGCCATCTGCTGAGCTATAACG

GCGCGTGCGTGACCCATCATGGCAGCCAGCAGCAGCTGTTTAACCAGACCATTAGC

AAAAGCCTGAGCCAGCAGATTCTGGAACATCTGAAACAGTTTGATGTGATTCCGAT

GATTAACGATGAAACCTTTATGTATGTGAACGATGTGTTTCATAACACCCTGCATCT

GGAAACCGGCGATTTTAACATTATTGAATATGAAAGCCGCGGCGGCAACTTTCAGCT

GTGCGAATGGCATGATCTGGCGGCGCGCCTGAACTTTCCGCTGAACAAAATTCTGAT

TGCGGGCGAACCGGCGTATCTGCAGAAATATCATGAAGCGATTTATGCGCCGTTTAA

AGAAACCGTGACCGCGGCGTTTAGCGCGCCGTTTTATTTTGAATTTACCGCGAAAAA

```
CATTGATAAAGCGCGCAGCCTGGAAAAACTGACCCTGCAGCTGGGCATTACCGCGG

AAGAAGTGATTGCGTTTGGCGATGGCCATAACGATTATACCATGCTGGAATGGGCG

GGCACCGGCATTGCGATGGAAAACGCGGTGGATGAACTGAAAAACATTGCGACCGA

AGTGACCCTGAGCAACGATAACGATGGCATTGCGGTGGCGCTGGCGAAAATTGTGG

GCGTTGTCGACTTATCCGGCC
                                            SEQ ID NO: 36
AATTGCAGAATTCATGCTGGAAAGCAGCGAAGTGAAAATGTATCAGACCATTCTGT

TTGATCTGGATGGCACCATTACCGATAGCGGCAGCGGCATTATGCGCAGCATTCTGT

ATGCGACCGAACAGCTGGGCTGGCCGGCGCCGAGCGAAGAAACCCTGCGCAGCTTT

ATTGGCCCGCCGCTGTATGAAAGCTTTCTGCATATGGCGCCGAGCGCGGAAGCGGC

GCAGCAGGCGGTGGGCCATTATCGCGCGTATTATCAGCGCAAAGGCATGTTTGAAA

ACCATGTGTATCCGGGCATTCCGGAAGTGCTGACCCGCCTGAAAGAAGCGGGCGCG

AAACTGTATATTGCGACCAGCAAACCGGAAGAATTTGCGAAAAAAATTATTACCCA

TTTTGATCTGGATCGCTATTTTACCGGCATTTATGGCGCGAGCATGGATGGCCATCG

CAGCAAAAAAGCGGATGTGATTCAGTATGCGCTGACCGAAGCGCAGCTGGATCCGA

CCAAAGAAGCGATTATTATGGTGGGCGATCGCAACCATGATATTCTGGGCGCGCAG

CAGAACGGCCTGGATAGCATTGGCGTGCTGTATGGCTTTGGCGAAGAAACCGAACT

GCAGGAAGCGGGCGCGACCTTTCTGGTGCAGAGCCCGAAAGATCTGGGCGCGATTC

TGCTGCAGAACAGCGTTGTCGACTTATCCGGCC
                                            SEQ ID NO: 37
AATTGCAGAATTCATGACCCGCATGCTGTTTCTGGATATTGATGGCACCCTGGTGGG

CAAAGATCAGCGCATTCCGCAGAGCGCGATTCGCGCGATTCGCGCGGCGCAGGGCA

ACGGCCATCTGGTGCTGATTTGCACTGGTCGTGCTGCGCGGGTGCGGCAGGCTGGC

GTTATGCGCTGCGTCCGGGCGCGTGGCAGCAGGGCCGCGGCACCGCGTTTCGCTGC

GGCCATCATGGCCGCGCGGCGCGCCGCCATGGCGGCGATCGCCGCCAGCGCCAGGT

TGTCGACTTAT
                                            SEQ ID NO: 38
AATTGCAGAATTCATGTATAGCATTGAAACCCTGGCGCATGTGGATACCCTGTGCCT

GGATAAAACCGGCACCATTACCGAAGGCAAAATGAAAGTGCAGAAAGCGATTATTC

TGCATGATAAATATGAAGAACTGTTTCCGCAGATTATTGGCAGCTATCTGAGCGAAA

GCACCGATAACAACATTACCATGCAGGCGATTCGCGATCATTATGAAGTGAGCAAC

CGCTTTGGCGCGAAAGAAGTGCTGGCGTTTAGCAGCGAACGCAAATGGGGCGCGAT

TGAATTTCCGGAAATTGGCACCGTGTATCTGGGCGCGCCGGAACGCCTGGTGGATG

ATAGCCGCCTGCCGGAAGCGGTGTTTACCGCGCAGGAAAACGGCTATCGCGTGCTG

ATGCTGGCGATTGCGGAACAGCAGCCGCTGAACGAAACCAAAATGCCGTATCTGGA

ACCGCTGGCGATTCTGGAAATTGATGATCCGATTCGCCAGAACGCGAAAGAAACCC

TGGCGTATCTGAAAGAAGAAGGCATTGATCTGAAAGTGATTAGCGGCGATAACCCG

GTGACCGTGAGCAACATTGCGCGCCGCGCGGGCCTGCCGGGCTATGAAAGCTATAT

TGATCTGAGCACCAAAACCACCGAAGCGGAAGTGCGCGAAGCGGTGCAGCAGTATA

CCGTGTTTGGCCGCGTGAGCCCGCAGCAGAAACGCACCATTGTGCGCGAACTGAAA

GATACCGAACATGTGGTGGCGATGACCGGCGATGGCGTGAACGATGTGCTGGCGCT

GCGCGAAGCGGATTGCAGCATTGCGATGGCGGAAGGCGATGGCGCGACCCGCCAGA
```

SEQ ID NO: 39
AATTGCAGAATTCATGTATAGCGTGGAAACCCTGGCGCGCGTGGATGTGCTGTGCCT

GGATAAAACCGGCACCATTACCCAGGGCAAAATGACCGTGAAAGGCCTGAAACTGC

TGAGCGAACGCTTTACCAAAGAAGAACTGGAACGCCTGCTGGCGGCGTATATGGAA

CATAGCAAAGATAACAACGCGACCGCGCAGGCGATTCGCAACGCGTATGAAGGCCT

GGAACATCATTATCAGGTGGGCGATATTATTCCGTTTAGCAGCGATCGCAAATGGGG

CGCGATGAGCATTGATGGCGTGGGCACCCTGTTTCTGGGCGCGCCGGAAATGCTGCT

GGAAGAAACCCGAAAGCGGTGGATCAGGCGCAGGCGCGCGGCAGCCGCGTGCTG

ATTCTGGCGTGGAGCCAGAGCGCGGTGGATACCGAAACCATGAGCCTGCCGAACGA

TGTGGAAGGCCTGGCGCTGCTGGAAATCGCGGATCCGATTCGTGAAGATGCGGCGG

AAACCCTGGAATATCTGCGTAGCGAAGATGTGACCCTGAAAATTATTAGCGGCGAT

AACCCGGTGACCGTGAGCCATATTGCGCATCAGGCGGGCTTTGCGGATTATCAGAG

CTATATTGATTGCAGCAAAGTGAGCGATGAAGAACTGGAAGCGCTGGCGGAAGATA

CCGCGATTTTTGGCCGCGTGAGCCCGCATCAGAAAAAACTGCTGATTCAGACCCTGA

ACGCGAACGGCCATACCACCGCGATGACCGGCGATGGCGTGAACGATATTCTGGCG

CTGCGCGAAGCGGATTGCAGCATTGTGATGGCGGAAGGCGATCCGGCGACCCGCCA

GATTGCGAACCTGGTGCTGATGGATAGCGAATTTAAAGATATTCCGGAAATTCTGTT

TGAAGGCCGCCGCGTGGTGAACAACGTTGTCGACTTATCCGGCC

SEQ ID NO: 40
AATTGCAGAATTCATGACCAACCCGGAACAGCGCCTGATTGTGACCGATCTGGATG

GCACCCTGCTGCATGATGCGCCGACCTTTGAAGAACGCTTTATTACCCAGCGCAGCA

TTGATACCGTGAAACGCATGCATGATGCGGGCTATCGCTTTGCGGTGGCGACCGCGC

GCCCGGTGAGCACCGGCTTTGAATATGCGGGCAAACTGCCGGTGGATGCGTATATTT

ATCTGAACGGCGCGCTGATTGATTTTGCGCCGGAACGCAGCGATTATGATCTGCTGA

CCAGCGGCCGCCTGCCGAGCGATGGCCATCTGCTGAAAGTGGGCTTTAGCAGCGCG

CGCGCGTGCGAAGTGTGCCGCTATCTGCTGGATGAAATTCCGGGCCTGAGCCTGGGC

ATTGTGATGGATGATGTGCGCTATACCAACTTTGATGTGAGCGTGTATTGGAAAACC

CAGACCTGGCAGTTTACCGATTTTACCGATGTGCCGGATGGCATTGCGGATAAAATT

ATTATTTTTCCGAAAAGCGAACAGTGGGCGCATCTGAAAACCCTGGTGCCGCCGGAT

TTTGATGTGGCGATTAGCGAAGGCAGCATGTGGATGCTGATGAGCCCGCTGGCGAA

CAAACGCCAGGCGCTGAAAACCCTGTGCGAACGCATGGATGTGCGCCTGGATGGCA

CCGTGAGCTTTGGCGATGATCTGATTGATATTGGCATGATGACCACCAGCGAAACCG

GCGTGGCGGTGGCGAACGCGAACCCGGAAGTGATTAAAATTGCGGATGAAATTTGC

CCGCCGAACAACGATGATGGCGTGGCGCAGTGGATTGAACGCCATCTGCTGGCGGT

TGTCGACTTATCCGGCC

SEQ ID NO: 41
AATTGCAGAATTCATGCGCAACGTGGTGCTGCTGGATCTGGATGGCACCCTGACCCA

GAGCGATCCGGGCATTATTGCGTGCGCGACCAAAGCGTTTGAAGAACTGAGCCTGC

CGGTGCCGGATGATCAGGAAATGCATCGCTTTATTGGCCCGGCGATTATTGAAAGCT

TCGCCGCAACCATATGCCGGATGAACTGCTGGATCGCGGCGTGGAAATTTATCGCG

```
AATATTATGCGGATAAAGCGGTGTTTGATGATCCGAACAACCCGGGCCATAAAATT

CCGGGCCGCCTGTATAACAGCGTGTATGCGGGCATTCCGGAACAGCTGGCGGCGCT

GCGCGCGGATGGCCTGCATCTGGCGATTGCGACCTGCAAACCGCAGTATCAGGCGG

AACCGGTGTGCGAACATTTTCATCTGGATACCATGGTGGATGGCATTTATGGCGCGA

GCACCGATAACAGCCGCATTGATAAAGATCAGGTGATTCGCTATTGCTTTGATAGCA

TTGGCTTTGATGCGGATGCGGGCGATCGCGCGCTGATGGTGGGCGATCGCTGGACC

GATGTGGATGGCGCGATTGCGTGCGGCCTGGATTGCCTGGGCTGCCGCTGGGGCTAT

GCGGAAGCGGGCGAACTGGAAGAACATGGCGCGTATCGCATTATTGATACCGTGGA

TGAACTGGCGGCGGCGGTGAACGATTATTTTGCGAAAGTTGTCGACTTATCCGGCC
```
SEQ ID NO: 42
```
AATTGCAGAATTCATGATTAAAGCGGCGTTTTTTGATATTGATGGCACCCTGACCAG

CTTTGTGACCCATGTGATTCCGCAGAGCAGCATTGATGCGCTGCATGAACTGCAGGA

TCGCGGCGTGAAAGTGTTTATTTGCAGCGGCCGCGCGCCGAGCCATATGACCGTGGT

GCTGGATATGATGCCGGTGCATTTTGATGGCATTATTGCGCTGAACGGCCAGTATTG

CTTTGATGATCATGGCCTGCTGGAAAAAGAAAGCCTGCTGCCGGAAGATATTGTGA

CCATTACCCGCTGGCTGGATGAACATCCGGATGTGGTGGCGAACTATTGCGAAAAA

GATTATGTGTATTTTAACCAGATTACCGATGCGATGCGCGCGACCTGGCGCCAGCTG

GGCAAAACCGCGCCGACCGTGAACATTGATGATCCGCATGAACGCGCGCTGAAACA

TGAAACCTTTCAGATTAGCCCGTATATTAGCTTTGAAGATGAAGCGAAACTGAGCGG

CATGTGCCGCAACGTGCGCGGCGTGCGCTGGCATCCGGATTTTACCGATCTGATTCC

GGCGGATGGCGGCAAACCGGAAGGCATGAAACGCTTTATGCGCCATTATGGCTGGA

CCCGCGAACAGACCATTGCGTTTGGCGATGGCGGCAACGATGCGGATATGCTGGCG

TTTGCGGGCATTGGCGTGGCGATGGGCAACGCGACCGAACCGGCGAAAGCGGCGGC

GGATTATATTACCGATGATGTGGATCATGATGGCATTATGAACGCGCTGAAACATTT

TAACGTGCTGGTTGTCGACTTATCCGGCC
```
SEQ ID NO: 43
```
ATGTCAATTAAGTTAGTTGCTATTGATATCGACGGAACATTGCTAAAATTCACAACAC

AAGATTACCCCACGGGTCAAAGAAGCGCTCCAAAAAGCAAATGAGCAAGGTGTTCG

TATTGTTTTATGTACAGGCCGTCCTTT
```
SEQ ID NO: 44
```
ACCGGCCATCATCGAGTCGTTCAGACGCAACCATATGCCGGACGAGCTGCTGGACC

GCGGCGTGGAGATATACCGCGAATACTATGCGGACAAGGCGGTGTTCGACGACCCG

AACAATCCCGGCCACAAAATTCCCGGACGAC
```
SEQ ID NO: 45
```
CCAACTCGGCAAGACCGCACCGACCGTGAACATCGACGATCCGCACGAGAGGGCGC

TGAAGCATGAGACGTTCCAGATCAGCCCGTACATCAGCTTTGAAGATGAAGCGAAG

CTGTCCGGCATGTGTCGC
```
(NCBI Reference Sequence: NP_814872.1)
SEQ ID NO: 46
```
MSIKLVAIDIDGTLLNSQHKITPRVKEALQKANEQGVRIVLCTGRPLPGVKEQLDELALY

GENDFVITYNGSLVQATKDNTIISRYTLSYEDFLEIEMYSRKVGAHLHTIDDSAIYTANR

NIGKYTIHEASLVNMPLKYRTVDEMTPEMNIIKMMMIDEPEVLDPAIAKLPLHFTEKYTT

VKSTPFYYEIMNKNASKGNALAKLADHLGLNKDEVMAIGDNENDLSMIDYAGIGVAM
```

GNATENVKTIADVHTTSNDEDGVAQIIEKMVLI (NCBI Reference Sequence: YP_003971091.1)

SEQ ID NO: 47

MSQHQVTTRQRRNVVLLDLDGTLTQSDPGIIACATKAFEELSLPVPDDQEMHRFIGPAII

ESFRRNHMPDELLDRGVEIYREYYADKAVFDDPNNPGHKIPGRLYNSVYAGIPEQLAAL

RADGLHLAIATCKPQYQAEPVCEHFHLDTMVDGIYGASTDNSRIDKDQVIRYCFDSIGF

DADAGDRALMVGDRWTDVDGAIACGLDCLGCRWGYAEAGELEEHGAYRIIDTVDELAAAV

NDYFAK (NCBI Reference Sequence: YP_003971333.1)

SEQ ID NO: 48

MASDDIMTAGAGGATATVRADIKAAFFDIDGTLTSFVTHVIPQSSIDALHELQDRGVKV

FICSGRAPSHMTVVLDMMPVHFDGIIALNGQYCFDDHGLLEKESLLPEDIVTITRWLDEH

PDVVANYCEKDYVYFNQITDAMRATWRQLGKTAPTVNIDDPHERALKHETFQISPYISF

EDEAKLSGMCRNVRGVRWHPDFTDLIPADGGKPEGMKRFMRHYGWTREQTIAFGDGGNDAD

MLAFAGIGVAMGNATEPAKAAADYITDDVDHDGIMNALKHFNVL

SEQ ID NO: 49

CCAACTCGGCAAGACCGCACCGACCGTGAACATCGACGATCCGCACGAGAGGGCGC

TGAAGCATGAGACGTTCCAGATCAGCCCGTACATCAGCTTTGAAGATGAAGCGAAG

CTGTCCGGCAT

SEQ ID NO: 50

ATGTCAATTAAGTTAGTTGCTATTGATATCGACGGAACATTGCTAAATTCACAACAC

AAGATTACCCCACGGGTCAAAGAAGCGCTCCAAAAAGCAAATGAGCAAGGTGTTCG

TATTGTTTTATGTACAGGCCGTCCTTTGCCAGGCGTGAAAGAACAATTGGATGAATT

AGCCTTATATGGTGAAAATGATTTCGTGATTACCTACAACGGTTCGCTTGTCCAAGC

AACCAAAGATAATACGATTATTTCACGCTATACCTTGAGTTATGAGGATTTTTTAGA

AATTGAAATGTATTCTCGTAAAGTCGGCGCTCACTTGCATACAATTGATGATTCCGC

TATTTACACTGCCAATCGCAATATTGGTAAATATACGATTCACGAAGCATCTTTAGT

GAACATGCCTTTAAAATATCGTACGGTGGATGAAATGACACCAGAGATGAACATTA

TTAAAATGATGATGATTGATGAGCCGGAAGTTTTAGATCCTGCCATTGCAAAATTAC

CATTACATTTTACCGAAAAATATACGACTGTTAAAAGTACGCCTTTTTACTATGAAA

TCATGAATAAAAATGCTAGCAAAGGCAATGCTCTAGCAAAATTGGCAGACCATTTA

GGCTTAAATAAAGACGAAGTGATGGCCATTGGTGACAATGAAAATGACTTATCCAT

GATTGATTACGCTGGGATTGGTGTTGCGATGGGCAATGCGACAGAAAATGTTAAAA

CAATTGCCGATGTGCATACCACTAGTAATGACGAAGATGGTGTCGCTCAAATTATTG

AAAAAATGGTTTTAATTTAA

SEQ ID NO: 51

ATGTCTCAGCATCAGGTCACGACCCGGCAGCGCAGGAACGTGGTGCTGCTCGACCTT

GACGGTACGTTGACGCAATCGGACCCGGGCATCATCGCCTGCGCCACCAAGGCGTT

CGAGGAGCTCAGCCTGCCGGTTCCCGACGATCAGGAGATGCACCGGTTCATCGGAC

CGGCCATCATCGAGTCGTTCAGACGCAACCATATGCCGGACGAGCTGCTGGACCGC

GGCGTGGAGATATACCGCGAATACTATGCGGACAAGGCGGTGTTCGACGACCCGAA

CAATCCCGGCCACAAAATTCCCGGACGACTGTACAACAGCGTGTACGCCGGTATTCC

CGAGCAGCTGGCGGCATTGCGCGCCGACGGCTTGCACCTGGCAATCGCCACGTGCA

AGCCGCAATATCAGGCCGAGCCAGTGTGCGAGCATTTCCATCTCGATACCATGGTCG

-continued

```
ACGGCATCTACGGCGCCAGCACAGACAATTCGCGCATCGACAAGGATCAGGTCATC

CGATACTGCTTCGACAGCATCGGATTCGATGCGGATGCCGGTGACCGCGCCCTGATG

GTCGGCGACCGTTGGACCGACGTCGACGGCGCCATCGCATGCGGGCTCGATTGCCT

GGGTTGCCGTTGGGGGTACGCCGAAGCCGGTGAGCTTGAGGAACATGGCGCATACC

GCATCATCGATACCGTCGATGAGCTTGCCGCCGCGGTGAATGATTATTTCGCAAAGTGA

SEQ ID NO: 52
ATGGCATCGGACGACATCATGACAGCGGGCGCCGGAGGCGCGACGGCCACCGTGCG

AGCCGACATCAAGGCGGCGTTCTTCGACATCGACGGCACGCTGACGAGTTTCGTGA

CGCATGTAATCCCGCAGTCCTCCATCGACGCGCTGCACGAGCTGCAGGATCGCGGG

GTGAAGGTGTTCATCTGCTCCGGTCGGGCGCCGTCGCACATGACCGTCGTGCTCGAC

ATGATGCCGGTGCACTTCGACGGCATCATCGCGCTGAACGGGCAGTACTGCTTCGAC

GACCACGGGCTCCTGGAGAAGGAGTCGCTGCTGCCCGAGGACATCGTCACCATCAC

CCGCTGGCTTGACGAGCACCCCGACGTGGTGGCGAACTACTGCGAGAAGGATTACG

TCTACTTCAACCAGATCACCGACGCGATGCGGGCCACGTGGCGCCAACTCGGCAAG

ACCGCACCGACCGTGAACATCGACGATCCGCACGAGAGGGCGCTGAAGCATGAGAC

GTTCCAGATCAGCCCGTACATCAGCTTTGAAGATGAAGCGAAGCTGTCCGGCATGTG

TCGCAATGTCAGAGGCGTGCGCTGGCATCCGGACTTCACCGACCTGATTCCCGCCGA

CGGCGGCAAACCCGAGGGAATGAAGCGGTTCATGCGGCATTACGGCTGGACGCGCG

AGCAGACCATCGCGTTCGGAGACGGCGGCAACGACGCCGACATGCTCGCCTTCGCC

GGCATCGGCGTGGCGATGGCAATGCGACCGAACCGGCGAAGGCCGCGGCCGACTA

CATCACCGATGACGTCGACCACGACGGCATCATGAACGCGCTCAAGCACTTCAACG

TCCTGTAG
```

Embodiments

Embodiment 1. A method of detecting an epoxide hydrolase gene in a biological sample from a subject, the method comprising detecting
(i) a gene that encodes an epoxide hydrolase having an amino acid sequence with at least about 95%, 96%, 97%, 98%, or 99% identity to SEQ ID NO:46, or the expression thereof, in the biological sample;
(ii) a gene that encodes an epoxide hydrolase having an amino acid sequence with at least about 95%, 96%, 97%, 98%, or 99% identity to SEQ ID NO:47, or the expression thereof, in the biological sample; and/or
(iii) a gene that encodes an epoxide hydrolase having an amino acid sequence with at least about 95%, 96%, 97%, 98%, or 99% identity to SEQ ID NO:48, or the expression thereof, in the biological sample.

Embodiment 2. The method of embodiment 1, wherein
(i) the gene that encodes an epoxide hydrolase having an amino acid sequence with at least about 95%, 96%, 97%, 98%, or 99% identity to SEQ ID NO:46 is an *Enterococcus* sp. gene;
(ii) the gene that encodes an epoxide hydrolase having an amino acid sequence with at least about 95%, 96%, 97%, 98%, or 99% identity to SEQ ID NO:47 is a *Bifidobacterium* sp. gene; and/or
(iii) the gene that encodes an epoxide hydrolase having an amino acid sequence with at least about 95%, 96%, 97%, 98%, or 99% identity to SEQ ID NO:48 is a *Bifidobacterium* sp. gene.

Embodiment 3. The method of embodiment 1 or 2, wherein
(i) the gene that encodes an epoxide hydrolase having an amino acid sequence with at least about 95%, 96%, 97%, 98%, or 99% identity to SEQ ID NO:46 is an *Enterococcus faecalis* gene;
(ii) the gene that encodes an epoxide hydrolase having an amino acid sequence with at least about 95%, 96%, 97%, 98%, or 99% identity to SEQ ID NO:47 is a *Bifidobacterium bifidum* gene; and/or
(iii) the gene that encodes an epoxide hydrolase having an amino acid sequence with at least about 95%, 96%, 97%, 98%, or 99% identity to SEQ ID NO:48 is a *Bifidobacterium bifidum* gene.

Embodiment 4. The method of any one of embodiments 1 to 3, comprising detecting the level of
(i) an epoxide hydrolase gene that encodes an enzyme that has the amino acid sequence of SEQ ID NO:46 (Gene 1), or the expression thereof, in the biological sample;
(ii) an epoxide hydrolase gene that encodes an enzyme that has the amino acid sequence of SEQ ID NO:47 (Gene 2), or the expression thereof, in the biological sample;
and/or
(iii) an epoxide hydrolase gene that encodes an enzyme that has the amino acid sequence of YP_003971333 (Gene 3), or the expression thereof, in the biological sample.

Embodiment 5. A method of detecting an epoxide hydrolase gene in a biological sample from a subject, the method comprising detecting (i) an epoxide hydrolase gene comprising a nucleotide sequence with at least about 95%, 96%, 97%, 98%, or 99% identity to SEQ ID NO:50, or the expression thereof, in the biological sample;
(ii) an epoxide hydrolase gene comprising a nucleotide sequence with at least about 95%, 96%, 97%, 98%, or 99% identity to SEQ ID NO:51, or the expression thereof, in the biological sample; and/or
(iii) an epoxide hydrolase gene comprising a nucleotide sequence with at least about 95%, 96%, 97%, 98%, or 99% identity to SEQ ID NO:52, or the expression thereof, in the biological sample.

Embodiment 6. A method of detecting an epoxide hydrolase gene in a biological sample from a subject, the method comprising detecting
(i) an epoxide hydrolase gene comprising the nucleotide sequence of SEQ ID NO:50 (Gene 1), or the expression thereof, in the biological sample;
(ii) an epoxide hydrolase gene comprising the nucleotide sequence of SEQ ID NO:51 (Gene 2), or the expression thereof, in the biological sample; and/or
(iii) an epoxide hydrolase gene comprising the nucleotide sequence of SEQ ID NO:52 (Gene 3), or the expression thereof, in the biological sample.

Embodiment 7. The method of any one of embodiments 1 to 6, wherein the biological sample is a fecal sample.

Embodiment 8. The method of any one of embodiments 1 or 7, wherein the subject is less than 1, 2, 3, 4, or 5 years old.

Embodiment 9. The method of any one of embodiments 1 to 8, wherein the subject is from 0 to 1 month old, from 0.5 to 2 months old, from 0 to 3 months old, 0.5 to 3 months old, from 3 to 6 months old, or from 0 to 6 months old.

Embodiment 10. The method of any one of embodiments 1 to 9, wherein the mother of the subject has or has had asthma.

Embodiment 11. The method of any one of embodiments 1 to 10, wherein the subject has been in a room with a cat 0 times during the first month after the subject was born.

Embodiment 12. The method of any one of embodiments 1 to 11, wherein the subject has not lived in a residence with a cat for at least 7, 14, or 21 days of the first month after the subject was born.

Embodiment 13. The method of any one of embodiments 1 to 12, wherein the subject has been in a room with a dog 0 times during the first month after the subject was born.

Embodiment 14. The method of any one of embodiments 1 to 13, wherein the subject has not lived in a residence with a dog for at least 7, 14, or 21 days of the first month after the subject was born.

Embodiment 15. The method of any one of embodiments 1 to 14, wherein the subject's mother has not lived in a residence with a dog for at least 30, 60, 90, 120, 150, 180, 210, 240, or 270 days between when the subject was conceived and when the subject was born.

Embodiment 16. The method of any one of embodiments 1 to 15, wherein the subject's mother has smoked at least once on a total of at least about 30, 60, 90, 120, 150, 180, 210, 240, or 270 days between when the subject was conceived and when the subject was born.

Embodiment 17. The method of any one of embodiments 12 or 14-16, wherein the days are consecutive days.

Embodiment 18. The method of any one of embodiments 1 to 17, wherein the subject has been fed formula in the first month of life.

Embodiment 19. The method of any one of embodiments 1 to 18, wherein the subject has not been fed breast milk in the first month of life.

Embodiment 20. The method of any one of embodiments 1 to 19, wherein the level of 12,13 DiHOME in feces of the subject is at least about >398 ng/g.

Embodiment 21. The method of any one of embodiments 1 to 20, wherein the level of 9,10 DiHOME in the feces of the subject is at least about >425 ng/g.

Embodiment 22. The method of any one of embodiments 1 to 21, wherein detecting a gene comprises detecting the level of the gene.

Embodiment 23. The method of embodiment 22, comprising detecting the level of Gene 1 in the biological sample.

Embodiment 24. The method of embodiment 22 or 23, comprising detecting the level of Gene 2 in the biological sample.

Embodiment 25. The method of any one of embodiments 22 to 24, comprising detecting the level of Gene 3 in the biological sample.

Embodiment 26. The method of any one of embodiments 22 to 25, wherein the level of a gene that encodes an epoxide hydrolase is the copy number of the gene or a portion thereof per an amount of weight of the biological sample.

Embodiment 27. The method of any one of embodiments 22 to 25, wherein the level of a gene that encodes an epoxide hydrolase is the copy number of the gene or a portion thereof per an amount of DNA in the biological sample.

Embodiment 28. The method of any one of embodiments 1 to 27, comprising determining whether there are at least about 1,598 or 13,318 copies of genomic DNA sequences encoding Gene 1, Gene 2, and/or Gene 3 per nanogram (ng) of fecal DNA in the fecal sample.

Embodiment 29. The method of any one of embodiments 1 to 28, comprising detecting the expression of:
(i) the gene that encodes an epoxide hydrolase having an amino acid sequence with at least about 95%, 96%, 97%, 98%, or 99% identity to SEQ ID NO:46 in the biological sample;
(ii) the gene that encodes an epoxide hydrolase having an amino acid sequence with at least about 95%, 96%, 97%, 98%, or 99% identity to SEQ ID NO:47 in the biological sample; and/or
(iii) a gene that encodes an epoxide hydrolase having an amino acid sequence with at least about 95%, 96%, 97%, 98%, or 99% identity to SEQ ID NO:48 in the biological sample.

Embodiment 30. The method of any one of embodiments 1 to 29, wherein detecting the expression of a gene comprises detecting an epoxide hydrolase mRNA transcribed from the gene or an epoxide hydrolase protein encoded by the gene.

Embodiment 31. The method of any one of embodiments 1 to 30, wherein detecting the expression of a gene comprises detecting the level of the expression of the gene.

Embodiment 32. The method of embodiment 31, wherein the level of expression is the level of mRNA transcribed from the gene or the level of an epoxide hydrolase protein encoded by the gene.

Embodiment 33. The method of any one of embodiments 1 to 32, wherein detecting comprises measuring with an assay.

Embodiment 34. The method of embodiment 33, wherein the assay comprises high-throughput sequencing, quantitative PCR, or microarray analysis.

Embodiment 35. The method of embodiment 33 or 34, wherein the assay comprises one or more probes or primers that hybridize to at least a portion of the gene or an mRNA transcribed from the gene under stringent conditions.

Embodiment 36. The method of any one of embodiments 33 to 35, wherein the assay comprises one or more probes or primers that hybridize to a portion of a genome within about 0.1, 0.5, 1, 2, 3, 4, or 5 kilobases of the gene under stringent conditions.

Embodiment 37. The method of any one of embodiments 1 to 36, further comprising detecting the level of an oxylipin in the biological sample.

Embodiment 38. The method of embodiment 37, wherein the oxylipin is 12,13 DiHOME and/or 9,10 DiHOME.

Embodiment 39. The method of any one of embodiments 1 to 38, further comprising calculating a Neonatal Atopy Score (NAtS) for the subject, wherein the subject's NAtS score comprises, one point for each of the following: (i) having at least about 13,318 copies of a genomic DNA sequence that encodes Gene 1, Gene 2, and/or Gene 3 per nanogram (ng) of fecal DNA in a fecal sample; (ii) having a mother who has or has had asthma; and (iii) having not lived in a residence with a cat for at least 7, 14, or 21 days of the first month after being born.

Embodiment 40. The method of embodiment 39, wherein the a NAtS of ≥2 is calculated for the subject.

Embodiment 41. The method of embodiment 40, further comprising identifying the subject as at risk of developing atopy compared to a corresponding subject with a NAtS of 1 or 0.

Embodiment 42. The method of embodiment 39, wherein a NAtS of 1 or 0 is calculated for the subject.

Embodiment 43. The method of embodiment 42, further comprising identifying the subject as less likely to develop atopy than a corresponding subject with a NAts of ≥2.

Embodiment 44. The method of any one of embodiments 1 to 43, further comprising calculating a Neonatal Asthma Predictive Score (NAPS) for the subject, wherein the subject's NAPS score comprises one point for each of the following: (i) having not lived in a residence with a dog for at least about 7, 14, or 21 days of the first month after being born; (ii) having a mother who has not lived in a residence with a dog for at least 30, 60, 90, 120, 150, 180, 210, 240, or 270 days between when the subject was conceived and when the subject was born; (iii) having a mother who has smoked at least once on a total of at least 30, 60, 90, 120, 150, 180, 210, 240, or 270 days between when the subject was conceived and when the subject was born; (iv) being fed formula in the first month of life; (v) having a fecal level of 12,13 DiHOME of at least about >398 ng/g; (vi) having a fecal level of 9,10 DiHOME of at least about >425 ng/g; and (vii) having at least about 1,598 copies of a genomic DNA sequence that encodes Gene 1, Gene 2, and/or Gene 3 per nanogram (ng) of fecal DNA in a fecal sample.

Embodiment 45. The method of embodiment 44, wherein a NAPS of ≥6 is calculated for the subject.

Embodiment 46. The method of embodiment 45, further comprising identifying the subject as at risk of developing atopy compared to a corresponding subject with a NAPS of <6.

Embodiment 47. The method of embodiment 44, wherein the a NAPS of <6 is calculated for the subject.

Embodiment 48. The method of embodiment 47, further comprising identifying the subject as less likely to develop atopy than a corresponding subject with a NAPS of ≥6.

Embodiment 49. A method of determining whether a subject is at risk of atopy or asthma, the method comprising:
(a) detecting
  (i) a gene that encodes an epoxide hydrolase having an amino acid sequence with at least about 95%, 96%, 97%, 98%, or 99% identity to SEQ ID NO:46, or the expression thereof, in a biological sample from the subject;
  (ii) a gene that encodes an epoxide hydrolase having an amino acid sequence with at least about 95%, 96%, 97%, 98%, or 99% identity to SEQ ID NO:47, or the expression thereof, in a biological sample from the subject; and/or
  (iii) a gene that encodes an epoxide hydrolase having an amino acid sequence with at least about 95%, 96%, 97%, 98%, or 99% identity to SEQ ID NO:48, or the expression thereof, in a biological sample from the subject, and
(b) identifying the subject as at risk of atopy or asthma if a level of the first epoxide hydrolase gene, the second epoxide hydrolase gene, and/or the third epoxide hydrolase gene is detected.

Embodiment 50. The method of any one of embodiments 39 to 43 or 49, further comprising monitoring the subject for atopy if the subject is identified as at risk for atopy, wherein the monitoring is more frequent than a corresponding subject who is identified as having less risk or a lower likelihood of developing atopy.

Embodiment 51. The method of any one of embodiments 39 to 43 or 49, further comprising monitoring the subject for atopy if the subject is identified as at risk for atopy, wherein the monitoring comprises an examination or diagnostic assay that is not administered to a corresponding subject who is identified as having less risk or a lower likelihood of developing atopy.

Embodiment 52. The method of any one of embodiments 44 to 49, further comprising monitoring the subject for asthma if the subject is identified as at risk for asthma, wherein the monitoring is more frequent than a corresponding subject who is identified as having less risk or a lower likelihood of developing asthma.

Embodiment 53. The method of any one of embodiments 44 to 49, further comprising monitoring the subject for asthma if the subject is identified as at risk for asthma, wherein the monitoring comprises an examination or diagnostic assay that is not administered to a corresponding subject who is identified as having less risk or a lower likelihood of developing asthma.

Embodiment 54. The method of any one of embodiments 39 to 43 or 49, further comprising administering a treatment to treat, reduce the likelihood of, or prevent atopy to the subject if the subject is identified as at risk for atopy.

Embodiment 55. The method of any one of embodiments 44 to 49, further comprising administering a treatment to treat, reduce the likelihood of, or prevent asthma to the subject if the subject is identified as at risk for asthma.

Embodiment 56. A method of reducing the likelihood that a subject will develop asthma or atopy, the method comprising administering to the subject a treatment that reduces the likelihood that the subject will develop atopy, wherein Gene 1, Gene 2, and/or Gene 3, or the expression thereof, has been detected in a biological sample from the subject.

Embodiment 57. A method of treating or preventing atopy or asthma in a subject in need thereof, the method comprising administering to the subject a treatment that prevents or treats atopy or asthma, wherein Gene 1, Gene 2, and/or Gene 3, or the expression thereof, has been detected in a biological sample from the subject.

Embodiment 58. The method of embodiment 56 or 57, wherein a level of Gene 1, Gene 2, and/or Gene 3 has been detected in the biological sample, wherein the level is at least about 1,598 or 13,318 copies of genomic DNA sequences encoding Gene 1, Gene 2, and/or Gene 3 per nanogram (ng) of fecal DNA of the subject.

Embodiment 59. The method of any one of embodiments 56 to 58, wherein the subject has been identified as at risk of atopy or asthma according to any one of embodiments 31-41.

Embodiment 60. The method of any one of embodiments 56 to 59, wherein the treatment comprises immunotherapy for a food allergen, immunotherapy for an aeroallergen, or a monoclonal antibody.

Embodiment 61. The method of any one of embodiments 56 to 60, wherein the treatment comprises the administration of an effective amount of omalizumab, montelukast, budesonide, levocetirizine, vitamin D supplementation, a probiotic organism, fish oil, or linoleic acid.

Embodiment 62. The method of any one of embodiments 56 to 61, wherein the treatment comprises oral mucosal immunoprophylaxis with a house dust mite, cat dander, or a grass pollen, vitamin E, supplementation with *Lactobacillus reuteri* with or without one or more leukotrienes, sublingual supplementation with grass pollen extract, or dust mite immunotherapy.

Embodiment 63. The method of any one of embodiments 56 to 62, wherein the treatment comprises administering an effective amount of at least one probiotic organism to the subject.

Embodiment 64. The method of embodiment 63, wherein the at least one probiotic organism comprises *Lactobacillus* sp., *Faecalibacterium* sp., *Akkermansia* sp., *Myxococcus* sp., *Pediococcus* sp., *Bifidobacterium* sp., and/or *Streptococcus* sp.

Embodiment 65. The method of embodiment 64, wherein (i) the *Lactobacillus* sp. is *Lactobacillus zeae, Lactobacillus acidipiscis, Lactobacillus acidophilus, Lactobacillus agilis, Lactobacillus aviarius, Lactobacillus brevis, Lactobacillus coleohominis, Lactobacillus crispatus, Lactobacillus crustorum, Lactobacillus curvatus, Lactobacillus diolivorans, Lactobacillus farraginis, Lactobacillus fermentum, Lactobacillus fuchuensis, Lactobacillus harbinensis, Lactobacillus helveticus, Lactobacillus hilgardii, Lactobacillus intestinalis, Lactobacillus jensenii, Lactobacillus kefiranofaciens, Lactobacillus kefiri, Lactobacillus lindneri, Lactobacillus mall, Lactobacillus manihotivorans, Lactobacillus mucosae, Lactobacillus oeni, Lactobacillus oligofermentans, Lactobacillus panis, Lactobacillus pantheris, Lactobacillus parabrevis, Lactobacillus paracollinoides, Lactobacillus parakefiri, Lactobacillus paraplantarum, Lactobacillus pentosus, Lactobacillus pontis, Lactobacillus reuteri, Lactobacillus rossiae, Lactobacillus salivarius, Lactobacillus siliginis, Lactobacillus sucicola, Lactobacillus vaccinostercus, Lactobacillus vaginalis, Lactobacillus vini, Lactococcus garvieae,* or *Lactococcus lactis*; (ii) the *Faecalibacterium* sp., is *Faecalibacterium prausnitzii*; (iii) the *Akkermansia* sp. is *Akkermansia muciniphila*; (iv) the *Myxococcus* sp. is *Myxococcus xanthus*; (v) the *Pediococcus* sp. is *Pediococcus pentosaceus, Pediococcus acidilactici, Pediococcus damnosus, Pediococcus ethanolidurans,* or *Pediococcus parvulus*; (vi) the *Bifidobacterium* sp. is *B. bifidum, B. infantis, B. reuteri, B. breve,* or *B. longum*; and/or (vii) the *Streptococcus* sp. is *Streptococcus thermophilis*.

Embodiment 66. The method of any one of embodiments 56 to 65, wherein the treatment comprises at least one antibiotic compound.

Embodiment 67. The method of embodiment 66, wherein the antibiotic is a cephalosporin, a penicillin, a carbapenem, or a glycopeptide.

What is claimed is:

1. A method of treating atopy or reducing the likelihood of atopy in a subject in need thereof, the method comprising:
    detecting an epoxide hydrolase gene in a biological sample from the subject, the gene comprising
    (i) a gene that encodes an epoxide hydrolase having an amino acid sequence with at least about 95%, 96%, 97%, 98%, or 99% identity to SEQ ID NO:46 (Gene 1), or the expression thereof, in the biological sample;
    (ii) a gene that encodes an epoxide hydrolase having an amino acid sequence with at least about 95%, 96%, 97%, 98%, or 99% identity to SEQ ID NO:47 (Gene 2), or the expression thereof, in the biological sample; and/or
    (iii) a gene that encodes an epoxide hydrolase having an amino acid sequence with at least about 95%, 96%, 97%, 98%, or 99% identity to SEQ ID NO:48 (Gene 3), or the expression thereof, in the biological sample;
    administering a treatment effective to treat or reduce the likelihood of developing atopy, wherein the treatment comprises:
    (a) immunotherapy for a food allergen, immunotherapy for an aeroallergen, or a monoclonal antibody;
    (b) administration of an effective amount of omalizumab, montelukast, budesonide, levocetirizine, vitamin D supplementation, a probiotic organism, fish oil, or linoleic acid;
    (c) oral mucosal immunoprophylaxis with a house dust mite, cat dander, or a grass pollen, vitamin E, supplementation with *Lactobacillus reuteri* with or without one or more leukotrienes, sublingual supplementation with grass pollen extract, or dust mite immunotherapy;
    (d) administering an effective amount of at least one probiotic organism to the subject;
    (e) administering an effective amount of at least one of a *Lactobacillus* sp., a *Faecalibacterium* sp., an *Akkermansia* sp., a *Myxococcus* sp., a *Pediococcus* sp., a *Bifidobacterium* sp., and/or a *Streptococcus* sp.;
    (f) administering an effective amount of at least one of a *Lactobacillus* sp., a *Faecalibacterium* sp., an *Akkermansia* sp., a *Myxococcus* sp., a *Pediococcus* sp., a *Bifidobacterium* sp., and/or a *Streptococcus* sp, and further wherein (i) the *Lactobacillus* sp. is selected from the group consisting of *Lactobacillus zeae, Lactobacillus acidipiscis, Lactobacillus acidophilus, Lactobacillus agilis, Lactobacillus avarius, Lactobacillus brevis, Lactobacillus coleohominis, Lactobacillus crispatus, Lactobacillus crustorum, Lactobacillus curvatus, Lactobacillus diolivorans, Lactobacillus farraginis, Lactobacillus fermentum, Lactobacillus fuchuensis, Lactobacillus harbinensis, Lactobacillus helveticus, Lactobacillus hilgardii, Lactobacillus intestinalis, Lactobacillus jensenii, Lactobacillus kefiranofaciens, Lactobacillus kefiri, Lactobacillus lindneri, Lactobacillus male, Lactobacillus manihotivorans, Lactobacillus mucosae, Lactobacillus oeni, Lactobacillus oligofermentans, Lactobacillus panes, Lactobacillus pantheris, Lactobacillus parabrevis, Lactobacillus paracollinoides, Lactobacillus parakefiri, Lactobacillus paraplantarum, Lactobacillus pentosus, Lactobacillus pontis, Lactobacillus reuteri, Lactobacillus rossiae, Lactobacillus salivarius, Lactobacillus siliginis, Lactobacillus sucicola, Lactobacillus vaccinostercus, Lactobacillus vaginalis, Lactobacillus vine, Lactococcus garvieae,* or *Lactococcus lactis*, (ii) the *Faecalibacterium* sp., is *Faecalibacterium prausnitzii*, (iii) the *Akkermansia* sp. is *Akkermansia muciniphila*, (iv) the *Myxococcus* sp. is *Myxococcus xanthus*, (v) the *Pediococcus* sp. is *Pediococcus pentosaceus, Pediococcus acidilactici, Pediococcus damnosus, Pediococcus ethanolidurans,* or *Pediococcus parvulus*, (vi) the *Bifidobacterium* sp. is *B. bifidum, B. infantis, B. reuteri, B. breve,* or *B. longum*, and/or (vii) the *Streptococcus* sp. is *Streptococcus* thermophiles;
    (g) at least one antibiotic compound; or
    (h) at least one of a cephalosporin, a penicillin, a carbapenem, or a glycopeptide.

2. The method of claim 1, wherein
    (i) the gene that encodes an epoxide hydrolase having an amino acid sequence with at least about 95%, 96%, 97%, 98%, or 99% identity to SEQ ID NO:46 is an *Enterococcus* sp. gene or an *Enterococcus faecalis* gene;
    (ii) the gene that encodes an epoxide hydrolase having an amino acid sequence with at least about 95%, 96%, 97%, 98%, or 99% identity to SEQ ID NO:47 is a *Bifidobacterium* sp. gene or a *Bifidobacterium bifidum* gene; and/or
    (iii) the gene that encodes an epoxide hydrolase having an amino acid sequence with at least about 95%, 96%, 97%, 98%, or 99% identity to SEQ ID NO:48 is a *Bifidobacterium* sp. gene or a *Bifidobacterium bifidum* gene.

3. The method of claim 1, wherein the biological sample is a fecal sample.

4. The method of claim 1, wherein
    (a) the subject is less than 1, 2, 3, 4, or 5 years old;
    (b) the subject is from 0 to 1 month old, from 0.5 to 2 months old, from 0 to 3 months old, 0.5 to 3 months old, from 3 to 6 months old, or from 0 to 6 months old;

(c) the mother of the subject has or has had asthma;
(d) the subject has been in a room with a cat 0 times during the first month after the subject was born;
(e) the subject has not lived in a residence with a cat for at least 7, 14, or 21 days of the first month after the subject was born;
(f) the subject has been in a room with a dog 0 times during the first month after the subject was born;
(g) the subject has not lived in a residence with a dog for at least 7, 14, or 21 days of the first month after the subject was born;
(h) the subject's mother has not lived in a residence with a dog for at least 30, 60, 90, 120, 150, 180, 210, 240, or 270 days between when the subject was conceived and when the subject was born;
(i) the subject's mother has smoked at least once on a total of at least about 30, 60, 90, 120, 150, 180, 210, 240, or 270 days between when the subject was conceived and when the subject was born;
(j) the subject has been fed formula in the first month of life;
(k) the subject has not been fed breast milk in the first month of life;
(l) a level of 12,13 DiHOME in feces of the subject is at least about >398 ng/g; or
(m) a level of 9,10 DiHOME in the feces of the subject is at least about >425 ng/g.

5. The method of claim 1, wherein detecting a gene comprises detecting a level of the gene.

6. The method of claim 5, wherein:
(a) the method comprises detecting the level of Gene 1 in the biological sample;
(b) the method comprises detecting the level of Gene 2 in the biological sample;
(c) the method comprises detecting the level of Gene 3 in the biological sample;
(d) the level of a gene that encodes an epoxide hydrolase is the copy number of the gene or a portion thereof per an amount of weight of the biological sample; or
(e) the level of a gene that encodes an epoxide hydrolase is the copy number of the gene or a portion thereof per an amount of DNA in the biological sample.

7. The method of claim 1, comprising determining whether there are at least about 1,598 or 13,318 copies of genomic DNA sequences encoding Gene 1, Gene 2, and/or Gene 3 per nanogram (ng) of fecal DNA in the fecal sample.

8. The method of claim 1, comprising detecting the expression of:
(i) the gene that encodes an epoxide hydrolase having an amino acid sequence with at least about 95%, 96%, 97%, 98%, or 99% identity to SEQ ID NO:46 in the biological sample;
(ii) the gene that encodes an epoxide hydrolase having an amino acid sequence with at least about 95%, 96%, 97%, 98%, or 99% identity to SEQ ID NO:47 in the biological sample; and/or
(iii) a gene that encodes an epoxide hydrolase having an amino acid sequence with at least about 95%, 96%, 97%, 98%, or 99% identity to SEQ ID NO:48 in the biological sample.

9. The method of claim 8, wherein:
(a) detecting the expression of a gene comprises detecting an epoxide hydrolase mRNA transcribed from the gene or an epoxide hydrolase protein encoded by the gene;
(b) detecting the expression of a gene comprises detecting a level of the expression of the gene; or
(c) detecting the expression of a gene comprises detecting a level of mRNA transcribed from the gene or the level of an epoxide hydrolase protein encoded by the gene.

10. The method of claim 1, wherein the detecting comprises:
(a) high-throughput sequencing, quantitative PCR, or microarray analysis;
(b) detection with one or more probes or primers that hybridize to at least a portion of the gene or an mRNA transcribed from the gene under stringent conditions; or
(c) detection with one or more probes or primers that hybridize to a portion of a genome within about 0.1, 0.5, 1, 2, 3, 4, or 5 kilobases of the gene under stringent conditions.

11. The method of claim 1, further comprising detecting the level of an oxylipin, 12,13 DiHOME, or 9,10 DiHOME in the biological sample.

12. The method of claim 1, further comprising calculating a Neonatal Atopy Score (NAtS) for the subject, wherein the subject's NAtS score comprises, one point for each of the following: (i) having at least about 13,318 copies of a genomic DNA sequence that encodes Gene 1, Gene 2, and/or Gene 3 per nanogram (ng) of fecal DNA in a fecal sample; (ii) having a mother who has or has had asthma; and (iii) having not lived in a residence with a cat for at least 7, 14, or 21 days of the first month after being born.

13. The method of claim 12, wherein:
(a) a NAtS of ≥2 is calculated for the subject;
(b) the method further comprises identifying the subject as at risk of developing atopy compared to a corresponding subject with a NAtS of 1 or 0;
(c) a NAtS of 1 or 0 is calculated for the subject; or
(d) the method further comprises identifying the subject as less likely to develop atopy than a corresponding subject with a NAts of ≥2.

14. The method of claim 12, further comprising
(a) monitoring the subject for atopy if the subject is identified as at risk for atopy, wherein the monitoring is more frequent than a corresponding subject who is identified as having less risk or a lower likelihood of developing atopy;
(b) monitoring the subject for atopy if the subject is identified as at risk for atopy, wherein the monitoring comprises an examination or diagnostic assay that is not administered to a corresponding subject who is identified as having less risk or a lower likelihood of developing atopy; or
(c) administering a treatment to treat, reduce the likelihood of, or prevent atopy to the subject if the subject is identified as at risk for atopy.

15. The method of claim 1, further comprising calculating a Neonatal Asthma Predictive Score (NAPS) for the subject, wherein the subject's NAPS score comprises one point for each of the following: (i) having not lived in a residence with a dog for at least about 7, 14, or 21 days of the first month after being born; (ii) having a mother who has not lived in a residence with a dog for at least 30, 60, 90, 120, 150, 180, 210, 240, or 270 days between when the subject was conceived and when the subject was born; (iii) having a mother who has smoked at least once on a total of at least 30, 60, 90, 120, 150, 180, 210, 240, or 270 days between when the subject was conceived and when the subject was born; (iv) being fed formula in the first month of life; (v) having a fecal level of 12,13 DiHOME of at least about ≥398 ng/g; (vi) having a fecal level of 9,10 DiHOME of at least about >425 ng/g; and (vii) having at least about 1,598 copies of a genomic DNA sequence that encodes Gene 1, Gene 2, and/or Gene 3 per nanogram (ng) of fecal DNA in a fecal sample.

16. The method of claim 15, wherein:
    (a) a NAPS of ≥6 is calculated for the subject;
    (b) the method further comprises identifying the subject as at risk of developing atopy compared to a corresponding subject with a NAPS of <6;
    (c) a NAPS of <6 is calculated for the subject; or
    (d) the method further comprises identifying the subject as less likely to develop atopy than a corresponding subject with a NAPS of ≥6.

17. The method of claim 15, further comprising
    (a) monitoring the subject for asthma if the subject is identified as at risk for asthma, wherein the monitoring is more frequent than a corresponding subject who is identified as having less risk or a lower likelihood of developing asthma;
    (b) monitoring the subject for asthma if the subject is identified as at risk for asthma, wherein the monitoring comprises an examination or diagnostic assay that is not administered to a corresponding subject who is identified as having less risk or a lower likelihood of developing asthma; or
    (c) administering a treatment to treat, reduce the likelihood of, or prevent asthma to the subject if the subject is identified as at risk for asthma.

18. A method of treating atopy or reducing the likelihood of atopy in a subject in need thereof, the method comprising:
    detecting an epoxide hydrolase gene in a biological sample from the subject, the gene comprising
    (i) an epoxide hydrolase gene comprising a nucleotide sequence with at least about 95%, 96%, 97%, 98%, or 99% identity to SEQ ID NO:50, or the expression thereof, in the biological sample;
    (ii) an epoxide hydrolase gene comprising a nucleotide sequence with at least about 95%, 96%, 97%, 98%, or 99% identity to SEQ ID NO:51, or the expression thereof, in the biological sample; and/or
    (iii) an epoxide hydrolase gene comprising a nucleotide sequence with at least about 95%, 96%, 97%, 98%, or 99% identity to SEQ ID NO:52, or the expression thereof, in the biological sample;
    administering a treatment effective to treat or reduce the likelihood of developing atopy, wherein the treatment comprises:
    (a) immunotherapy for a food allergen, immunotherapy for an aeroallergen, or a monoclonal antibody;
    (b) administration of an effective amount of omalizumab, montelukast, budesonide, levocetirizine, vitamin D supplementation, a probiotic organism, fish oil, or linoleic acid;
    (c) oral mucosal immunoprophylaxis with a house dust mite, cat dander, or a grass pollen, vitamin E, supplementation with *Lactobacillus reuteri* with or without one or more leukotrienes, sublingual supplementation with grass pollen extract, or dust mite immunotherapy;
    (d) administering an effective amount of at least one probiotic organism to the subject;
    (e) administering an effective amount of at least one of a *Lactobacillus* sp., a *Faecalibacterium* sp., an *Akkermansia* sp., a *Myxococcus* sp., a *Pediococcus* sp., a *Bifidobacterium* sp., and/or a *Streptococcus* sp.;
    (f) administering an effective amount of at least one of a *Lactobacillus* sp., a *Faecalibacterium* sp., an *Akkermansia* sp., a *Myxococcus* sp., a *Pediococcus* sp., a *Bifidobacterium* sp., and/or a *Streptococcus* sp, and further wherein (i) the *Lactobacillus* sp. is selected from the group consisting of *Lactobacillus zeae, Lactobacillus acidipiscis, Lactobacillus acidophilus, Lactobacillus agilis, Lactobacillus aviarius, Lactobacillus brevis, Lactobacillus coleohominis, Lactobacillus crispatus, Lactobacillus crustorum, Lactobacillus curvatus, Lactobacillus diolivorans, Lactobacillus farraginis, Lactobacillus fermentum, Lactobacillus fuchuensis, Lactobacillus harbinensis, Lactobacillus helveticus, Lactobacillus hilgardii, Lactobacillus intestinalis, Lactobacillus jensenii, Lactobacillus kefiranofaciens, Lactobacillus kefiri, Lactobacillus lindneri, Lactobacillus mali, Lactobacillus manihotivorans, Lactobacillus mucosae, Lactobacillus oeni, Lactobacillus oligofermentans, Lactobacillus panis, Lactobacillus pantheris, Lactobacillus parabrevis, Lactobacillus paracollinoides, Lactobacillus parakefiri, Lactobacillus paraplantarum, Lactobacillus pentosus, Lactobacillus pontis, Lactobacillus reuteri, Lactobacillus rossiae, Lactobacillus salivarius, Lactobacillus siliginis, Lactobacillus sucicola, Lactobacillus vaccinostercus, Lactobacillus vaginalis, Lactobacillus vini, Lactococcus garvieae*, or *Lactococcus lactis*, (ii) the *Faecalibacterium* sp., is *Faecalibacterium prausnitzii*, (iii) the *Akkermansia* sp. is *Akkermansia muciniphila*, (iv) the *Myxococcus* sp. is *Myxococcus xanthus*, (v) the *Pediococcus* sp. is *Pediococcus pentosaceus, Pediococcus acidilactici, Pediococcus damnosus, Pediococcus ethanolidurans*, or *Pediococcus parvulus*, (vi) the *Bifidobacterium* sp. is *B. bifidum, B. infantis, B. reuteri, B. breve*, or *B. longum*, and/or (vii) the *Streptococcus* sp. is *Streptococcus thermophiles*;
    (g) at least one antibiotic compound; or
    (h) at least one of a cephalosporin, a penicillin, a carbapenem, or a glycopeptide.

\* \* \* \* \*

SEQUENCE LISTING

<160> NUMBER OF SEQ ID NOS: 52

<210> SEQ ID NO 1
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 1
taatacgact cactataggg                    20

<210> SEQ ID NO 2
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 2
gctagttatt gctcagcgg                                                  19

<210> SEQ ID NO 3
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 3
atcaacactg ccagtgtggc t                                               21

<210> SEQ ID NO 4
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 4
agtgtcatgc ccactattcc c                                               21

<210> SEQ ID NO 5
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 5
ggatggaaaa tcaaccacca                                                 20

<210> SEQ ID NO 6
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 6
ggaagtgacg cctttcatga                                                 20

<210> SEQ ID NO 7
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 7
acctgtcctg tcgggtgaa                                                  19

<210> SEQ ID NO 8
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 8
cccacggaac tgtgatgct                                                  19

<210> SEQ ID NO 9

```
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 9
tctttcctgc agcccaatg                                              19

<210> SEQ ID NO 10
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 10
agcctctgtt ccaactgata gtga                                        24

<210> SEQ ID NO 11
<211> LENGTH: 27
<212> TYPE: DNA
<213> ORGANISM: Artificial sequence
<220> FEATURE:
<223> OTHER INFORMATION: Synthetic polynucleotide

<400> SEQUENCE: 11
aagatgaccc agatcatgtt tgagacc                                     27

<210> SEQ ID NO 12
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 12
agccagtcca gacgcaggat                                             20

<210> SEQ ID NO 13
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 13
cgaagactac agttctgcca tt                                          22

<210> SEQ ID NO 14
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 14
gacgtttcag aggttctcag ag                                          22

<210> SEQ ID NO 15
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 15
```

```
gaaatgccac cttttgacag tg                                              22

<210> SEQ ID NO 16
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 16
tggatgctct catcaggaca g                                               21

<210> SEQ ID NO 17
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 17
ccctcacact cagatcatct tct                                             23

<210> SEQ ID NO 18
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 18
gctacgacgt gggctacag                                                  19

<210> SEQ ID NO 19
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 19
cctcgtcccg tagacaaaat g                                               21

<210> SEQ ID NO 20
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 20
tctccacttt gccactgcaa                                                 20

<210> SEQ ID NO 21
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 21
cgacggaaca ttgctaaatt cac                                             23

<210> SEQ ID NO 22
<211> LENGTH: 21
<212> TYPE: DNA
```

```
<213> ORGANISM: Artificial sequence
<220> FEATURE:
<223> OTHER INFORMATION: Synthetic polynucleotide

<400> SEQUENCE: 22
caaaggacgg cctgtacata a                                              21

<210> SEQ ID NO 23
<211> LENGTH: 23
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' 6-carboxyfluorescin
<220> FEATURE:
<221> NAME/KEY: misc_feature
<222> LOCATION: (9)..(10)
<223> OTHER INFORMATION: Internal ZEN quencher
<220> FEATURE:
<221> NAME/KEY: misc_feature
<222> LOCATION: (23)..(23)
<223> OTHER INFORMATION: 3' Iowa Black FQ quencher

<400> SEQUENCE: 23
acgggtcaaa gaagcgctcc aaa                                            23

<210> SEQ ID NO 24
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 24
gtcgttcaga cgcaaccata                                                20

<210> SEQ ID NO 25
<211> LENGTH: 18
<212> TYPE: DNA
<213> ORGANISM: Artificial sequence
<220> FEATURE:
<223> OTHER INFORMATION: Synthetic polynucleotide

<400> SEQUENCE: 25
tttgtggccg ggattgtt                                                  18

<210> SEQ ID NO 26
<211> LENGTH: 24
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' 6-carboxyfluorescin
<220> FEATURE:
<221> NAME/KEY: misc_feature
<222> LOCATION: (9)..(10)
<223> OTHER INFORMATION: Internal ZEN quencher
<220> FEATURE:
<221> NAME/KEY: misc_feature
<222> LOCATION: (24)..(24)
<223> OTHER INFORMATION: 3' Iowa Black FQ quencher

<400> SEQUENCE: 26
tactatgcgg acaaggcggt gttc                                           24
```

<210> SEQ ID NO 27
<211> LENGTH: 17
<212> TYPE: DNA
<213> ORGANISM: Artificial sequence
<220> FEATURE:
<223> OTHER INFORMATION: Synthetic polynucleotide

<400> SEQUENCE: 27
gcaccgaccg tgaacat                                                       17

<210> SEQ ID NO 28
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 28
ggacagcttc gcttcatctt                                                    20

<210> SEQ ID NO 29
<211> LENGTH: 24
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' 6-carboxyfluorescin
<220> FEATURE:
<221> NAME/KEY: misc_feature
<222> LOCATION: (9)..(10)
<223> OTHER INFORMATION: Internal ZEN quencher
<220> FEATURE:
<221> NAME/KEY: misc_feature
<222> LOCATION: (24)..(24)
<223> OTHER INFORMATION: 3' Iowa Black FQ quencher

<400> SEQUENCE: 29
cgctgaagca tgagacgttc caga                                               24

<210> SEQ ID NO 30
<211> LENGTH: 899
<212> TYPE: DNA
<213> ORGANISM: Artificial sequence
<220> FEATURE:
<223> OTHER INFORMATION: Synthetic polynucleotide

<400> SEQUENCE: 30
aattgcagaa ttcatgatta aactgattgc gagcgatatg gatggcaccc tgctggatgc        60
gaaaatgagc attaccaacg ataacgcgag cgcgattcgc gaagcggaac gcctgggcat       120
tgaatttatg gtggcgaccg gccgcgcgta taccgaagcg aaaccggcgc tggaagaagc       180
gggcattgat tgcgcgatga ttaccctgaa cggcgcgcag gtgtttgata agatggccca       240
tagcctgttt accgcgggca ttgaaaaaga aaccgtgacc gaagtgctga ccattctgag       300
ccagcataac gtgtattatg aaattagcac caacaaaggc attttttagcg aacatcagga     360 aaaacgcatt gaaaactttg cggcgcatat tgcggaaagc atgccgcatc tgacctataa       420
agtggcgatt gcgatggcga gcgcgcatct gagcctgctg catattaccct atgtggatcg      480 cctggatgat attctgaaag atgatagcat tgaagtgctg aaaattattg gctttagcat       540
ggatggcccg aaagtgctgg gcccggcggg catggaagtg gaagaactgg atgatctggt       600

```
ggtgaccagc agcgcgctga caacattga aattaaccat cgcctggcgc agaaaggcat      660
tgcggtggcg cgcgtggcga aagaacgcgg cattccggcg gaacaggtga tgaccattgg      720
cgataacctg aacgatgtga gcatgattca gtgggcgggc gtgagctttg cgatgggcaa      780
cgcggaactg gaactgaaag aatatgcgaa atatgaaacc gcgaccaacc tggaaaacgg      840
cgtgggcgaa gcgattctgc gcgcgattcg cgaagatctg gttgtcgact tatccggcc      899
```

<210> SEQ ID NO 31
<211> LENGTH: 833
<212> TYPE: DNA
<213> ORGANISM: Artificial sequence
<220> FEATURE:
<223> OTHER INFORMATION: Synthetic polynucleotide

<400> SEQUENCE: 31

```
aattgcagaa ttcatgaaaa aactgattgc gattgatctg gatggcacca ccctgaacgc       60
gcagagcctg attagcccga aaaccgaaca gaccctgaaa aaagcgattg ataacggcca      120
ttatgtgagc attgcgaccg ccgcccgta tcgcatgagc catcagtttt atcagcagct      180
gggcctgacc accccgatgg tgaactttaa cggcgcgctg gtgcatattc cggaaaaaaa      240
atgggatctg gaaagcgaag cgaacattga acgcgatctg gtgtttgata ttctggcgca      300 gaaaaagaa ctgcagctgg attttgtggc ggcggaaaac aaagaaacct tttatattga      360 tacccctggat ggcttttgatc cgaaattttt tgcgagcaaa gcgaccctgg ataacctgct      420
gaccgcgaaa aacctgcgca ccaacccgac cagcatgatg gtgcgcacca ccccgaacca      480
ggcggaaaaa gtggcggata ccctgaccaa acagtatggc gattatattg atgtgcgcac      540
ctggggcggc ccgatgccga ttctggaaat ggtggcgaaa ggcattcaga aagcgcatgg      600
cgtggatcag gtggcgaact ttctgagcgt gaaaccggcg gatattattg cgtttggcga      660
tgaacataac gatgaagaaa tgctgagcta tgcgggctgg ggcgtggcga tgaacaacgc      720
gaccgataaa attaaaagcg tggcgaacga tgtgaccgaa aaaaccaacg atcaggatgg      780
cctggcggat tatctggaaa actatctgga tctggttgtc gacttatccg gcc             833
```

<210> SEQ ID NO 32
<211> LENGTH: 842
<212> TYPE: DNA
<213> ORGANISM: Artificial sequence
<220> FEATURE:
<223> OTHER INFORMATION: Synthetic polynucleotide

<400> SEQUENCE: 32

```
aattgcagaa ttcatgagca ttaaactggt ggcgattgat attgatggca ccctgctgaa       60
cagccagcat aaaattaccc cgcgcgtgaa agaagcgctg cagaaagcga acgaacaggg      120
cgtgcgcatt gtgctgtgca ccggccgccc gctgccgggc gtgaaagaac agctggatga      180
actggcgctg tatggcgaaa cgattttgt gattacctat aacggcagcc tggtgcaggc      240
gaccaaagat aacaccatta ttagccgcta taccctgagc tatgaagatt ttctggaaat      300
tgaaatgtat agccgcaaag tgggcgcgca tctgcatacc attgatgata gcgcgattta      360
taccgcgaac cgcaacattg gcaaatatac cattcatgaa gcgagcctgg tgaacatgcc      420
gctgaaatat cgcaccgtgg atgaaatgac cccggaaatg aacattatta aatgatgat      480 gattgatgaa ccggaagtgc tggatccgga gattgcgaaa ctgccgctgc attttaccga      540 aaatatacc accgtgaaaa gcaccccgtt ttattatgaa attatgaaca aaaacgcgag      600
caaaggcaac gcgctggcga aactggcgga tcatctgggc ctgaacaaag atgaagtgat      660
```

```
ggcgattggc gataacgaaa acgatctgag catgattgat tatgcgggca ttggcgtggc    720
gatgggcaac gcgaccgaaa acgtgaaaac cattgcggat gtgcatacca ccagcaacga    780
tgaagatggc gtggcgcaga ttattgaaaa aatggtgctg attgttgtcg acttatccgg    840
cc                                                                    842
```

<210> SEQ ID NO 33
<211> LENGTH: 809
<212> TYPE: DNA
<213> ORGANISM: Artificial sequence
<220> FEATURE:
<223> OTHER INFORMATION: Synthetic polynucleotide

<400> SEQUENCE: 33

```
aattgcagaa ttcatggata aaatgaaagc gattaccttt tttgatctgg atggcaccct     60
gctggatggc accagccaga ttaccccgga aattaccgcg gcggtggcgg cgctgaaaga    120
taaccagatt ctgccgctga ttgcgaccgg ccgcaccctg tgcgaaattc agccgattat    180
gaaagcgagc ggcattgata gcgcgattgt gatgaacggc cagtttattc attatgaagg    240
caaaaccatt tatagcgatg aatttaccac cgaagaatgc gtgagcctgc atgaacatgt    300
gaaacagcgc ggccatgaac tggcgtttta taacgaacgc cgcattttt gcaccggcca    360 taccggcacc gtgaaacagg cgtatgatta tattcatagc gcggtgccgg aaattgatcc    420
gaccggctat gaaaacgatg cggtgaacat gatgctggtg ctgagccagc atggcgatga    480
tgatgaatat tattatgaac gctttccgga actgaccttt tatcgcaacg gcccgtttag    540
cattgatatt gtgcgcaaag gcgtgagcaa aggcagcggc gtgaaaaacc tgtttaacac    600
cctgggcctg aacggcattc cgacctatgc gtttggcgat ggcattaacg atctggcgct    660
gtttgaagcg tgcgattatg gcattgcgat gggcaacgcg cgcgaagaac tgaaagaaaa    720
agcgaccttt attagcacca aaaacaccga aaacggcatt gtgaacggcc tgaaaaaatt    780
tgatctgctg gttgtcgact tatccggcc                                      809
```

<210> SEQ ID NO 34
<211> LENGTH: 446
<212> TYPE: DNA
<213> ORGANISM: Artificial sequence
<220> FEATURE:
<223> OTHER INFORMATION: Synthetic polynucleotide

<400> SEQUENCE: 34

```
aattgcagaa ttcatgaaag cggtgctgac cgatctggat aacaccctga ttgcgtggaa     60
caacccggat ggcaccgaag aactgaaaac ctggctgctg gaaatgaaaa acgcgggcat    120
taccgtgctg gtggtgagca acaacaaaga tagccgcatt aaacgcgtgg tggaaaaatt    180
tgatctggat tatgtggcgc gcgcgctgaa accgaccgcg cgcggcttta aactggcgga    240
aaaaaaactg ggcctgaaac cgagcgaaat gctgatggtg ggcgatcaga ttatgaccga    300
tattcgcggc gcgaacgcgg cgggcattcg caacgtgctg gtgcagccga ttgtggatac    360
cgatggctgg aacacccgca ttaaccgctt ttttgaacgc aaaattatga aatatctgag    420
caaaaaagtt gtcgacttat ccggcc                                         446
```

<210> SEQ ID NO 35
<211> LENGTH: 866
<212> TYPE: DNA
<213> ORGANISM: Artificial sequence
<220> FEATURE:

<223> OTHER INFORMATION: Synthetic polynucleotide

<400> SEQUENCE: 35

| aattgcagaa ttcatggcgg tgaaagcgat tgtgatggat attgatggca ccctgctgac | 60 |
| cagcgaaaaa aaaattagcc cgaaaacccg ccaggcgctg gtggcggcgc agaaacaggg | 120 |
| cctgagcctg attctggcga gcggccgccc gaccaacggc atgcgccgc tggcggatga | 180 |
| actggaaatg gcgcattata acggccatct gctgagctat aacggcgcgt gcgtgaccca | 240 |
| tcatggcagc cagcagcagc tgtttaacca gaccattagc aaaagcctga gccagcagat | 300 |
| tctggaacat ctgaaacagt ttgatgtgat tccgatgatt aacgatgaaa cctttatgta | 360 |
| tgtgaacgat gtgttttcata acccctgca tctggaaacc ggcgatttta acattattga | 420 |
| atatgaaagc cgcggcggca ctttcagct gtgcgaatgg catgatctgg cggcgcgcct | 480 |
| gaactttccg ctgaacaaaa ttctgattgc gggcgaaccg gcgtatctgc agaaatatca | 540 |
| tgaagcgatt tatgcgccgt ttaaagaaac cgtgaccgcg gcgtttagcg cgccgtttta | 600 |
| ttttgaattt accgcgaaaa acattgataa agcgcgcagc ctggaaaaac tgaccctgca | 660 |
| gctgggcatt accgcggaag aagtgattgc gtttggcgat ggccataacg attataccat | 720 |
| gctggaatgg gcgggcaccg gcattgcgat ggaaaacgcg gtggatgaac tgaaaaacat | 780 |
| tgcgaccgaa gtgaccctga gcaacgataa cgatggcatt gcggtggcgc tggcgaaaat | 840 |
| tgtgggcgtt gtcgacttat ccggcc | 866 |

<210> SEQ ID NO 36
<211> LENGTH: 707
<212> TYPE: DNA
<213> ORGANISM: Artificial sequence
<220> FEATURE:
<223> OTHER INFORMATION: Synthetic polynucleotide

<400> SEQUENCE: 36

| aattgcagaa ttcatgctgg aaagcagcga agtgaaaatg tatcagacca ttctgtttga | 60 |
| tctggatggc accattaccg atagcggcag cggcattatg cgcagcattc tgtatgcgac | 120 |
| cgaacagctg ggctggccgg cgccgagcga agaaacccctg cgcagcttta ttggcccgcc | 180 |
| gctgtatgaa agctttctgc atatggcgcc gagcgcggaa gcggcgcagc aggcggtggg | 240 |
| ccattatcgc gcgtattatc agcgcaaagg catgttgaa aaccatgtgt atccgggcat | 300 |
| tccggaagtg ctgacccgcc tgaaagaagc gggcgcgaaa ctgtatattg cgaccagcaa | 360 |
| accggaagaa tttgcgaaaa aaattattac ccatttttgat ctggatcgct attttaccgg | 420 |
| catttatggc gcgagcatgg atggccatcg cagcaaaaaa gcggatgtga ttcagtatgc | 480 |
| gctgaccgaa gcgcagctgg atccgaccaa agaagcgatt attatggtgg gcgatcgcaa | 540 |
| ccatgatatt ctgggcgcgc agcagaacgg cctggatagc attggcgtgc tgtatggctt | 600 |
| tggcgaagaa accgaactgc aggaagcggg cgcgacctt ctggtgcaga gcccgaaaga | 660 |
| tctgggcgcg attctgctgc agaacagcgt tgtcgactta ccggcc | 707 |

<210> SEQ ID NO 37
<211> LENGTH: 293
<212> TYPE: DNA
<213> ORGANISM: Artificial sequence
<220> FEATURE:
<223> OTHER INFORMATION: Synthetic polynucleotide

<400> SEQUENCE: 37

| aattgcagaa ttcatgaccc gcatgctgtt tctggatatt gatggcaccc tggtgggcaa | 60 | agatcagcgc attccgcaga gcgcgattcg cgcgattcgc gcggcgcagg gcaacggcca     120 tctggtgctg atttgcactg gtcgtgctcg cgcgggtgcg gcaggctggc gttatgcgct     180 gcgtccgggc gcgtggcagc agggccgcgg caccgcgttt cgctgcggcc atcatggccg     240 cgcggcgcgc cgccatggcg gcgatcgccg ccagcgccag gttgtcgact tat            293

<210> SEQ ID NO 38
<211> LENGTH: 941
<212> TYPE: DNA
<213> ORGANISM: Artificial sequence
<220> FEATURE:
<223> OTHER INFORMATION: Synthetic polynucleotide

<400> SEQUENCE: 38
aattgcagaa ttcatgtata gcattgaaac cctggcgcat gtggataccc tgtgcctgga      60
taaaaccggc accattaccg aaggcaaaat gaaagtgcag aaagcgatta ttctgcatga     120
taaatatgaa gaactgtttc gcagattat tggcagctat ctgagcgaaa gcaccgataa      180
caacattacc atgcaggcga ttcgcgatca ttatgaagtg agcaaccgct tggcgcgaa      240 agaagtgctg gcgtttagca gcgaacgcaa atggggcgcg attgaatttc cggaaattgg     300
caccgtgtat ctgggcgcgc cggaacgcct ggtggatgat agccgcctgc cggaagcggt     360
gtttaccgcg caggaaaacg gctatcgcgt gctgatgctg gcgattgcgg aacagcagcc     420
gctgaacgaa accaaaatgc cgtatctgga accgctggcg attctggaaa ttgatgatcc     480
gattcgccag aacgcgaaag aaaccctggc gtatctgaaa gaagaaggca ttgatctgaa     540
agtgattagc ggcgataacc cggtgaccgt gagcaacatt gcgcgccgcg cgggcctgcc     600
gggctatgaa agctatattg atctgagcac caaaaccacc gaagcggaag tgcgcgaagc     660
ggtgcagcag tataccgtgt ttggccgcgt gagcccgcag cagaaacgca ccattgtgcg     720
cgaactgaaa gataccgaac atgtggtggc gatgaccggc gatggcgtga acgatgtgct     780
ggcgctgcgc gaagcggatt gcagcattgc gatggcggaa ggcgatggcg cgacccgcca     840
gattagcaac ctggtgctgc tggatagcga ttttaccacc ctgccggatg tgctgtttga     900
aggccgccgc gtggtgaaca cgttgtcga cttatccggc c                         941

<210> SEQ ID NO 39
<211> LENGTH: 944
<212> TYPE: DNA
<213> ORGANISM: Artificial sequence
<220> FEATURE:
<223> OTHER INFORMATION: Synthetic polynucleotide

<400> SEQUENCE: 39
aattgcagaa ttcatgtata gcgtggaaac cctggcgcgc gtggatgtgc tgtgcctgga      60
taaaaccggc accattaccc agggcaaaat gaccgtgaaa ggcctgaaac tgctgagcga     120
acgctttacc aaagaagaac tggaacgcct gctggcggcg tatatggaac atagcaaaga     180
taacaacgcg accgcgcagg cgattcgcaa cgcgtatgaa ggcctggaac atcattatca     240
ggtgggcgat attattccgt ttagcagcga tcgcaaatgg ggcgcgatga gcattgatgg     300
cgtgggcacc ctgtttctgg gcgcgccgga atgctgctg gaagaaaacc cgaaagcggt     360
ggatcaggcg caggcgcgcg gcagccgcgt gctgattctg gcgtggagcc agagcgcggt     420
ggataccgaa accatgagcc tgccgaacga tgtggaaggc ctggcgctgc tggaaatcgc     480
ggatccgatt cgtgaagatg cggcggaaac cctggaatat ctgcgtagcg aagatgtgac     540

```
cctgaaaatt attagcggcg ataacccggt gaccgtgagc catattgcgc atcaggcggg    600
ctttgcggat tatcagagct atattgattg cagcaaagtg agcgatgaag aactggaagc    660
gctggcggaa gataccgcga tttttggccg cgtgagcccg catcagaaaa aactgctgat    720
tcagaccctg aacgcgaacg gccataccac cgcgatgacc ggcgatggcg tgaacgatat    780
tctggcgctg cgcgaagcgg attgcagcat tgtgatggcg gaaggcgatc cggcgacccg    840
ccagattgcg aacctggtgc tgatggatag cgaatttaaa gatattccgg aaattctgtt    900
tgaaggccgc cgcgtggtga caacgttgt cgacttatcc ggcc                     944
```

```
<210> SEQ ID NO 40
<211> LENGTH: 866
<212> TYPE: DNA
<213> ORGANISM: Artificial sequence
<220> FEATURE:
<223> OTHER INFORMATION: Synthetic polynucleotide

<400> SEQUENCE: 40
aattgcagaa ttcatgacca acccggaaca gcgcctgatt gtgaccgatc tggatggcac     60
cctgctgcat gatgcgccga cctttgaaga acgctttatt acccagcgca gcattgatac    120
cgtgaaacgc atgcatgatg cgggctatcg ctttgcggtg gcgaccgcgc gcccggtgag    180
caccggcttt gaatatgcgg gcaaactgcc ggtggatgcg tatatttatc tgaacggcgc    240
gctgattgat tttgcgccgg aacgcagcga ttatgatctg ctgaccagcg gccgcctgcc    300
gagcgatggc catctgctga agtgggctt tagcagcgcg cgcgcgtgcg aagtgtgccg    360
ctatctgctg gatgaaattc cgggcctgag cctgggcatt gtgatggatg atgtgcgcta    420
taccaacttt gatgtgagcg tgtattggaa aacccagacc tggcagttta ccgattttac    480
cgatgtgccg gatggcattg cggataaaat tattatttt ccgaaaagcg aacagtgggc    540
gcatctgaaa accctggtgc gccggattt tgatgtggcg attagcgaag cagcatgtg    600 gatgctgatg agcccgctgg cgaacaaacg ccaggcgctg aaaaccctgt gcgaacgcat    660
ggatgtgcgc ctggatggca ccgtgagctt tggcgatgat ctgattgata ttggcatgat    720
gaccaccagc gaaaccggcg tggcggtggc gaacgcgaac ccggaagtga ttaaaattgc    780
ggatgaaatt tgcccgccga caacgatga tggcgtggcg cagtggattg aacgccatct    840
gctggcggtt gtcgacttat ccggcc                                        866
```

```
<210> SEQ ID NO 41
<211> LENGTH: 734
<212> TYPE: DNA
<213> ORGANISM: Artificial sequence
<220> FEATURE:
<223> OTHER INFORMATION: Synthetic polynucleotide

<400> SEQUENCE: 41
aattgcagaa ttcatgcgca acgtggtgct gctggatctg gatggcaccc tgacccagag     60
cgatccgggc attattgcgt gcgcgaccaa agcgtttgaa gaactgagcc tgccggtgcc    120
ggatgatcag gaaatgcatc gctttattgg cccggcgatt attgaaagct tcgccgcaa    180 ccatatgccg gatgaactgc tggatcgcgg cgtggaaatt tatcgcgaat attatgcgga    240
taaagcggtg tttgatgatc cgaacaaccc gggccataaa attccgggcc gcctgtataa    300
cagcgtgtat gcgggcattc cggaacagct ggcggcgctg cgcgcggatg gcctgcatct    360
ggcgattgcg acctgcaaac gcagtatca ggcggaaccg gtgtgcgaac attttcatct    420
ggataccatg gtggatggca tttatggcgc gagcaccgat aacagccgca ttgataaaga    480
```

```
tcaggtgatt cgctattgct ttgatagcat tggctttgat gcggatgcgg gcgatcgcgc      540
gctgatggtg ggcgatcgct ggaccgatgt ggatggcgcg attgcgtgcg gcctggattg      600
cctgggctgc cgctggggct atgcggaagc gggcgaactg aagaacatg gcgcgtatcg       660 cattattgat accgtggatg aactggcggc ggcggtgaac gattattttg cgaaagttgt      720
cgacttatcc ggcc                                                        734
```

<210> SEQ ID NO 42
<211> LENGTH: 821
<212> TYPE: DNA
<213> ORGANISM: Artificial sequence
<220> FEATURE:
<223> OTHER INFORMATION: Synthetic polynucleotide

<400> SEQUENCE: 42

```
aattgcagaa ttcatgatta aagcggcgtt ttttgatatt gatggcaccc tgaccagctt      60
tgtgacccat gtgattccgc agagcagcat tgatgcgctg catgaactgc aggatcgcgg     120
cgtgaaagtg tttatttgca gcggccgcgc gccgagccat atgaccgtgg tgctggatat     180
gatgccggtg catttgatg gcattattgc gctgaacggc cagtattgct ttgatgatca     240
tggcctgctg gaaaaagaaa gcctgctgcc ggaagatatt gtgaccatta cccgctggct     300
ggatgaacat ccggatgtgg tggcgaacta ttgcgaaaaa gattatgtgt attttaacca     360
gattaccgat gcgatgcgcg cgacctggcg ccagctgggc aaaaccgcgc cgaccgtgaa     420
cattgatgat ccgcatgaac gcgcgctgaa acatgaaacc tttcagatta gcccgtatat     480
tagctttgaa gatgaagcga aactgagcgg catgtgccgc aacgtgcgcg cgtgcgctg      540 gcatccggat tttaccgatc tgattccggc ggatggcggc aaaccggaag gcatgaaacg     600
ctttatgcgc cattatggct ggacccgcga acagaccatt gcgtttggcg atggcggcaa     660
cgatgcggat atgctggcgt ttgcgggcat tggcgtggcg atgggcaacg cgaccgaacc     720
ggcgaaagcg gcggcggatt atattaccga tgatgtggat catgatggca ttatgaacgc     780
gctgaaacat tttaacgtgc tggttgtcga cttatccggc c                         821
```

<210> SEQ ID NO 43
<211> LENGTH: 140
<212> TYPE: DNA
<213> ORGANISM: Artificial sequence
<220> FEATURE:
<223> OTHER INFORMATION: Synthetic polynucleotide

<400> SEQUENCE: 43

```
atgtcaatta agttagttgc tattgatatc gacggaacat tgctaaattc acaacacaag      60
attaccccac gggtcaaaga agcgctccaa aaagcaaatg agcaaggtgt tcgtattgtt     120
ttatgtacag gccgtccttt                                                 140
```

<210> SEQ ID NO 44
<211> LENGTH: 143
<212> TYPE: DNA
<213> ORGANISM: Artificial sequence
<220> FEATURE:
<223> OTHER INFORMATION: Synthetic polynucleotide

<400> SEQUENCE: 44

```
accggccatc atcgagtcgt tcagacgcaa ccatatgccg gacgagctgc tggaccgcgg      60
cgtggagata taccgcgaat actatgcgga caaggcggtg ttcgacgacc cgaacaatcc     120
```
cggccacaaa attcccggac gac                                              143

<210> SEQ ID NO 45
<211> LENGTH: 130
<212> TYPE: DNA
<213> ORGANISM: Artificial sequence
<220> FEATURE:
<223> OTHER INFORMATION: Synthetic polynucleotide

<400> SEQUENCE: 45
ccaactcggc aagaccgcac cgaccgtgaa catcgacgat ccgcacgaga gggcgctgaa    60
gcatgagacg ttccagatca gcccgtacat cagctttgaa gatgaagcga agctgtccgg   120
catgtgtcgc                                                          130

<210> SEQ ID NO 46
<211> LENGTH: 270
<212> TYPE: PRT
<213> ORGANISM: Artificial sequence
<220> FEATURE:
<223> OTHER INFORMATION: Synthetic polypeptide

<400> SEQUENCE: 46

Met Ser Ile Lys Leu Val Ala Ile Asp Ile Asp Gly Thr Leu Leu Asn
1               5                   10                  15

Ser Gln His Lys Ile Thr Pro Arg Val Lys Glu Ala Leu Gln Lys Ala
            20                  25                  30

Asn Glu Gln Gly Val Arg Ile Val Leu Cys Thr Gly Arg Pro Leu Pro
        35                  40                  45

Gly Val Lys Glu Gln Leu Asp Glu Leu Ala Leu Tyr Gly Glu Asn Asp
    50                  55                  60

Phe Val Ile Thr Tyr Asn Gly Ser Leu Val Gln Ala Thr Lys Asp Asn
65                  70                  75                  80

Thr Ile Ile Ser Arg Tyr Thr Leu Ser Tyr Glu Asp Phe Leu Glu Ile
                85                  90                  95

Glu Met Tyr Ser Arg Lys Val Gly Ala His Leu His Thr Ile Asp Asp
            100                 105                 110

Ser Ala Ile Tyr Thr Ala Asn Arg Asn Ile Gly Lys Tyr Thr Ile His
        115                 120                 125

Glu Ala Ser Leu Val Asn Met Pro Leu Lys Tyr Arg Thr Val Asp Glu
    130                 135                 140

Met Thr Pro Glu Met Asn Ile Ile Lys Met Met Ile Asp Glu Pro
145                 150                 155                 160

Glu Val Leu Asp Pro Ala Ile Ala Lys Leu Pro Leu His Phe Thr Glu
                165                 170                 175

Lys Tyr Thr Thr Val Lys Ser Thr Pro Phe Tyr Tyr Glu Ile Met Asn
            180                 185                 190

Lys Asn Ala Ser Lys Gly Asn Ala Leu Ala Lys Leu Ala Asp His Leu
        195                 200                 205

Gly Leu Asn Lys Asp Glu Val Met Ala Ile Gly Asp Asn Glu Asn Asp
    210                 215                 220

Leu Ser Met Ile Asp Tyr Ala Gly Ile Gly Val Ala Met Gly Asn Ala
225                 230                 235                 240

Thr Glu Asn Val Lys Thr Ile Ala Asp Val His Thr Thr Ser Asn Asp
                245                 250                 255

Glu Asp Gly Val Ala Gln Ile Ile Glu Lys Met Val Leu Ile
            260                 265                 270

<210> SEQ ID NO 47
<211> LENGTH: 244
<212> TYPE: PRT
<213> ORGANISM: Artificial sequence
<220> FEATURE:
<223> OTHER INFORMATION: Synthetic polypeptide

<400> SEQUENCE: 47

```
Met Ser Gln His Gln Val Thr Thr Arg Gln Arg Asn Val Val Leu
1               5                   10                  15

Leu Asp Leu Asp Gly Thr Leu Thr Gln Ser Asp Pro Gly Ile Ile Ala
            20                  25                  30

Cys Ala Thr Lys Ala Phe Glu Glu Leu Ser Leu Pro Val Pro Asp Asp
            35                  40                  45

Gln Glu Met His Arg Phe Ile Gly Pro Ala Ile Ile Glu Ser Phe Arg
    50                  55                  60

Arg Asn His Met Pro Asp Glu Leu Leu Asp Arg Gly Val Glu Ile Tyr
65                  70                  75                  80

Arg Glu Tyr Tyr Ala Asp Lys Ala Val Phe Asp Pro Asn Asn Pro
                85                  90                  95

Gly His Lys Ile Pro Gly Arg Leu Tyr Asn Ser Val Tyr Ala Gly Ile
                100                 105                 110

Pro Glu Gln Leu Ala Ala Leu Arg Ala Asp Gly Leu His Leu Ala Ile
                115                 120                 125

Ala Thr Cys Lys Pro Gln Tyr Gln Ala Glu Pro Val Cys Glu His Phe
            130                 135                 140

His Leu Asp Thr Met Val Asp Gly Ile Tyr Gly Ala Ser Thr Asp Asn
145                 150                 155                 160

Ser Arg Ile Asp Lys Asp Gln Val Ile Arg Tyr Cys Phe Asp Ser Ile
                165                 170                 175

Gly Phe Asp Ala Asp Ala Gly Asp Arg Ala Leu Met Val Gly Asp Arg
                180                 185                 190

Trp Thr Asp Val Asp Gly Ala Ile Ala Cys Gly Leu Asp Cys Leu Gly
            195                 200                 205

Cys Arg Trp Gly Tyr Ala Glu Ala Gly Glu Leu Glu Glu His Gly Ala
            210                 215                 220

Tyr Arg Ile Ile Asp Thr Val Asp Glu Leu Ala Ala Ala Val Asn Asp
225                 230                 235                 240

Tyr Phe Ala Lys
```

<210> SEQ ID NO 48
<211> LENGTH: 283
<212> TYPE: PRT
<213> ORGANISM: Artificial sequence
<220> FEATURE:
<223> OTHER INFORMATION: Synthetic polypeptide

<400> SEQUENCE: 48

```
Met Ala Ser Asp Asp Ile Met Thr Ala Gly Ala Gly Gly Ala Thr Ala
1               5                   10                  15

Thr Val Arg Ala Asp Ile Lys Ala Ala Phe Phe Asp Ile Asp Gly Thr
            20                  25                  30

Leu Thr Ser Phe Val Thr His Val Ile Pro Gln Ser Ser Ile Asp Ala
        35                  40                  45

Leu His Glu Leu Gln Asp Arg Gly Val Lys Val Phe Ile Cys Ser Gly
    50                  55                  60
```

```
Arg Ala Pro Ser His Met Thr Val Val Leu Asp Met Met Pro Val His
 65                  70                  75                  80

Phe Asp Gly Ile Ile Ala Leu Asn Gly Gln Tyr Cys Phe Asp Asp His
                 85                  90                  95

Gly Leu Leu Glu Lys Glu Ser Leu Leu Pro Glu Asp Ile Val Thr Ile
            100                 105                 110

Thr Arg Trp Leu Asp Glu His Pro Asp Val Val Ala Asn Tyr Cys Glu
        115                 120                 125

Lys Asp Tyr Val Tyr Phe Asn Gln Ile Thr Asp Ala Met Arg Ala Thr
    130                 135                 140

Trp Arg Gln Leu Gly Lys Thr Ala Pro Thr Val Asn Ile Asp Asp Pro
145                 150                 155                 160

His Glu Arg Ala Leu Lys His Glu Thr Phe Gln Ile Ser Pro Tyr Ile
                165                 170                 175

Ser Phe Glu Asp Glu Ala Lys Leu Ser Gly Met Cys Arg Asn Val Arg
            180                 185                 190

Gly Val Arg Trp His Pro Asp Phe Thr Asp Leu Ile Pro Ala Asp Gly
        195                 200                 205

Gly Lys Pro Glu Gly Met Lys Arg Phe Met Arg His Tyr Gly Trp Thr
    210                 215                 220

Arg Glu Gln Thr Ile Ala Phe Gly Asp Gly Gly Asn Asp Ala Asp Met
225                 230                 235                 240

Leu Ala Phe Ala Gly Ile Gly Val Ala Met Gly Asn Ala Thr Glu Pro
                245                 250                 255

Ala Lys Ala Ala Ala Asp Tyr Ile Thr Asp Asp Val Asp His Asp Gly
            260                 265                 270

Ile Met Asn Ala Leu Lys His Phe Asn Val Leu
        275                 280

<210> SEQ ID NO 49
<211> LENGTH: 123
<212> TYPE: DNA
<213> ORGANISM: Artificial sequence
<220> FEATURE:
<223> OTHER INFORMATION: Synthetic polynucleotide

<400> SEQUENCE: 49
ccaactcggc aagaccgcac cgaccgtgaa catcgacgat ccgcacgaga gggcgctgaa      60
gcatgagacg ttccagatca gcccgtacat cagctttgaa gatgaagcga agctgtccgg     120
cat                                                                  123

<210> SEQ ID NO 50
<211> LENGTH: 813
<212> TYPE: DNA
<213> ORGANISM: Artificial sequence
<220> FEATURE:
<223> OTHER INFORMATION: Synthetic polynucleotide

<400> SEQUENCE: 50
atgtcaatta agttagttgc tattgatatc gacggaacat tgctaaattc acaacacaag      60
attaccccac gggtcaaaga agcgctccaa aaagcaaatg agcaaggtgt tcgtattgtt     120
ttatgtacag gccgtccttt gccaggcgtg aaagaacaat tggatgaatt agccttatat     180
ggtgaaaatg atttcgtgat tacctacaac ggttcgcttg tccaagcaac caaagataat     240
acgattattt cacgctatac cttgagttat gaggattttt tagaaattga atgtattct      300 cgtaaagtcg gcgctcactt gcatacaatt gatgattccg ctatttacac tgccaatcgc     360
```

-continued

| | |
|---|---|
| aatattggta aatatacgat tcacgaagca tctttagtga acatgccttt aaaatatcgt | 420 |
| acggtggatg aaatgacacc agagatgaac attattaaaa tgatgatgat tgatgagccg | 480 |
| gaagttttag atcctgccat tgcaaaatta ccattacatt ttaccgaaaa atatacgact | 540 |
| gttaaaagta cgcctttta ctatgaaatc atgaataaaa atgctagcaa aggcaatgct | 600 |
| ctagcaaaat tggcagacca tttaggctta aataaagacg aagtgatggc cattggtgac | 660 |
| aatgaaaatg acttatccat gattgattac gctgggattg tgttgcgat gggcaatgcg | 720 |
| acagaaaatg ttaaaacaat tgccgatgtg cataccacta gtaatgacga agatggtgtc | 780 |
| gctcaaatta ttgaaaaaat ggttttaatt taa | 813 |

<210> SEQ ID NO 51
<211> LENGTH: 735
<212> TYPE: DNA
<213> ORGANISM: Artificial sequence
<220> FEATURE:
<223> OTHER INFORMATION: Synthetic polynucleotide

<400> SEQUENCE: 51

| | |
|---|---|
| atgtctcagc atcaggtcac gacccggcag cgcaggaacg tggtgctgct cgaccttgac | 60 |
| ggtacgttga cgcaatcgga cccgggcatc atcgcctgcg ccaccaaggc gttcgaggag | 120 |
| ctcagcctgc cggttcccga cgatcaggag atgcaccggt tcatcggacc ggccatcatc | 180 |
| gagtcgttca gacgcaacca tatgccggac gagctgctgg accgcggcgt ggagatatac | 240 |
| cgcgaatact atgcggacaa gcggtgttc gacgacccga acaatcccgg ccacaaaatt | 300 |
| cccggacgac tgtacaacag cgtgtacgcc ggtattcccg agcagctggc ggcattgcgc | 360 |
| gccgacggct tgcacctggc aatcgccacg tgcaagccgc aatatcaggc cgagccagtg | 420 |
| tgcgagcatt tccatctcga taccatggtc gacggcatct acggcgccag cacagacaat | 480 |
| tcgcgcatcg acaaggatca ggtcatccga tactgcttcg acagcatcgg attcgatgcg | 540 |
| gatgccggtg accgcgccct gatggtcggc gaccgttgga ccgacgtcga cggcgccatc | 600 |
| gcatgcgggc tcgattgcct gggttgccgt tgggggtacg ccgaagccgg tgagcttgag | 660 |
| gaacatggcg cataccgcat catcgatacc gtcgatgagc ttgccgccgc ggtgaatgat | 720 |
| tatttcgcaa agtga | 735 |

<210> SEQ ID NO 52
<211> LENGTH: 852
<212> TYPE: DNA
<213> ORGANISM: Artificial sequence
<220> FEATURE:
<223> OTHER INFORMATION: Synthetic polynucleotide

<400> SEQUENCE: 52

| | |
|---|---|
| atggcatcgg acgacatcat gacagcgggc gccggaggcg cgacggccac cgtgcgagcc | 60 |
| gacatcaagg cggcgttctt cgacatcgac ggcacgctga cgagtttcgt gacgcatgta | 120 |
| atcccgcagt cctccatcga cgcgctgcac gagctgcagg atcgcggggt gaaggtgttc | 180 |
| atctgctccg gtcgggcgcc gtcgcacatg accgtcgtgc tcgacatgat gccggtgcac | 240 |
| ttcgacggca tcatcgcgct gaacgggcag tactgcttcg acgaccacgg gctcctggag | 300 |
| aaggagtcgc tgctgcccga ggacatcgtc accatcaccc gctggcttga cgagcacccc | 360 |
| gacgtggtgg cgaactactg cgagaaggat tacgtctact tcaaccagat caccgacgcg | 420 |
| atgcgggcca cgtggcgcca actcggcaag accgcaccga ccgtgaacat cgacgatccg | 480 |

```
cacgagaggg cgctgaagca tgagacgttc cagatcagcc cgtacatcag ctttgaagat    540
gaagcgaagc tgtccggcat gtgtcgcaat gtcagaggcg tgcgctggca tccggacttc    600
accgacctga ttcccgccga cggcggcaaa cccgagggaa tgaagcggtt catgcggcat    660
tacggctgga cgcgcgagca gaccatcgcg ttcggagacg gcggcaacga cgccgacatg    720
ctcgccttcg ccggcatcgg cgtggcgatg ggcaatgcga ccgaaccggc gaaggccgcg    780
gccgactaca tcaccgatga cgtcgaccac gacggcatca tgaacgcgct caagcacttc    840
aacgtcctgt ag                                                       852
```